United States Patent
Yan et al.

(10) Patent No.: US 12,187,684 B2
(45) Date of Patent: *Jan. 7, 2025

(54) BENZIMIDAZOLE DERIVATIVES AS MODULATORS OF RETINOID-RELATED ORPHAN RECEPTOR GAMMA (RORγ) AND PHARMACEUTICAL USE THEREOF

(71) Applicants: Jiangsu Hengrui Medicine Co., Ltd., Lianyungang (CN); Shanghai Hengrui Pharmaceutical Co., Ltd., Shanghai (CN)

(72) Inventors: Yinfa Yan, Bedminster, NJ (US); Minsheng Zhang, Warren, NJ (US); Dong Liu, Basking Ridge, NJ (US); Fengqi Zhang, Edison, NJ (US); Suxing Liu, Edison, NJ (US); Rumin Zhang, Edison, NJ (US); Feng He, Shanghai (CN); Weikang Tao, North Brunswick, NJ (US)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,537

(22) Filed: Nov. 21, 2022

(65) Prior Publication Data
US 2023/0130361 A1  Apr. 27, 2023

Related U.S. Application Data

(63) Continuation of application No. 17/052,451, filed as application No. PCT/US2019/030526 on May 3, 2019, now Pat. No. 11,512,055.

(60) Provisional application No. 62/666,312, filed on May 3, 2018.

(51) Int. Cl.
| | |
|---|---|
| *C07D 235/06* | (2006.01) |
| *C07D 235/12* | (2006.01) |
| *C07D 235/14* | (2006.01) |
| *C07D 235/16* | (2006.01) |
| *C07D 401/04* | (2006.01) |
| *C07D 409/04* | (2006.01) |
| *C07D 413/12* | (2006.01) |

(52) U.S. Cl.
CPC ........ *C07D 235/06* (2013.01); *C07D 235/12* (2013.01); *C07D 235/14* (2013.01); *C07D 235/16* (2013.01); *C07D 401/04* (2013.01); *C07D 409/04* (2013.01); *C07D 413/12* (2013.01)

(58) Field of Classification Search
CPC .............. A61K 31/4184; C07D 235/04; C07D 235/12; C07D 235/14; C07D 235/16; C07D 401/04; C07D 409/04
See application file for complete search history.

(56) References Cited

U.S. PATENT DOCUMENTS

| | | | |
|---|---|---|---|
| 11,512,055 B2* | 11/2022 | Yan | C07D 409/04 |
| 2004/0138255 A1 | 7/2004 | Huang et al. | |
| 2011/0190364 A1* | 8/2011 | Player | A61P 1/04 |
| | | | 514/394 |
| 2013/0065896 A1 | 3/2013 | Masaki et al. | |
| 2013/0345436 A1 | 12/2013 | Jiang et al. | |
| 2015/0152065 A1 | 6/2015 | Brookings et al. | |
| 2015/0291607 A1 | 10/2015 | Bakonyi et al. | |
| 2017/0253605 A1 | 9/2017 | Yu et al. | |

FOREIGN PATENT DOCUMENTS

| | | |
|---|---|---|
| WO | 2012027965 A1 | 3/2012 |
| WO | 2013029338 A1 | 3/2013 |
| WO | 2015066241 A1 | 5/2015 |

OTHER PUBLICATIONS

Benoit G, et al, Pharmacological Reviews, 58 (4):798-836, 2006.
Zhang, Y., et al., Acta Pharmacogica Sinica, 36:71-87, 2015.
Villey I, et al, Eur. J. Immunol., 29(12):4072-80, 1999.
Ruan, Q., et al., J. Exp. Med., 208(11):2321-2333, 2011.
Ivanov, I. I. et al., Cell, 126:1121-1133, 2006.
Buonocore, S., et al., Nature, 464:1371-1375, 2010.
Jetten, A. M., Nucl. Recep. Signal, 7:e300, DOI:10.1621/nrs.07003, 2009.
Guillaumond, F. et al, J. Biol. Rhythms, 20 (5):391-403, 2005.

(Continued)

*Primary Examiner* — Clinton A Brooks
*Assistant Examiner* — George W Kosturko
(74) *Attorney, Agent, or Firm* — Fox Rothschild LLP

(57) ABSTRACT

The present invention relates to benzimidazole derivatives of formula (I) as inhibitors of retinoid-related orphan receptor gamma (RORγ) protein, pharmaceutical compositions containing the compounds, preparation methods thereof, and the use of the compounds as therapeutic agents for the treatment of RORγ-mediated diseases or disorders.

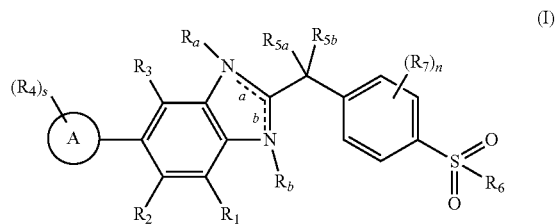

18 Claims, No Drawings

(56) References Cited

OTHER PUBLICATIONS

Akashi M and Takumi T., Nat. Struct. Mol. Biol., 12 (5):441-448, 2005.
Louten et al, J. Allergy Clin. Immunol., 123 : 1004-1011, (2009).
Annuziato, F., et al, Nat. Rev. Rheumatol., 5(6): 325-331,2009.
Lizuka, M., et al., J. Immunol., 194:56-67, 2014.
Chen, Y., et al., Mucosal. Immunol., 7(1):38-45, 2014.
Jia, S., et al., Clin. Exp. Immunol., 162:131-137, 2010.
Boaventura, V. S., et al, Eur. J. Immunol., 40: 2830-2836, 2010.
Figueroa-Vega, N., et al, J. Clin. Endocrinol. Metab., 95: 953-62, 2010.
Jun R. Huh and Dan R. Littman, Eur. J. Immunol., 42(9): 2232-2237.

\* cited by examiner

BENZIMIDAZOLE DERIVATIVES AS MODULATORS OF RETINOID-RELATED ORPHAN RECEPTOR GAMMA (RORγ) AND PHARMACEUTICAL USE THEREOF

CROSS-REFERENCE TO RELATED APPLICATIONS

This application is a continuation of U.S. patent application Ser. No. 17/052,451, filed on Nov. 2, 2020, which is a U.S. national phase application of International Application No. PCT/US2019/030526, filed on May 3, 2019, which claims priority under 35 U.S.C. § 119 (e) to U.S. Provisional Patent Application No. 62/666,312, filed on May 3, 2018, the disclosures of which are incorporated herein by reference in their entirety.

FIELD OF THE INVENTION

The present invention relates to modulators of retinoid-related orphan receptor gamma (RORγ) and their uses as therapeutic agents for treatment of RORγ-mediated diseases or conditions, including various inflammation and autoimmune diseases and cancers.

BACKGROUND OF THE INVENTION

Nuclear receptors are ligand-regulated transcription factors that regulate development, immunity, and cellular metabolism, one of the major classes of drug targets for human diseases. The retinoid-related orphan receptor gamma (RORγ) protein is a member of the NR1 subfamily of nuclear receptors and exhibits a typical nuclear receptor domain structure, consisting of the DNA binding domain; ligand binding domain; a hinge domain and activation function 2 domain (Benoit G, et al, *Pharmacological Reviews*, 58 (4):798-836, 2006; Zhang, Y., et al., *Acta Pharmacogica Sinica*, 36:71-87, 2015). RORγ recognizes and binds as monomers, as opposed to most other nuclear receptors, which bind as dimers. It binds to specific DNA sequences, typically consisting of TAAA/TNTAGGTCA, termed ROR response elements (ROREs).

There are two isoforms of RORγ, RORγ1 and RORγ2, which are produced from the same RORC gene, probably by selection of alternative promoters (Villey I, et al, *Eur. J. Immunol.*, 29(12):4072-80, 1999). RORγ2 (also known as RORγt) produced from an mRNA identical to that of RORγ1 except for a replacement of an alternative exon with two 5'-most exons, leading to a truncated form of RORγ1. The two isoforms exhibit distinct patterns of tissue-specific expression. RORγt is preferentially expressed in the thymus and several distinct cell types of the immune system, whereas RORγ1 is expressed in many tissues, thymus, lung, kidney, muscle, and liver.

RORγt is a master regulator of the development of T helper 17 cells (Th17 cells) (Ruan, Q., et al., *J. Exp. Med.*, 208(11):2321-2333, 2011; Ivanov, I. I. et al., *Cell*, 126:1121-1133, 2006). Th17 cells produce numerous cytokines, including interleukin-17 (IL-17), that are known to enhance inflammatory processes. In addition, a critical role of RORγt was shown in non-Th17 lymphoid cells expressing Thy1, SCA-1 and IL-23R proteins (Buonocore, S., et al., *Nature*, 464:1371-1375, 2010). RORγt plays an important role in the development of secondary lymphoid tissues, thymopoiesis, lymphocyte development ((Jetten, A. M., *Nucl. Recep. Signal*, 7:e300, DOI:10.1621/nrs.07003, 2009). RORγ1 appears to be involved in the regulation of circadian rhythms (Guil-laumond, F. et al, *J. Biol. Rhythms*, 20 (5):391-403, 2005; Akashi M and Takumi T., *Nat. Struct. Mol. Biol.*, 12 (5): 441-448, 2005).

RORγ has been identified as a key mediator in the pathogenesis of several diseases such as rheumatoid arthritis, psoriasis, multiple sclerosis, inflammatory bowel disease, Crohn's disease, Sjögren's syndrome and asthma, etc. (Louten et al, *J. Allergy Clin. Immunol.*, 123: 1004-1011, (2009); Annuziato, F., et al, *Nat. Rev. Rheumatol.*, 5(6): 325-331, 2009; Lizuka, M., et al., *J. Immunol.*, 194:56-67, 2014). Some other diseases, such as chronic dry eye disease, Kawasaki Disease, mucosal leishmaniasis, and Hashimoto's thyroiditis, are characterized by increased Th17 proportions and/or elevated levels of Th17 hallmark cytokines such as IL-17, IL-22 and IL-23 (Chen, Y., et al., *Mucosal. Immunol.*, 7(1):38-45, 2014; Jia, S., et al., *Clin. Exp. Immunol.*, 162: 131-137, 2010; Boaventura, V. S., et al, *Eur. J. Immunol.*, 40: 2830-2836, 2010; Figueroa-Vega, N., et al, *J. Clin. Endocrinol. Metab.*, 95: 953-62, 2010). In each of the above examples the inhibition may be enhanced by simultaneous inhibition of RORα. RORγt inhibitors are currently under development for the treatment of autoimmune diseases such as psoriasis and rheumatoid arthritis. See Jun R. Huh and Dan R. Littman, *Eur. J. Immunol.*, 42(9): 2232-2237 (2012), WO 2012/027965, WO 2013/029338, and US 2015/291607.

The present invention describes a series of new compounds that display potent inhibition against RORγ, therefore, can provide a potential therapeutic approach to RORγ-mediated diseases or conditions.

SUMMARY OF THE INVENTION

In one aspect, the present invention is directed to a compound of formula (I):

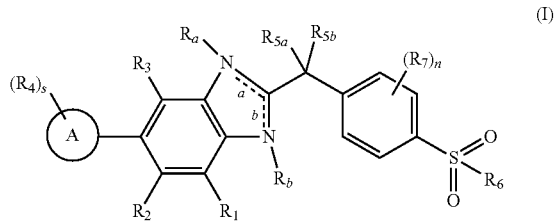

or a tautomer, mesomer, racemate, enantiomer, diastereomer, or mixture thereof, or a pharmaceutically acceptable salt, solvate, or prodrug thereof,
wherein:
  ==== is selected from single bond and double bond, when $\overset{a}{====}$ is double bond, then $\overset{b}{====}$ is single bond, $R_a$ is absent and $R_b$ is hydrogen; when $\overset{b}{====}$ is double bond, then $\overset{a}{====}$ is single bond, $R_a$ is hydrogen and $R_b$ is absent;
  ring A is selected from the group consisting of cycloalkyl, heterocyclyl, aryl and heteroaryl;
  $R_1$, $R_2$ and $R_3$ are identical or different and each is independently selected from the group consisting of hydrogen, halogen, alkyl, haloalkyl, alkenyl, alkynyl, alkoxy, cyano, amino, hydroxy, cycloalkyl, heterocyclyl, aryl and heteroaryl;
  each $R_4$ is identical or different and each is independently selected from the group consisting of hydrogen, halogen, alkyl, haloalkyl, alkenyl, alkynyl, alkoxy, haloalkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$ and —S(O)$_2$NR$_{11}$R$_{12}$, wherein said alkyl, alkenyl, alkynyl, alkoxy, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

R$_{5a}$ and R$_{5b}$ are identical or different and each is independently selected from the group consisting of hydrogen, halogen, alkyl, haloalkyl, hydroxy, hydroxyalkyl, alkoxy, cyano, amino, cycloalkyl, heterocyclyl, aryl, heteroaryl, —OR$_8$, —NR$_{10}$COR$_9$, —NR$_{10}$COCH$_2$OR$_8$, —(CH$_2$)$_x$C(O)OR$_8$, —(CH$_2$)$_x$CONR$_{11}$R$_{12}$ and —(CH$_2$)$_x$NR$_{11}$R$_{12}$, wherein said alkyl, alkoxy, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, —CONR$_{11}$R$_{12}$, —NR$_{10}$COR$_9$, cycloalkyl, heterocyclyl, aryl and heteroaryl;

or R$_{5a}$ and R$_{5b}$ are together form

R$_6$ is selected from the group consisting of alkyl, haloalkyl, alkenyl, alkynyl, cycloalkyl, heterocyclyl, aryl, heteroaryl and NR$_{11}$R$_{12}$, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

each R$_7$ is identical or different and each is independently selected from the group consisting of hydrogen, halogen, alkyl, haloalkyl, alkenyl, alkynyl, alkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$ and —S(O)$_2$NR$_{11}$R$_{12}$, wherein said alkyl, alkenyl, alkynyl, alkoxy, cycloalkyl, heterocyclyl, aryl and heteroaryl are each optionally substituted by one or more group(s) selected from the group consisting of halogen, alkyl, alkenyl, alkynyl, alkoxy, cyano, amino, nitro, hydroxy, cycloalkyl, heterocyclyl, aryl and heteroaryl;

R$_8$ is selected from the group consisting of hydrogen, alkyl, haloalkyl, cycloalkyl and heterocyclyl, wherein said alkyl, aryl and heteroaryl are each optionally substituted by one or more groups selected from the group consisting of halogen and alkoxy;

R$_9$ is selected from the group consisting of hydrogen, alkyl, hydroxyl, alkoxy, cycloalkyl, aryl and heteroaryl, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

R$_{10}$ is selected from the group consisting of hydrogen, alkyl, haloalkyl, cycloalkyl and heterocyclyl;

R$_{11}$ and R$_{12}$ are identical or different and each is independently selected from the group consisting of hydrogen, alkyl, alkenyl, alkynyl, haloalkyl, cycloalkyl, heterocyclyl, —COR$_{13}$, aryl and heteroaryl, wherein said alkyl, alkenyl, alkynyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

or R$_{11}$ and R$_{12}$ together with the nitrogen atom to which they are attached form heterocyclyl, wherein heterocyclyl has one or more heteroatoms selected from the group consisting of O, N and S, and is optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

R$_{13}$ is selected from the group consisting of hydrogen, alkyl, hydroxyl, alkoxy, cycloalkyl, aryl and heteroaryl, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

n is 0, 1, 2, 3, or 4;

s is 0, 1, 2, 3 or 4; and x is 0, 1, 2, 3 or 4.

In another aspect, the present invention is directed to a compound of formula (IA),

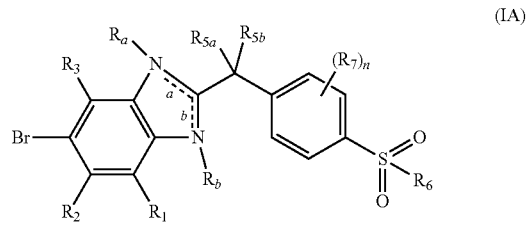

or a tautomer, mesomer, racemate, enantiomer, diastereomer, or mixture thereof, or a pharmaceutically acceptable salt, solvate or prodrug thereof, which is an intermediate for the synthesis of the compound of formula (I), wherein:

$\underline{\overset{a}{\text{----}}}$, $\underline{\overset{b}{\text{----}}}$, R$_a$, R$_b$, R$_1$~R$_3$, R$_{5a}$, R$_{5b}$, R$_6$, R$_7$ and n are as defined in formula (I).

In another aspect, the present invention is directed to a compound of formula (IC) or formula (ID) as an intermediate for the synthesis of compounds of formula (I), or a tautomer, mesomer, racemate, enantiomer, diastereomer, or mixture thereof, or a pharmaceutically acceptable salt, solvate or prodrug thereof,

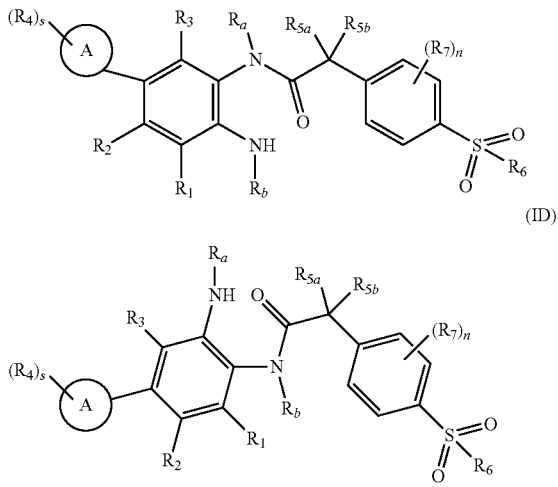

wherein:
R$_a$ and R$_b$ is hydrogen;
ring A, R$_1$–R$_4$, R$_{5a}$, R$_{5b}$, R$_6$, R$_7$, n and s are as defined in formula (I).

In another aspect, the present invention is directed to various processes for preparing the compound of formula (I).

In another aspect, the present invention is directed to a pharmaceutical composition comprising a compound of formula (I), or a tautomer, mesomer, racemate, enantiomer, diastereomer, or mixture thereof, or a pharmaceutically acceptable salt, solvate or prodrug thereof, and one or more pharmaceutically acceptable carriers, diluents or excipients.

In another aspect, the present invention is directed to a method for inhibiting a retinoid-related orphan receptor gamma (RORγ) or treating a retinoid-related orphan receptor gamma (RORγ) protein mediated disease or disorder in a subject using a therapeutically effective amount of the compound of formula (I), or the tautomer, mesomer, racemate, enantiomer, diastereomer, or mixture thereof, or a pharmaceutically acceptable salt, solvate or prodrug thereof.

Other aspects and advantages of the present invention will be better appreciated in view of the following detailed description and claims.

DETAILED DESCRIPTION OF THE INVENTION

In one aspect, the present invention is directed to a compound of formula (I):

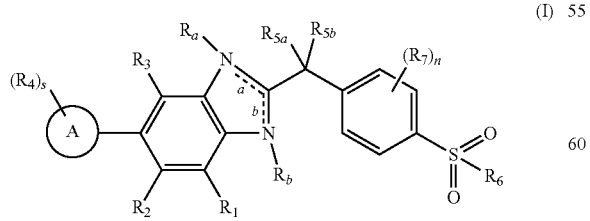

or a tautomer, mesomer, racemate, enantiomer, diastereomer, or mixture thereof, or a pharmaceutically acceptable salt, solvate, or prodrug thereof, wherein:
═══ is selected from single bond and double bond, when $\overset{a}{═══}$ is double bond, then $\overset{b}{═══}$ is single bond, R$_a$ is absent and R$_b$ is hydrogen; when $\overset{b}{═══}$ is double bond, then $\overset{a}{═══}$ is single bond, R$_a$ is hydrogen and R$_b$ is absent;

ring A is selected from the group consisting of cycloalkyl, heterocyclyl, aryl and heteroaryl;

R$_1$, R$_2$ and R$_3$ are identical or different and each is independently selected from the group consisting of hydrogen, halogen, alkyl, haloalkyl, alkenyl, alkynyl, alkoxy, cyano, amino, hydroxy, cycloalkyl, heterocyclyl, aryl and heteroaryl;

each R$_4$ is identical or different and each is independently selected from the group consisting of hydrogen, halogen, alkyl, haloalkyl, alkenyl, alkynyl, alkoxy, haloalkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$ and —S(O)$_2$NR$_{11}$R$_{12}$, wherein said alkyl, alkenyl, alkynyl, alkoxy, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

R$_{5a}$ and R$_{5b}$ are identical or different and each is independently selected from the group consisting of hydrogen, halogen, alkyl, haloalkyl, hydroxy, hydroxyalkyl, alkoxy, cyano, amino, cycloalkyl, heterocyclyl, aryl, heteroaryl, —OR$_8$, —NR$_{10}$COR$_9$, —NR$_{10}$COCH$_2$OR$_8$, —(CH$_2$)$_x$C(O)OR$_8$, —(CH$_2$)$_x$CONR$_{11}$R$_{12}$ and —(CH$_2$)$_x$NR$_{11}$R$_{12}$, wherein said alkyl, alkoxy, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, —CONR$_{11}$R$_{12}$, —NR$_{10}$COR$_9$, cycloalkyl, heterocyclyl, aryl and heteroaryl;

or R$_{5a}$ and R$_{5b}$ are together form

R$_6$ is selected from the group consisting of alkyl, haloalkyl, alkenyl, alkynyl, cycloalkyl, heterocyclyl, aryl, heteroaryl and NR$_{11}$R$_{12}$, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

each R$_7$ is identical or different and each is independently selected from the group consisting of hydrogen, halogen, alkyl, haloalkyl, alkenyl, alkynyl, alkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$ and —S(O)$_2$NR$_{11}$R$_{12}$, wherein said alkyl, alkenyl, alkynyl, alkoxy, cycloalkyl, heterocyclyl, aryl and heteroaryl are each optionally substituted by one or more group(s) selected from the group consisting of halogen, alkyl, alkenyl, alkynyl, alkoxy, cyano, amino, nitro, hydroxy, cycloalkyl, heterocyclyl, aryl and heteroaryl;

$R_8$ is selected from the group consisting of hydrogen, alkyl, haloalkyl, cycloalkyl and heterocyclyl, wherein said alkyl, aryl and heteroaryl are each optionally substituted by one or more groups selected from the group consisting of halogen and alkoxy;

$R_9$ is selected from the group consisting of hydrogen, alkyl, hydroxyl, alkoxy, cycloalkyl, aryl and heteroaryl, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

$R_{10}$ is selected from the group consisting of hydrogen, alkyl, haloalkyl, cycloalkyl and heterocyclyl;

$R_{11}$ and $R_{12}$ are identical or different and each is independently selected from the group consisting of hydrogen, alkyl, alkenyl, alkynyl, haloalkyl, cycloalkyl, heterocyclyl, —$COR_{13}$, aryl and heteroaryl, wherein said alkyl, alkenyl, alkynyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

or $R_{11}$ and $R_{12}$ together with the nitrogen atom to which they are attached form heterocyclyl, wherein heterocyclyl has one or more heteroatoms selected from the group consisting of O, N and S, and is optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R_{13}$ is selected from the group consisting of hydrogen, alkyl, hydroxyl, alkoxy, cycloalkyl, aryl and heteroaryl, wherein said alkyl, cycloalkyl, heterocyclyl, aryl and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl and heteroaryl;

n is 0, 1, 2, 3, or 4;

s is 0, 1, 2, 3 or 4; and x is 0, 1, 2, 3 or 4.

In some embodiments of the present invention, the compound of formula (I), or a tautomer, mesomer, racemate, enantiomer, diastereomer, or mixture thereof, or a pharmaceutically acceptable salt, solvate or prodrug thereof, is a compound of formula (Ia) or formula (Ib):

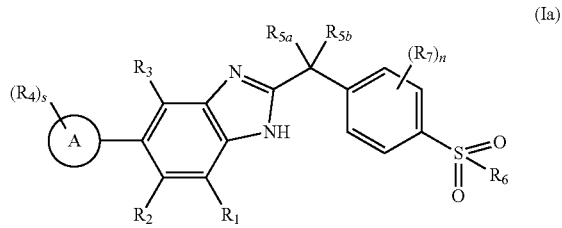

(Ia)

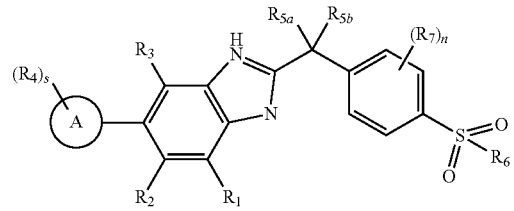

(Ib)

wherein:
$R_1$~$R_4$, $R_{5a}$, $R_{5b}$, $R_6$, $R_7$, n and s are as defined in formula (I).

In some embodiments of the present invention, in a compound of formula (I), or a tautomer, mesomer, racemate, enantiomer, diastereomer, or mixture thereof, or a pharmaceutically acceptable salt, solvate or prodrug thereof, ring A is selected from the group consisting of phenyl, $C_{3-6}$ cycloalkyl and 5 or 6 member heteroaryl, preferably piperidinyl, phenyl, thienyl, furyl and pyridinyl.

In some embodiments of the present invention, the compound of formula (I), or a tautomer, mesomer, racemate, enantiomer, diastereomer, or mixture thereof, or a pharmaceutically acceptable salt, solvate or prodrug thereof, is a compound of formula (II):

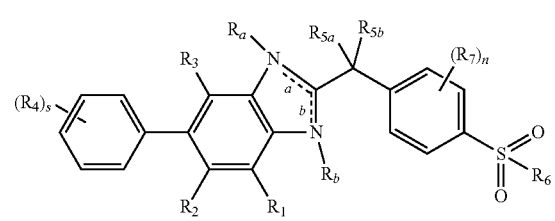

(II)

wherein:
$\underset{\text{a}}{\text{-----}}$, $\underset{\text{b}}{\text{-----}}$, $R_a$, $R_b$, $R_1$~$R_4$, $R_{5a}$, $R_{5b}$, $R_6$, $R_7$, n and s are as defined in formula (I).

In some embodiments of the present invention, the compound of formula (I), or a tautomer, mesomer, racemate, enantiomer, diastereomer, or mixture thereof, or a pharmaceutically acceptable salt, solvate or prodrug thereof, is a compound of formula (Ia):

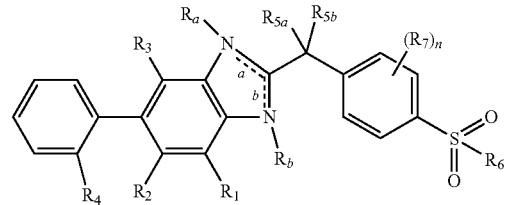

(IIa)

wherein:
$\underset{\text{a}}{\text{-----}}$, $\underset{\text{b}}{\text{-----}}$, $R_a$, $R_b$, $R_1$~$R_4$, $R_{5a}$, $R_{5b}$, $R_6$, $R_7$ and n are as defined in formula (I).

In some embodiments of the present invention, the compound of formula (I), or a tautomer, mesomer, racemate, enantiomer, diastereomer, or mixture thereof, or a pharmaceutically acceptable salt, solvate or prodrug thereof, is a compound of formula (III):

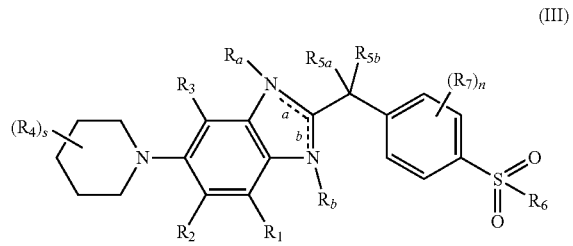

(III)

wherein:

$\stackrel{a}{\text{-----}}$, $\stackrel{b}{\text{-----}}$, $R_a$, $R_b$, $R_1$~$R_4$, $R_{5a}$, $R_{5b}$, $R_6$, $R_7$, n and s are as defined in formula (I).

In some embodiments of the present invention, the compound of formula (I), or a tautomer, mesomer, racemate, enantiomer, diastereomer, or mixture thereof, or a pharmaceutically acceptable salt, solvate or prodrug thereof, is a compound of formula (IIIa):

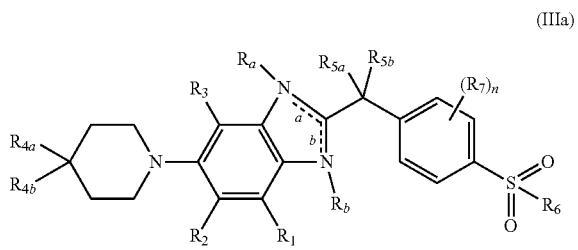

(IIIa)

wherein:

$R_{4a}$ and $R_{4b}$ are identical or different and each is independently selected from the group consisting of halogen, hydrogen, alkyl and haloalkyl;

$\stackrel{a}{\text{-----}}$, $\stackrel{b}{\text{-----}}$, $R_a$, $R_b$, $R_1$~$R_3$, $R_{5a}$, $R_{5b}$, $R_6$, $R_7$ and n are as defined in formula (I).

In some embodiments of the present invention, in the compound of formula (I), or a tautomer, mesomer, racemate, enantiomer, diastereomer, or mixtures thereof, or a pharmaceutically acceptable salt, solvate or prodrug thereof, each $R_4$ is identical or different and each is independently selected from the group consisting of hydrogen, halogen, alkyl, haloalkyl, alkoxy, haloalkoxy, cyano, amino, —$OR_8$ and —$NR_{11}R_{12}$;

$R_8$, $R_{11}$ and $R_{12}$ are as defined in formula (I).

In some embodiments of the present invention, in the compound of formula (I), or a tautomer, mesomer, racemate, enantiomer, diastereomer, or mixtures thereof, or a pharmaceutically acceptable salt, solvate or prodrug thereof, $R_1$, $R_2$, and $R_3$ are identical or different and each is independently selected from the group consisting of hydrogen, halogen and alkyl.

In some embodiments of the present invention, in the compound of formula (I), or a tautomer, mesomer, racemate, enantiomer, diastereomer, or mixtures thereof, or a pharmaceutically acceptable salt, solvate or prodrug thereof, $R_{5a}$ and $R_{5b}$ are identical or different and each is independently selected from the group consisting of hydrogen, hydroxy, hydroxyalkyl, —$OR_8$, —$NR_{10}COR_9$, —$NR_{10}COCH_2OR_8$, —$(CH_2)_xC(O)OR_8$, —$(CH_2)_xCONR_{11}R_{12}$ and —$(CH_2)_xNR_{11}R_{12}$;

or $R_{5a}$ and $R_{5b}$ are together form

$R_8$ to $R_{12}$ and x are as defined in formula (I).

In some embodiments of the present invention, in the compound of formula (I), or a tautomer, mesomer, racemate, enantiomer, diastereomer, or mixtures thereof, or a pharmaceutically acceptable salt, solvate or prodrug thereof, $R_6$ is selected from the group consisting of alkyl, haloalkyl, cycloalkyl, heterocyclyl and —$NR_{11}R_{12}$, wherein said alkyl is optionally substituted by one or more groups selected from the group consisting of alkoxy and cycloalkyl.

In some embodiments of the present invention, in the compound of formula (I), or a tautomer, mesomer, racemate, enantiomer, diastereomer, or mixtures thereof, or a pharmaceutically acceptable salt, solvate or prodrug thereof, $R_7$ is selected from the group consisting of hydrogen, halogen and alkyl.

Typical compounds of the present invention include, but are not limited to,

| Example No. | Compound Name |
|---|---|
| 1 | ![structure]<br>1<br>4,6-dichloro-2-(4-(ethylsulfonyl)benzyl)-5-phenyl-1H-benzo[d]imidazole |

| Example No. | Compound Name |
|---|---|
| 2 | 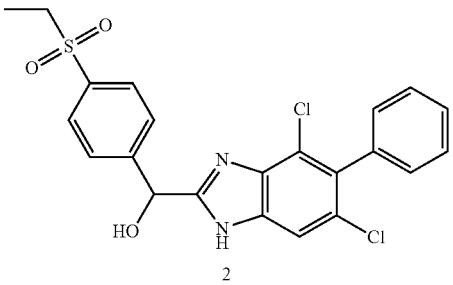 [SMILES: CCS(=O)(=O)c1ccc(C(O)c2nc3c(Cl)c(-c4ccccc4)c(Cl)cc3[nH]2)cc1]
(4,6-dichloro-5-phenyl-1H-benzo[d]imidazol-2-yl)(4-(ethylsulfonyl)phenyl)methanol |
| 3 | 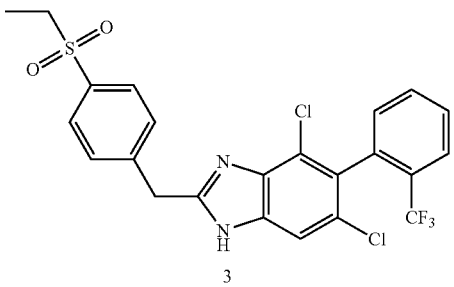 [SMILES: CCS(=O)(=O)c1ccc(Cc2nc3c(Cl)c(-c4ccccc4C(F)(F)F)c(Cl)cc3[nH]2)cc1]
4,6-dichloro-2-(4-(ethylsulfonyl)benzyl)-5-(2-(trifluoromethyl)phenyl)-1H-benzo[d]imidazole |
| 4 | 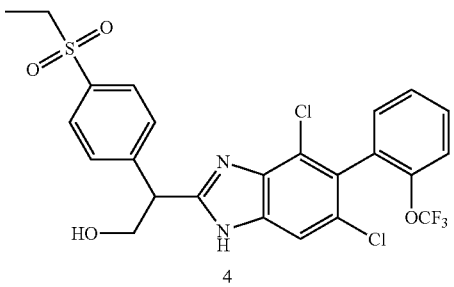 [SMILES: CCS(=O)(=O)c1ccc(C(CO)c2nc3c(Cl)c(-c4ccccc4OC)c(Cl)cc3[nH]2)cc1]
2-(4,6-dichloro-5-(2-(trifluoromethoxy)phenyl)-1H-benzo[d]imidazol-2-yl)-2-(4-(ethylsulfonyl)phenyl)ethanol |
| 5 | 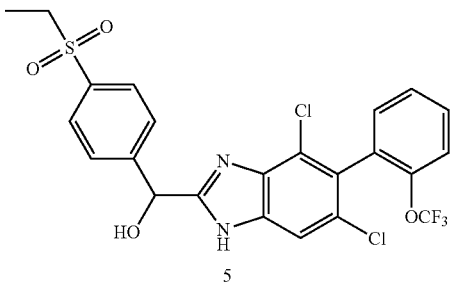
(4,6-dichloro-5-(2-(trifluoromethoxy)phenyl)-1H-benzo[d]imidazol-2-yl)(4-(ethylsulfonyl)phenyl)methanol |

| Example No. | Compound Name |
|---|---|
| 6 | 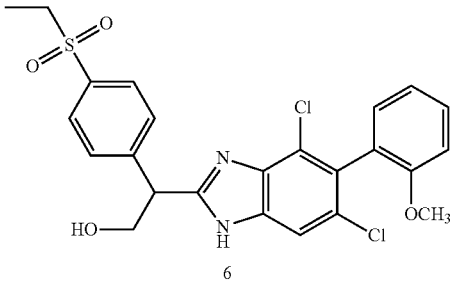
2-(4,6-dichloro-5-(2-methoxyphenyl)-1H-benzo[d]imidazol-2-yl)-2-(4-(ethylsulfonyl)phenyl)ethanol |
| 7 | 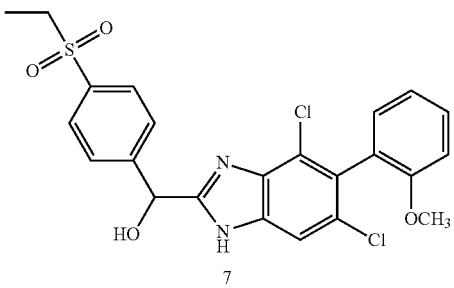 [SMILES: CCS(=O)(=O)c1ccc(C(O)c2nc3c(Cl)c(-c4ccccc4OC)c(Cl)cc3[nH]2)cc1]
(4,6-dichloro-5-(2-methoxyphenyl)-1H-benzo[d]imidazol-2-yl)(4-(ethylsulfonyl)phenyl)methanol |
| 8 | 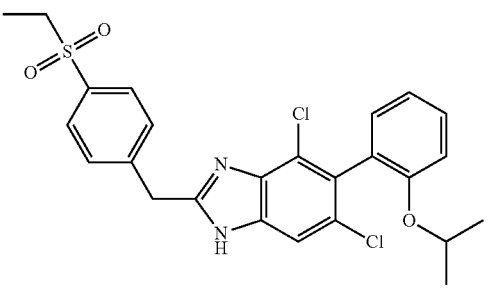
4,6-dichloro-2-(4-(ethylsulfonyl)benzyl)-5-(2-isopropoxyphenyl)-1H-benzo[d]imidazole |
| 9 | 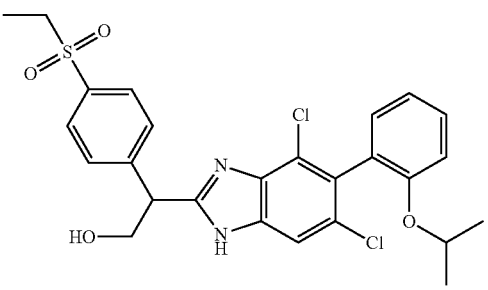
2-(4,6-dichloro-5-(2-isopropoxyphenyl)-1H-benzo[d]imidazol-2-yl)-2-(4-(ethylsulfonyl)phenyl)ethanol |

-continued
| Example No. | Compound Name |
|---|---|
| 10 | 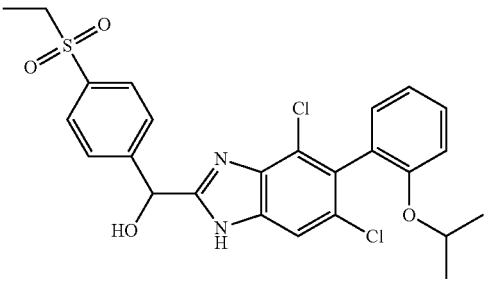
(4,6-dichloro-5-(2-isopropoxyphenyl)-1H-benzo[d]imidazol-2-yl)(4-(ethylsulfonyl)phenyl)methanol |
| 11 | 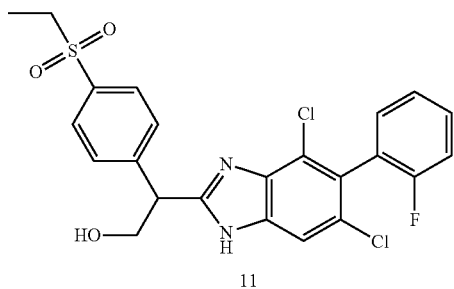 [SMILES: CCS(=O)(=O)c1ccc(C(CO)c2nc3c(Cl)c(-c4ccccc4F)c(Cl)cc3[nH]2)cc1]
2-(4,6-dichloro-5-(2-fluorophenyl)-1H-benzo[d]imidazol-2-yl)-2-(4-(ethylsulfonyl)phenyl)ethanol |
| 12 | 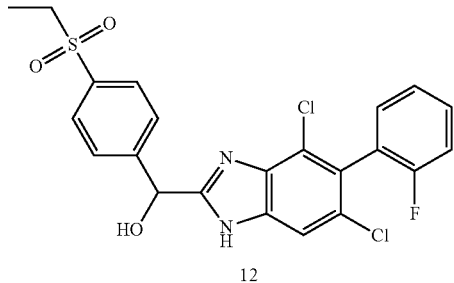 [SMILES: CCS(=O)(=O)c1ccc(C(O)c2nc3c(Cl)c(-c4ccccc4F)c(Cl)cc3[nH]2)cc1]
(4,6-dichloro-5-(2-fluorophenyl)-1H-benzo[d]imidazol-2-yl)(4-(ethylsulfonyl)phenyl)methanol |
| 13 | 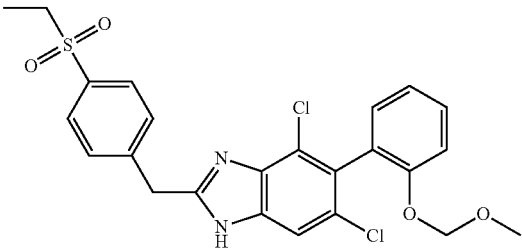
4,6-dichloro-2-(4-(ethylsulfonyl)benzyl)-5-(2-(methoxymethoxy)phenyl)-1H-benzo[d]imidazole |

-continued
| Example No. | Compound Name |
|---|---|
| 14 | 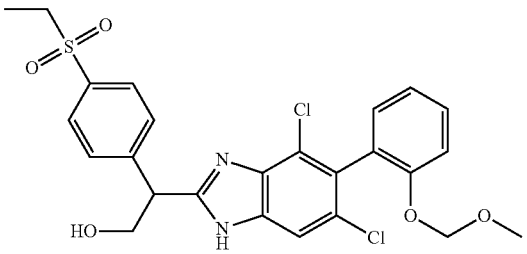
2-(4,6-dichloro-5-(2-methoxymethoxyphenyl)-1H-benzo[d]imidazol-2-yl)-2-(4-(ethylsulfonyl)phenyl)ethanol |
| 15 | 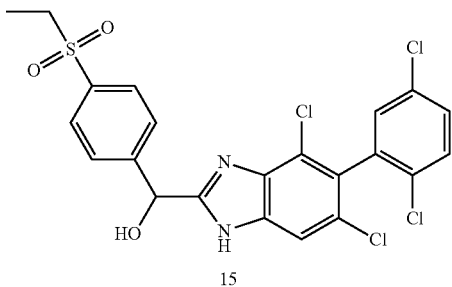 [SMILES: CCS(=O)(=O)c1ccc(C(O)c2nc3c(Cl)c(-c4cc(Cl)ccc4Cl)c(Cl)cc3[nH]2)cc1]
(4,6-dichloro-5-(2,5-dichlorophenyl)-1H-benzo[d]imidazol-2-yl)(4-(ethylsulfonyl)phenyl)methanol |
| 16 | 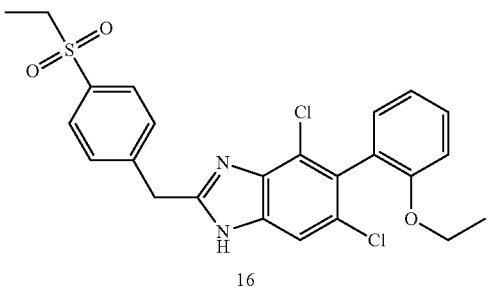 [SMILES: CCOc1ccccc1-c1c(Cl)cc2[nH]c(Cc3ccc(S(=O)(=O)CC)cc3)nc2c1Cl]
4,6-dichloro-5-(2-ethoxyphenyl)-2-(4-(ethylsulfonyl)benzyl)-1H-benzo[d]imidazole |
| 17 | 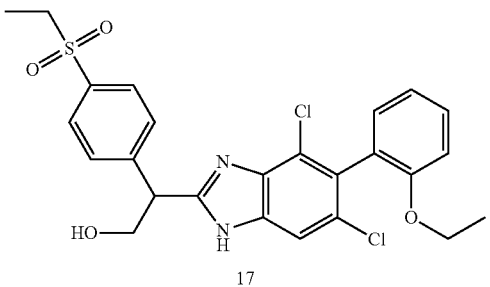 [SMILES: CCOc1ccccc1-c1c(Cl)cc2[nH]c(C(CO)c3ccc(S(=O)(=O)CC)cc3)nc2c1Cl]
2-(4,6-dichloro-5-(2-ethoxyphenyl)-1H-benzo[d]imidazol-2-yl)-2-(4-(ethylsulfonyl)phenyl)ethanol |

| Example No. | Compound Name |
|---|---|
| 18 | 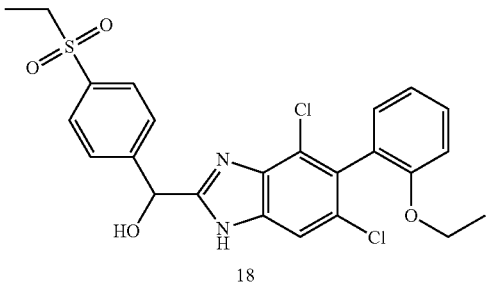 [SMILES: CCOc1ccccc1-c1c(Cl)cc2[nH]c(C(O)c3ccc(S(=O)(=O)CC)cc3)nc2c1Cl]<br>4,6-dichloro-5-(2-ethoxyphenyl)-1H-benzo[d]imidazol-2-yl)(4-(ethylsulfonyl)phenyl)methanol |
| 19 | 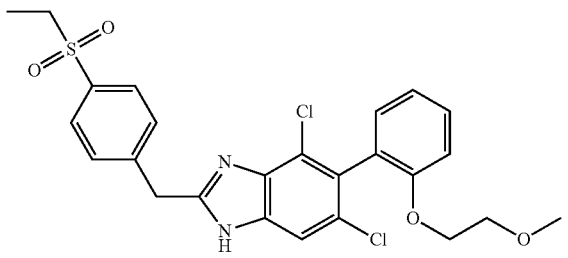<br>4,6-dichloro-2-(4-(ethylsulfonyl)benzyl)-5-(2-(2-methoxyethoxy)phenyl)-1H-benzo[d]imidazole |
| 20 | 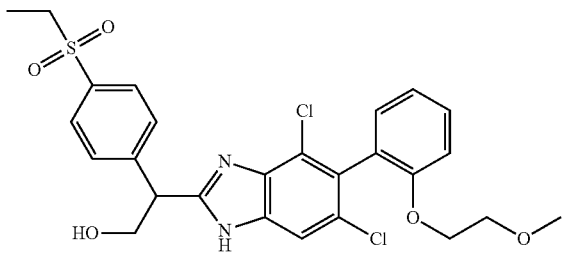<br>2-(4,6-dichloro-5-(2-(2-methoxyethoxy)phenyl)-1H-benzo[d]imidazol-2-yl)-2-(4-(ethylsulfonyl)phenyl)ethanol |
| 21 | 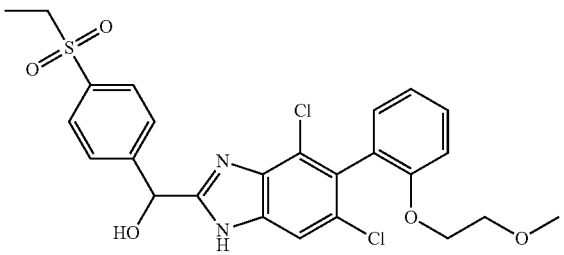<br>(4,6-dichloro-5-(2-(2-methoxyethoxy)phenyl)-1H-benzo[d]imidazol-2-yl)(4-(ethylsulfonyl)phenyl)methanol |

-continued
| Example No. | Compound Name |
|---|---|
| 22 | 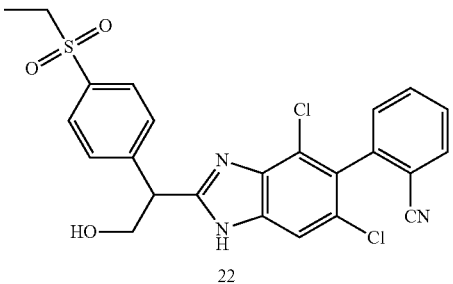 [SMILES: CCS(=O)(=O)c1ccc(C(CO)c2nc3c(Cl)c(-c4ccccc4C#N)c(Cl)cc3[nH]2)cc1]<br>2-(4,6-dichloro-2-(1-(4-(ethylsulfonyl)phenyl)-2-hydroxyethyl)-1H-benzo[d]imidazol-5-yl)benzonitrile |
| 23 | 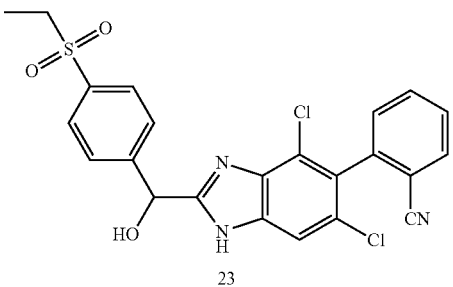 [SMILES: CCS(=O)(=O)c1ccc(C(O)c2nc3c(Cl)c(-c4ccccc4C#N)c(Cl)cc3[nH]2)cc1]<br>2-(4,6-dichloro-2-((4-(ethylsulfonyl)phenyl)(hydroxy)methyl)-1H-benzo[d]imidazol-5-yl)benzonitrile |
| 24 | 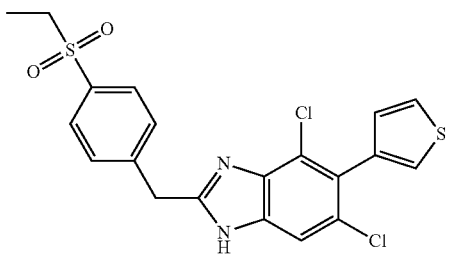<br>4,6-dichloro-2-(4-(ethylsulfonyl)benzyl)-5-(thiophen-3-yl)-1H-benzo[d]imidazole |
| 25 | 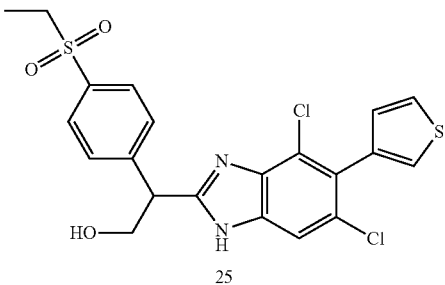 [SMILES: CCS(=O)(=O)c1ccc(C(CO)c2nc3c(Cl)c(-c4ccsc4)c(Cl)cc3[nH]2)cc1]<br>2-(4,6-dichloro-5-(thiophen-3-yl)-1H-benzo[d]imidazol-2-yl)-2-(4-(ethylsulfonyl)phenyl)ethanol |

| Example No. | Compound Name |
|---|---|
| 26 | 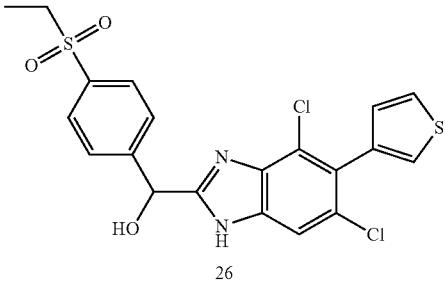 [SMILES: CCS(=O)(=O)c1ccc(C(O)c2nc3c(Cl)c(-c4ccsc4)c(Cl)cc3[nH]2)cc1]<br>(4,6-dichloro-5-(thiophen-3-yl)-1H-benzo[d]imidazol-2-yl)(4-(ethylsulfonyl)phenyl)methanol |
| 27 | 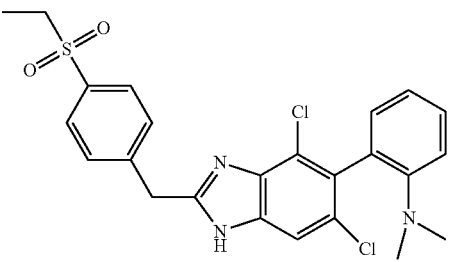<br>2-(4,6-dichloro-2-(4-(ethylsulfonyl)benzyl)-1H-benzo[d]imidazol-5-yl)-N,N-dimethylaniline |
| 28 | 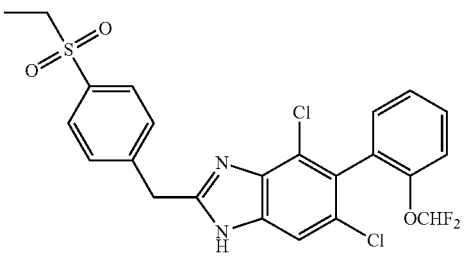<br>4,6-dichloro-5-(2-(difluoromethoxy)phenyl)-2-(4-(ethylsulfonyl)benzyl)-1H-benzo[d]imidazole |
| 29 | 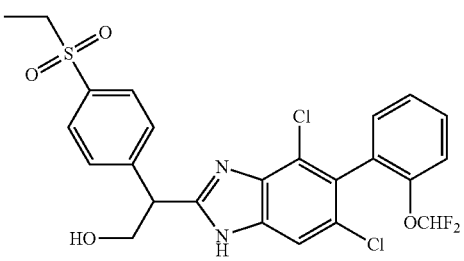<br>2-(4,6-dichloro-5-(2-(difluoromethoxy)phenyl)-1H-benzo[d]imidazol-2-yl)-2-(4-(ethylsulfonyl)phenyl)ethanol |

| Example No. | Compound Name |
|---|---|
| 30 | 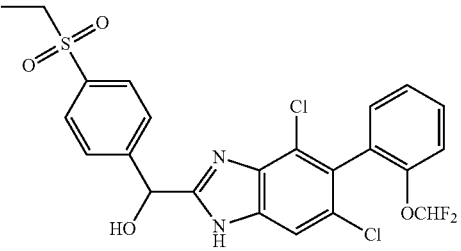<br>(4,6-dichloro-5-(2-(difluoromethoxy)phenyl)-1H-benzo[d]imidazol-2-yl)(4-(ethylsulfonyl)phenyl)methanol |
| 31 | 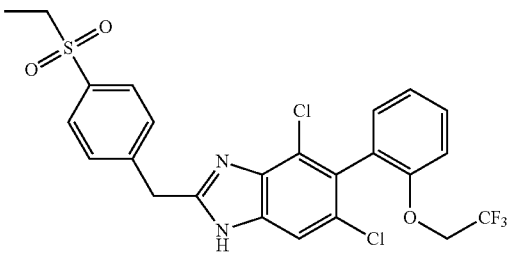<br>4,6-dichloro-2-(4-(ethylsulfonyl)benzyl)-5-(2-(2,2,2-trifluoroethoxy)phenyl)-1H-benzo[d]imidazole |
| 32 | 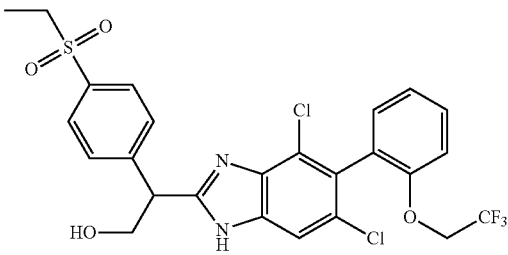<br>2-(4,6-dichloro-5-(2-(2,2,2-trifluoroethoxy)phenyl)-1H-benzo[d]imidazol-2-yl)-2-(4-(ethylsulfonyl)phenyl)ethanol |
| 33 | 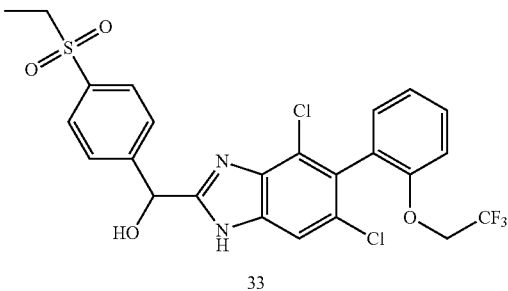 [SMILES: CCS(=O)(=O)c1ccc(C(O)c2nc3c(Cl)c(-c4ccccc4OCC(F)(F)F)c(Cl)cc3[nH]2)cc1]<br>(4,6-dichloro-5-(2-(2,2,2-trifluoroethoxy)phenyl)-1H-benzo[d]imidazol-2-yl)(4-(ethylsulfonyl)phenyl)methanol |

| Example No. | Compound Name |
|---|---|
| 34 | 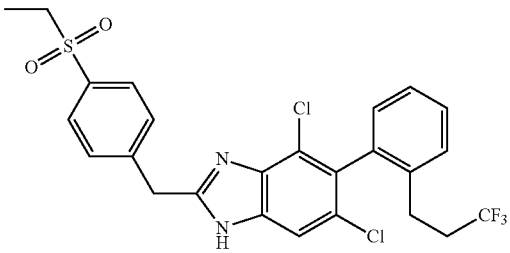
4,6-dichloro-2-(4-(ethylsulfonyl)benzyl)-5-(2-(3,3,3-trifluoropropyl)phenyl)-1H-benzo[d]imidazole |
| 35 | 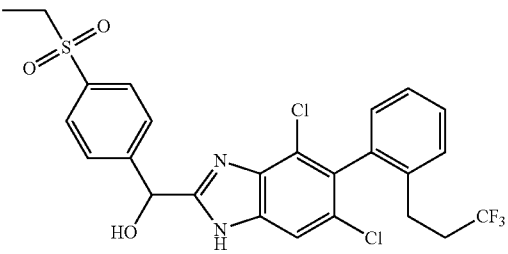
(4,6-dichloro-5-(2-(3,3,3-trifluoropropyl)phenyl)-1H-benzo[d]imidazol-2-yl)(4-(ethylsulfonyl)phenyl)methanol |
| 36 | 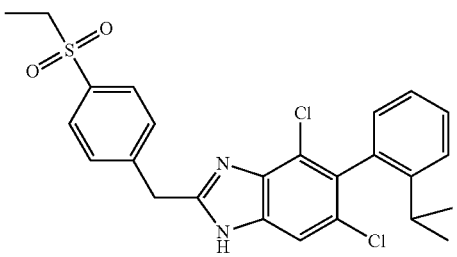
4,6-dichloro-2-(4-(ethylsulfonyl)benzyl)-5-(2-isopropylphenyl)-1H-benzo[d]imidazole |
| 37 | 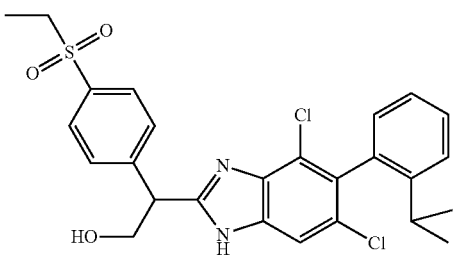
2-(4,6-dichloro-5-(2-isopropylphenyl)-1H-benzo[d]imidazol-2-yl)-2-(4-(ethylsulfonyl)phenyl)ethanol |

| Example No. | Compound Name |
|---|---|
| 38 | 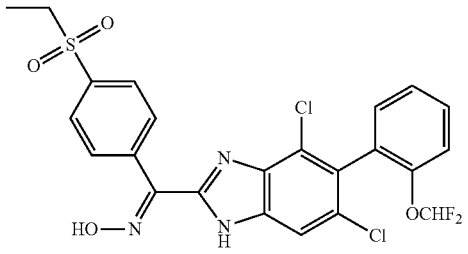<br>38<br><br>(E,Z)-(4,6-dichloro-5-(2-(difluoromethoxy)phenyl)-1H-benzo[d]imidazol-2-yl)(4-(ethylsulfonyl)phenyl)methanone oxime |
| 39 | 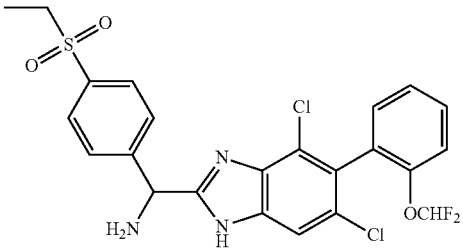<br>39<br><br>1H-benzo[d]imidazol-2-yl)(4-(ethylsulfonyl)phenyl) methanamine(4,6-dichloro-5-(2-(difluoromethoxy)phenyl)- |
| 40 | 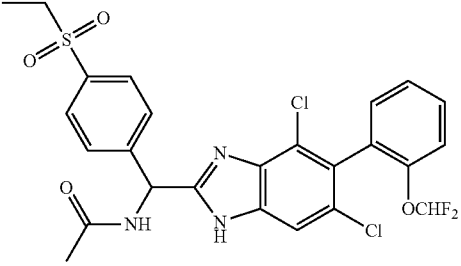<br>40<br><br>N-((4,6-dichloro-5-(2-(difluoromethoxy)phenyl)-1H-benzo[d]imidazol-2-yl)(4-(ethylsulfonyl)phenyl)methyl) acetamide |
| 41 | 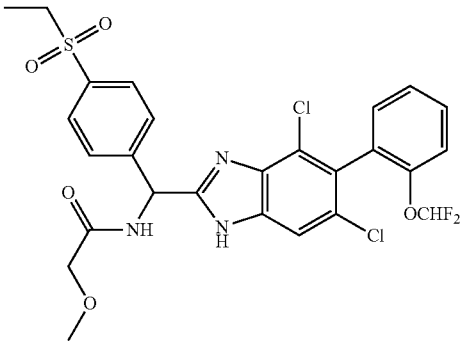<br>41<br><br>N-((4,6-dichloro-5-(2-(difluoromethoxy)phenyl)-1H-benzo[d]imidazol-2-yl)(4-(ethylsulfonyl)phenyl)methyl)-2-methoxyacetamide |

| Example No. | Compound Name |
|---|---|
| 42 | 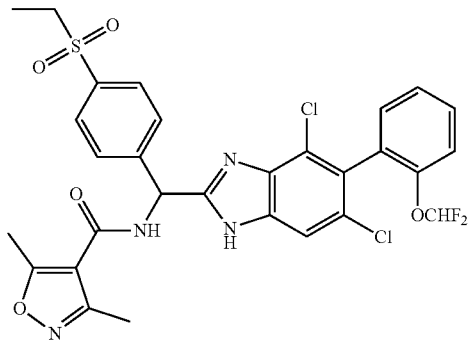<br>42<br>N-((4,6-dichloro-5-(2-(difluoromethoxy)phenyl)-1H-benzo[d]imidazol-2-yl)(4-(ethylsulfonyl)phenyl)methyl)-3,5-dimethylisoxazole-4-carboxamide |
| 43 | 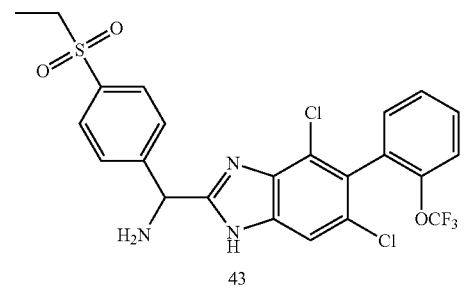<br>43<br>(4,6-dichloro-5-(2-(trifluoromethoxy)phenyl)-1H-benzo[d]imidazol-2-yl)(4-(ethylsulfonyl)phenyl)methanamine |
| 44 | 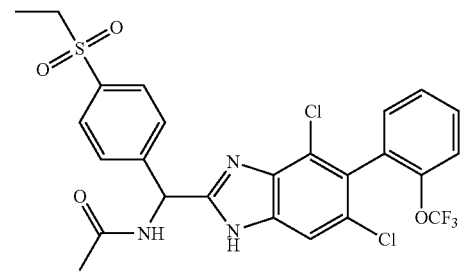<br>44<br>N-((4,6-dichloro-5-(2-(trifluoromethoxy)phenyl)-1H-benzo[d]imidazol-2-yl)(4-(ethylsulfonyl)phenyl)methyl)acetamide |
| 45 | 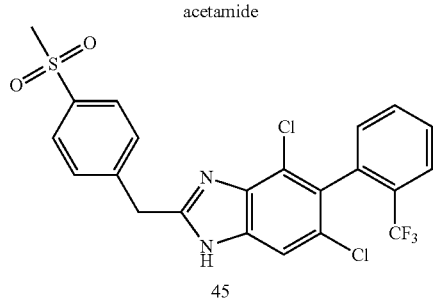<br>45<br>4,6-dichloro-2-(4-(methylsulfonyl)benzyl)-5-(2-(trifluoromethyl)phenyl)-1H-benzo[d]imidazole |

-continued

| Example No. | Compound Name |
|---|---|
| 46 | 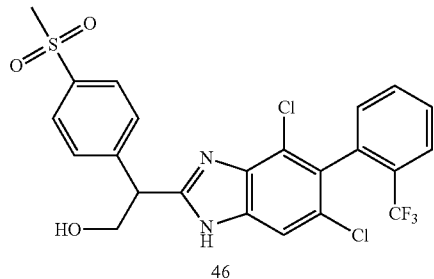 [SMILES: CS(=O)(=O)c1ccc(C(CO)c2nc3c(Cl)c(-c4ccccc4C(F)(F)F)c(Cl)cc3[nH]2)cc1]<br>2-(4,6-dichloro-5-(2-(trifluoromethyl)phenyl)-1H-benzo[d]imidazol-2-yl)-2-(4-(methylsulfonyl)phenyl) ethanol |
| 47 | 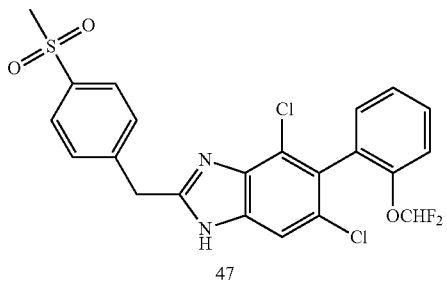 [SMILES: CS(=O)(=O)c1ccc(Cc2nc3c(Cl)c(-c4ccccc4OC(F)F)c(Cl)cc3[nH]2)cc1]<br>4,6-dichloro-5-(2-(difluoromethoxyl)phenyl)-2-(4-(methylsulfonyl)benzyl)-1H-benzo[d]imidazole |
| 48 | 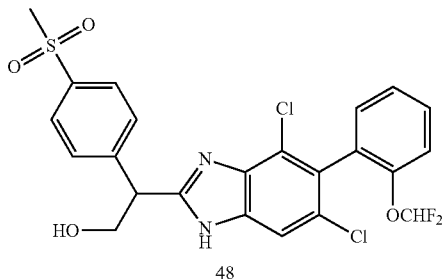 [SMILES: CS(=O)(=O)c1ccc(C(CO)c2nc3c(Cl)c(-c4ccccc4OC(F)F)c(Cl)cc3[nH]2)cc1]<br>2-(4,6-dichloro-5-(2-(difluoromethoxy)phenyl)-1H-benzo[d]imidazol-2-yl)-2-(4-(methylsulfonyl)phenyl) ethanol |
| 49 | 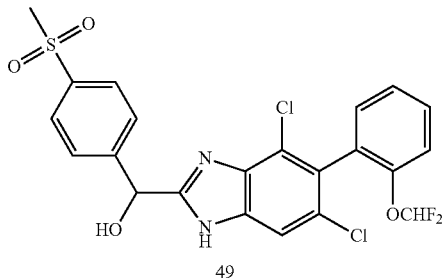 [SMILES: CS(=O)(=O)c1ccc(C(O)c2nc3c(Cl)c(-c4ccccc4OC(F)F)c(Cl)cc3[nH]2)cc1]<br>(4,6-dichloro-5-(2-(difluoromethoxy)phenyl)-1H-benzo[d]imidazol-2-yl)(4-(methylsulfonyl)phenyl) methanol |

| Example No. | Compound Name |
|---|---|
| 50 | 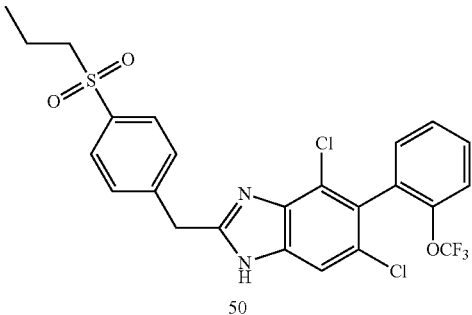 [SMILES: CCCS(=O)(=O)c1ccc(Cc2nc3c(Cl)c(-c4ccccc4OC(F)(F)F)c(Cl)cc3[nH]2)cc1]

4,6-dichloro-2-(4-(propylsulfonyl)benzyl)-5-(2-(trifluoromethoxy)phenyl)-1H-benzo[d]imidazole |
| 51 | 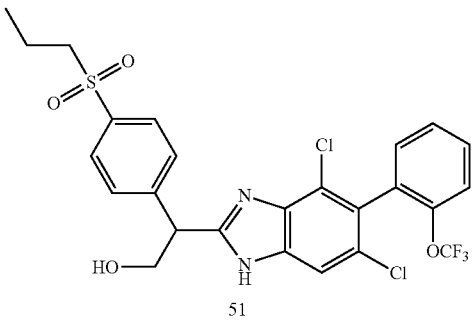 [SMILES: CCCS(=O)(=O)c1ccc(C(CO)c2nc3c(Cl)c(-c4ccccc4OC(F)(F)F)c(Cl)cc3[nH]2)cc1]

2-(4,6-dichloro-5-(2-(trifluoromethoxy)phenyl)-1H-benzo[d]imidazol-2-yl)-2-(4-(propylsulfonyl)phenyl)ethanol |
| 52 | 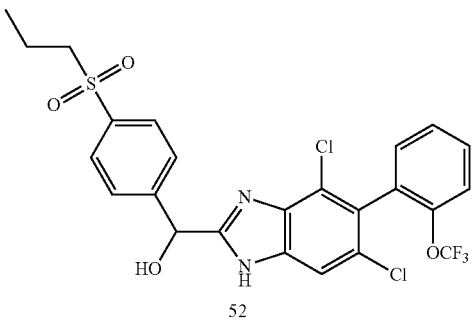 [SMILES: CCCS(=O)(=O)c1ccc(C(O)c2nc3c(Cl)c(-c4ccccc4OC(F)(F)F)c(Cl)cc3[nH]2)cc1]

(4,6-dichloro-5-(2-(trifluoromethoxy)phenyl)-1H-benzo[d]imidazol-2-yl)(4-(propylsulfonyl)phenyl)methanol |
| 53 | 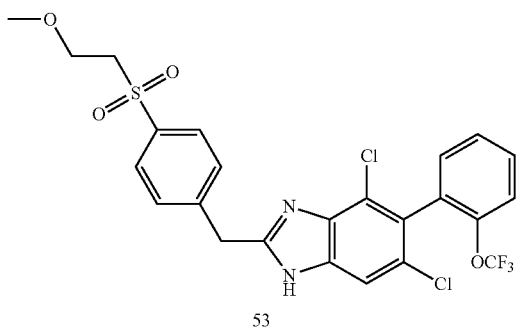 [SMILES: COCCS(=O)(=O)c1ccc(Cc2nc3c(Cl)c(-c4ccccc4OC(F)(F)F)c(Cl)cc3[nH]2)cc1]

4,6-dichloro-2-(4-((2-methoxyethyl)sulfonyl)benzyl)-5-(2-(trifluoromethoxy)phenyl)-1H-benzo[d]imidazole |

| Example No. | Compound Name |
|---|---|
| 54 | 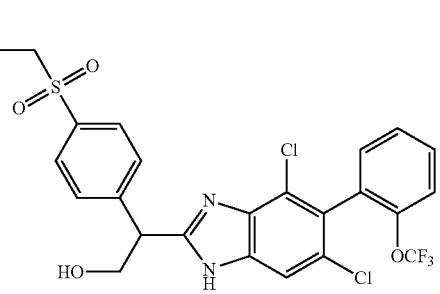<br>2-(4,6-dichloro-5-(2-(trifluoromethoxy)phenyl)-1H-benzo[d]imidazol-2-yl)-2-(4-((2-methoxyethyl)sulfonyl)phenyl)ethanol |
| 55 | 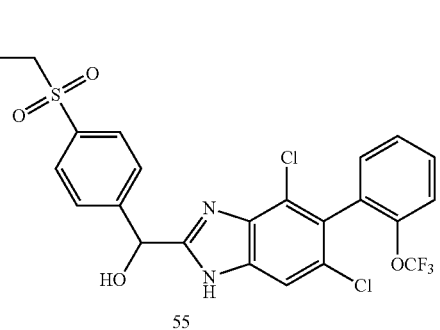<br>(4,6-dichloro-5-(2-(trifluoromethoxy)phenyl)-1H-benzo[d]imidazol-2-yl)(4-((2-methoxyethyl)sulfonyl)phenyl)methanol |
| 56 | 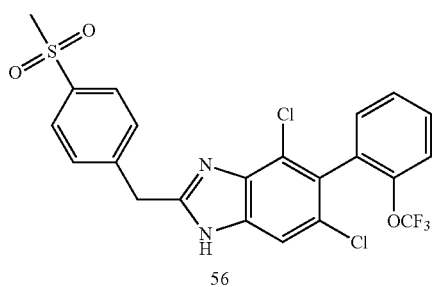 [SMILES: CS(=O)(=O)c1ccc(Cc2nc3c(Cl)c(-c4ccccc4OC(F)(F)F)c(Cl)cc3[nH]2)cc1]<br>4,6-dichloro-2-(4-(methylsulfonyl)benzyl)-5-(2-(trifluoromethoxy)phenyl)-1H-benzo[d]imidazole |
| 57 | 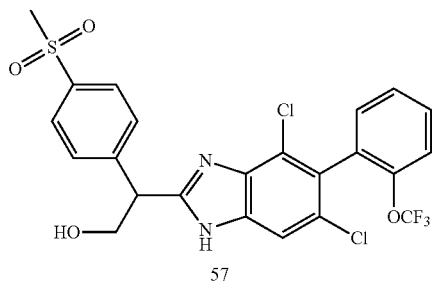 [SMILES: CS(=O)(=O)c1ccc(C(CO)c2nc3c(Cl)c(-c4ccccc4OC(F)(F)F)c(Cl)cc3[nH]2)cc1]<br>2-(4,6-dichloro-5-(2-(trifluoromethoxy)phenyl)-1H-benzo[d]imidazol-2-yl)-2-(4-(methylsulfonyl)phenyl)ethanol |

| Example No. | Compound Name |
|---|---|
| 58 | 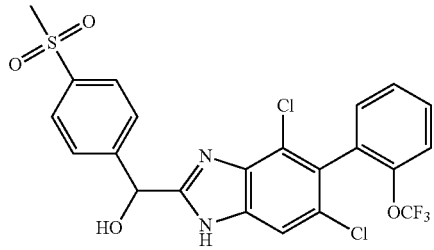<br>(4,6-dichloro-5-(2-(trifluoromethoxy)phenyl)-1H-benzo[d]imidazol-2-yl)(4-(methylsulfonyl)phenyl)methanol |
| 59 | 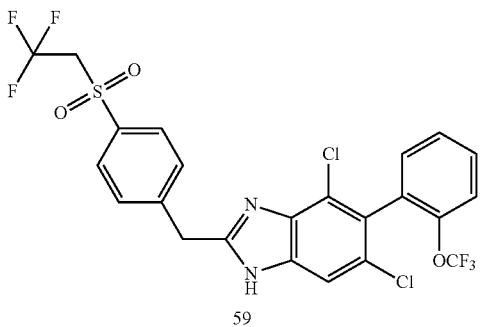 [SMILES: O=S(=O)(CC(F)(F)F)c1ccc(Cc2nc3c(Cl)c(-c4ccccc4OC(F)(F)F)c(Cl)cc3[nH]2)cc1]<br>4,6-dichloro-2-(4-((2,2,2-trifluoroethyl)sulfonyl)benzyl)-5-(2-(trifluoromethoxy)phenyl)-1H-benzo[d]imidazole |
| 60 | 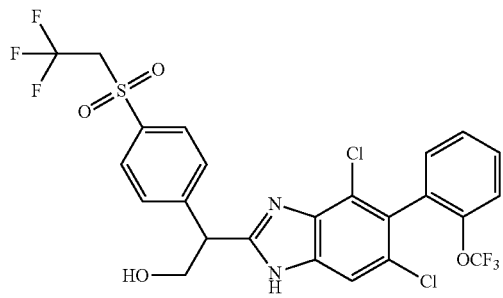<br>2-(4,6-dichloro-5-(2-(trifluoromethoxy)phenyl)-1H-benzo[d]imidazol-2-yl)-2-(4-((2,2,2-trifluoroethyl)sulfonyl)phenyl)ethanol |
| 61 | 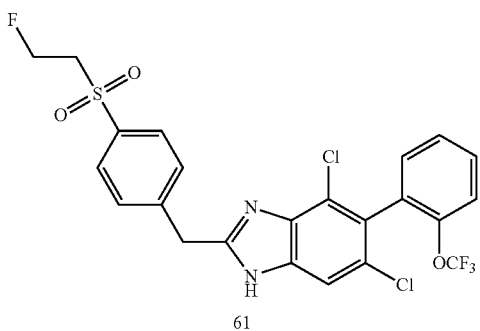 [SMILES: O=S(=O)(CCF)c1ccc(Cc2nc3c(Cl)c(-c4ccccc4OC(F)(F)F)c(Cl)cc3[nH]2)cc1]<br>4,6-dichloro-2-(4-((2-fluoroethyl)sulfonyl)benzyl)-5-(2-(trifluoromethoxy)phenyl)-1H-benzo[d]imidazole |

| Example No. | Compound Name |
|---|---|
| 62 | 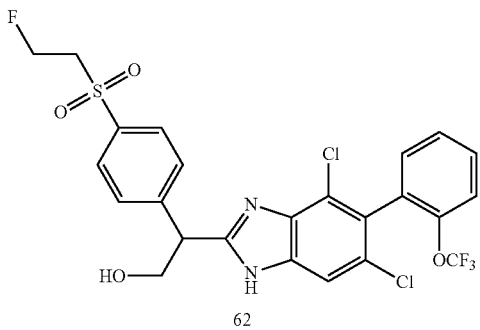 [SMILES: O=S(=O)(CCF)c1ccc(C(CO)c2nc3c(Cl)c(-c4ccccc4OC(F)(F)F)c(Cl)cc3[nH]2)cc1]
2-(4,6-dichloro-5-(2-(trifluoromethoxy)phenyl)-1H-benzo[d]imidazol-2-yl)-2-(4-((2-fluoroethyl)sulfonyl)phenyl)ethanol |
| 63 | 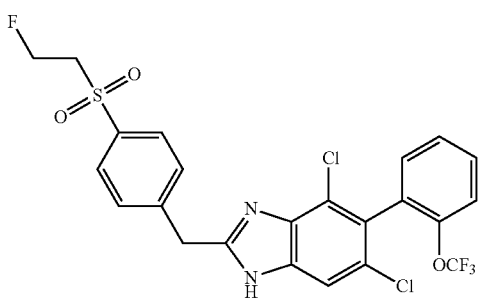
4,6-dichloro-2-(4-((2-fluoroethyl)sulfonyl)benzyl)-5-(2-(trifluoromethyl)phenyl)-1H-benzo[d]imidazole |
| 64 | 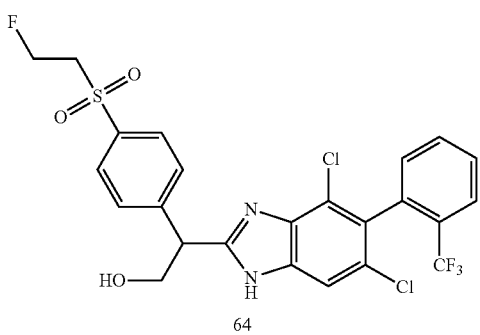 [SMILES: O=S(=O)(CCF)c1ccc(C(CO)c2nc3c(Cl)c(-c4ccccc4C(F)(F)F)c(Cl)cc3[nH]2)cc1]
2-(4,6-dichloro-5-(2-(trifluoromethyl)phenyl)-1H-benzo[d]imidazol-2-yl)-2-(4-((2-fluoroethyl)sulfonyl)phenyl)ethanol |
| 65 | 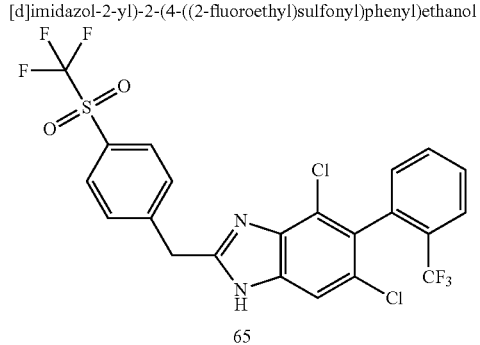
4,6-dichloro-5-(2-(trifluoromethyl)phenyl)-2-(4-((trifluoromethyl)sulfonyl)benzyl)-1H-benzo[d]imidazole |

| Example No. | Compound Name |
|---|---|
| 66 | 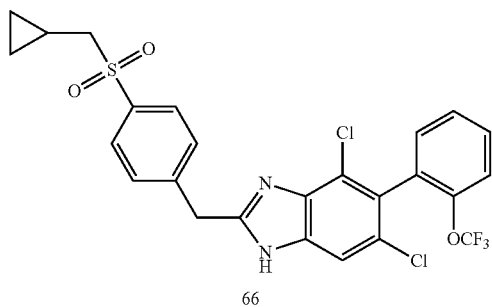 [SMILES: O=S(=O)(CC1CC1)c1ccc(Cc2nc3c(Cl)c(-c4ccccc4OC(F)(F)F)c(Cl)cc3[nH]2)cc1]<br>4,6-dichloro-2-(4-((cyclopropylmethyl)sulfonyl)benzyl)-5-(2-(trifluoromethoxy)phenyl)-1H-benzo[d]imidazole |
| 67 | 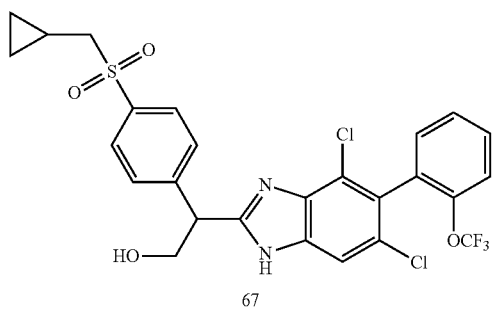 [SMILES: O=S(=O)(CC1CC1)c1ccc(C(CO)c2nc3c(Cl)c(-c4ccccc4OC(F)(F)F)c(Cl)cc3[nH]2)cc1]<br>2-(4-((cyclopropylmethyl)sulfonyl)phenyl)-2-(4,6-dichloro-5-(2-(trifluoromethoxy)phenyl)-1H-benzo[d]imidazol-2-yl)ethanol |
| 68 | 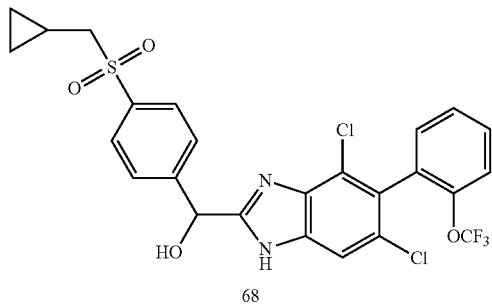 [SMILES: O=S(=O)(CC1CC1)c1ccc(C(O)c2nc3c(Cl)c(-c4ccccc4OC(F)(F)F)c(Cl)cc3[nH]2)cc1]<br>(4-((cyclopropylmethyl)sulfonyl)phenyl)(4,6-dichloro-5-(2-(trifluoromethoxy)phenyl)-1H-benzo[d]imidazol-2-yl)methanol |
| 69 | 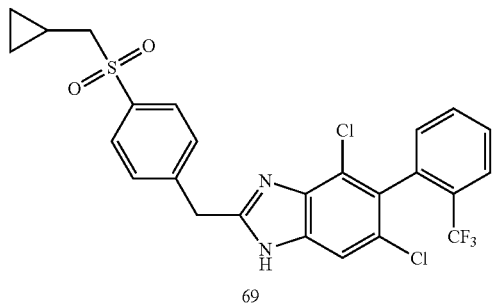 [SMILES: O=S(=O)(CC1CC1)c1ccc(Cc2nc3c(Cl)c(-c4ccccc4C(F)(F)F)c(Cl)cc3[nH]2)cc1]<br>4,6-dichloro-2-(4-((cyclopropylmethyl)sulfonyl)benzyl)-5-(2-(trifluoromethyl)phenyl)-1H-benzo[d]imidazole |

-continued

| Example No. | Compound Name |
|---|---|
| 70 | 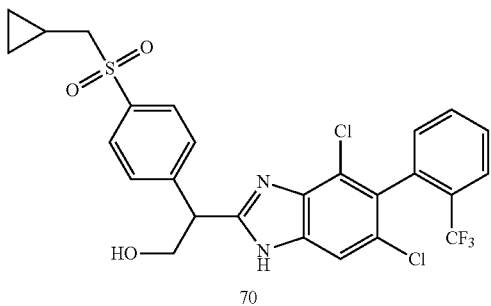 [SMILES: O=S(=O)(CC1CC1)c1ccc(C(CO)c2nc3c(Cl)c(-c4ccccc4C(F)(F)F)c(Cl)cc3[nH]2)cc1]

2-(4-((cyclopropylmethyl)sulfonyl)phenyl)-2-(4,6-dichloro-5-(2-(trifluoromethyl)phenyl)-1H-benzo[d]imidazol-2-yl)ethanol |
| 71 | 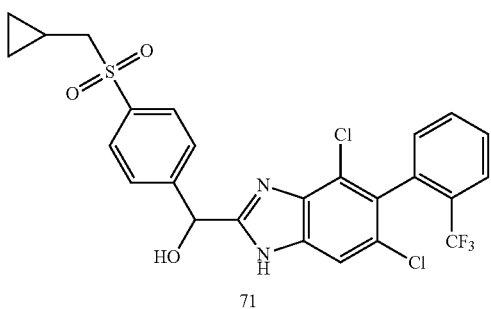 [SMILES: O=S(=O)(CC1CC1)c1ccc(C(O)c2nc3c(Cl)c(-c4ccccc4C(F)(F)F)c(Cl)cc3[nH]2)cc1]

(4-((cyclopropylmethyl)sulfonyl)phenyl)(4,6-dichloro-5-(2-(trifluoromethyl)phenyl)-1H-benzo[d]imidazol-2-yl)methanol |
| 72 | 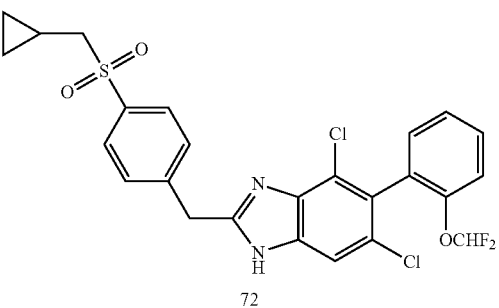 [SMILES: O=S(=O)(CC1CC1)c1ccc(Cc2nc3c(Cl)c(-c4ccccc4OC(F)F)c(Cl)cc3[nH]2)cc1]

4,6-dichloro-2-(4-((cyclopropylmethyl)sulfonyl)benzyl)-5-(2-(difluoromethoxy)phenyl)-1H-benzo[d]imidazole |
| 73 | 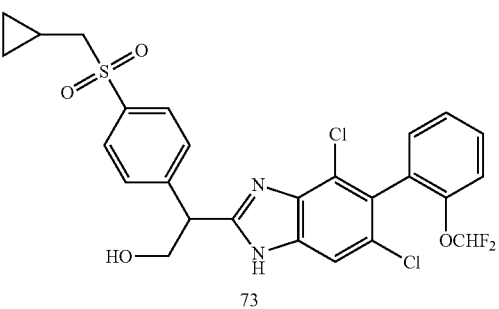 [SMILES: O=S(=O)(CC1CC1)c1ccc(C(CO)c2nc3c(Cl)c(-c4ccccc4OC(F)F)c(Cl)cc3[nH]2)cc1]

2-(4-((cyclopropylmethyl)sulfonyl)phenyl)-2-(4,6-dichloro-5-(2-(difluoromethoxy)phenyl)-1H-benzo[d]imidazol-2-yl)ethanol |

| Example No. | Compound Name |
|---|---|
| 74 | 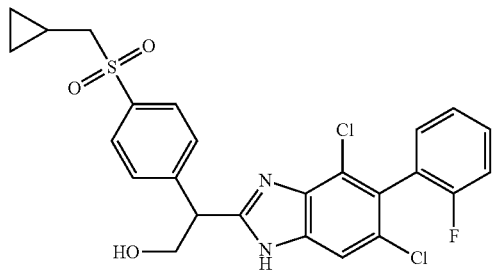<br>2-(4-((cyclopropylmethyl)sulfonyl)phenyl)-2-(4,6-dichloro-5-(2-fluorophenyl)-1H-benzo[d]imidazol-2-yl)ethanol |
| 75 | 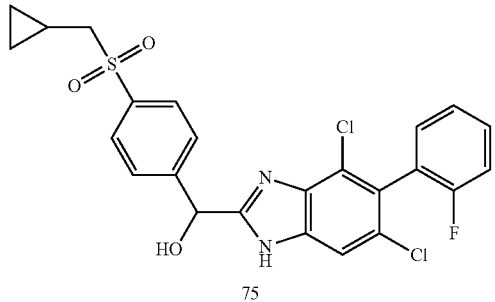 [SMILES: O=S(=O)(CC1CC1)c1ccc(C(O)c2nc3c(Cl)c(-c4ccccc4F)c(Cl)cc3[nH]2)cc1]<br>(4-((cyclopropylmethyl)sulfonyl)phenyl)(4,6-dichloro-5-(2-fluorophenyl)-1H-benzo[d]imidazol-2-yl)methanol |
| 76 | 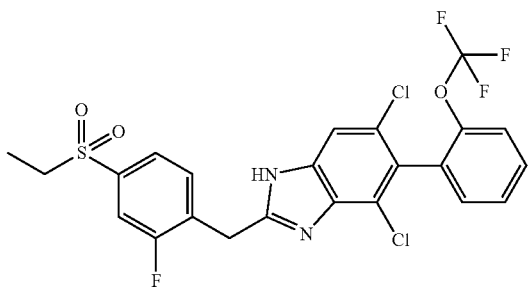<br>4,6-dichloro-2-(4-(ethylsulfonyl)-2-fluorobenzyl)-5-(2-(trifluoromethoxy)phenyl)-1H-benzo[d]imidazole |
| 77 | 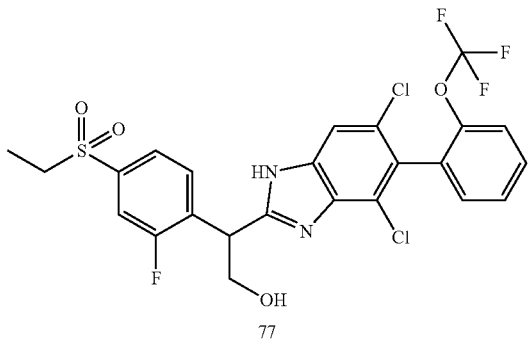 [SMILES: CCS(=O)(=O)c1ccc(C(CO)c2nc3c(Cl)c(-c4ccccc4OC(F)(F)F)c(Cl)cc3[nH]2)c(F)c1]<br>2-(4,6-dichloro-5-(2-(trifluoromethoxy)phenyl)-1H-benzo[d]imidazol-2-yl)-2-(4-(ethylsulfonyl)-2-fluorophenyl)ethanol |

| Example No. | Compound Name |
|---|---|
| 78 | 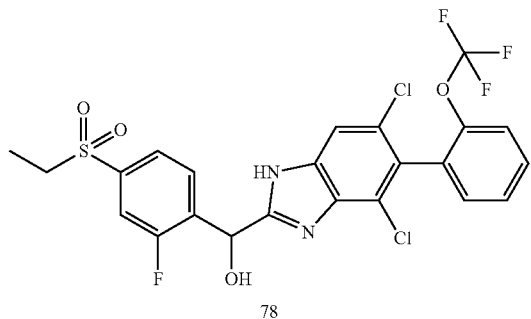 [SMILES: CCS(=O)(=O)c1ccc(C(O)c2nc3c(Cl)c(-c4ccccc4OC(F)(F)F)c(Cl)cc3[nH]2)c(F)c1]

(4,6-dichloro-5-(2-(trifluoromethoxy)phenyl)-1H-benzo[d]imidazol-2-yl)(4-(ethylsulfonyl)-2-fluorophenyl)methanol |
| 79 | 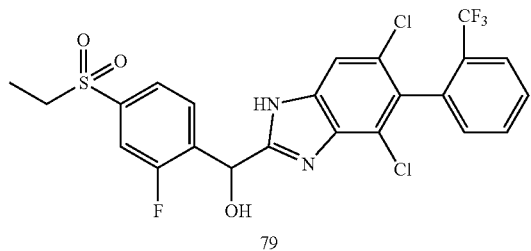 [SMILES: CCS(=O)(=O)c1ccc(C(O)c2nc3c(Cl)c(-c4ccccc4C(F)(F)F)c(Cl)cc3[nH]2)c(F)c1]

(4,6-dichloro-5-(2-(trifluoromethyl)phenyl)-1H-benzo[d]imidazol-2-yl)(4-(ethylsulfonyl)-2-fluorophenyl)methanol |
| 80 | 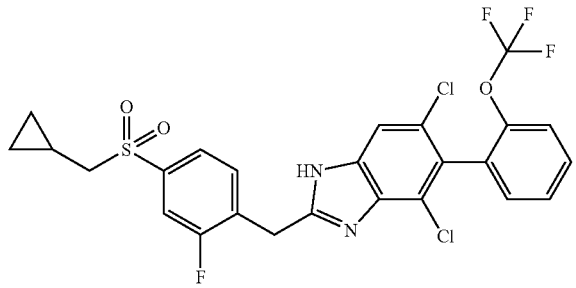

4,6-dichloro-2-(4-((cyclopropylmethyl)sulfonyl)-2-fluorobenzyl)-5-(2-(trifluoromethoxy)phenyl)-1H-benzo[d]imidazole |
| 81 | 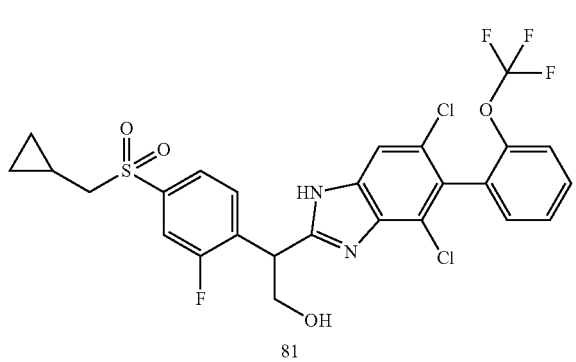 [SMILES: O=S(=O)(CC1CC1)c1ccc(C(CO)c2nc3c(Cl)c(-c4ccccc4OC(F)(F)F)c(Cl)cc3[nH]2)c(F)c1]

2-(4-((cyclopropylmethyl)sulfonyl)-2-fluorophenyl)-2-(4,6-dichloro-5-(2-(trifluoromethoxy)phenyl)-1H-benzo[d]imidazol-2-yl)ethanol |

| Example No. | Compound Name |
|---|---|
| 82 | 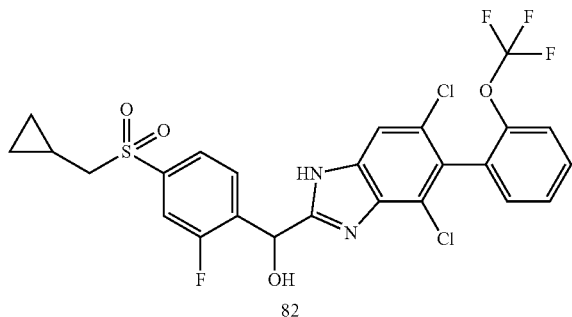 [SMILES: O=S(=O)(CC1CC1)c1ccc(C(O)c2nc3c(Cl)c(-c4ccccc4OC(F)(F)F)c(Cl)cc3[nH]2)c(F)c1]

(4-((cyclopropylmethyl)sulfonyl)-2-fluorophenyl)(4,6-dichloro-5-(2-(trifluoromethoxy)phenyl)-1H-benzo[d]imidazol-2-yl)methanol |
| 83 | 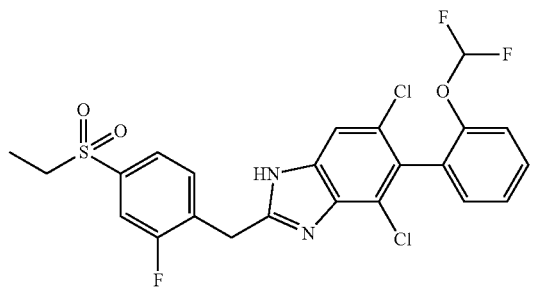

4,6-dichloro-5-(2-(difluoromethoxy)phenyl)-2-(4-(ethylsulfonyl)-2-fluorobenzyl)-1H-benzo[d]imidazole |
| 84 | 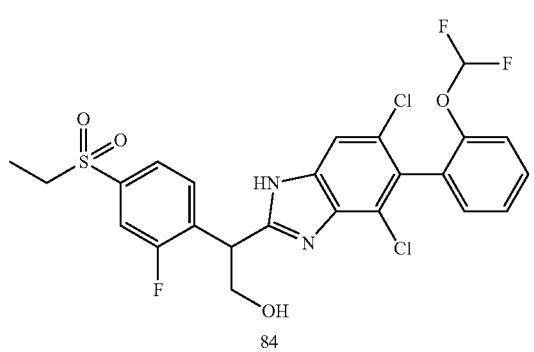 [SMILES: CCS(=O)(=O)c1ccc(C(CO)c2nc3c(Cl)c(-c4ccccc4OC(F)F)c(Cl)cc3[nH]2)c(F)c1]

2-(4,6-dichloro-5-(2-(difluoromethoxy)phenyl)-1H-benzo[d]imidazol-2-yl)-2-(4-(ethylsulfonyl)-2-fluorophenyl)ethanol |
| 85 | 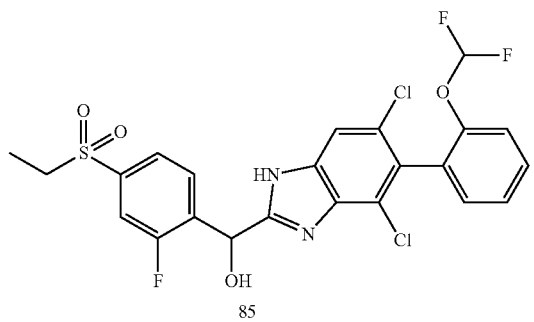 [SMILES: CCS(=O)(=O)c1ccc(C(O)c2nc3c(Cl)c(-c4ccccc4OC(F)F)c(Cl)cc3[nH]2)c(F)c1]

(4,6-dichloro-5-(2-(difluoromethoxy)phenyl)-1H-benzo[d]imidazol-2-yl)(4-(ethylsulfonyl)-2-fluorophenyl)methanol |

| Example No. | Compound Name |
|---|---|
| 86 | 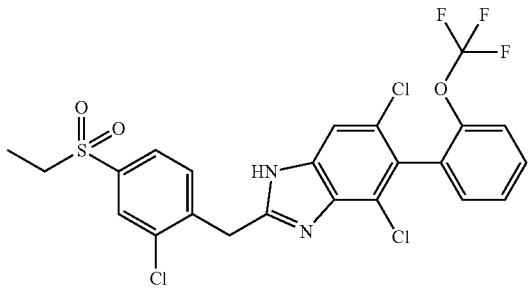
4,6-dichloro-2-(2-chloro-4-(ethylsulfonyl)benzyl)-5-(2-(trifluoromethoxy)phenyl)-1H-benzo[d]imidazole |
| 87 | 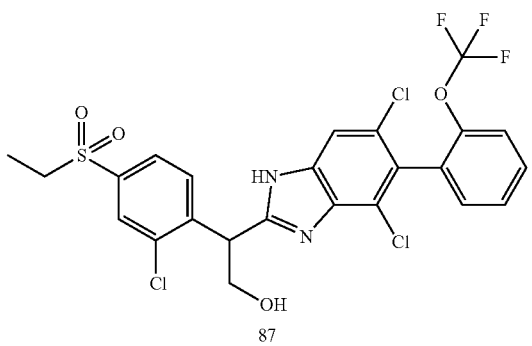 [SMILES: CCS(=O)(=O)c1ccc(C(CO)c2nc3c(Cl)c(-c4ccccc4OC(F)(F)F)c(Cl)cc3[nH]2)c(Cl)c1]
2-(2-chloro-4-(ethylsulfonyl)phenyl)-2-(4,6-dichloro-5-(2-(trifluoromethoxy)phenyl)-1H-benzo[d]imidazol-2-yl)ethanol |
| 88 | 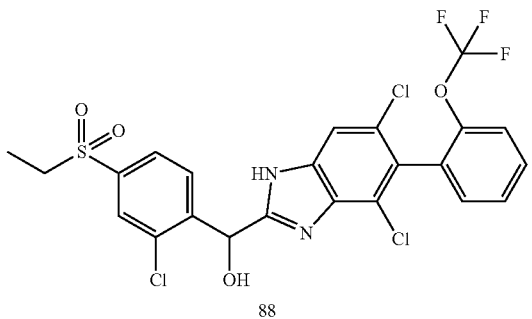 [SMILES: CCS(=O)(=O)c1ccc(C(O)c2nc3c(Cl)c(-c4ccccc4OC(F)(F)F)c(Cl)cc3[nH]2)c(Cl)c1]
(2-chloro-4-(ethylsulfonyl)phenyl)(4,6-dichloro-5-(2-(trifluoromethoxy)phenyl)-1H-benzo[d]imidazol-2-yl)methanol |
| 89 | 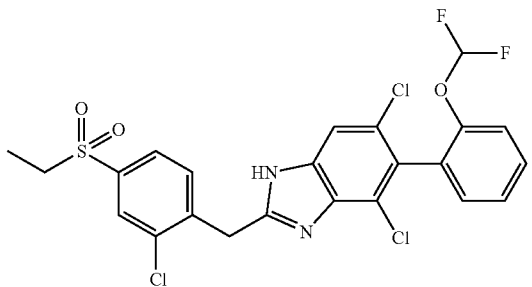
4,6-dichloro-2-(2-chloro-4-(ethylsulfonyl)benzyl)-5-(2-(difluoromethoxy)phenyl)-1H-benzo[d]imidazole |

| Example No. | Compound Name |
|---|---|
| 90 | 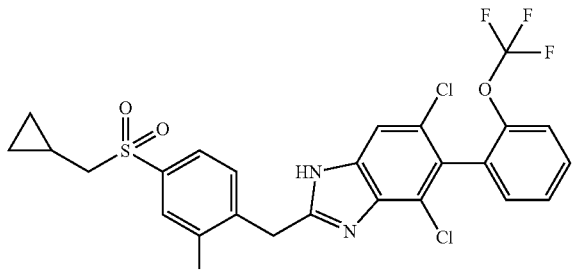

4,6-dichloro-2-(2-chloro-4-((cyclopropylmethyl)sulfonyl)benzyl)-5-(2-(trifluoromethoxy)phenyl)-1H-benzo[d]imidazole |
| 91 | 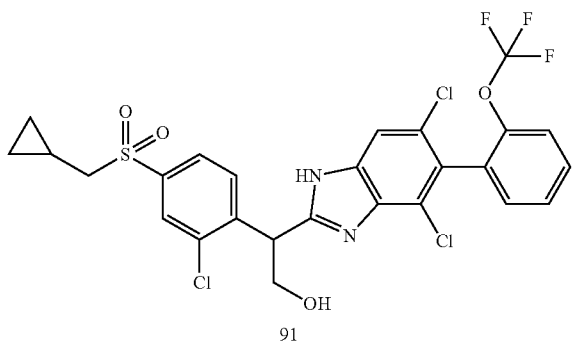

2-(2-chloro-4-((cyclopropylmethyl)ethylsulfonyl)phenyl)-2-(4,6-dichloro-5-(2-(trifluoromethoxy)phenyl)-1H-benzo[d]imidazol-2-yl)ethanol |
| 92 | 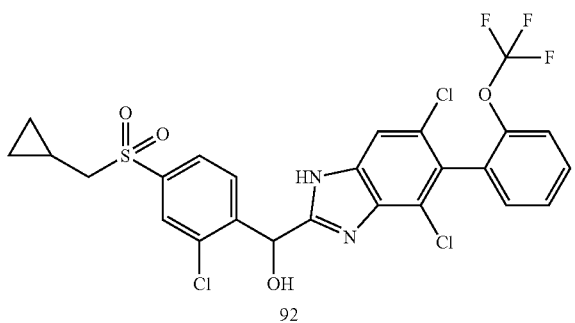

(2-chloro-4-((cyclopropylmethyl)sulfonyl)phenyl)(4,6-dichloro-5-(2-(trifluoromethoxy)phenyl)-1H-benzo[d]imidazol-2-yl)methanol |
| 93 | 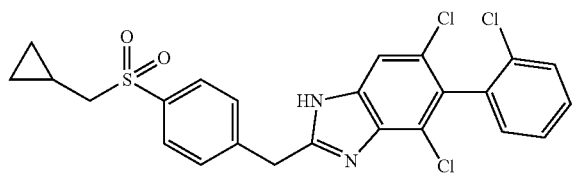

4,6-dichloro-2-(2-chloro-4-((cyclopropylmethyl)sulfonyl)benzyl)-5-(2-chlorophenyl)-1H-benzo[d]imidazole |

| Example No. | Compound Name |
|---|---|
| 94 | 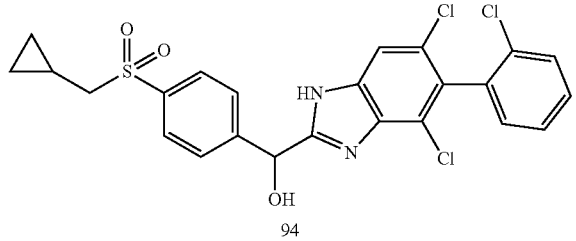 [SMILES: O=S(=O)(CC1CC1)c1ccc(C(O)c2nc3c(Cl)c(-c4ccccc4Cl)c(Cl)cc3[nH]2)cc1]

(2-chloro-4-((cyclopropylmethyl)sulfonyl)phenyl)(4,6-dichloro-5-(2-chlorophenyl)-1H-benzo[d]imidazol-2-yl)methanol |
| 95 | 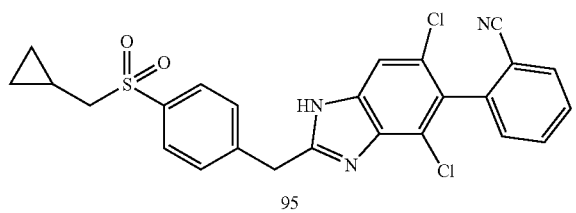 [SMILES: N#Cc1ccccc1-c1c(Cl)cc2[nH]c(Cc3ccc(S(=O)(=O)CC4CC4)cc3)nc2c1Cl]

4,6-dichloro-2-(2-chloro-4-((cyclopropylmethyl)sulfonyl)benzyl)-5-(2-cyanophenyl)-1H-benzo[d]imidazole |
| 96 | 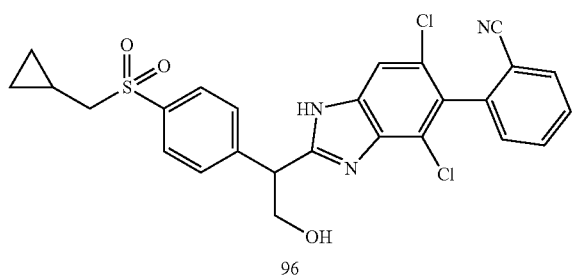 [SMILES: N#Cc1ccccc1-c1c(Cl)cc2[nH]c(C(CO)c3ccc(S(=O)(=O)CC4CC4)cc3)nc2c1Cl]

2-(2-chloro-4-((cyclopropylmethyl)ethylsulfonyl)phenyl)-2-(4,6-dichloro-5-(2-cyanophenyl)-1H-benzo[d]imidazol-2-yl)ethanol |
| 97 | 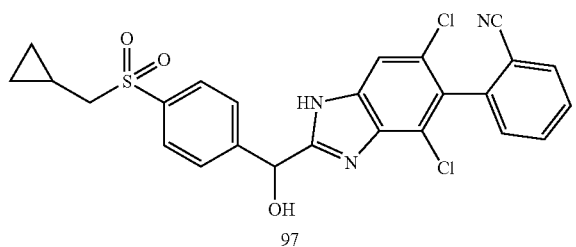 [SMILES: N#Cc1ccccc1-c1c(Cl)cc2[nH]c(C(O)c3ccc(S(=O)(=O)CC4CC4)cc3)nc2c1Cl]

(4-((cyclopropylmethyl)sulfonyl)phenyl)(4,6-dichloro-5-(2-cyanophenyl)-1H-benzo[d]imidazol-2-yl)methanol |

| Example No. | Compound Name |
|---|---|
| 98 | 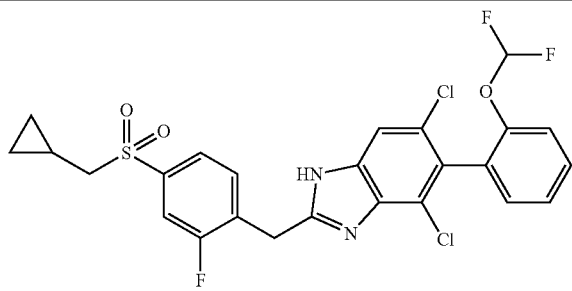

4,6-dichloro-2-(4-((cyclopropylmethyl)sulfonyl)-2-fluorobenzyl)-
5-(2-(difluoromethoxy)phenyl)-1H-benzo[d]imidazole |
| 99 | 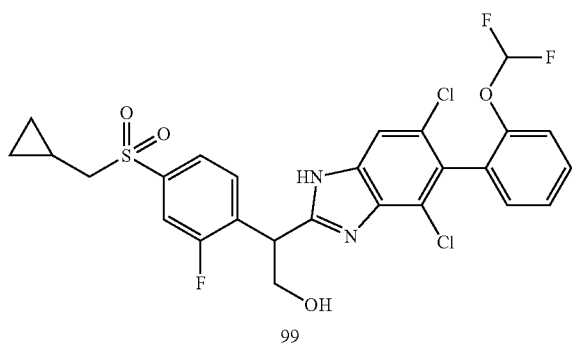 [SMILES: O=S(=O)(CC1CC1)c1ccc(C(CO)c2nc3c(Cl)c(-c4ccccc4OC(F)F)c(Cl)cc3[nH]2)c(F)c1]

2-(4-((cyclopropylmethyl)sulfonyl)-2-fluorophenyl)-2-(4,6-dichloro-5-
(2-(difluoromethoxy)phenyl)-1H-benzo[d]imidazol-2-yl)ethanol |
| 100 | 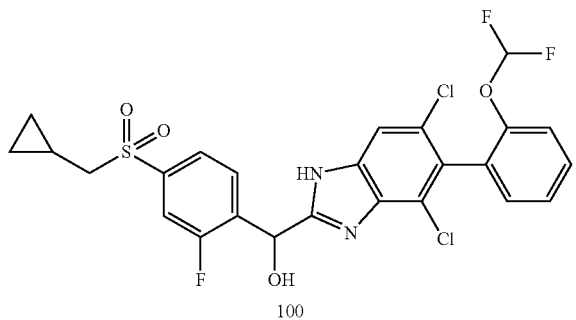 [SMILES: O=S(=O)(CC1CC1)c1ccc(C(O)c2nc3c(Cl)c(-c4ccccc4OC(F)F)c(Cl)cc3[nH]2)c(F)c1]

(4-((cyclopropylmethyl)sulfonyl)-2-fluorophenyl)(4,6-dichloro-5-(2-
(difluoromethoxy)phenyl)-1H-benzo[d]imidazol-2-yl)methanol |
| 101 | 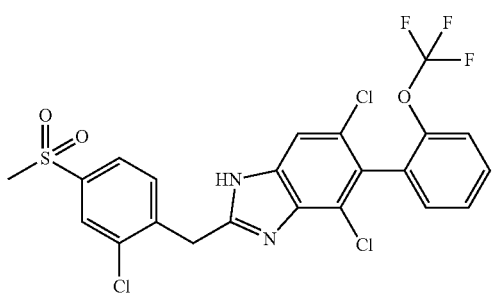

4,6-dichloro-2-(2-chloro-4-(methylsulfonyl)benzyl)-5-
(2-(trifluoromethoxy)phenyl)-1H-benzo[d]imidazole |

| Example No. | Compound Name |
|---|---|
| 102 | 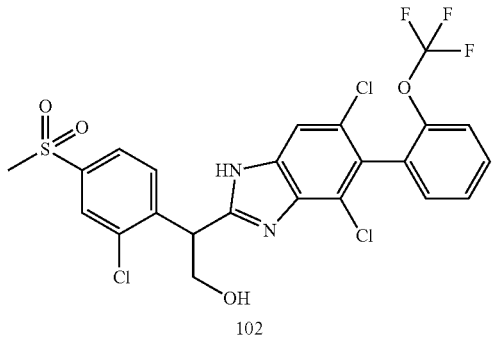 [SMILES: CS(=O)(=O)c1ccc(C(CO)c2nc3c(Cl)c(-c4ccccc4OC(F)(F)F)c(Cl)cc3[nH]2)c(Cl)c1]

2-(2-chloro-4-(methylsulfonyl)phenyl)-2-(4,6-dichloro-5-(2-(trifluoromethoxy)phenyl)-1H-benzo[d]imidazol-2-yl)ethanol |
| 103 | 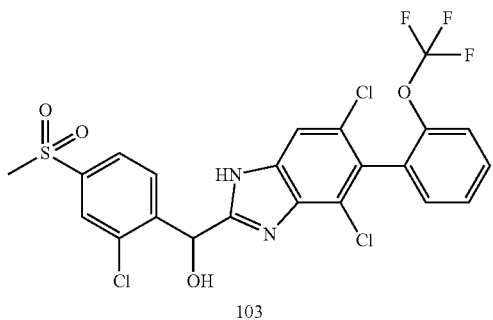 [SMILES: CS(=O)(=O)c1ccc(C(O)c2nc3c(Cl)c(-c4ccccc4OC(F)(F)F)c(Cl)cc3[nH]2)c(Cl)c1]

(2-chloro-4-(methylsulfonyl)phenyl)(4,6-dichloro-5-(2-(trifluoromethoxy)phenyl)-1H-benzo[d]imidazol-2-yl)methanol |
| 104 | 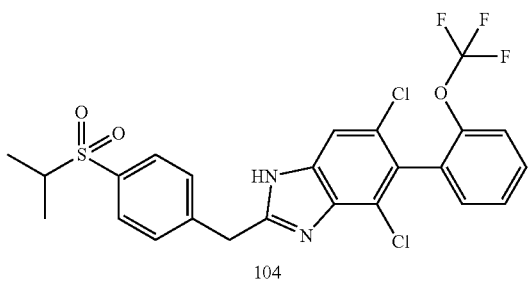 [SMILES: CC(C)S(=O)(=O)c1ccc(Cc2nc3c(Cl)c(-c4ccccc4OC(F)(F)F)c(Cl)cc3[nH]2)cc1]

4,6-dichloro-2-(4-((iso-propyl)sulfonyl)benzyl)-5-(2-(trifluoromethoxy)phenyl)-1H-benzo[d]imidazole |
| 105 | 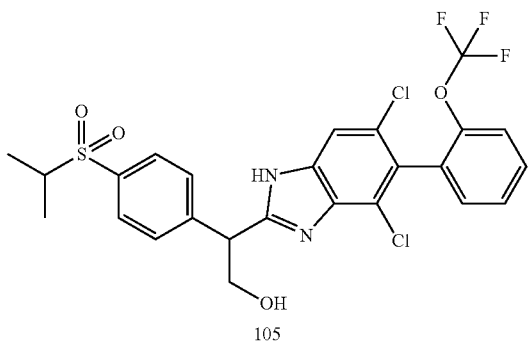 [SMILES: CC(C)S(=O)(=O)c1ccc(C(CO)c2nc3c(Cl)c(-c4ccccc4OC(F)(F)F)c(Cl)cc3[nH]2)cc1]

2-(4-((iso-propyl)sulfonyl)phenyl)-2-(4,6-dichloro-5-(2-(trifluoromethoxy)phenyl)-1H-benzo[d]imidazol-2-yl)ethanol |

| Example No. | Compound Name |
|---|---|
| 106 | 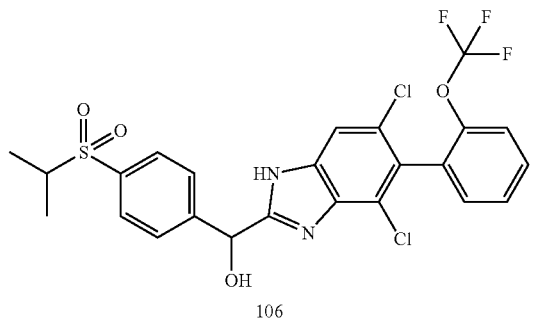

(4-((iso-propyl)sulfonyl)phenyl)(4,6-dichloro-5-(2-(trifluoromethoxy)phenyl)-1H-benzo[d]imidazol-2-yl)methanol |
| 107 | 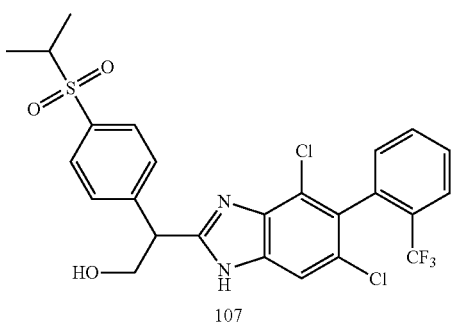 [SMILES: CC(C)S(=O)(=O)c1ccc(C(CO)c2nc3c(Cl)c(-c4ccccc4C(F)(F)F)c(Cl)cc3[nH]2)cc1]

2-(4,6-dichloro-5-(2-(trifluoromethyl)phenyl)-1H-benzo[d]imidazol-2-yl)-2-(4-((iso-propyl)sulfonyl)phenyl)ethanol |
| 108 | 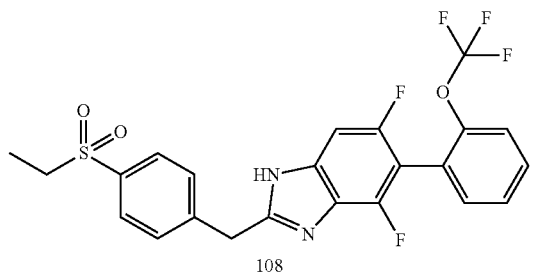 [SMILES: CCS(=O)(=O)c1ccc(Cc2nc3c(F)c(-c4ccccc4OC(F)(F)F)c(F)cc3[nH]2)cc1]

2-(4-(ethylsulfonyl)benzyl)-4,6-difluoro-5-(2-(trifluoromethoxy)phenyl)-1H-benzo[d]imidazole |
| 109 | 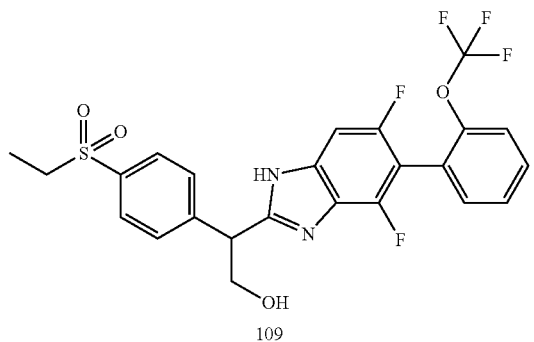 [SMILES: CCS(=O)(=O)c1ccc(C(CO)c2nc3c(F)c(-c4ccccc4OC(F)(F)F)c(F)cc3[nH]2)cc1]

2-(4,6-difluoro-5-(2-(trifluoromethoxy)phenyl)-1H-benzo[d]imidazol-2-yl)-2-(4-(ethylsulfonyl)phenyl)ethanol |

| Example No. | Compound Name |
|---|---|
| 110 | 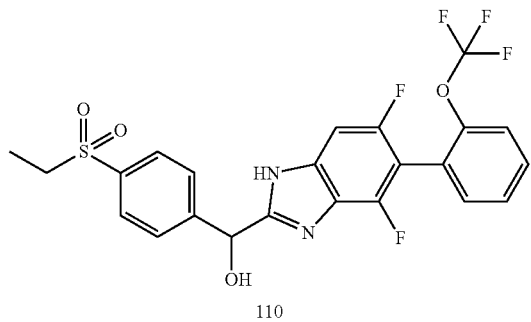 [SMILES: CCS(=O)(=O)c1ccc(C(O)c2nc3c(F)c(-c4ccccc4OC(F)(F)F)c(F)cc3[nH]2)cc1]<br>(4,6-difluoro-5-(2-(trifluoromethoxy)phenyl)-1H-benzo[d]imidazol-2-yl)(4-(ethylsulfonyl)phenyl)methanol |
| 111 | 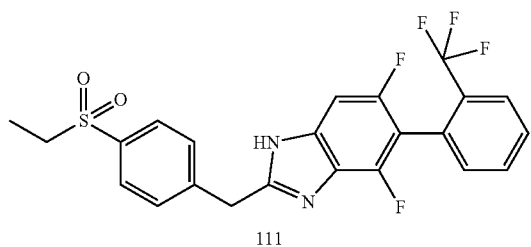 [SMILES: CCS(=O)(=O)c1ccc(Cc2nc3c(F)c(-c4ccccc4C(F)(F)F)c(F)cc3[nH]2)cc1]<br>2-(4-(ethylsulfonyl)benzyl)-4,6-difluoro-5-(2-(trifluoromethyl)phenyl)-1H-benzo[d]imidazole |
| 112 | 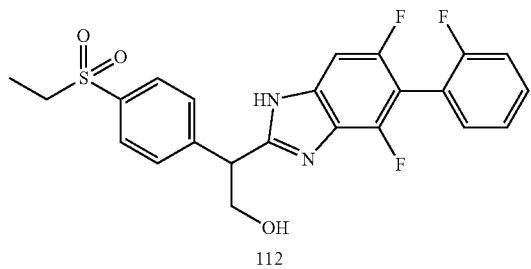 [SMILES: CCS(=O)(=O)c1ccc(C(CO)c2nc3c(F)c(-c4ccccc4F)c(F)cc3[nH]2)cc1]<br>2-(4,6-difluoro-5-(2-fluorophenyl)-1H-benzo[d]imidazol-2-yl)-2-(4-(ethylsulfonyl)phenyl)ethanol |
| 113 | 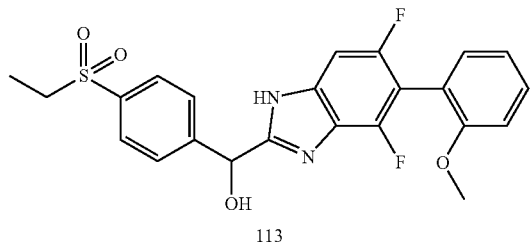 [SMILES: CCS(=O)(=O)c1ccc(C(O)c2nc3c(F)c(-c4ccccc4OC)c(F)cc3[nH]2)cc1]<br>(4,6-difluoro-5-(2-methoxyphenyl)-1H-benzo[d]imidazol-2-yl)(4-(ethylsulfonyl)phenyl)methanol |

| Example No. | Compound Name |
|---|---|
| 114 | 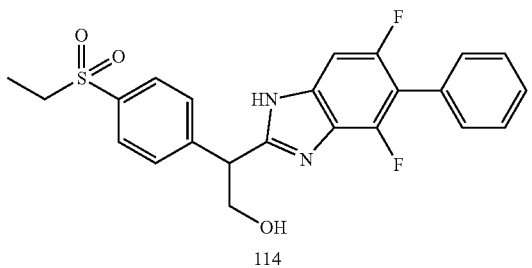 [SMILES: CCS(=O)(=O)c1ccc(C(CO)c2nc3c(F)c(-c4ccccc4)c(F)cc3[nH]2)cc1]
2-(4,6-difluoro-5-phenyl-1H-benzo[d]imidazol-2-yl)-2-(4-(ethylsulfonyl)phenyl)ethanol |
| 115 | 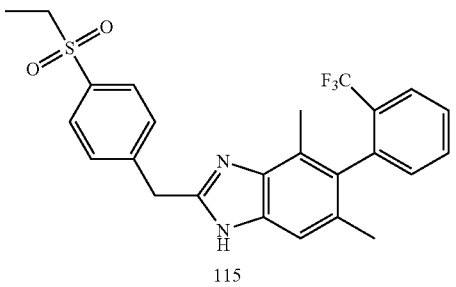 [SMILES: CCS(=O)(=O)c1ccc(Cc2nc3c(C)c(-c4ccccc4C(F)(F)F)c(C)cc3[nH]2)cc1]
2-(4-(ethylsulfonyl)benzyl)-4,6-dimethyl-5-(2-(trifluoromethyl)phenyl)-1H-benzo[d]imidazole |
| 116 | 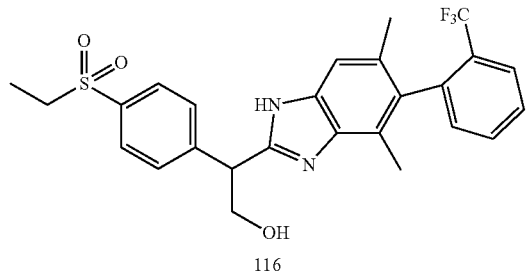 [SMILES: CCS(=O)(=O)c1ccc(C(CO)c2nc3c(C)c(-c4ccccc4C(F)(F)F)c(C)cc3[nH]2)cc1]
2-(4,6-dimethyl-5-(2-(trifluoromethyl)phenyl)-1H-benzo[d]imidazol-2-yl)-2-(4-(ethylsulfonyl)phenyl)ethanol |
| 117 | 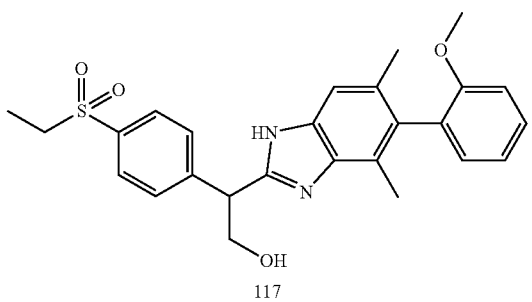 [SMILES: CCS(=O)(=O)c1ccc(C(CO)c2nc3c(C)c(-c4ccccc4OC)c(C)cc3[nH]2)cc1]
2-(4-(ethylsulfonyl)phenyl)-2-(5-(2-methoxyphenyl)-4,6-dimethyl-1H-benzo[d]imidazol-2-yl)ethanol |

| Example No. | Compound Name |
|---|---|
| 118 | 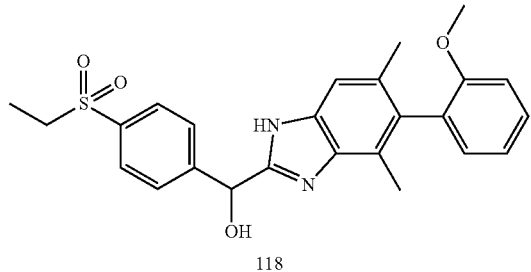 [SMILES: CCS(=O)(=O)c1ccc(C(O)c2nc3c(C)c(-c4ccccc4OC)c(C)cc3[nH]2)cc1]

118

(4-(ethylsulfonyl)phenyl)(5-(2-methoxyphenyl)-4,6-dimethyl-1H-benzo[d]imidazol-2-yl)methanol |
| 119 | 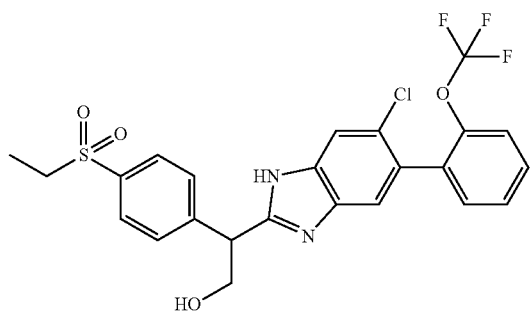

119

2-(6-chloro-5-(2-(trifluoromethoxy)phenyl)-1H-benzo[d]imidazol-2-yl)-2-(4-(ethylsulfonyl)phenyl)ethanol |
| 120 | 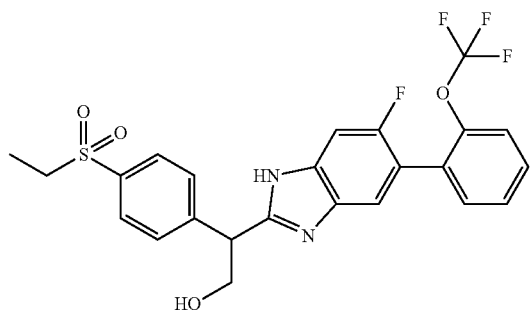

120

2-(4-(ethylsulfonyl)phenyl)-2-(6-fluoro-5-(2-(trifluoromethoxy)phenyl)-1H-benzo[d]imidazol-2-yl)ethanol |
| 121 | 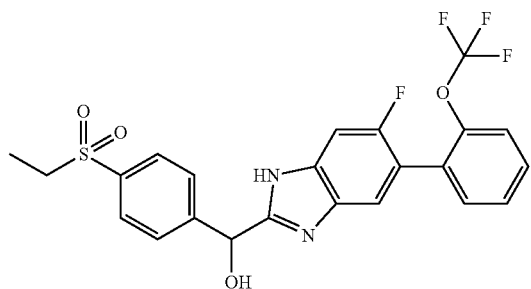

121

(4-(ethylsulfonyl)phenyl)(6-fluoro-5-(2-(trifluoromethoxy)phenyl)-1H-benzo[d]imidazol-2-yl)methanol |

| Example No. | Compound Name |
|---|---|
| 122 | 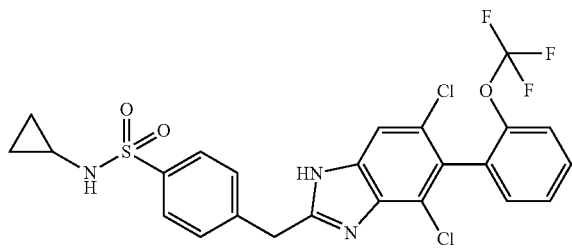<br>N-cyclopropyl-4-((4,6-dichloro-5-(2-(trifluoromethoxy)phenyl)-1H-benzo[d]imidazol-2-yl)methyl)benzenesulfonamide |
| 123 | 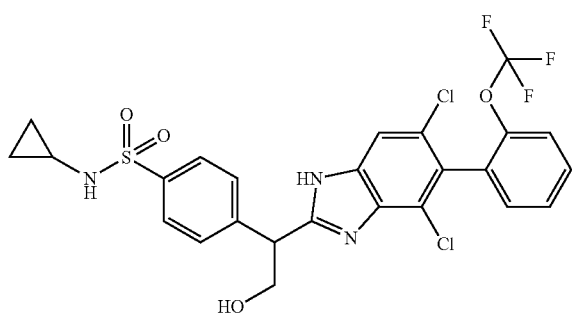<br>N-cyclopropyl-4-(1-(4,6-dichloro-5-(2-(trifluoromethoxy)phenyl)-1H-benzo[d]imidazol-2-yl)-2-hydroxyethyl)benzenesulfonamide |
| 124 | 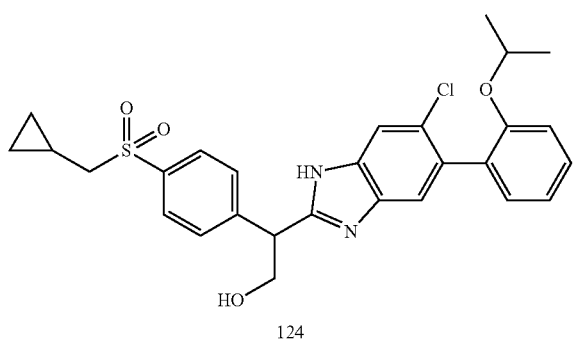 [SMILES: CC(C)Oc1ccccc1-c1cc2nc(C(CO)c3ccc(S(=O)(=O)CC4CC4)cc3)[nH]c2cc1Cl]<br>2-(6-chloro-5-(2-isopropoxyphenyl)-1H-benzo[d]imidazol-2-yl)-2-(4-((cyclopropylmethyl)sulfonyl)phenyl)ethanol |
| 124-1 | 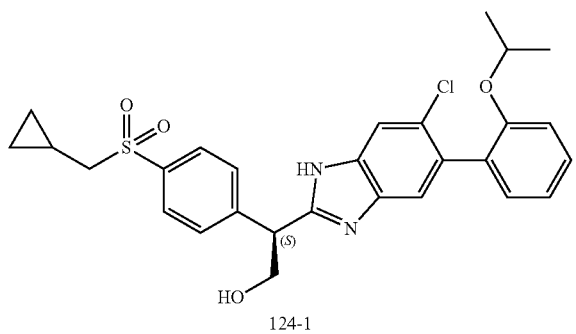<br>(S)-2-(6-chloro-5-(2-isopropoxyphenyl)-1H-benzo[d]imidazol-2-yl)-2-(4-((cyclopropylmethyl)sulfonyl)phenyl)ethanol |

| Example No. | Compound Name |
|---|---|
| 124-2 | 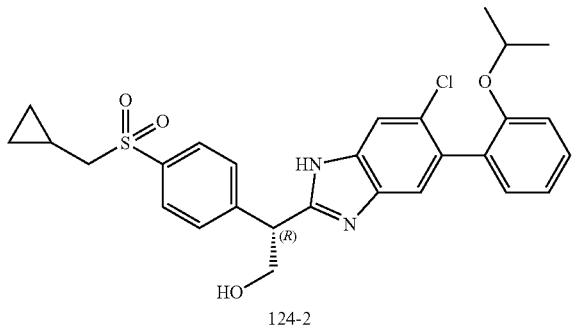

(R)-2-(6-chloro-5-(2-isopropoxyphenyl)-1H-benzo[d]imidazol-2-yl)-2-(4-((cyclopropylmethyl)sulfonyl)phenyl)ethanol |
| 125 | 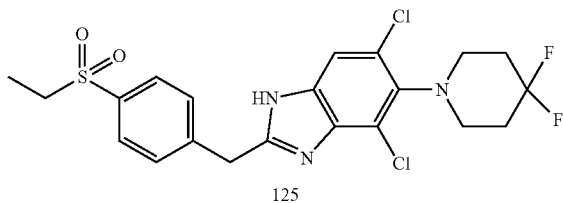 [SMILES: CCS(=O)(=O)c1ccc(Cc2nc3c(Cl)c(N4CCC(F)(F)CC4)c(Cl)cc3[nH]2)cc1]

4,6-dichloro-5-(4,4-difluoropiperidin-1-yl)-2-(4-(ethylsulfonyl)benzyl)-1H-benzo[d]imidazole |
| 126 | 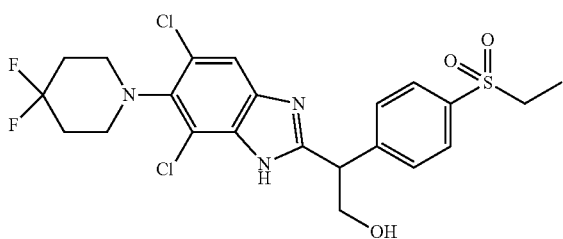

2-(5,7-dichloro-6-(4,4-difluoropiperidin-1-yl)-1H-benzo[d]imidazol-2-yl)-2-(4-(ethylsulfonyl)phenyl)ethanol |
| 126-1 | 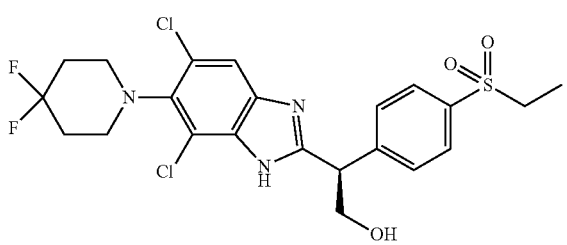

(R)-2-(5,7-dichloro-6-(4,4-difluoropiperidin-1-yl)-1H-benzo[d]imidazol-2-yl)-2-(4-(ethylsulfonyl)phenyl)ethanol |

| Example No. | Compound Name |
|---|---|
| 126-2 | 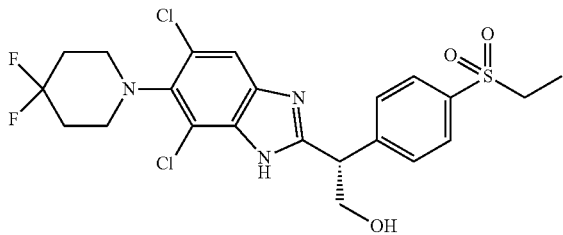

(S)-2-(5,7-dichloro-6-(4,4-difluoropiperidin-1-yl)-1H-benzo[d]imidazol-2-yl)-2-(4-(ethylsulfonyl)phenyl)ethanol |
| 127 | 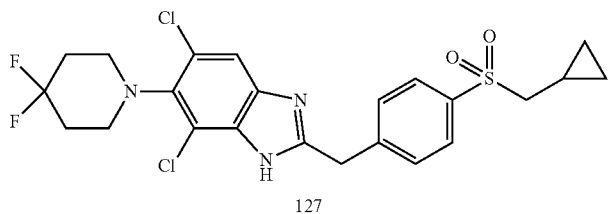 [SMILES: O=S(=O)(CC1CC1)c1ccc(Cc2nc3cc(Cl)c(N4CCC(F)(F)CC4)c(Cl)c3[nH]2)cc1]

5,7-dichloro-2-(4-((cyclopropylmethyl)sulfonyl)benzyl)-6-(4,4-difluoropiperidin-1-yl)-1H-benzo[d]imidazole |
| 128 | 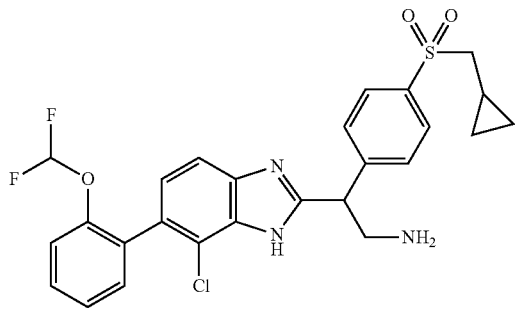

2-(7-chloro-6-(2-(difluoromethoxy)phenyl)-1H-benzo[d]imidazol-2-yl)-2-(4-((cyclopropylmethyl)sulfonyl)phenyl)ethanamine |
| 129 | 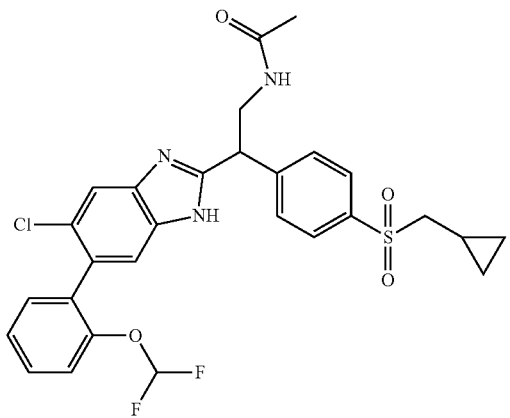

N-(2-(7-chloro-6-(2-(difluoromethoxy)phenyl)-1H-benzo[d]imidazol-2-yl)-2-(4-((cyclopropylmethyl)sulfonyl)phenyl)ethyl)acetamide |

| Example No. | Compound Name |
|---|---|
| 130 | 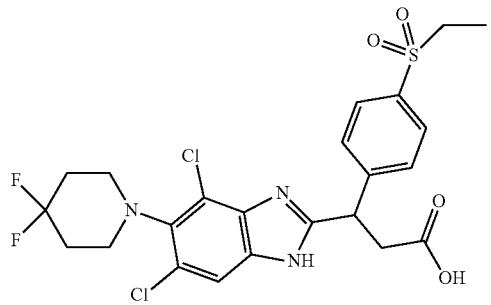

130

3-(4,6-dichloro-5-(4,4-difluoropiperidin-1-yl)-1H-benzo[d]imidazol-2-yl)-3-(4-(ethylsulfonyl)phenyl)propanoic acid |
| 131 | 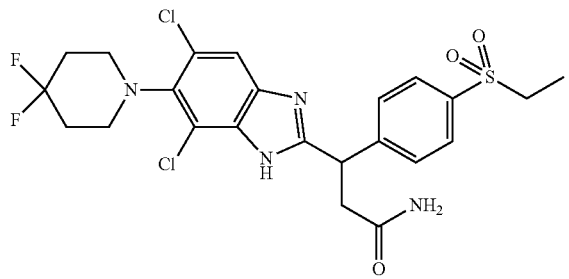

131

3-(4,6-dichloro-5-(4,4-difluoropiperidin-1-yl)-1H-benzo[d]imidazol-2-yl)-3-(4-(ethylsulfonyl)phenyl)propanamide |
| 132 | 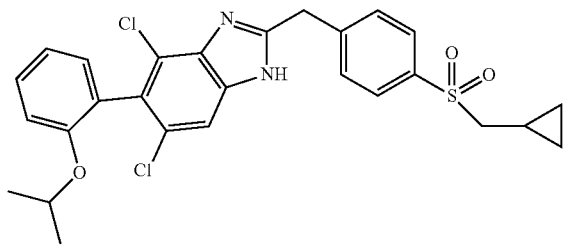

132

4,6-dichloro-2-(4-((cyclopropylmethyl)sulfonyl)benzyl)-5-(2-isopropoxyphenyl)-1H-benzo[d]imidazole |
| 133 | 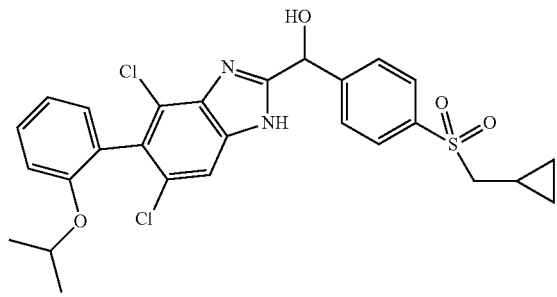

133

(4-((cyclopropylmethyl)sulfonyl)phenyl)(5,7-dichloro-6-(2-isopropoxyphenyl)-1H-benzo[d]imidazol-2-yl)methanol |

| Example No. | Compound Name |
|---|---|
| 134 | 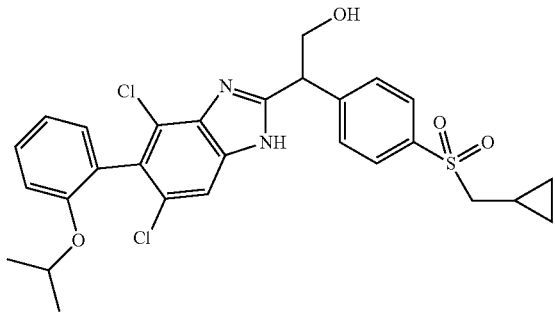

134

2-(4-((cyclopropylmethyl)sulfonyl)phenyl)-2-(4,6-dichloro-5-(2-isopropoxyphenyl)-1H-benzo[d]imidazol-2-yl)ethanol |
| 135 | 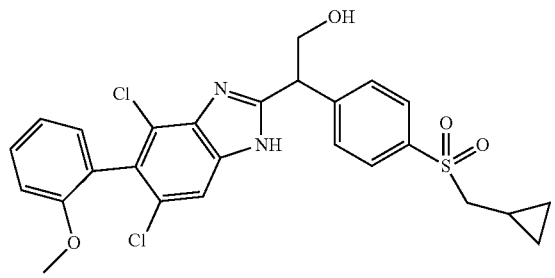

135

2-(4-((cyclopropylmethyl)sulfonyl)phenyl)-2-(4,6-dichloro-5-(2-methoxyphenyl)-1H-benzo[d]imidazol-2-yl)ethanol |
| 136 | 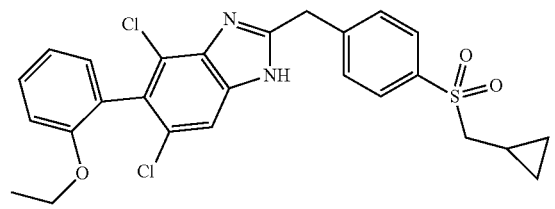

136

4,6-dichloro-2-(4-((cyclopropylmethyl)sulfonyl)benzyl)-5-(2-ethoxyphenyl)-1H-benzo[d]imidazole |
| 137 | 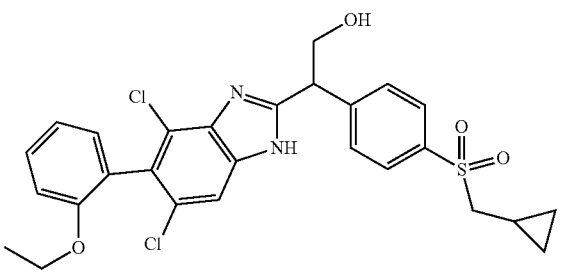

137

2-(4-((cyclopropylmethyl)sulfonyl)phenyl)-2-(4,6-dichloro-5-(2-ethoxyphenyl)-1H-benzo[d]imidazol-2-yl)ethanol |

| Example No. | Compound Name |
|---|---|
| 138 | 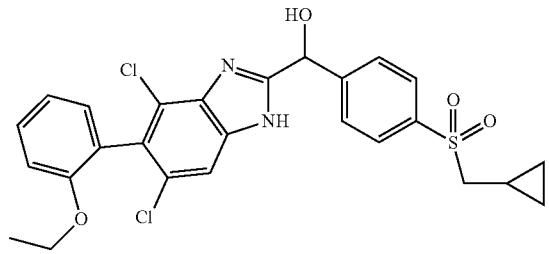

(4-((cyclopropylmethyl)sulfonyl)phenyl)(4,6-dichloro-5-(2-ethoxyphenyl)-1H-benzo[d]imidazol-2-yl)methanol

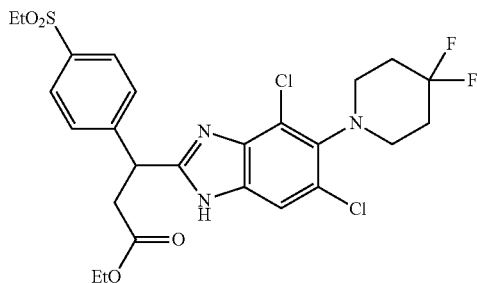

ethyl 3-(4,6-dichloro-5-(4,4-difluoropiperidin-1-yl)-1H-benzo[d]imidazol-2-yl)-3-(4-(ethylsulfonyl)phenyl)propanoate

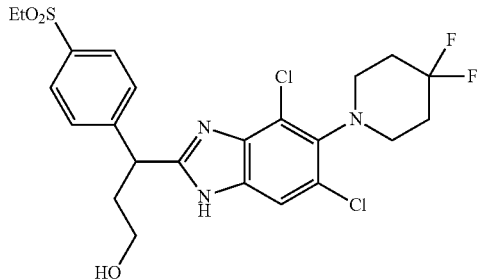

3-(4,6-dichloro-5-(4,4-difluoropiperidin-1-yl)-1H-benzo[d]imidazol-2-yl)-3-(4-(ethylsulfonyl)phenyl)propan-1-ol |
| 139 | 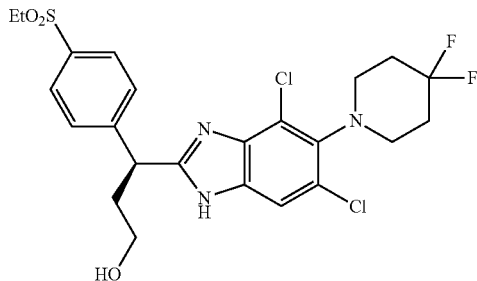

(S)-3-(4,6-dichloro-5-(4,4-difluoropiperidin-1-yl)-1H-benzo[d]imidazol-2-yl)-3-(4-(ethylsulfonyl)phenyl)propan-1-ol |

| Example No. | Compound Name |
|---|---|
| 140 | 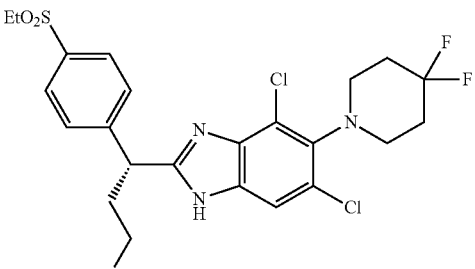
140
(R)-3-(4,6-dichloro-5-(4,4-difluoropiperidin-1-yl)-1H-benzo[d]imidazol-2-yl)-3-(4-(ethylsulfonyl)phenyl)propan-1-ol |
| 141 | 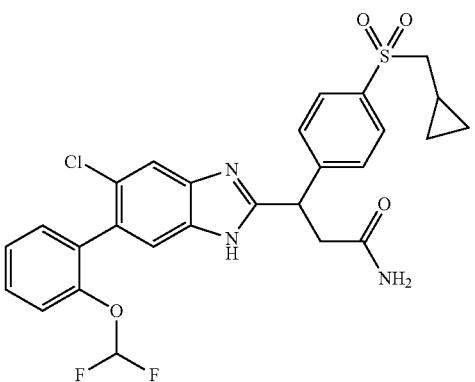
141
3-(5-chloro-6-(2-(difluoromethoxy)phenyl)-1H-benzo[d]imidazol-2-yl)-3-(4-((cyclopropylmethyl)sulfonyl)phenyl)propanamide |
| 142 | 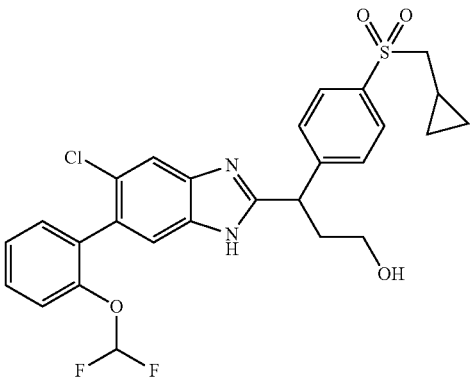
142
3-(5-chloro-6-(2-(difluoromethoxy)phenyl)-1H-benzo[d]imidazol-2-yl)-3-(4-((cyclopropylmethyl)sulfonyl)phenyl)propan-1-ol |

| Example No. | Compound Name |
|---|---|
| 143 | 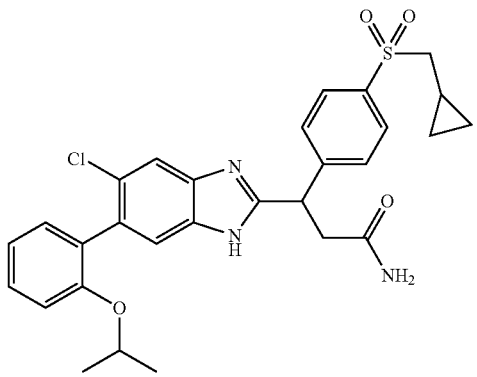
143
3-(5-chloro-6-(2-isopropoxyphenyl)-1H-benzo[d]imidazol-2-yl)-3-(4-((cyclopropylmethyl)sulfonyl)phenyl)propanamide |
| 144 | 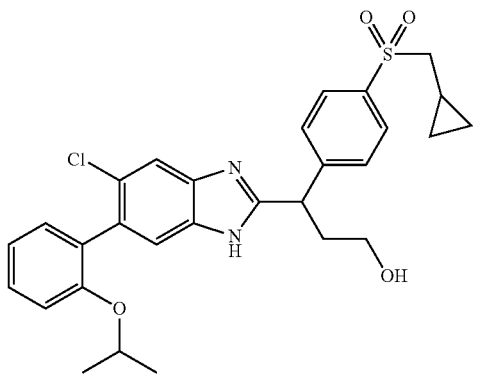
144
3-(5-chloro-6-(2-isopropoxyphenyl)-1H-benzo[d]imidazol-2-yl)-3-(4-((cyclopropylmethyl)sulfonyl)phenyl)propan-1-ol |
| 145 | 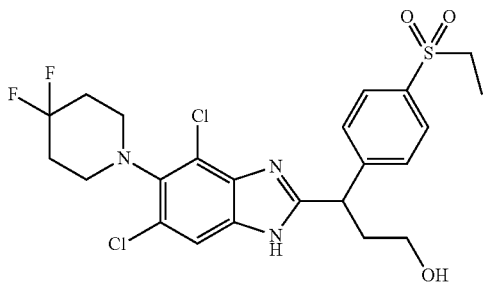
145
3-(4,6-dichloro-5-(4,4-difluoropiperidin-1-yl)-1H-benzo[d]imidazol-2-yl)-3-(4-(ethylsulfonyl)phenyl)propan-1-ol |

| Example No. | Compound Name |
|---|---|
| | 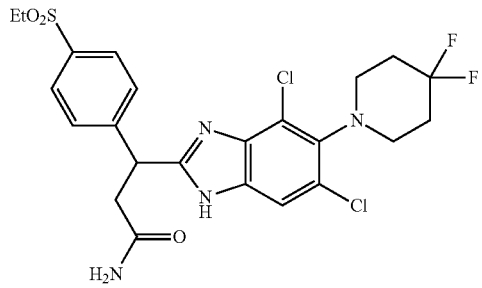<br>3-(4,6-dichloro-5-(4,4-difluoropiperidin-1-yl)-1H-benzo[d]imidazol-2-yl)-3-(4-(ethylsulfonyl)phenyl)propanamide |
| 146 | 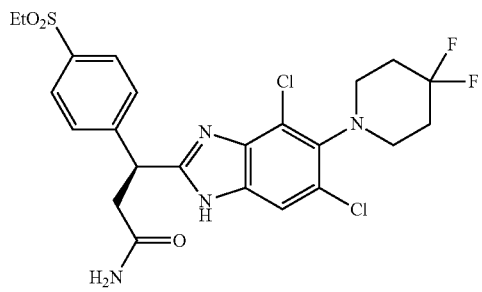<br>(S)-3-(4,6-dichloro-5-(4,4-difluoropiperidin-1-yl)-1H-benzo[d]imidazol-2-yl)-3-(4-(ethylsulfonyl)phenyl)propanamide |
| 147 | 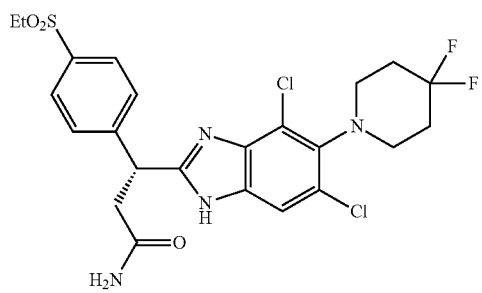<br>(R)-3-(4,6-dichloro-5-(4,4-difluoropiperidin-1-yl)-1H-benzo[d]imidazol-2-yl)-3-(4-(ethylsulfonyl)phenyl)propanamide |
| | 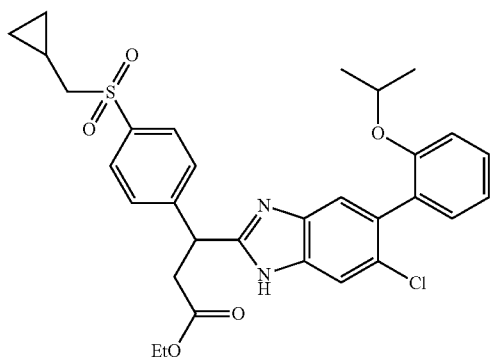 [SMILES: CCOC(=O)CC(c1ccc(S(=O)(=O)CC2CC2)cc1)c1nc2cc(-c3ccccc3OC(C)C)c(Cl)cc2[nH]1]<br>ethyl 3-(6-chloro-5-(2-isopropoxyphenyl)-1H-benzo[d]imidazol-2-yl)-3-(4-((cyclopropylmethyl)sulfonyl)phenyl)propanoate |

| Example No. | Compound Name |
|---|---|
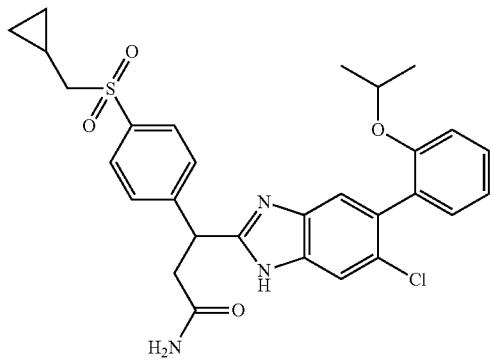
3-(6-chloro-5-(2-isopropoxyphenyl)-1H-benzo[d]imidazol-2-yl)-3-(4-((cyclopropylmethyl)sulfonyl)phenyl)propanamide
148
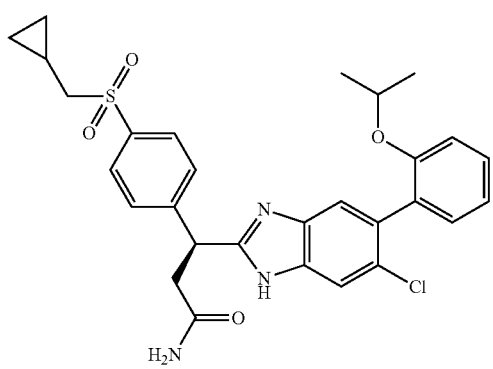
148
(S)-3-(6-chloro-5-(2-isopropoxyphenyl)-1H-benzo[d]imidazol-2-yl)-3-(4-((cyclopropylmethyl)sulfonyl)phenyl)propanamide
149
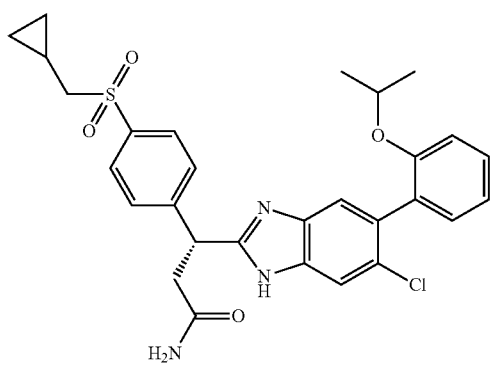 [SMILES: CC(C)Oc1ccccc1-c1cc2nc(C(CC(N)=O)c3ccc(S(=O)(=O)CC4CC4)cc3)[nH]c2cc1Cl]
149
(R)-3-(6-chloro-5-(2-isopropoxyphenyl)-1H-benzo[d]imidazol-2-yl)-3-(4-((cyclopropylmethyl)sulfonyl)phenyl)propanamide -continued
| Example No. | Compound Name |
|---|---|
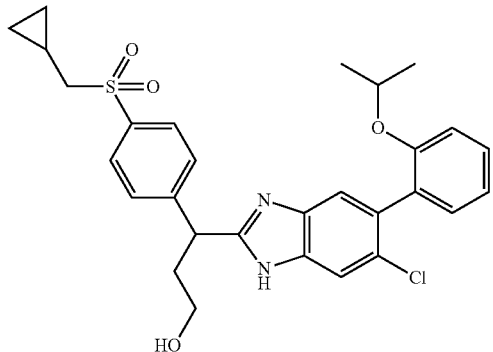
3-(6-chloro-5-(2-isopropoxyphenyl)-1H-benzo[d]imidazol-2-yl)-3-(4-((cyclopropylmethyl)sulfonyl)phenyl)propan-1-ol
150
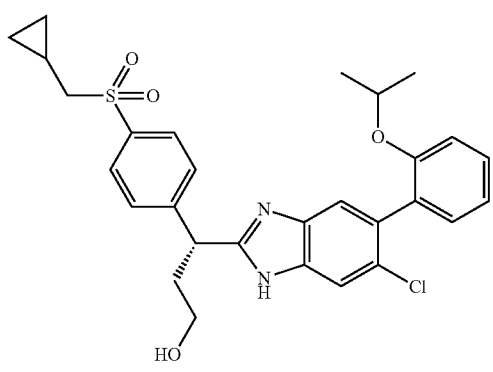 [SMILES: CC(C)Oc1ccccc1-c1cc2nc(C(CCO)c3ccc(S(=O)(=O)CC4CC4)cc3)[nH]c2cc1Cl]
150
(R)-3-(6-chloro-5-(2-isopropoxyphenyl)-1H-benzo[d]imidazol-2-yl)-3-(4-((cyclopropylmethyl)sulfonyl)phenyl)propan-1-ol
151
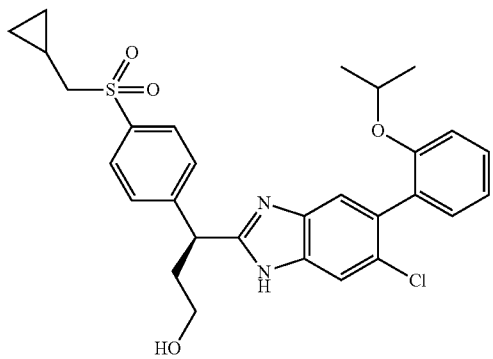
151
(S)-3-(6-chloro-5-(2-isopropoxyphenyl)-1H-benzo[d]imidazol-2-yl)-3-(4-((cyclopropylmethyl)sulfonyl)phenyl)propan-1-ol

| Example No. | Compound Name |
|---|---|
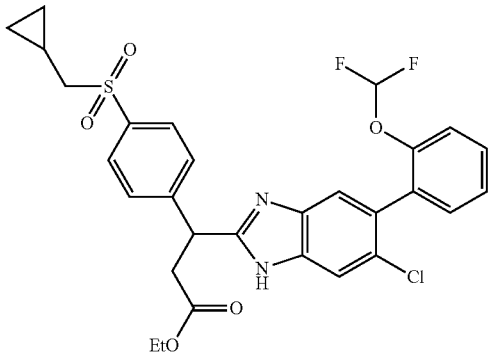 [SMILES: CCOC(=O)CC(c1ccc(S(=O)(=O)CC2CC2)cc1)c1nc2cc(-c3ccccc3OC(F)F)c(Cl)cc2[nH]1]
ethyl 3-(6-chloro-5-(2-(difluoromethoxy)phenyl)-
1H-benzo[d]imidazol-2-yl)-3-(4-
((cyclopropylmethyl)sulfonyl)phenyl)propanoate
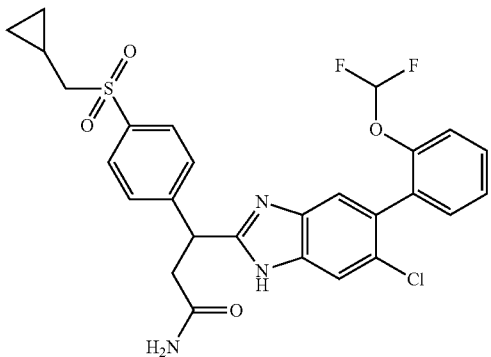 [SMILES: NC(=O)CC(c1ccc(S(=O)(=O)CC2CC2)cc1)c1nc2cc(-c3ccccc3OC(F)F)c(Cl)cc2[nH]1]
3-(6-chloro-5-(2-(difluoromethoxy)phenyl)-1H-benzo[d]
imidazol-2-yl)-3-(4-((cyclopropylmethyl)sulfonyl)phenyl)
propanamide
152
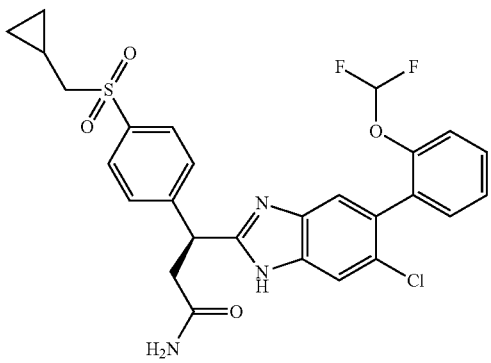
152
(S)-3-(6-chloro-5-(2-(difluoromethoxy)phenyl)-
1H-benzo[d]imidazol-2-yl)-3-(4-
((cyclopropylmethyl)sulfonyl)phenyl)propanamide -continued
| Example No. | Compound Name |
|---|---|
| 153 | 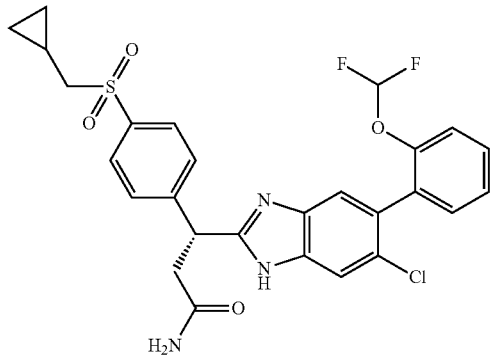<br>(R)-3-(6-chloro-5-(2-(difluoromethoxy)phenyl)-1H-benzo[d]imidazol-2-yl)-3-(4-((cyclopropylmethyl)sulfonyl)phenyl)propanamide |
| 154 | 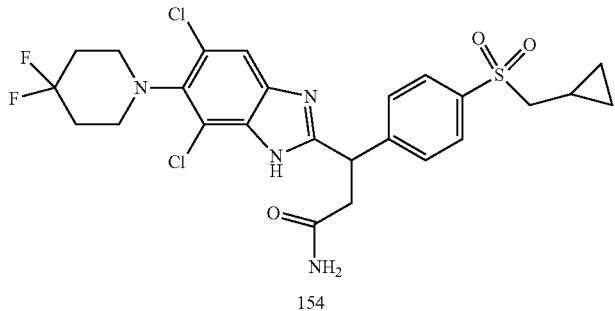 [SMILES: NC(=O)CC(c1ccc(S(=O)(=O)CC2CC2)cc1)c1nc2cc(Cl)c(N3CCC(F)(F)CC3)c(Cl)c2[nH]1]<br>3-(4-((cyclopropylmethyl)sulfonyl)phenyl)-3-(5,7-dichloro-6-(4,4-difluoropiperidin-1-yl)-1H-benzo[d]imidazol-2-yl)propanamide |
|  | 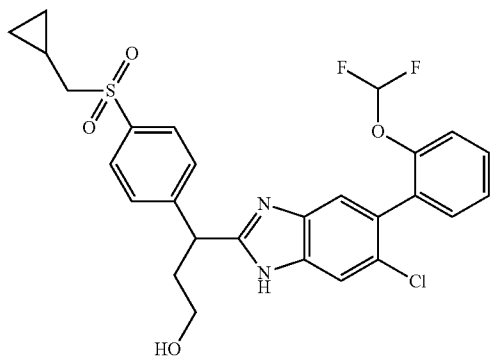<br>3-(6-chloro-5-(2-(difluoromethoxy)phenyl)-1H-benzo[d]imidazol-2-yl)-3-(4-((cyclopropylmethyl)sulfonyl)phenyl)propan-1-ol |

| Example No. | Compound Name |
|---|---|
| 155 | 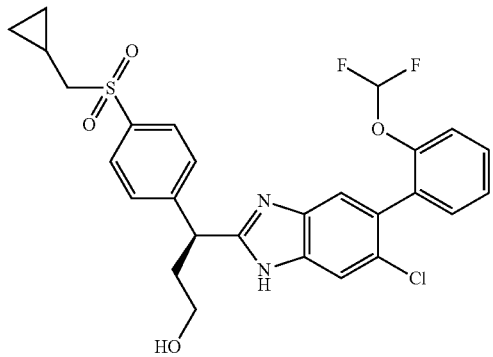
(S)-3-(6-chloro-5-(2-(difluoromethoxy)phenyl)-1H-benzo[d]imidazol-2-yl)-3-(4-((cyclopropylmethyl)sulfonyl)phenyl)propan-1-ol |
| 156 | 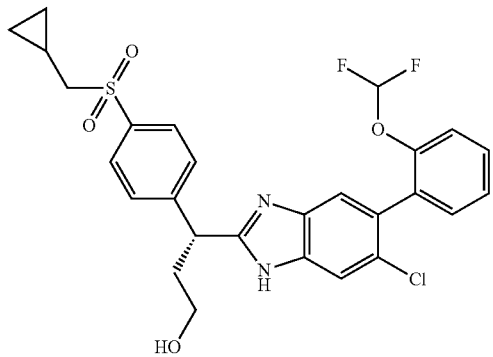 [SMILES: O=S(=O)(CC1CC1)c1ccc(C(CCO)c2nc3cc(-c4ccccc4OC(F)F)c(Cl)cc3[nH]2)cc1]
(R)-3-(6-chloro-5-(2-(difluoromethoxy)phenyl)-1H-benzo[d]imidazol-2-yl)-3-(4-((cyclopropylmethyl)sulfonyl)phenyl)propan-1-ol |
| 157 | 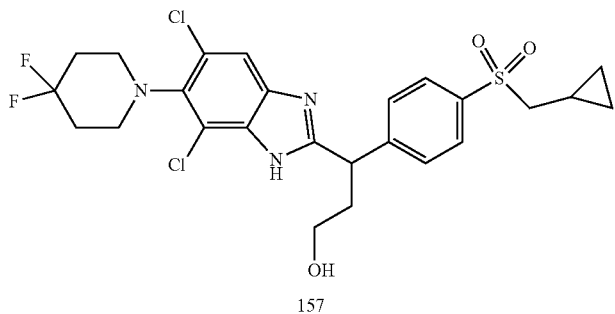 [SMILES: O=S(=O)(CC1CC1)c1ccc(C(CCO)c2nc3cc(Cl)c(N4CCC(F)(F)CC4)c(Cl)c3[nH]2)cc1]
3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol |

| Example No. | Compound Name |
|---|---|
| 158 | 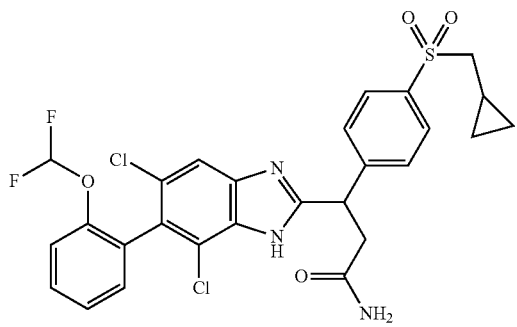<br>3-(4-((cyclopropylmethyl)sulfonyl)phenyl)-3-(5,7-dichloro-6-(2-(difluoromethoxy)phenyl)-1H-benzo[d]imidazol-2-yl)propanamide |
| 159 | 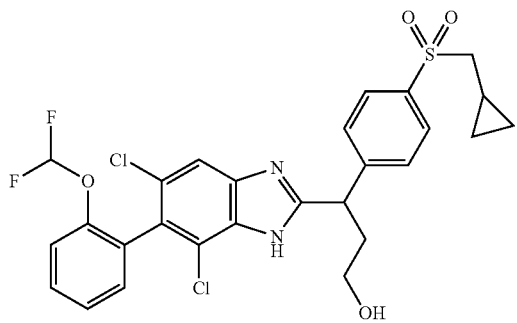<br>3-(4-((cyclopropylmethyl)sulfonyl)phenyl)-3-(5,7-dichloro-6-(2-(difluoromethoxy)phenyl)-1H-benzo[d]imidazol-2-yl)propan-1-ol |
| 160 | 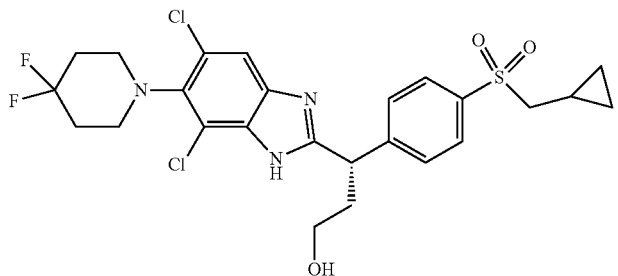<br>(S)-3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol |

| Example No. | Compound Name |
|---|---|
| 161 | 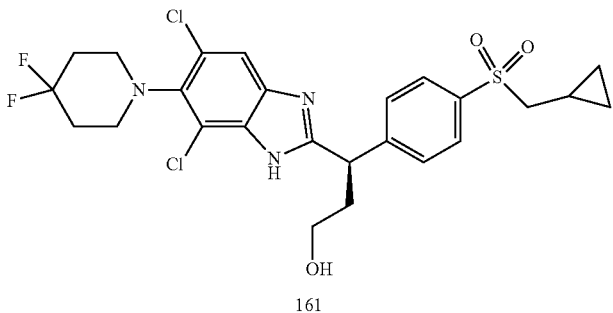 [SMILES: O=S(=O)(CC1CC1)c1ccc([C@@H](CCO)c2nc3cc(Cl)c(N4CCC(F)(F)CC4)c(Cl)c3[nH]2)cc1]<br>(R)-3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol |
| 162 | 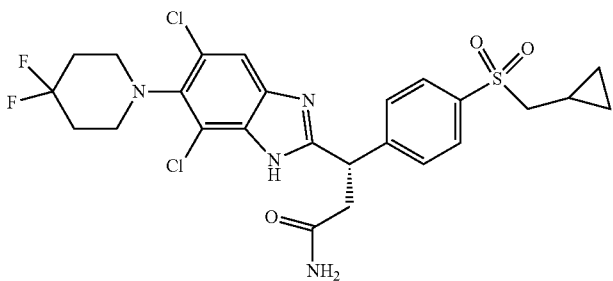<br>(S)-3-(4-((cyclopropylmethyl)sulfonylphenyl)-3-(5,7-dichloro-6-(4,4-difluoropiperidin-1-yl)-1H-benzo[d]imidazol-2-yl)propanamide |
| 163 | 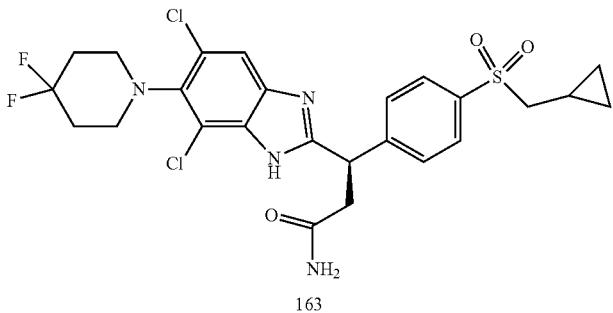 [SMILES: NC(=O)C[C@H](c1ccc(S(=O)(=O)CC2CC2)cc1)c1nc2cc(Cl)c(N3CCC(F)(F)CC3)c(Cl)c2[nH]1]<br>(R)-3-(4-((cyclopropylmethyl)sulfonyl)phenyl)-3-(5,7-dichloro-6-(4,4-difluoropiperidin-1-yl)-1H-benzo[d]imidazol-2-yl)propanamide |

| Example No. | Compound Name |
|---|---|
| 164 | 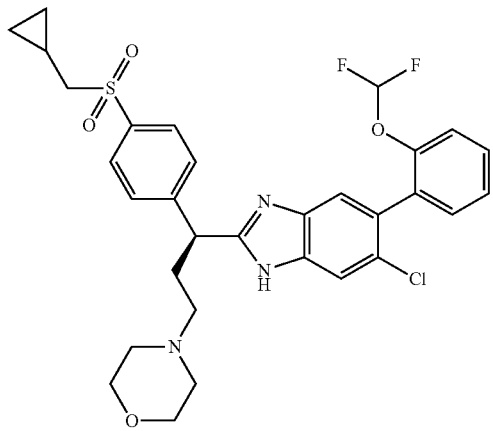<br>(S)-4-(3-(6-chloro-5-(2-(difluoromethoxy)phenyl)-1H-benzo[d]imidazol-2-yl)-3-(4-((cyclopropylmethyl)sulfonyl)phenyl)propyl)morpholine |
| 165 | 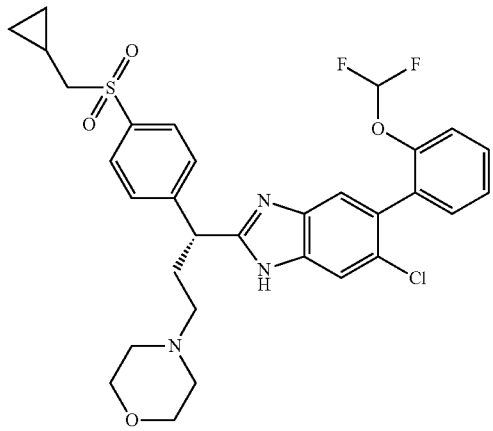<br>(R)-4-(3-(6-chloro-5-(2-(difluoromethoxy)phenyl)-1H-benzo[d]imidazol-2-yl)-3-(4-((cyclopropylmethyl)sulfonyl)phenyl)propyl)morpholine |

| Example No. | Compound Name |
|---|---|
| 166 | 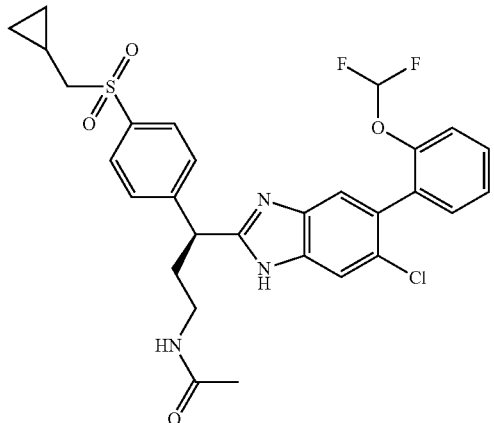 |
(S)-N-(3-(6-chloro-5-(2-(difluoromethoxy)phenyl)-
1H-benzo[d]imidazol-2-yl)-3-
(4-((cyclopropylmethyl)sulfonyl)phenyl)propyl)acetamide
| 167 | 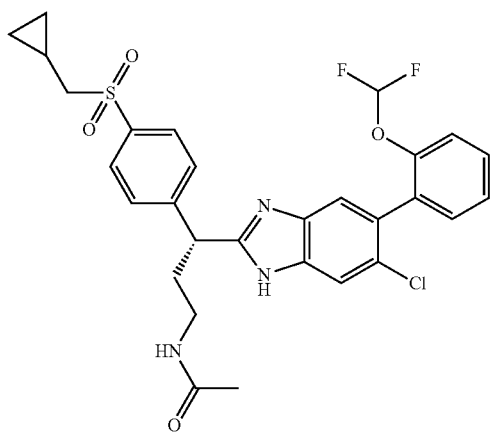 |
(R)-N-(3-(6-chloro-5-(2-(difluoromethoxy)phenyl)-
1H-benzo[d]imidazol-2-yl)-3-(4-
((cyclopropylmethyl)sulfonyl)phenyl)propyl)acetamide
| 168 | 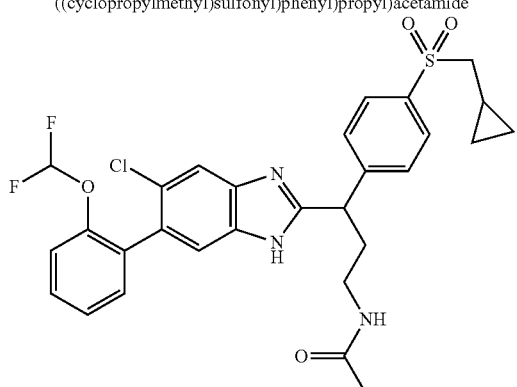 |
N-(3-(5-chloro-6-(2-(difluoromethoxy)phenyl)-1H-benzo[d]
imidazol-2-yl)-3-(4-((cyclopropylmethyl)sulfonyl)phenyl)propyl)
acetamide

| Example No. | Compound Name |
|---|---|
| 169 | 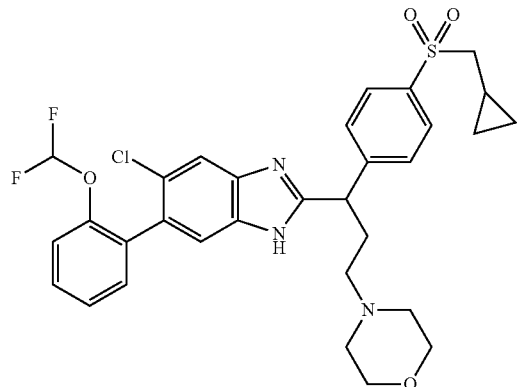
4-(3-(5-chloro-6-(2-(difluoromethoxy)phenyl)-1H-benzo[d]imidazol-2-yl)-3-(4-((cyclopropylmethyl)sulfonyl)phenyl)propyl)morpholine |
| 170 | 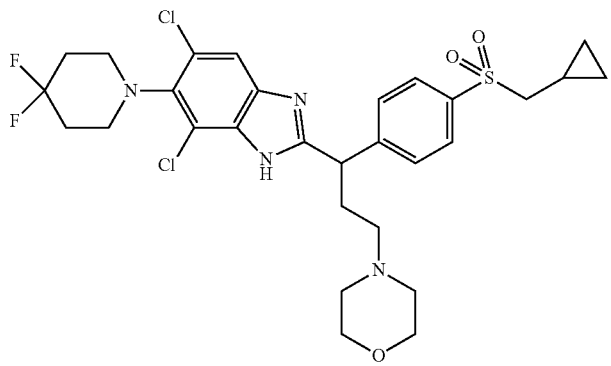
4-(3-(4-((cyclopropylmethyl)sulfonyl)phenyl)-3-(5,7-dichloro-6-(4,4-difluoropiperidin-1-yl)-1H-benzo[d]imidazol-2-yl)propyl)morpholine |
| 171 | 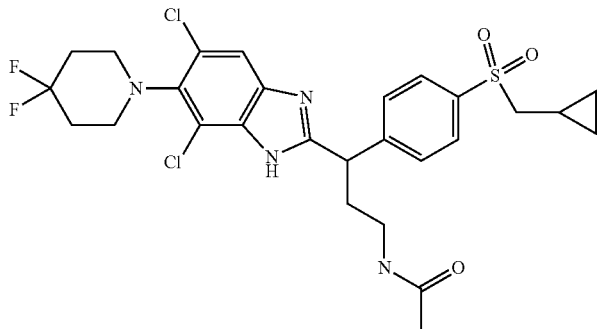
N-(3-(4-((cyclopropylmethyl)sulfonyl)phenyl)-3-(5,7-dichloro-6-(4,4-difluoropiperidin-1-yl)-1H-benzo[d]imidazol-2-yl)propyl)acetamide |

In another aspect, the present invention is directed to a compound of formula (IA,

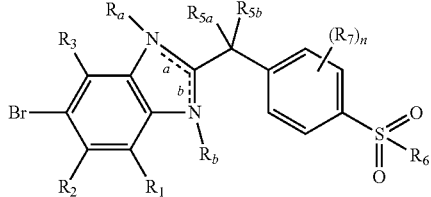
(IA)

or a tautomer, mesomer, racemate, enantiomer, diastereomer, or mixture thereof, or a pharmaceutically acceptable salt, solvate or prodrug thereof, which is an intermediate for the synthesis of the compound of formula (I), wherein:

$\underset{a}{====}$, $\underset{b}{====}$, $R_a$, $R_b$, $R_1 \sim R_3$, $R_{5a}$, $R_{5b}$, $R_6$, $R_7$ and n are as defined in formula (I).

In another aspect, the present invention is directed to a compound of formula (IC) or formula (ID), or a tautomer, mesomer, racemate, enantiomer, diastereomer, or mixture thereof, or a pharmaceutically acceptable salt, solvate or prodrug thereof,

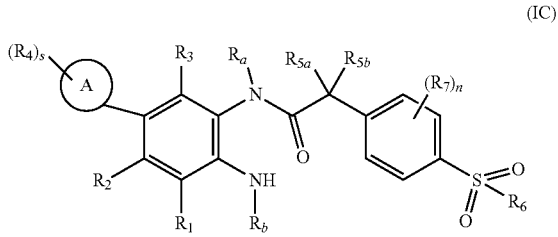
(IC)

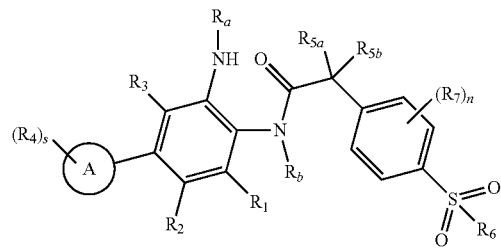
(ID)

wherein:

$R_a$ and $R_b$ is hydrogen;

ring A, $R_1 \sim R_4$, $R_{5a}$, $R_{5b}$, $R_6$, $R_7$, n and s are as defined in formula (I).

In some embodiments of the present invention, in a compound of formula (IC) or formula (ID), or a tautomer, mesomer, racemate, enantiomer, diastereomer, or mixture thereof, or a pharmaceutically acceptable salt, solvate or prodrug thereof, ring A is selected from the group consisting of phenyl, $C_{3-6}$ cycloalkyl and 5 or 6 member heteroaryl, preferably piperidinyl, phenyl, thienyl, furyl and pyridinyl.

Typical intermediate compounds of the present invention include, but are not limited to, the compounds listed in the following table.

| Example No. | Compound Name |
|---|---|
|  | 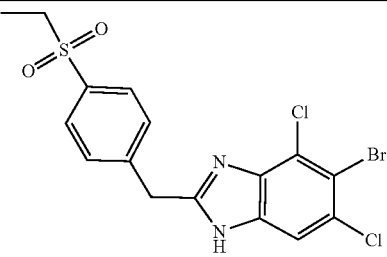<br>5-bromo-4,6-dichloro-2-(4-(ethylsulfonyl)benzyl)-1H-benzo[d]imidazole |
|  | 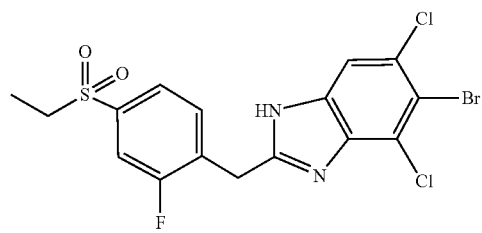 [SMILES: CCS(=O)(=O)c1ccc(Cc2nc3c(Cl)c(Br)c(Cl)cc3[nH]2)c(F)c1]<br>5-bromo-4,6-dichloro-2-(4-(ethylsulfonyl)-2-fluorobenzyl)-1H-benzo[d]imidazole |

| Example No. | Compound Name |
|---|---|
| | 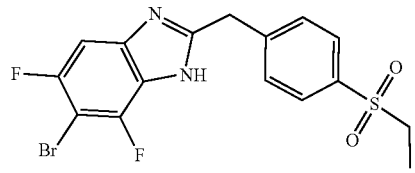 [SMILES: CCS(=O)(=O)c1ccc(Cc2nc3cc(F)c(Br)c(F)c3[nH]2)cc1]<br>6-bromo-2-(4-(ethylsulfonyl)benzyl)-5,7-difluoro-1H-benzo[d]imidazole |
| | 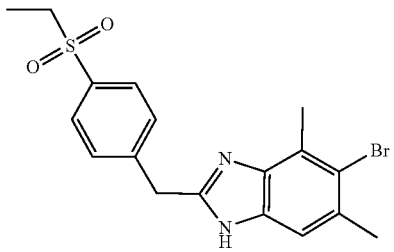 [SMILES: CCS(=O)(=O)c1ccc(Cc2nc3c(C)c(Br)c(C)cc3[nH]2)cc1]<br>5-bromo-2-(4-(ethylsulfonyl)benzyl)-4,6-dimethyl-1H-benzo[d]imidazole |
| | 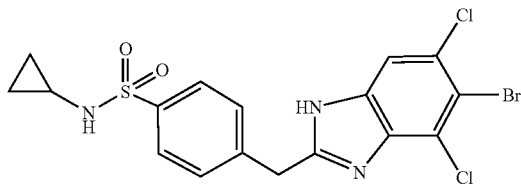 [SMILES: O=S(=O)(NC1CC1)c1ccc(Cc2nc3c(Cl)c(Br)c(Cl)cc3[nH]2)cc1]<br>4-((5-bromo-4,6-dichloro-1H-benzo[d]imidazol-2-yl)methyl)-N-cyclopropylbenzenesulfonamide |
| | 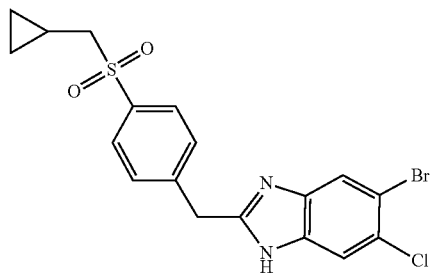 [SMILES: O=S(=O)(CC1CC1)c1ccc(Cc2nc3cc(Br)c(Cl)cc3[nH]2)cc1]<br>5-bromo-6-chloro-2-(4-((cyclopropylmethyl)sulfonyl)benzyl)-1H-benzo[d]imidazole |
| | 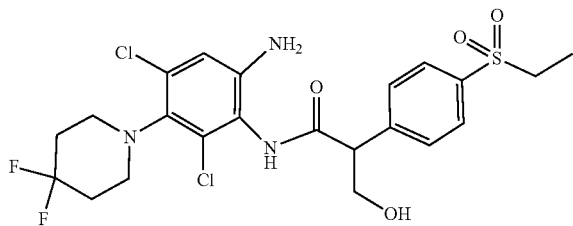 [SMILES: CCS(=O)(=O)c1ccc(C(CO)C(=O)Nc2c(N)cc(Cl)c(N3CCC(F)(F)CC3)c2Cl)cc1]<br>N-(6-amino-2,4-dichloro-3-(4,4-difluoropiperidin-1-yl)phenyl)-2-(4-(ethylsulfonyl)phenyl)-3-hydroxypropanamide |

-continued

| Example No. | Compound Name |
|---|---|

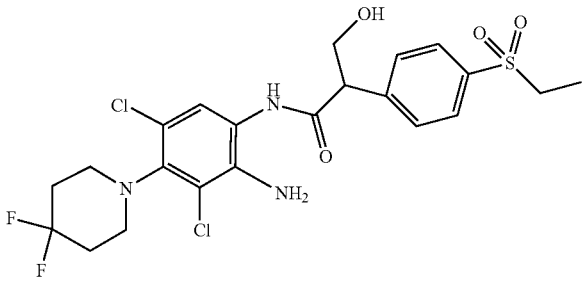 [SMILES: CCS(=O)(=O)c1ccc(C(CO)C(=O)Nc2cc(Cl)c(N3CCC(F)(F)CC3)c(Cl)c2N)cc1]

N-(2-amino-3,5-dichloro-4-(4,4-difluoropiperidin-1-yl)phenyl)-2-(4-(ethylsulfonyl)phenyl)-3-hydroxypropanamide

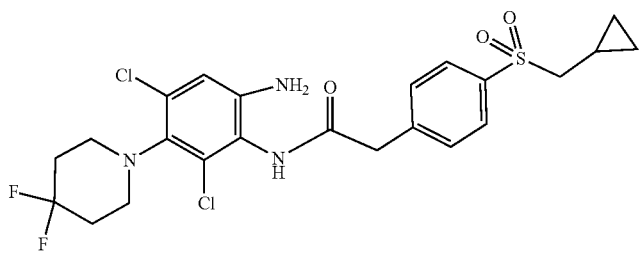 [SMILES: Nc1cc(Cl)c(N2CCC(F)(F)CC2)c(Cl)c1NC(=O)Cc1ccc(S(=O)(=O)CC2CC2)cc1]

N-(6-amino-2,4-dichloro-3-(4,4-difluoropiperidin-1-yl)phenyl)-2-(4-((cyclopropylmethyl)sulfonyl)phenyl)acetamide

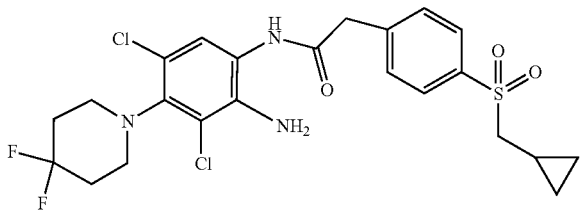 [SMILES: Nc1c(NC(=O)Cc2ccc(S(=O)(=O)CC3CC3)cc2)cc(Cl)c(N2CCC(F)(F)CC2)c1Cl]

N-(2-amino-3,5-dichloro-4-(4,4-difluoropiperidin-1-yl)phenyl)-2-(4-((cyclopropylmethyl)sulfonyl)phenyl)acetamide

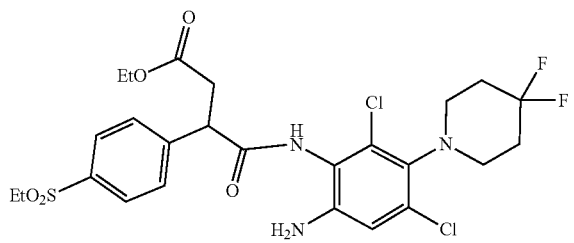

ethyl 4-((6-amino-2,4-dichloro-3-(4,4-difluoropiperidin-1-yl)phenyl)amino)-3-(4-(ethylsulfonyl)phenyl)-4-oxobutanoate

| Example No. | Compound Name |
|---|---|

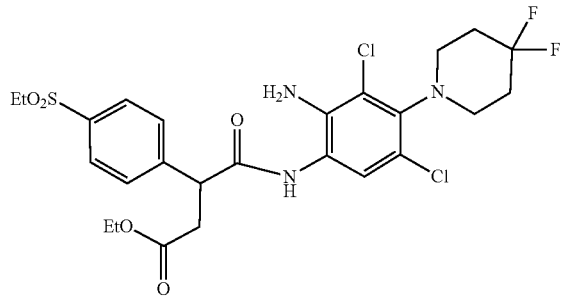

ethyl 4-((2-amino-3,5-dichloro-4-(4,4-difluoropiperidin-1-yl)phenyl)amino)-3-(4-(ethylsulfonyl)phenyl)-4-oxobutanoate

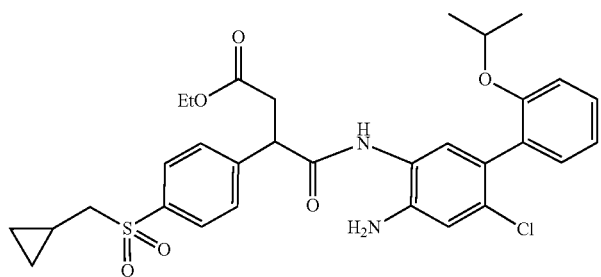 [SMILES: CCOC(=O)CC(C(=O)Nc1cc(-c2ccccc2OC(C)C)c(Cl)cc1N)c1ccc(S(=O)(=O)CC2CC2)cc1]

ethyl 4-((4-amino-6-chloro-2'-isopropoxy-[1,1'-biphenyl]-3-yl)amino)-3-(4-((cyclopropylmethyl)sulfonyl)phenyl)-4-oxobutanoate

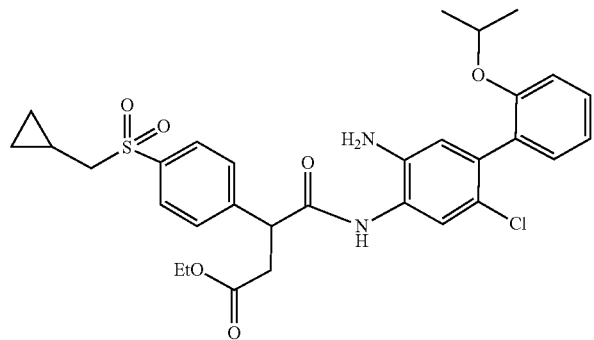 [SMILES: CCOC(=O)CC(C(=O)Nc1cc(Cl)c(-c2ccccc2OC(C)C)cc1N)c1ccc(S(=O)(=O)CC2CC2)cc1]

ethyl 4-((5-amino-2-chloro-2'-isopropoxy-[1,1'-biphenyl]-4-yl)amino)-3-(4-((cyclopropylmethyl)sulfonyl)phenyl)-4-oxobutanoate

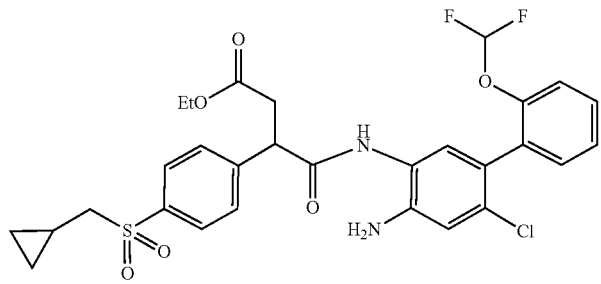 [SMILES: CCOC(=O)CC(C(=O)Nc1cc(-c2ccccc2OC(F)F)c(Cl)cc1N)c1ccc(S(=O)(=O)CC2CC2)cc1]

ethyl 4-((4-amino-6-chloro-2'-(difluoromethoxy)-[1,1'-biphenyl]-3-yl)amino)-3-(4-((cyclopropylmethyl)sulfonyl)phenyl)-4-oxobutanoate

| Example No. | Compound Name |
|---|---|
| | 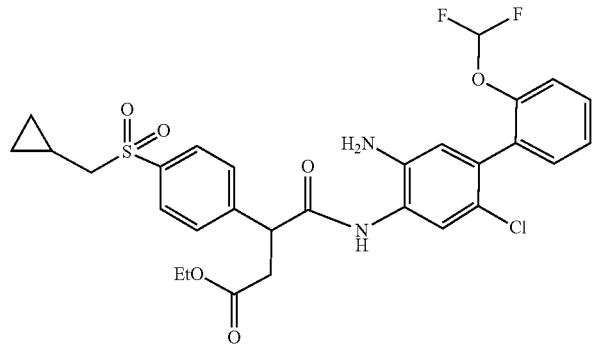 [SMILES: CCOC(=O)CC(C(=O)Nc1cc(Cl)c(-c2ccccc2OC(F)F)cc1N)c1ccc(S(=O)(=O)CC2CC2)cc1]<br>ethyl 4-((5-amino-2-chloro-2'-(difluoromethoxy)-[1,1'-biphenyl]-4-yl)amino)-3-(4-((cyclopropylmethyl)sulfonyl)phenyl)-4-oxobutanoate |

In another aspect, the present invention is directed to a process for preparing the compound of formula (I), comprising a step of coupling a compound of formula (IA) with a compound of formula (IB) under an alkaline condition in the presence of a catalyst to give the compound of formula (I):

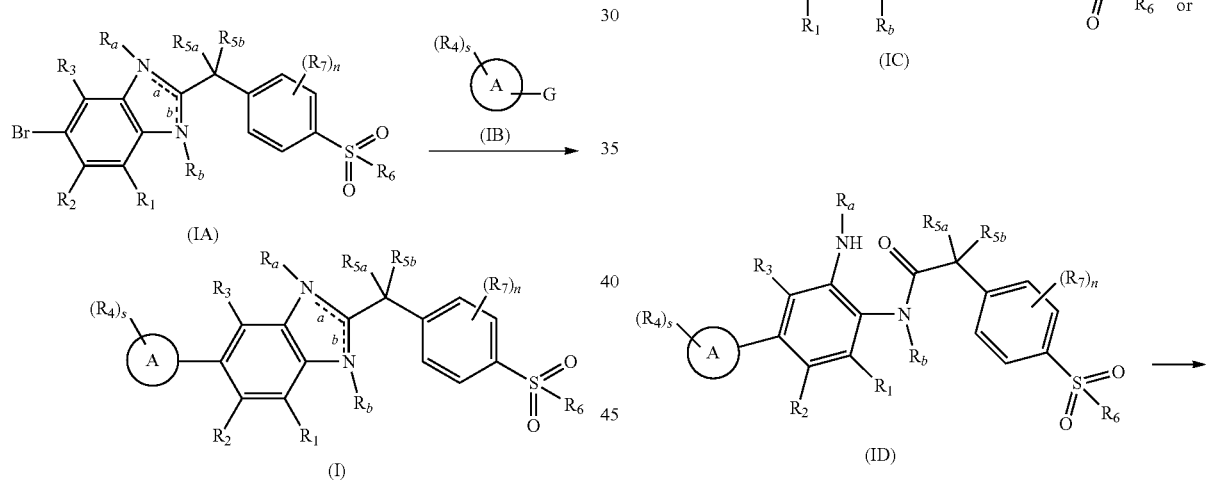

wherein:
G is leaving group, preferably boronic acid or borate, and more preferably

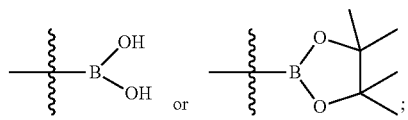

ring A, $\stackrel{a}{=\!=\!=}$, $\stackrel{b}{=\!=\!=}$, $R_a$, $R_b$, $R_1 \sim R_4$, $R_{5a}$, $R_{5b}$, $R_6$, $R_7$, n and s are as defined in formula (I).

In another aspect, the present invention is directed to a process for preparing the compound of formula (I), comprising a step of cyclization of a compound of formula (IC) or (ID) to give the compound of formula (I):

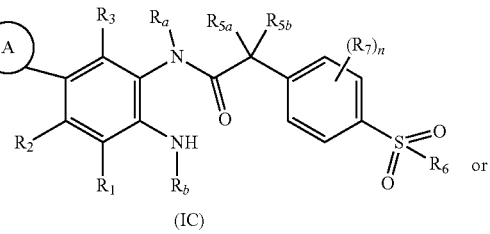

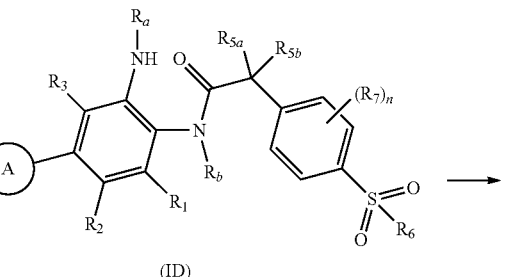

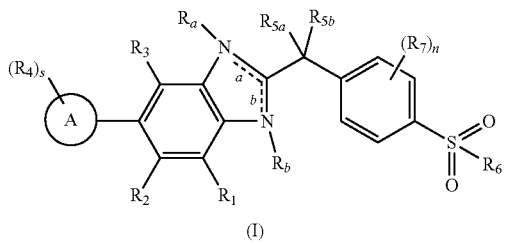

wherein:
ring A, $\stackrel{a}{=\!=\!=}$, $\stackrel{b}{=\!=\!=}$, $R_a$, $R_b$, $R_1 \sim R_4$, $R_{5a}$, $R_{5b}$, $R_6$, $R_7$, n and s are as defined in formula (I).

In another aspect, the present invention is directed to a process for preparing the compound of formula (II), comprising a step of cyclization of a compound of formula (IIC) or formula (IID) to give the compound of formula (II):

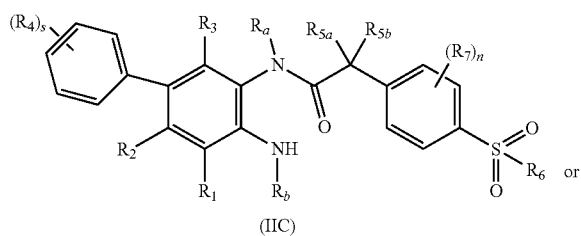

(IIC)

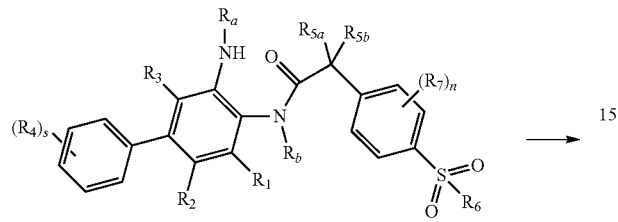

(IID)

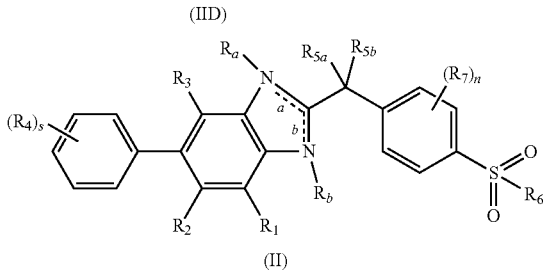

(II)

wherein:

$\stackrel{a}{\text{-----}}$, $\stackrel{b}{\text{-----}}$, $R_a$, $R_b$, $R_1 \sim R_4$, $R_{5a}$, $R_{5b}$, $R_6$, $R_7$, n and s are as defined in formula (II).

In another aspect, the present invention is directed to a process for preparing the compound of formula (III), comprising a step of cyclization of a compound of formula (IIIC) or formula (IIID) is subject to intramolecular reaction to give a formula (III):

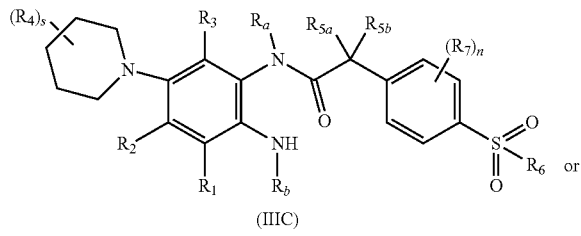

(IIIC)

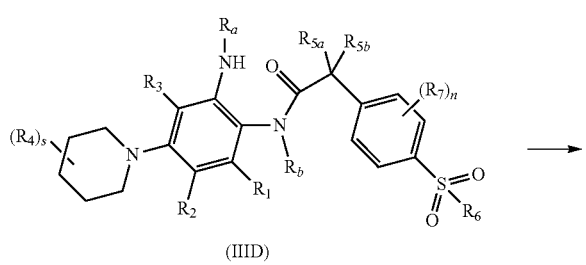

(IIID)

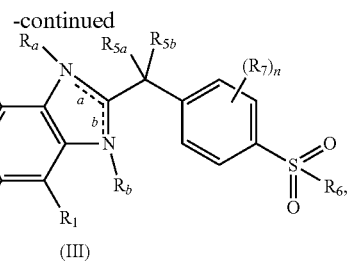

(III)

wherein:

$\stackrel{a}{\text{-----}}$, $\stackrel{b}{\text{-----}}$, $R_a$, $R_b$, $R_1 \sim R_4$, $R_{5a}$, $R_{5b}$, $R_6$, $R_7$, n and s are as defined in formula (III).

In another aspect, the present invention is directed to a pharmaceutical composition comprising a therapeutically effective amount of the compound of formula (I), or a tautomer, mesomer, racemate, enantiomer, diastereomer, or mixture thereof, or a pharmaceutically acceptable salt, solvate or prodrug thereof, and one or more pharmaceutically acceptable carriers, diluents or excipients.

In another aspect, the present invention is directed to a method for inhibiting a retinoid-related orphan receptor gamma (RORγ) in a subject, comprising administering to the subject a therapeutically effective amount of the compound of formula (I), or the tautomer, mesomer, racemate, enantiomer, diastereomer, or mixture thereof, or the pharmaceutically acceptable salt, solvate or prodrug thereof.

In another aspect, the present invention is directed to a method for treating a retinoid-related orphan receptor gamma (RORγ) protein mediated disease or disorder in a subject, comprising administering to the subject a therapeutically effective amount of the compound of formula (I), or the tautomer, mesomer, racemate, enantiomer, diastereomer, or mixture thereof, or a pharmaceutically acceptable salt, solvate or prodrug thereof.

In another aspect, the present invention is directed to use of the compound of formula (I), or a tautomer, mesomer, racemate, enantiomer, diastereomer, or mixture thereof, or a pharmaceutically acceptable salt, solvate or prodrug thereof, in the preparation of a medicament for inhibiting RORγ.

In another aspect, the present invention is directed to use of the compound of formula (I), or a tautomer, mesomer, racemate, enantiomer, diastereomer, or mixture thereof, or a pharmaceutically acceptable salt, solvate or prodrug thereof, in the preparation of a medicament for treating a RORγ protein mediated disease or disorder.

In another aspect, the present invention further relates to a compound of the formula (I), or a tautomer, a mesomer, a racemate, an enantiomer, a diastereomer or a mixture thereof, or a pharmaceutically acceptable salt thereof for use as a medicament.

In another aspect, the present invention further relates to a compound of the formula (I), or a tautomer, a mesomer, a racemate, an enantiomer, a diastereomer, or a mixture thereof, or a pharmaceutically acceptable salt thereof for use as a RORγ inhibitor.

In another aspect, the present invention further relates to a compound of the formula (I), or a tautomer, a mesomer, a racemate, an enantiomer, a diastereomer, or a mixture thereof, or a pharmaceutically acceptable salt thereof for use as a medicament for treating a RORγ protein mediated disease or disorder.

RORγ protein mediated diseases or disorders include, but are not limited to, inflammation and autoimmune diseases and cancers, wherein inflammation and autoimmune diseases include, but are not limited to, arthritis, rheumatoid arthritis, juvenile rheumatoid arthritis, psoriasis, psoriatic arthritis, osteoarthritis, regional enteritis, ulcerative colitis, ankylosing spondylitis, autoimmune diabetes, type I diabetes, autoimmune ocular disease, autoimmune thyroid disease, autoimmune polyedocrine syndrome type I, autoimmune polyendocrine syndrome type II, multiple sclerosis, inflammatory bowel disease, inflammatory bowel syndrome, juvenile idiopathic arthritis, Sjögren's syndrome, Crohn's disease, asthma, Kawasaki Disease, Hashimoto's thyroiditis, infectious diseases, ankylosing spondylitis, chronic obstructive pulmonary disease (COPD), pulmonary disease, glomerulonephritis, myocarditis, thyroiditis, dry eye, Uveitis, Behcet's disease, asthma, atopic dermatitis, contact dermatitis, allograft rejection, polymyocitis, grad versus host disease, acne, ulcerative colitis, systemic lupus erythematosus, scleroderma, bronchitis, dermatomyositis and allergic rhinitis; and wherein cancers include, but are not limited to, non-Hodgkin's lymphoma, diffuse large B-cell lymphoma, follicular lymphoma, synovial sarcoma, breast cancer, cervical cancer, colon cancer, lung cancer, stomach cancer, rectal cancer, pancreatic cancer, brain cancer, skin cancer, oral cancer, prostate cancer, bone cancer, kidney cancer, ovarian cancer, bladder cancer, liver cancer, fallopian tube tumor, ovarian tumor, peritoneal tumor, melanoma, solid tumor, glioma, nerve Glioblastoma, hepatocellular carcinoma, mastoid renal tumor, head and neck tumor, leukemia, lymphoma, myeloma and non-small cell lung cancer.

Definitions

Unless otherwise stated, the terms used herein have the following meanings.

"Alkyl" refers to a linear or branched saturated aliphatic hydrocarbon group having 1 to 20 carbon atoms, preferably $C_1$-$C_{12}$ alkyl, more preferably $C_1$-$C_6$ alkyl, sometimes more preferably $C_1$-$C_4$ alkyl. Nonlimiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the branched isomers thereof. More preferably an alkyl group is a lower alkyl having 1 to 6 carbon atoms, and the nonlimiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, carboxyl, and carboxylic ester.

"Alkylene" refers to a hydrogen atom of an alkyl which is further substituted. For example, methylene(—$CH_2$—), 1,2-ethylene(—$CH_2CH_2$—), 1,3-propylene(—$CH_2CH_2CH_2$—), 1,4-butylene(—$CH_2CH_2CH_2CH_2$—), and the like.

"Alkenyl" refers to an alkyl defined as above that has at least two carbon atoms, preferably 2-10 carbons, more preferably 2-6 carbons, sometimes more preferably 2-4 carbons, and at least one carbon-carbon double bond, for example, ethenyl, 1-propenyl, 2-propenyl, 1-, 2- or 3-butenyl and the like. The alkenyl group may be substituted or unsubstituted. When substituted, the substituent group(s) is preferably one or more groups independently selected from the group consisting of alkyl, alkenyl, alkynyl, alkoxyl, alkylthio, alkylamino, halogen, thiol, hydroxyl, nitro, cyano, cycloalkyl, heterocyclyl, aryl, heteroaryl, cycloalkoxyl, heterocylic alkoxyl, cycloalkylthio and heterocyclylthio.

"Cycloalkyl" refers to a saturated and/or partially unsaturated monocyclic or polycyclic hydrocarbon group having 3 to 20 carbon atoms, preferably 3 to 12 carbon atoms, more preferably 3 to 8 carbon atoms, and most preferably 3 to 6 carbon atoms. Nonlimiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more rings may contain one or more double bonds, but none of the rings has a completely conjugated pi-electron system, preferably 6 to 14 membered spiro cycloalkyl, and more preferably 7 to 10 membered spiro cycloalkyl. According to the number of the common spiro atoms, spiro cycloalkyl may be divided into mono-spiro cycloalkyl, di-spiro cycloalkyl, or poly-spiro cycloalkyl, and preferably a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Nonlimiting examples of spiro cycloalkyls include, but are not limited to:

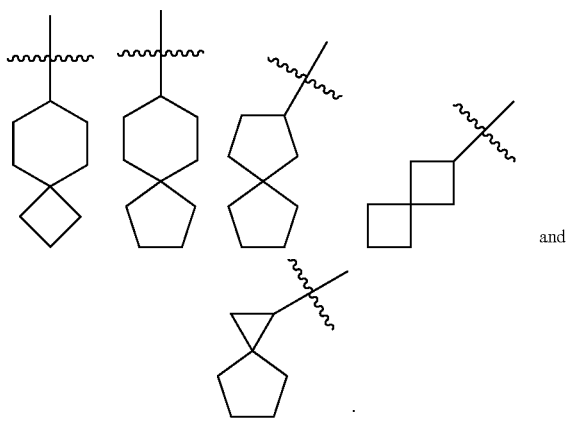

and

.

"Fused cycloalkyl" refers to a 5 to 20 membered full-carbon polycyclic group, wherein each ring in the system shares an adjacent pair of carbon atoms with another ring, wherein one or more rings may contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl may be divided into bicyclic, tricyclic, tetracyclic or polycyclic fused cycloalkyl, preferably bicyclic, tricyclic or tetracyclic fused cycloalkyl, and more preferably bicyclic or tricyclic. Nonlimiting examples of fused cycloalkyl include, but are not limited to:

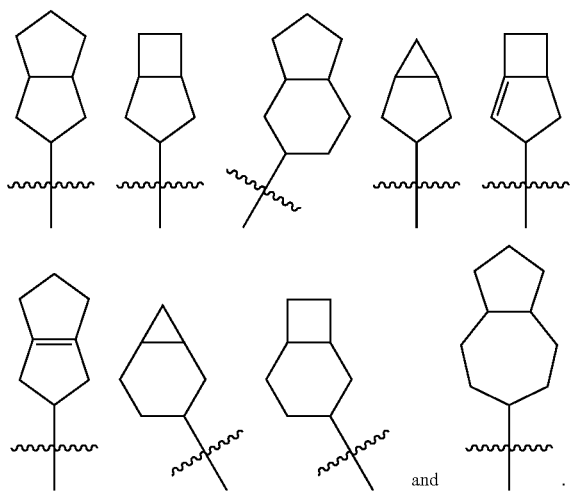

"Bridged cycloalkyl" refers to a 5 to 20 membered full-carbon polycyclic group, wherein every two rings in the system share two disconnected atoms, wherein the rings may have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl may be divided into bicyclic, tricyclic, tetracyclic or polycyclic bridged cycloalkyl, and preferably bicyclic, tricyclic or tetracyclic bridged cycloalkyl, and more preferably bicyclic or tricyclic bridged cycloalkyl. Nonlimiting examples of bridged cycloalkyls include, but are not limited to:

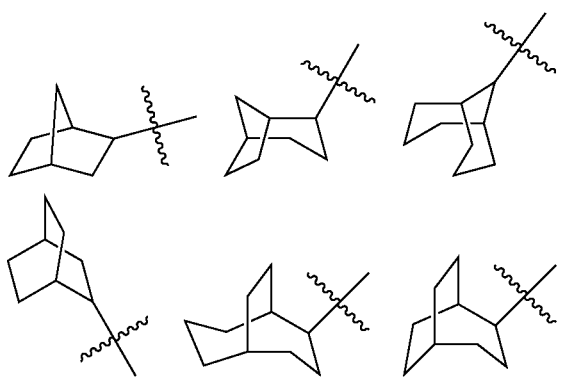

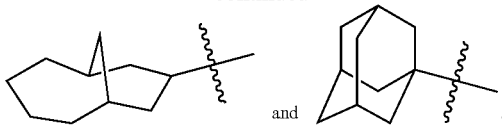

Said cycloalkyl include above cycloalkyl fused to aryl, heteroaryl or heterocyclyl, wherein the ring bound to the parent structure is cycloalkyl. Nonlimiting examples include indanyl, tetrahydronaphthyl, benzocycloheptyl and the like. The cycloalkyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, carboxyl, carboxylic ester.

"Heterocyclyl" refers to a 3 to 20 membered saturated and/or partially unsaturated monocyclic or polycyclic hydrocarbon group having one or more heteroatoms selected from the group consisting of N, O, and $S(O)_m$ (wherein m is an integer selected from 0 to 2) as ring atoms, but excluding —O—O—, —O—S— or —S—S— in the ring, and the remaining ring atoms being carbon atoms. Preferably, heterocyclyl has 3 to 12 atoms with 1 to 4 heteroatoms, more preferably 3 to 6 atoms. Nonlimiting examples of monocyclic heterocyclyl include, but are not limited to, pyrrolidinyl, imidazolidinyl, tetrahydrofuranyl, tetrahydrothiophenyl, dihydroimidazolyl, dihydrofuranyl, dihydropyrazolyl, dihydropyrrolyl, piperidyl, piperazinyl, morpholinyl, thiomorpholinyl, homopiperazinyl and the like. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein said rings have one or more heteroatoms selected from the group consisting of N, O, and $S(O)_m$ (wherein m is an integer selected from 0 to 2) as ring atoms and the remaining ring atoms being carbon atoms, wherein one or more rings may contain one or more double bonds, but none of the rings has a completely conjugated pi-electron system; preferably 6 to 14 membered spiro heterocyclyl, and more preferably 7 to 10 membered spiro heterocyclyl. According to the number of common spiro atoms, spiro heterocyclyl may be divided into mono-spiro heterocyclyl, di-spiro heterocyclyl, or poly-spiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Nonlimiting examples of spiro heterocyclyls include, but are not limited to:

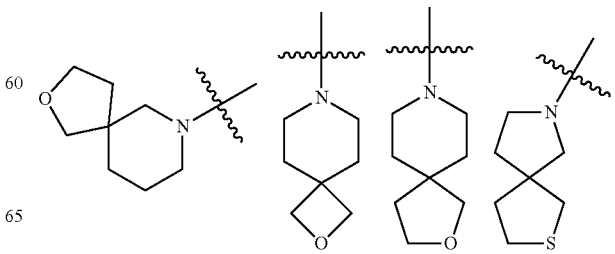

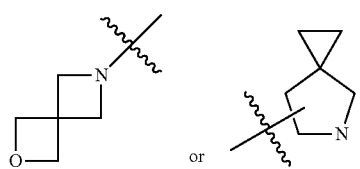

or

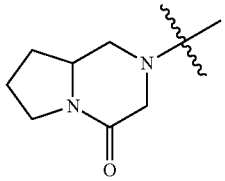

"Fused heterocyclyl" refers to a 5 to 20 membered polycyclic heterocyclyl group, wherein each ring in the system shares an adjacent pair of atoms with another ring, wherein one or more rings may contain one or more double bonds, but none of the rings has a completely conjugated pi-electron system, and wherein said rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered fused heterocyclyl, and more preferably 7 to 10 membered fused heterocyclyl. According to the number of membered rings, fused heterocyclyl may be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Nonlimiting examples of fused heterocyclyl include, but are not limited to:

"Bridged heterocyclyl" refers to a 5 to 14 membered polycyclic heterocyclyl group, wherein every two rings in the system share two disconnected atoms, wherein the rings may have one or more double bonds, but none of the rings has a completely conjugated pi-electron system, and the rings have one or more heteroatoms selected from the group consisting of N, O, and $S(O)_m$ (wherein m is an integer selected from 0 to 2) as ring atoms, and the remaining ring atoms being carbon atoms; preferably 6 to 14 membered bridged heterocyclyl, and more preferably 7 to 10 membered bridged heterocyclyl. According to the number of membered rings, bridged heterocyclyl may be divided into bicyclic, tricyclic, tetracyclic or polycyclic bridged heterocyclyl, and preferably bicyclic, tricyclic or tetracyclic bridged heterocyclyl, and more preferably bicyclic or tricyclic bridged heterocyclyl. Nonlimiting examples of bridged heterocyclyls include, but are not limited to:

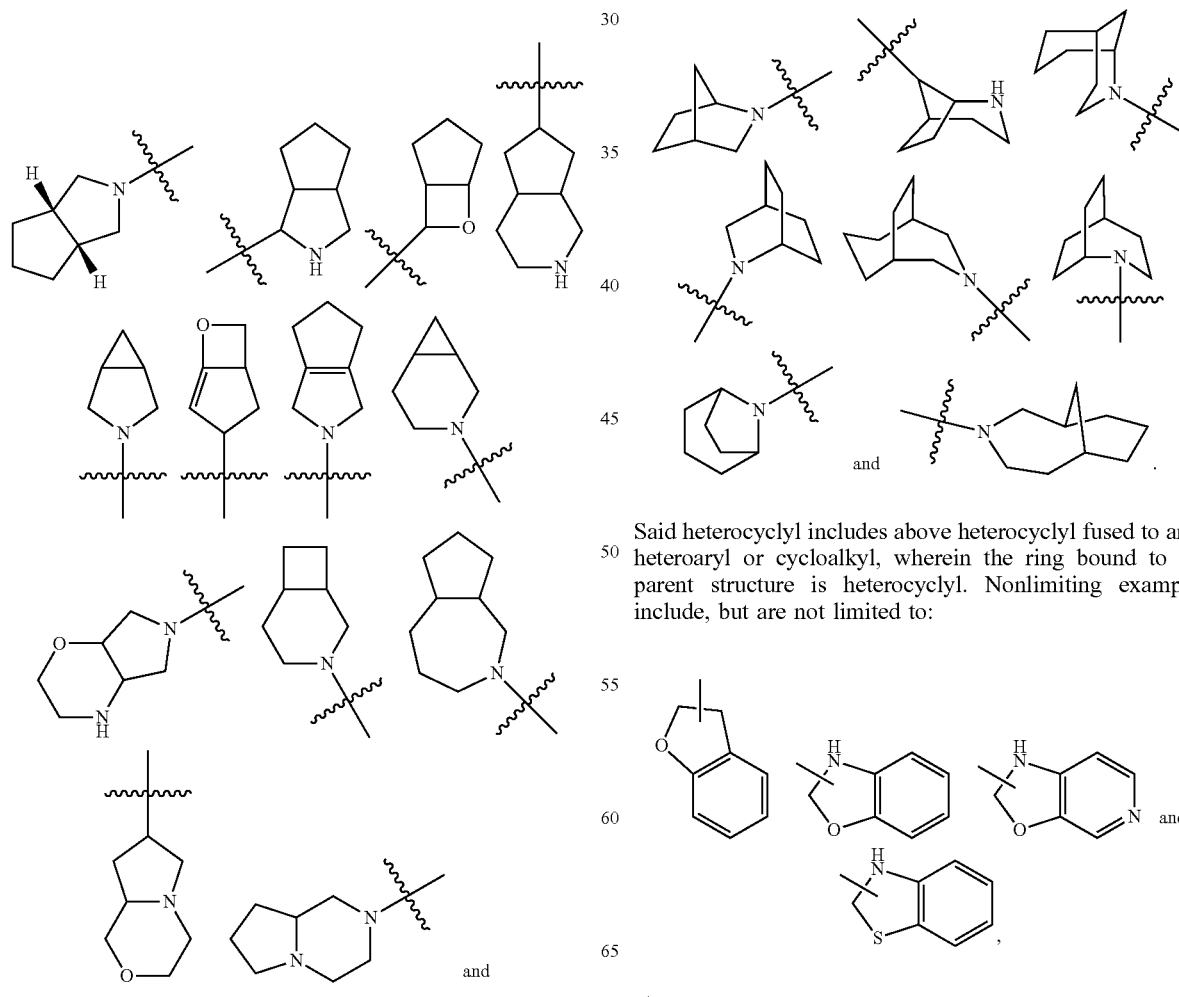

Said heterocyclyl includes above heterocyclyl fused to aryl, heteroaryl or cycloalkyl, wherein the ring bound to the parent structure is heterocyclyl. Nonlimiting examples include, but are not limited to:

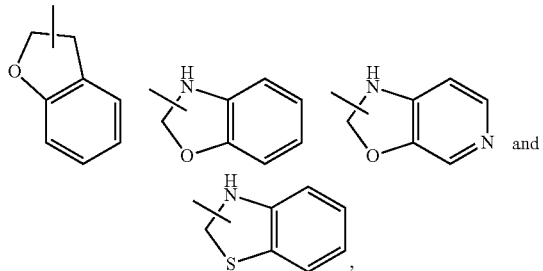

etc.

The heterocyclyl may be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, oxo, carboxyl, carboxylic ester.

"Aryl" refers to a 6 to 14 membered full-carbon monocyclic ring or polycyclic fused ring (i.e. each ring in the system shares an adjacent pair of carbon atoms with another ring in the system) group having a completely conjugated pi-electron system; preferably 6 to 10 membered aryl, more preferably phenyl and naphthyl, and most preferably phenyl. The aryl includes above aryl fused to heteroaryl, heterocyclyl or cycloalkyl, wherein the ring bound to parent structure is aryl. Nonlimiting examples include, but are not limited to:

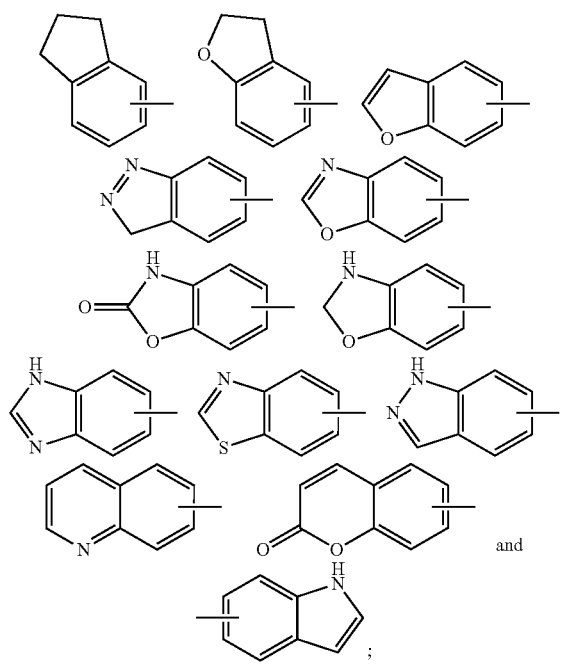

preferably

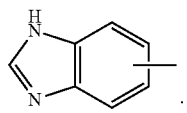

The aryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, and carboxylic ester.

"Heteroaryl" refers to 5 to 14 membered aryl having 1 to 4 heteroatoms selected from the group consisting of O, S and N as ring atoms and remaining ring atoms being carbon atoms; preferably 5 to 10 membered heteroaryl, more preferably 5- or 6-membered heteroaryl such as imidazolyl, furyl, thienyl, pyrazolyl, oxazolyl, pyrrolyl, tetrazolyl, pyridyl, pyrimidinyl, thiadiazole, pyrazinyl, and the like, preferably imidazolyl, pyrazolyl, pyrimidinyl or thiadiazole; more preferably pyrazolyl. The heteroaryl includes above heteroaryl fused to aryl, heterocyclyl or cycloalkyl, wherein the ring bound to parent structure is heteroaryl. Nonlimiting examples include, but are not limited to:

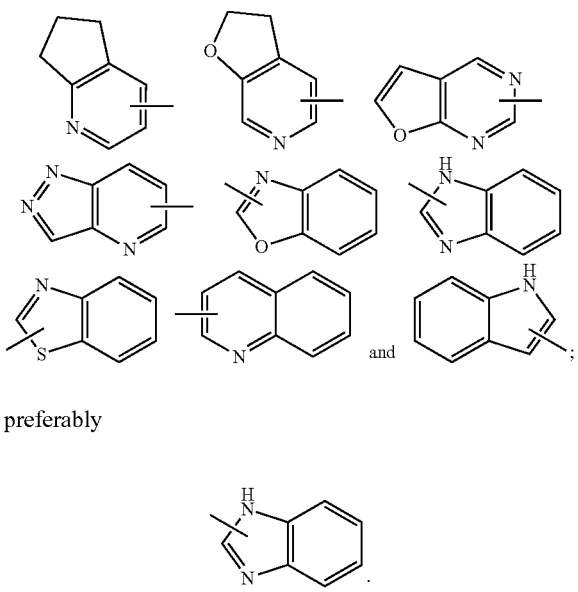

preferably

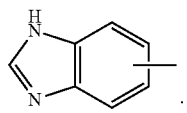

The heteroaryl may be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, carboxyl, and carboxylic ester.

"Alkoxy" refers to an —O-(alkyl) or an —O-(unsubstituted cycloalkyl) group, wherein the alkyl is as defined above. Nonlimiting examples include, but are not limited to, methoxy, ethoxy, propoxy, butoxy, cyclopropyloxy, cyclobutyloxy, cyclopentyloxy, cyclohexyloxy, and the like. The alkoxy may be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclylthio, amino, haloalkyl, hydroxyalkyl, carboxyl, and carboxylic ester.

"Haloalkyl" refers to an alkyl substituted with one or more halogen, wherein alkyl is as defined above.

"Haloalkoxy" refers to an alkoxy substituted with one or more halogen, wherein alkoxy is as defined above.

"Hydroxyalkyl" refers to an alkyl substituted with hydroxy, wherein alkyl is as defined above.

"Hydroxy" refers to an —OH group.

"Halogen" refers to fluorine, chlorine, bromine or iodine.

"Amino" refers to an —NH$_2$ group.

"Cyano" refers to a —CN group.

"Nitro" refers to an —NO$_2$ group.

"Oxo" refers to =O.

"Carboxyl" refers to a —C(O)OH group.

"Carboxylic ester" refers to a —C(O)O(alkyl) or —C(O)O(cycloalkyl) group, wherein the alkyl and cycloalkyl are as defined above.

"Optional" or "optionally" means that the event or circumstance described subsequently can be, but need not be, and such descriptions include the situation in which the event or circumstance may or may not occur. For example, "the heterocyclic group optionally substituted with an alkyl" means that an alkyl group can be, but need not be, present, and such description includes the situation of the heterocyclic group being substituted with an alkyl and the heterocyclic group being not substituted with an alkyl.

"Substituted" refers to one or more hydrogen atoms in a group, preferably up to 5, more preferably 1 to 3 hydrogen atoms, independently substituted with a corresponding number of substituents. It goes without saying that the substituents only exist in their possible chemical position. The person skilled in the art is able to determine whether the substitution is possible or impossible by experiments or theory without paying excessive efforts. For example, when amino or hydroxy with free hydrogen is bound to a carbon atoms having unsaturated bonds (such as olefinic) may be unstable.

For any substituents alkyl, alkenyl, alkynyl, alkoxy, alkylthio, alkylamino, cycloalkyl, heterocyclyl, aryl, heteroaryl, cycloalkoxy, heterocylic alkoxy, cycloalkylthio, heterocyclylthio, and carboxylic ester mentioned throughout the application, any alkyl is preferably $C_1$-$C_6$ alkyl, sometimes more preferably $C_1$-$C_4$ alkyl; any alkenyl is preferably $C_2$-$C_6$ alkenyl, sometimes more preferably $C_1$-$C_4$ alkenyl; any alkynyl is preferably $C_2$-$C_6$ alkynyl, sometimes more preferably $C_1$-$C_4$ alkynyl; any cycloalkyl is preferably $C_3$-$C_6$ cycloalkyl; any heterocyclyl is preferably 5- to 10-membered, sometimes more preferably 5- or 6-membered heterocyclyl; any aryl is preferably $C_6$-$C_{10}$ aryl, more preferably phenyl; any heteroaryl is 5- to 10-membered, sometimes more preferably 5- or 6-membered, heteroaryl; and any carboxylic ester is preferably $C_1$-$C_4$ alkyl ester, sometimes more preferably methyl or ethyl ester.

A "pharmaceutical composition" refers to a mixture of one or more of the compounds according to the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism and the absorption of the active ingredient and thus displaying biological activity.

The compounds of the present disclosure can exist as pharmaceutically acceptable salts or solvates. Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid, or the like.

"Solvate" refers to a physical association of a compound of this invention with one or more, preferably one to three, solvent molecules, whether organic or inorganic. This physical association includes hydrogen bonding. In certain instances the solvate will be capable of isolation, for example, when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

"Therapeutically effective amount" refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

"Pharmaceutically acceptable" refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

"Patient" or "subject" includes both human and other mammalian animals, including but not limited to cats, dogs, cows, horses, or the like.

"Treating" or "treatment" refers to: (i) inhibiting the disease, disorder, or condition, i.e., arresting its development; and (ii) relieving the disease, disorder, or condition, i.e., causing regression of the disease, disorder, and/or condition. In some embodiments, the present invention also includes use of a compound according to any embodiment disclosed for preventing a disease, disorder or condition from occurring in a patient that may be predisposed to the disease, disorder, and/or condition but has not yet been diagnosed as having it;

Any terms in the present application, unless specifically defined, will take the ordinary meanings as understood by a person of ordinary skill in the art. All references cited herein are incorporated by reference in their entireties.

Synthesis Method of the Present Invention

In order to obtain the object of the present invention, the present invention applies the following synthetic technical solutions:

A process for preparing a compound of formula (I) of the present invention, or a tautomer, mesomer, racemate, enantiomer, diastereomer, or mixtures thereof, or pharmaceutically acceptable salts thereof, comprising the following steps:

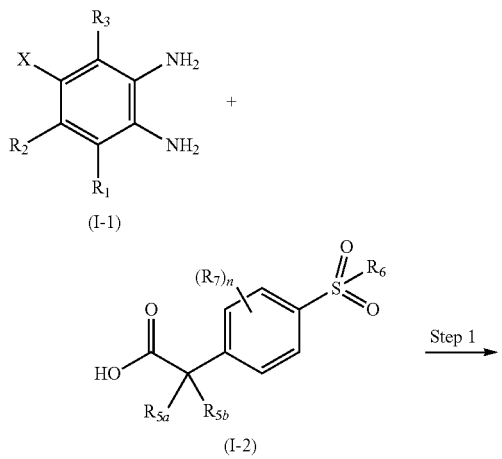

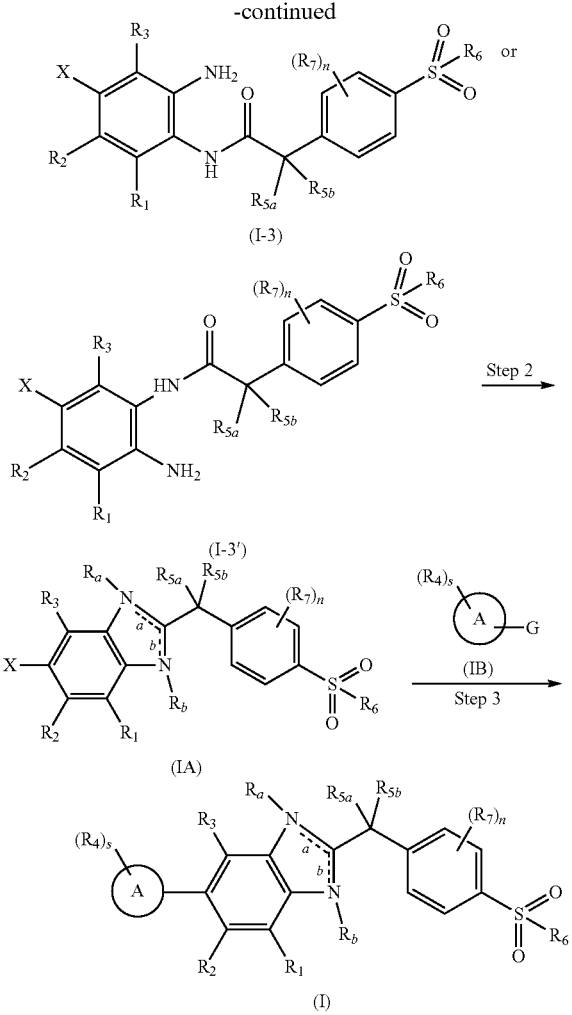

Step 1, the compound of the formula (I-1) is subjected to a condensation reaction with formula (I-2) under alkaline conditions to obtain a compound of the formula (I-3) or formula (I-3');

Step 2, the formula (I-3) or formula (I-3') is subjected to an intramolecular reaction in the presence of an acid to give a compound of the formula (IA);

Step 3, the compound of formula (IA) is subject to coupling reaction with formula (IB) under an alkaline condition in the presence of catalyst to give a formula (I);

wherein:

X is halogen, preferably bromine;

G is leaving group, preferably boronic acid or borate; more preferably

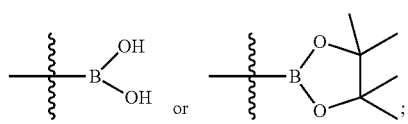

ring A, $\stackrel{a}{=\!=\!=}$, $\stackrel{b}{=\!=\!=}$, $R_a$, $R_b$, $R_1 \sim R_4$, $R_{5a}$, $R_{5b}$, $R_6$, $R_7$, n and s are as defined in formula (I).

Alkaline reagents include organic base and inorganic base, wherein said organic base includes, but is not limited to, triethylamine, N,N-disopropylethylamine, n-butyllithium, lithium diisopropylamide, potassium acetate, sodium tert-butoxide or potassium tert-butoxide, wherein said inorganic base includes, but is not limited to, sodium hydride, potassium phosphate, sodium carbonate, potassium carbonate or cesium carbonate.

Phosphine palladium-based catalysts include, but are not limited to, 2-(dicyclohexylphosphino)-2,4,6-triisopropylbiphenyl, (±)-2,2'-bis(diphenylphosphino)-1,1'-binaphthyl, tris(dibenzylideneacetone)dipalladium(0), palladium diacetate, [1,1'-bis(diphenylphosphino)ferrocene]dichloropalladium, triphenylphosphine and tetrakis(triphenylphosphine) palladium.

The above reactions are preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

A process for preparing a compound of formula (I) of the present invention, or a tautomer, mesomer, racemate, enantiomer, diastereomer, or mixtures thereof, or pharmaceutically acceptable salts thereof, comprising the following steps:

Scheme 2

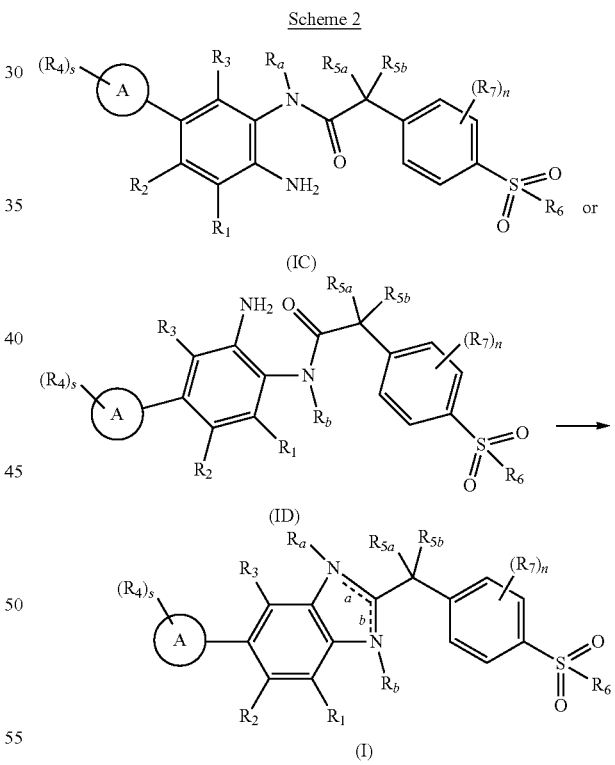

The formula (IC) or formula (ID) is subjected to an intramolecular reaction in the presence of an acid to give a compound of the formula (I);

wherein:

ring A, $\stackrel{a}{=\!=\!=}$, $\stackrel{b}{=\!=\!=}$, $R_a$, $R_b$, $R_1 \sim R_4$, $R_{5a}$, $R_{5b}$, $R_6$, $R_7$, n and s are as defined formula (I).

The reagents that provide an acidic condition include, but are not limited to, acetic acid, pyridine hydrobromide, trifluoroacetic acid, formic acid, hydrochloric acid, sulfuric acid and methanesulfonic acid, preferably pyridine hydrobromide or hydrochloric acid.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

A process for preparing a compound of formula (II) of the present invention, or a tautomer, mesomer, racemate, enantiomer, diastereomer, or mixtures thereof, or pharmaceutically acceptable salts thereof, comprising the following steps:

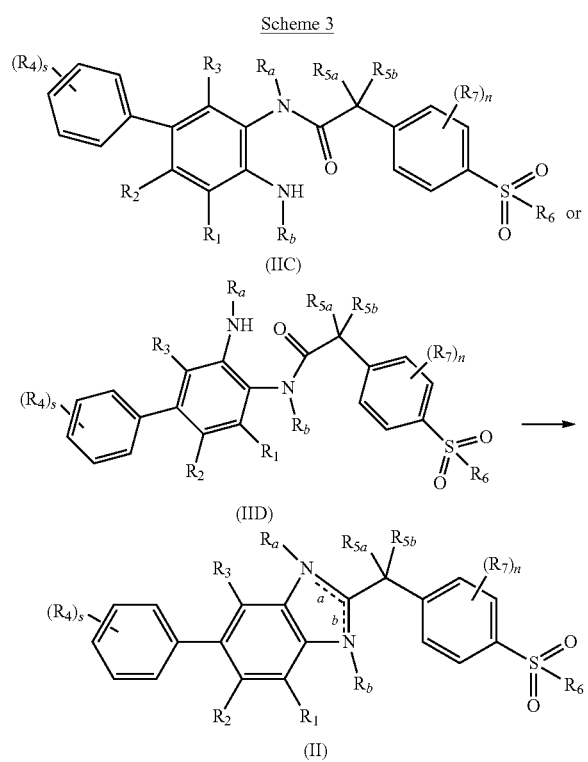

(II)

The formula (IIC) or formula (IID) is subjected to an intramolecular reaction in the presence of an acid to give a compound of the formula (II);
wherein:

$\underset{\text{-----}}{a}$, $\underset{\text{-----}}{b}$, $R_a$, $R_b$, $R_1 \sim R_4$, $R_{5a}$, $R_{5b}$, $R_6$, $R_7$, n and s are as defined in formula (II).

The reagents that provide an acidic condition include, but are not limited to, acetic acid, pyridine hydrobromide, trifluoroacetic acid, formic acid, hydrochloric acid, sulfuric acid and methanesulfonic acid, preferably pyridine hydrobromide or hydrochloric acid.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

A process for preparing a compound of formula (III) of the present invention, or a tautomer, mesomer, racemate, enantiomer, diastereomer, or mixtures thereof, or pharmaceutically acceptable salts thereof, comprising the following steps:

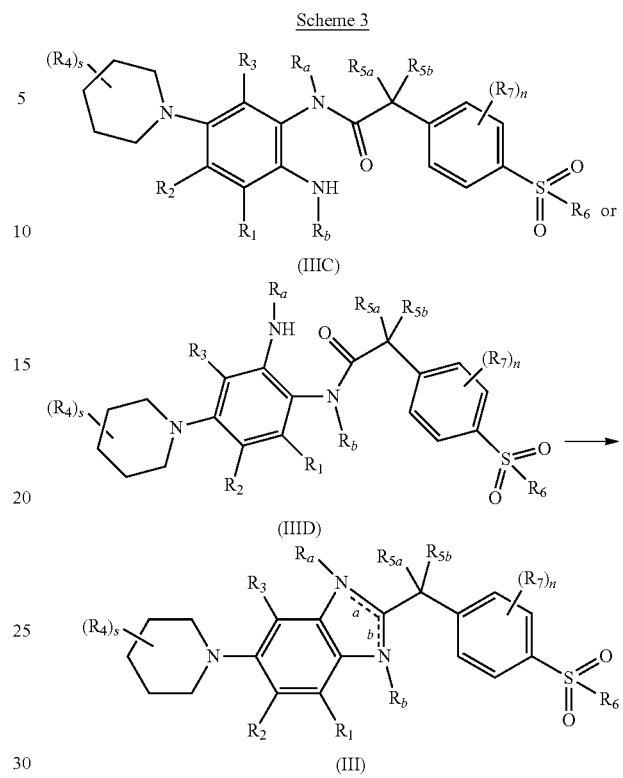

(III)

The formula (IIIC) or formula (IIID) is subjected to an intramolecular reaction in the presence of an acid to give a compound of the formula (III);
wherein:

$\underset{\text{-----}}{a}$, $\underset{\text{-----}}{b}$, $R_a$, $R_b$, $R_1 \sim R_4$, $R_{5a}$, $R_{5b}$, $R_6$, $R_7$, n and s are as defined formula (III).

The reagents that provide an acidic condition include, but are not limited to, acetic acid, pyridine hydrobromide, trifluoroacetic acid, formic acid, hydrochloric acid, sulfuric acid and methanesulfonic acid, preferably pyridine hydrobromide or hydrochloric acid.

The above reactions are preferably carried out in a solvent. The solvent used includes, but not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

The present invention will be further described with the following examples, but the examples should not be considered as limiting the scope of the invention.

EXAMPLES

The structures of the compounds were identified by nuclear magnetic resonance (NMR) and/or mass spectrometry (MS). NMR was determined by a Bruker AVANCE-400 or AVANCE III 500. The solvents are deuterated-dimethyl sulfoxide (DMSO-$d_6$), deuterated-chloroform (CDCl$_3$) and deuterated-methanol (CD$_3$OD) with tetramethylsilane (TMS) as an internal standard. NMR chemical shifts (δ) are given in $10^{-6}$ (ppm).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

Chiral high performance liquid chromatography (HPLC) was determined on LC-10A vp (Shimadzu) or SFC-analytical (Berger Instruments Inc.)

MS was determined by a SHIMADZU (ESI) liquid chromatography-mass spectrometer (manufacturer: Shimadzu, type: LC-20AD, LCMS-2020).

The known raw materials of the present invention were prepared by the conventional synthesis methods in the art, or purchased from Aldrich Chemical Company, Fisher Scientific or Combi-Blocks, etc.

Unless otherwise stated, the reactions were carried out under nitrogen atmosphere or argon atmosphere.

The term "nitrogen atmosphere" or "argon atmosphere" means that a reaction flask was equipped with a 1 L nitrogen or argon balloon.

The term "hydrogen atmosphere" means that a reaction flask was equipped with a 1 L hydrogen balloon.

Unless otherwise stated, the reaction temperature in the reactions refers to room temperature, and the range of the temperature was 20° C. to 30° C.

The reaction process was monitored by thin layer chromatography (TLC), and the developing solvent system includes: A: dichloromethane and methanol, B: hexane and ethyl acetate. The ratio of the volume of the solvent was adjusted according to the polarity of the compounds. The elution system for purification of the compounds by column chromatography, thin layer chromatography and Combi-Flash flash rapid preparation instrument includes: A: dichloromethane and methanol, B: hexane and ethyl acetate. The ratio of the volume of the solvent was adjusted according to the polarity of the compounds, and sometimes a small amount of basic reagent such as ammonia or acidic reagent such as acetic acid was added.

Final compounds were purified by Shimadzu (LC-20AD, SPD20A) Prepative HPLC (Phenomenex Gemini-NX 5 uM C18 21.2×100 mm column) with an elution system: C: 0.075% TFA in water and 0.075% TFA in MeOH or D: 0.075% TFA in water and 0.075% TFA in $CH_3CN$.

The following abbreviations are used:

TEA is triethylamine,

DIPEA is N,N-diisopropylethylamine,

EDCI is N-(3-Dimethylaminopropyl)-N'-ethylcarbodiimide hydrochloride,

HOBt is 1-Hydroxybenzotriazole hydrate,

DCM is dichloromathene,

HBTU is O-(Benzotriazol-1-yl)-N,N,N',N'-tetramethyluronium hexafluorophosphate,

DMF is N,N-dimethylformamide,

NMR is proton nuclear magnetic resonance, and

MS is mass spectroscopy with (+) referring to the positive mode which generally gives a M+1 (or M+H) absorption where M=the molecular mass.

Prep HPLC is Prepative High performance liquid chromatography.

Example 1

Preparation of 4,6-dichloro-2-(4-(ethylsulfonyl)benzyl)-5-phenyl-1H-benzo[d]imidazole

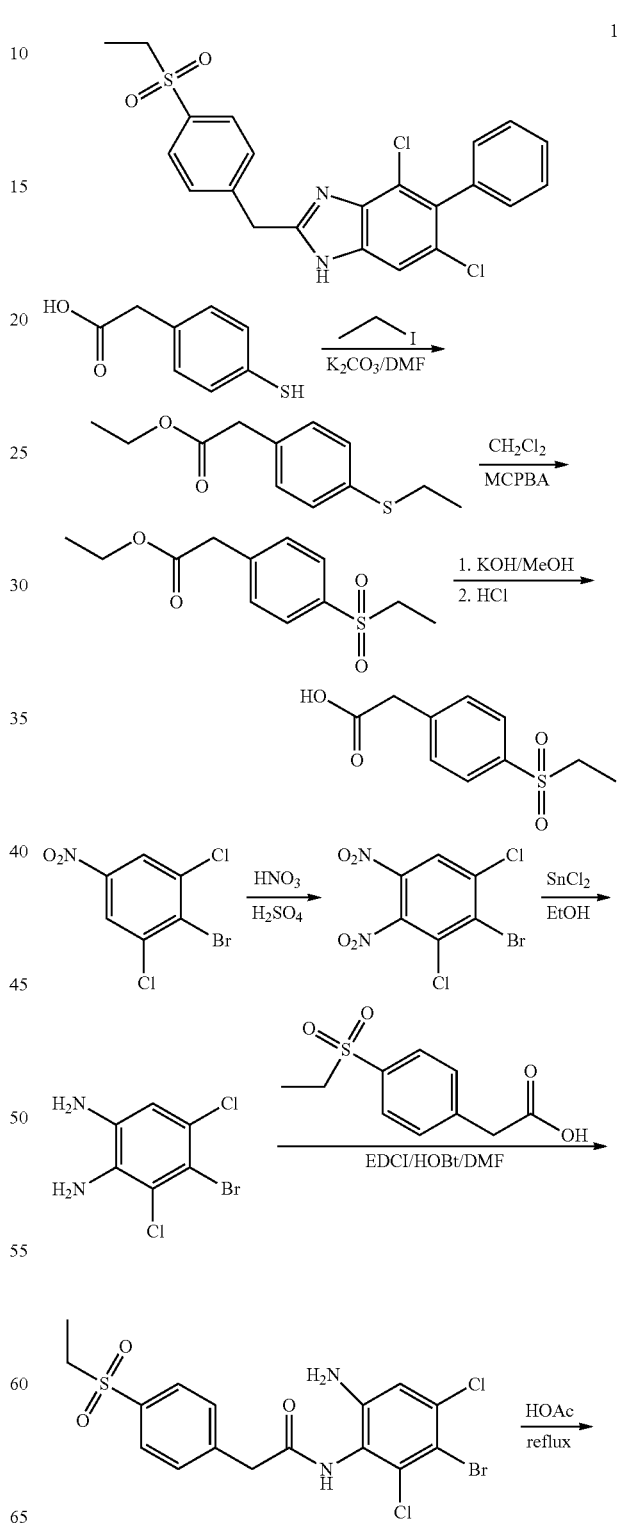

-continued

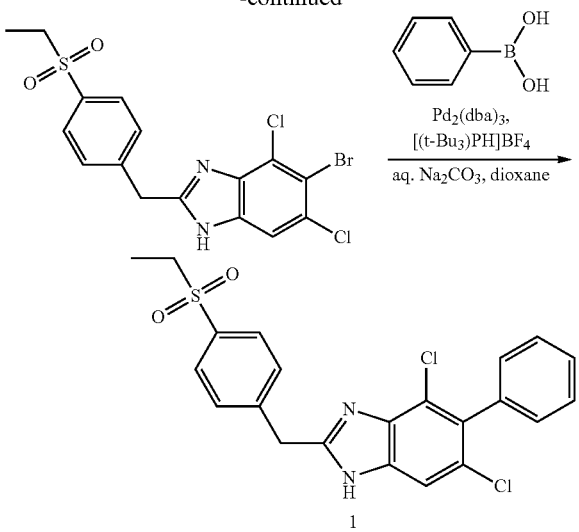

Step 1. Preparation of ethyl 2-(4-(ethylthio)phenyl)acetate

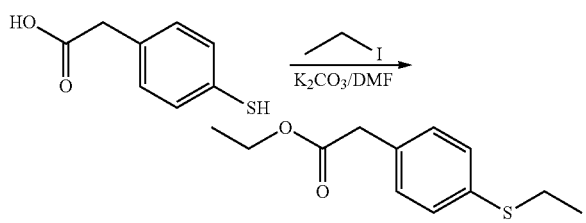

To a solution of 2-(4-mercaptophenyl) acetic acid (3.4 g, 0.02 mol) in N,N-dimethylformamide (DMF) (20 ml) was added $K_2CO_3$ (11 g, 0.04 mol) and iodoethane (6.4 g, 0.06 mol). The reaction mixture was stirred at RT. After 2.5 hours, the starting material was totally consumed. The reaction mixture was partitioned between ethyl acetate (30 ml) and water (30 ml). The organic phase was washed with water (30 ml) and brine (20 ml), dried over sodium sulphate, filtered, and concentrated to give the desired product ethyl [4-(ethylthio)phenyl]acetate (3.6 g, 80%) as a pale yellow solid, MS (+) ES: 225 $(M+H)^+$.

Step 2. Preparation of ethyl 2-(4-(ethylsulfonyl)phenyl)acetate

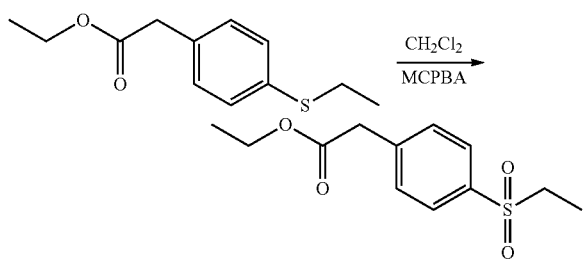

To a 250 ml round bottom flask, were added ethyl 2-(4-(ethylthio)phenyl)acetate (5.5 g, 0.0245 mol) and dichloromethane (82.5 ml). The reaction mixture was cooled to 0° C. To the same flask, m-chloroperbenzoic acid (12.6 g, 0.073 mol) was added at 0° C. The reaction mixture was stirred at room temperature for 12 h. The resulting suspension was filtered through a pad of celite. The filtrate was washed with water. The organic layer was separated, washed with saturated sodium bicarbonate solution followed by brine and dried over anhydrous sodium sulfate. The solvent was evaporated under reduced pressure to get the crude product. The crude product was purified by flash column chromatography with hexane/ethyl acetate to get the title compound as an oil that was solidified upon standing (4.7 g, 75%), MS (+) ES: 257 $(M+H)^+$.

Step 3. Preparation of 2-(4-(ethylsulfonyl)phenyl)acetic acid

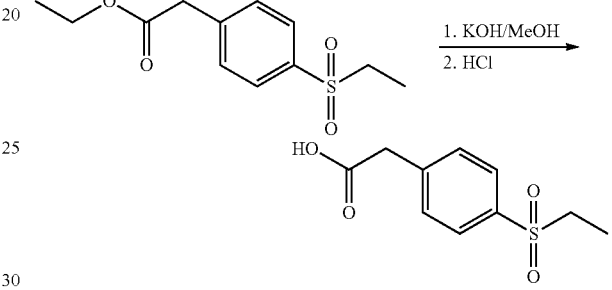

To a 50 mL round bottom flask, were added ethyl 2-(4-(ethylsulfonyl)phenyl)acetate (2.56 g, 0.01 mol) and ethanol (18 ml). To the same flask, a solution of sodium hydroxide in water (1.42 g, 0.0355 mol in 18 ml of water) was added. The reaction mixture was stirred at room temperature for 12 h. The volatiles were evaporated under reduced pressure. The residue was acidified with 1N HCl to pH 5.0 and extracted with ethyl acetate (15 ml×3). The organic layer was separated and combined, washed with brine and dried over sodium sulfate. The solvent was evaporated under reduced pressure to get the title compound as a colorless oil that was solidified upon standing (2.0 g, 85%), MS (+) ES: 229 $(M+H)^+$.

Step 4. Preparation of 2-bromo-1,3-dichloro-4,5-dinitrobenzene

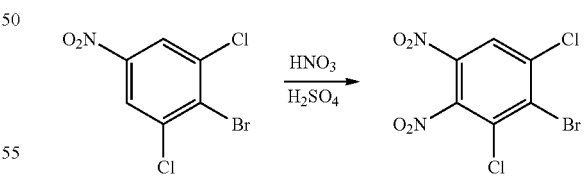

2-bromo-1,3-dichloro-5-nitrobenzene (2.7 g, 0.01 mol) was carefully added into a pre-prepared solution of fuming nitric acid (10 ml) and concentrated sulfuric acid (10 ml) with stirring. After the addition, the mixture was heated to 50° C. in a water bath for two hours until the completion of the reaction (LCMS monitor). The mixture was then cooled and poured onto ice. The yellow precipitate was collected by filtration and washed thoroughly with water and dried to afford the product as a yellow solid (3 g, 95%), MS (+) ES: 314 $(M+H)^+$.

Step 5. Preparation of 4-bromo-3,5-dichlorobenzene-1,2-diamine

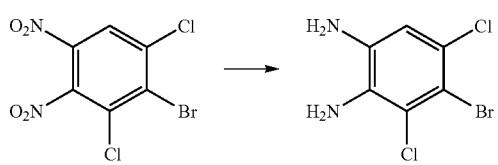 [SMILES: O=[N+]([O-])c1cc(Cl)c(Br)c(Cl)c1[N+](=O)[O-] ; Nc1cc(Cl)c(Br)c(Cl)c1N]

To a stirred mixture of AcOH (50 ml) and EtOH (100 ml) was suspended 2-bromo-1,3-dichloro-4,5-dinitrobenzene (3.1 g, 0.01 mol) and iron powder (4.4 g, 0.08 mol). The reaction mixture was heated slowly to a gentle reflux and allowed to stir for 1 hour. The reaction mixture then was cooled to room temperature, diethyl ether (50 ml) and water (50 ml) were added. The solution was carefully neutralized by the addition of solid sodium carbonate. The organic phase was separated and the water phase was extracted with ethyl acetate (20 ml). The organic phases were combined and washed with saturated $NaHCO_3$ (2×30 ml), $H_2O$ (2×30 ml) and brine (1×30 ml), then dried over $MgSO_4$, filtered and concentrated to dryness under vacuum to yield the title compound as a off-white solid (2.0 g, 78%), MS (+) ES: 255 $(M+H)^+$.

Step 6. Preparation of N-(6-amino-3-bromo-2,4-dichlorophenyl)-2-(4-(ethylsulfonyl)phenyl)acetamide

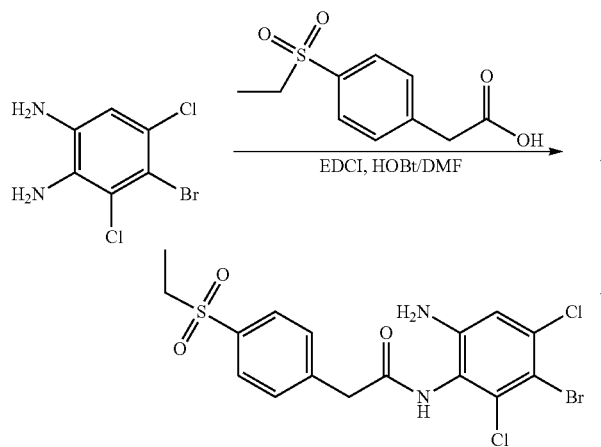

1-Ethyl-(3-(3-dimethylamino)propyl)-carbodiimide hydrochloride (2.0 g, 0.01 mol) and benzotriazol-1-ol (1.35 g, 0.01 mol) were added into a cooled solution (ice water bath) of 4-bromo-3,5-dichlorobenzene-1,2-diamine (2.55 g, 0.01 mol) and 2-(4-(ethylsulfonyl)phenyl)acetic acid (step 3, 2.28 g, 0.01 mol) in DMF (10 ml), portionwise, over 30 min. After the addition was completed, the mixture was stirred for 60 min and was allowed to warm-up to room temp, stirred overnight. The mixture was partitioned between water (50 ml) and ethyl acetate (50 ml). The organic phase was separated and dried over $MgSO_4$, filtered. The solvent was evaporated under reduced pressure to leave a off-white solid which was purified by flash chromatography with hexane/ethyl acetate to afford the product as a off-white solid (3.5 g, 75%), MS (+) ES: 466 $(M+H)^+$.

Step 7. Preparation of 5-bromo-4,6-dichloro-2-(4-(ethylsulfonyl)benzyl)-1H-benzo[d]imidazole

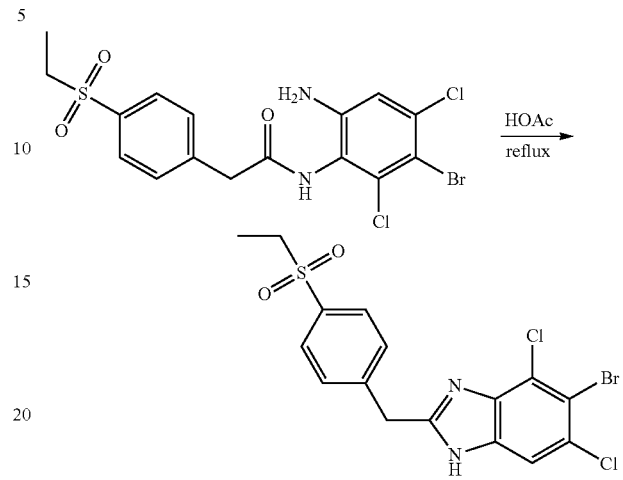

N-(6-amino-3-bromo-2,4-dichlorophenyl)-2-(4-(ethylsulfonyl)phenyl)acetamide (step 6) (3.5 g, 0.0075 mol) was mixed with acetic acid (25 ml) and the mixture was heated to 100° C. for 4 hours, cooled. The solvent was evaporated under reduce pressure and the residue was dissolved in dichloromethane and washed with saturated sodium bicarbonate, dried over $MgSO_4$. This product was purified by flash chromatography with hexane/ethyl acetate to afford the product as a white solid (2.7 g, 80%), MS (+) ES: 448 $(M+H)^+$.

Step 8. Preparation of 4,6-dichloro-2-(4-(ethylsulfonyl)benzyl)-5-phenyl-1H-benzo[d]imidazole

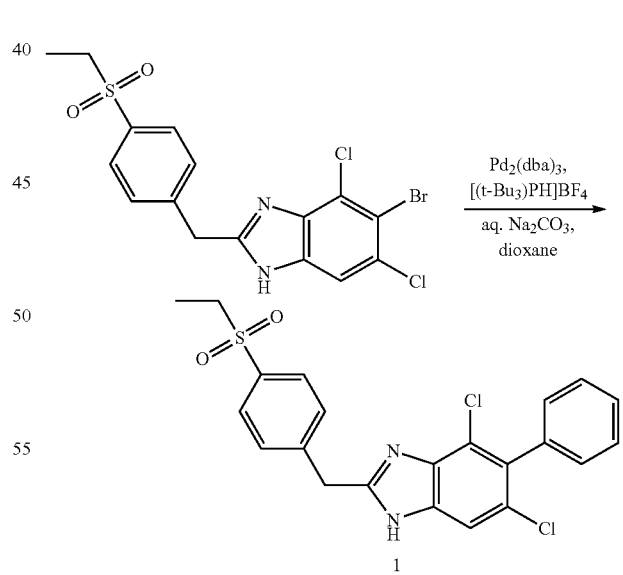

A mixture of 5-bromo-4,6-dichloro-2-(4-(ethylsulfonyl)benzyl)-1H-benzo[d]imidazole (step 7) (448 mg, 1 mmol), phenylboronic acid (363 mg, 3 mmol), tris-(dibenzylideneacetone)dipalladium(0) (60 mg), tri(tert-butyl)phosphonium tetrafluoroboronate (60 mg) and sodium carbonate (2M solution) in 1,4-dioxane (3 ml) was degassed, sealed and heated to 100° C. under Microwave irradiation for 1 h. The volatile solvents were removed under reduced pressure. The residue was directly loaded onto a ISCO solid cartridge and flashed with hexane/ethyl acetate to afford a white solid product 320 mg (72% yield), MS (+) ES: 445 (M+H)$^+$.

Example 2

Preparation of (4,6-dichloro-5-phenyl-1H-benzo[d]imidazol-2-yl)(4-(ethylsulfonyl)phenyl)methanol

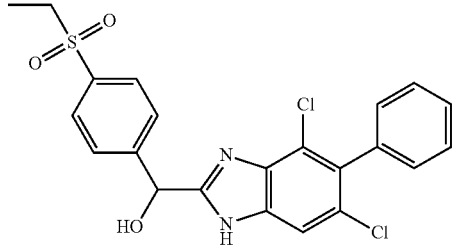

Step 1. Preparation of (4,6-dichloro-5-phenyl-1H-benzo[d]imidazol-2-yl)(4-(ethylsulfonyl)phenyl)methanone

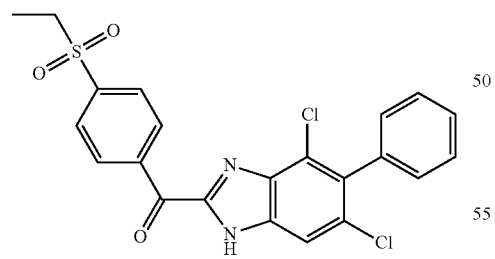

4,6-dichloro-2-(4-(ethylsulfonyl)benzyl)-5-phenyl-1H-benzo[d]imidazole (example 1) (4.5 mg, 0.01 mmol) was dissolved in 1,4-dioxane (0.5 ml), MnO$_2$ (5 mg, 0.058 mmol) was added at room temp. The mixture was stirred and heated to 60° C. for 60 min until the completion (LCMS monitor). After cooling, the solid was filtered off and the product was purified by flash chromatography with hexane/ethyl acetate to afford a white solid (4 mg. 87%), MS (+) ES: 459 (M+H)$^+$.

Step 2. Preparation of (4,6-dichloro-5-phenyl-1H-benzo[d]imidazol-2-yl)(4-(ethylsulfonyl)phenyl)methanol

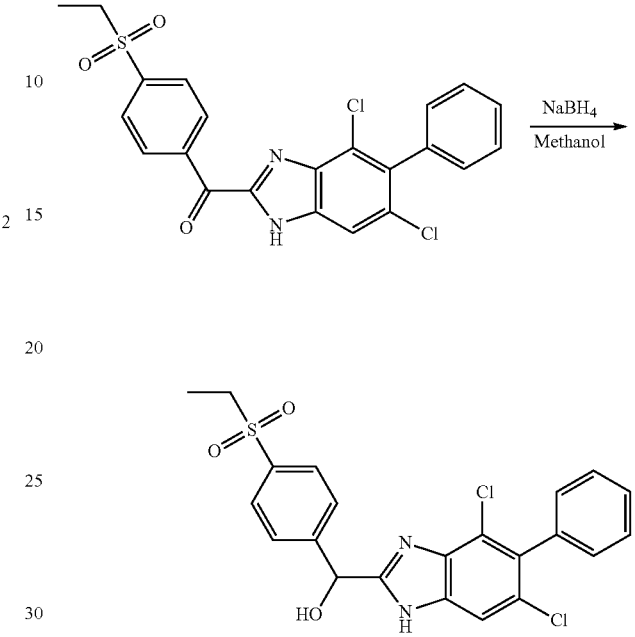

(4,6-dichloro-5-phenyl-1H-benzo[d]imidazol-2-yl)(4-(ethylsulfonyl)phenyl)methanone (example 3, step 1) (4 mg, 0.0087 mmol) was dissolved in methanol (0.5 ml), sodium borohydride (1.6 mg, 0.044 mmol) was added and the mixture was stirred for 30 min until completion. The product was purified by Prep HPLC with elution system C to afford a white solid (3.3 mg, 82%), MS (+) ES: 461 (M+H)$^+$.

Example 3

Preparation of 4,6-dichloro-2-(4-(ethylsulfonyl)benzyl)-5-(2-(trifluoromethyl)phenyl)-1H-benzo[d]imidazole

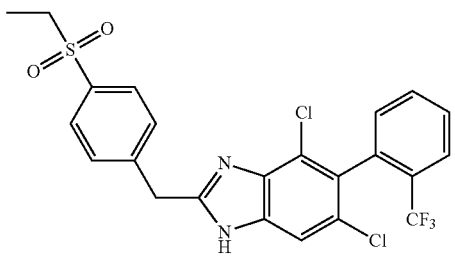

In accordance with the synthetic route of example 1, the starting material, phenylboronic acid in step 8 was replaced with 2-trifluoromethylphenylboronic acid, accordingly, the title compound was obtain as a white solid, MS (+) ES: 513 (M+H)$^+$.

Example 4

Preparation of 2-(4,6-dichloro-5-(2-(trifluoromethoxy)phenyl)-1H-benzo[d]imidazol-2-yl)-2-(4-(ethylsulfonyl)phenyl)ethanol

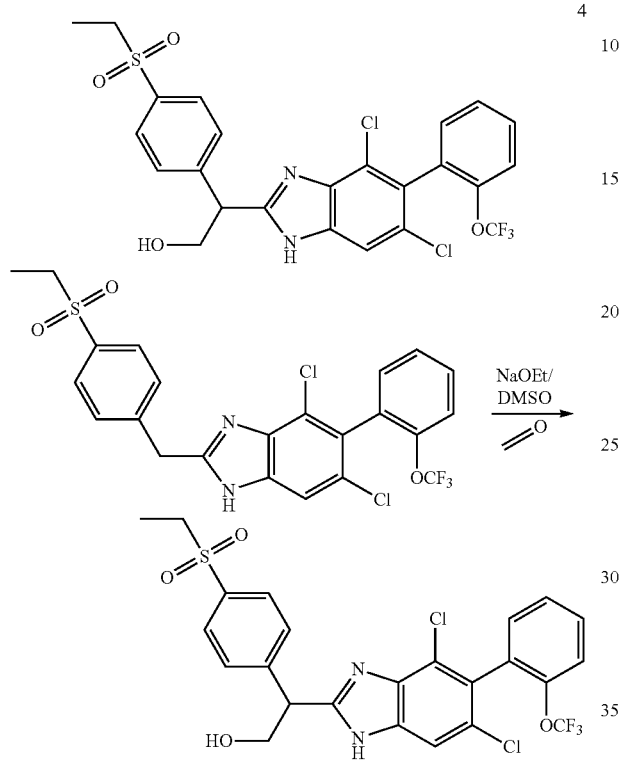

4,6-dichloro-2-(4-(ethylsulfonyl)benzyl)-5-(2-(trifluoromethoxy)phenyl)-1H-benzo[d]imidazole (5.3 mg, 0.01 mmol) was dissolved in 0.1 ml anhydrous DMSO, paraformylaldehyde (0.6 mg, 0.02 mmol) wan added with stirring, followed by the addition of powder sodium ethoxide (1.2 mg, 0.02 mmol). The mixture was stirred at room temp for 60 min. The mixture was treated with small amount of diluted HCl and directly purified by Prep HPLC with elution system C to afford the product as a white solid (3.8 mg, 70% yield), MS (+) ES: 559 (M+H)+.

Example 5

Preparation of (4,6-dichloro-5-(2-(trifluoromethoxy)phenyl)-1H-benzo[d]imidazol-2-yl)(4-(ethylsulfonyl)phenyl)methanol

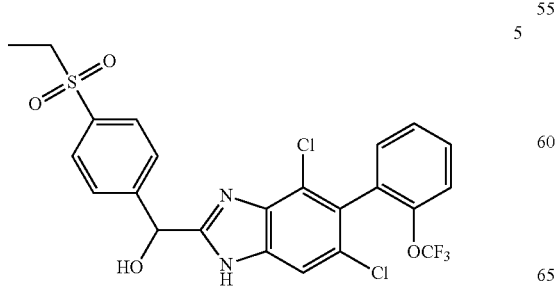

This product was prepared by essentially the same method as of example 2 to afford the product as a white solid, MS (+) ES: 545 (M+H)+.

Example 6

Preparation of 2-(4,6-dichloro-5-(2-methoxyphenyl)-1H-benzo[d]imidazol-2-yl)-2-(4-(ethylsulfonyl)phenyl)ethanol

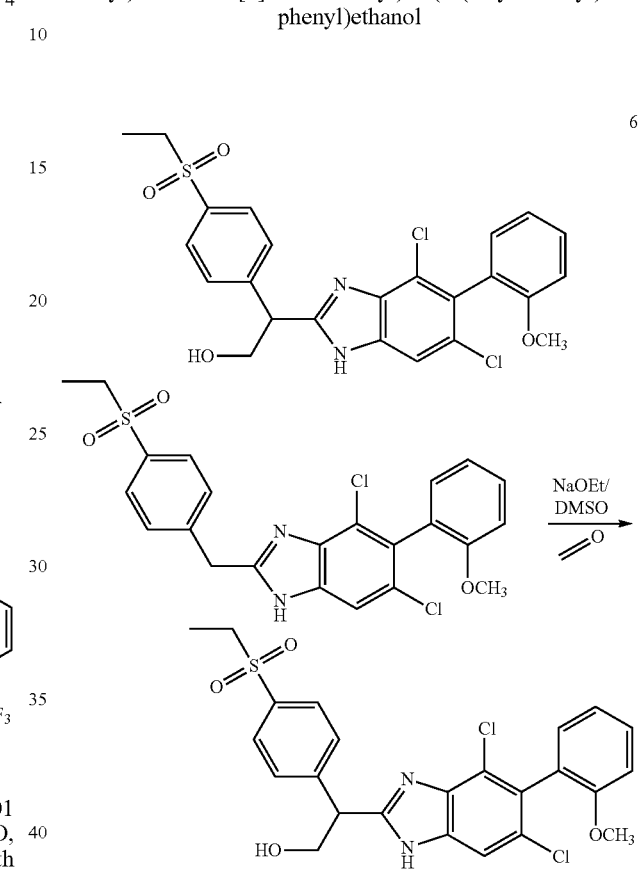

This compound was prepared by essential the same method as of example 4 to afford the product as a white solid, MS (+) ES: 505 (M+H)+.

Example 7

Preparation of (4,6-dichloro-5-(2-methoxyphenyl)-1H-benzo[d]imidazol-2-yl)(4-(ethylsulfonyl)phenyl)methanol

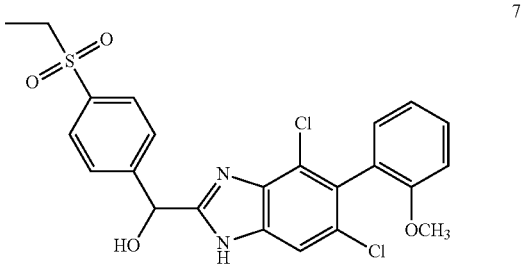 [SMILES: CCS(=O)(=O)c1ccc(C(O)c2nc3c(Cl)c(-c4ccccc4OC)c(Cl)cc3[nH]2)cc1]

This product was prepared by essentially the same method as of example 2 to afford the product as a white solid, MS (+) ES: 491 (M+H)⁺.

Example 8

Preparation of 4,6-dichloro-2-(4-(ethylsulfonyl)benzyl)-5-(2-isopropoxyphenyl)-1H-benzo[d]imidazole

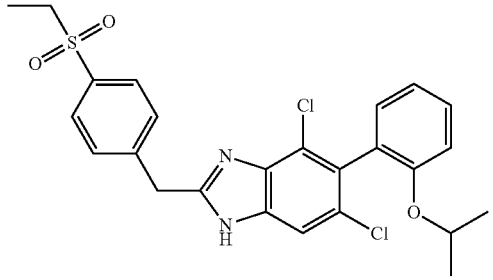

This compound was prepared by using essentially the same scope of example 1 except by using 2-isopropyloxyphenylboronic acid instead of phenylboronic acid in step 8 to afford the product as a white solid, MS (+) ES: 503 (M+H)⁺.

Example 9

Preparation of 2-(4,6-dichloro-5-(2-isopropoxyphenyl)-1H-benzo[d]imidazol-2-yl)-2-(4-(ethylsulfonyl)phenyl)ethanol

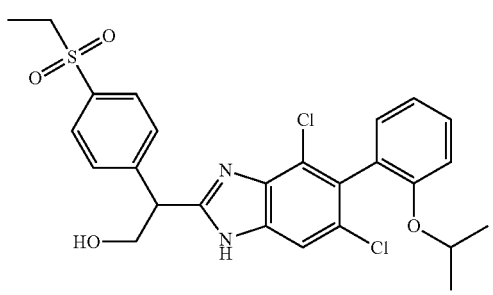

This compound was prepared by essential the same method as of example 4 to afford the product as a white solid, MS (+) ES: 533 (M+H)⁺.

Example 10

Preparation of (4,6-dichloro-5-(2-isopropoxyphenyl)-1H-benzo[d]imidazol-2-yl)(4-(ethylsulfonyl)phenyl)methanol

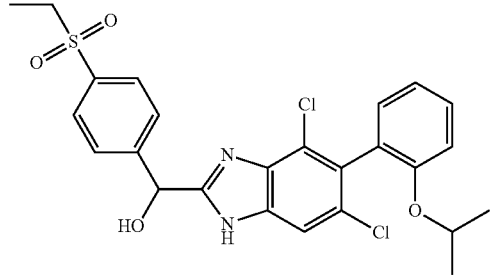

This product was prepared by essentially the same method as of example 2 to afford the product as a white solid, MS (+) ES: 519 (M+H)⁺.

Example 11

Preparation of 2-(4,6-dichloro-5-(2-fluorophenyl)-1H-benzo[d]imidazol-2-yl)-2-(4-(ethylsulfonyl)phenyl)ethanol

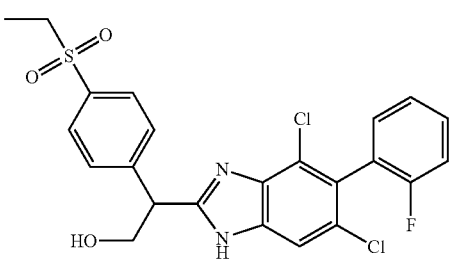

This compound was prepared by essential the same method as of example 4 to afford the product as a white solid, MS (+) ES: 493 (M+H)⁺.

Example 12

Preparation of (4,6-dichloro-5-(2-fluorophenyl)-1H-benzo[d]imidazol-2-yl)(4-(ethylsulfonyl)phenyl)methanol

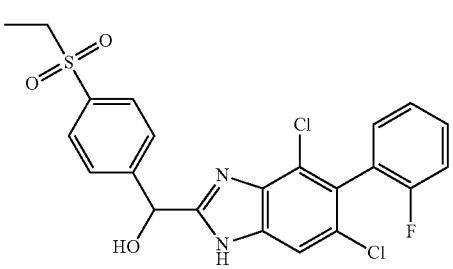

This product was prepared by essentially the same method as of example 2 to afford the product as a white solid, MS (+) ES: 479 (M+H)+.

Example 13

Preparation of 4,6-dichloro-2-(4-(ethylsulfonyl)benzyl)-5-(2-(methoxymethoxy)phenyl)-1H-benzo[d]imidazole

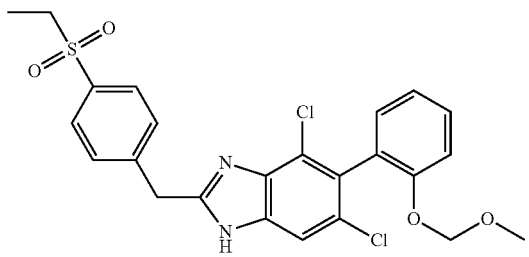

13

This compound was prepared by using essentially the same scope of example 1 except by using 2-methoxymethoxyphenylboronic acid instead of phenylboronic acid in step 8 to afford the product as a white solid, MS (+) ES: 505 (M+H)+.

Example 14

Preparation of 2-(4,6-dichloro-5-(2-methoxymethoxyphenyl)-1H-benzo[d]imidazol-2-yl)-2-(4-(ethylsulfonyl)phenyl)ethanol

14

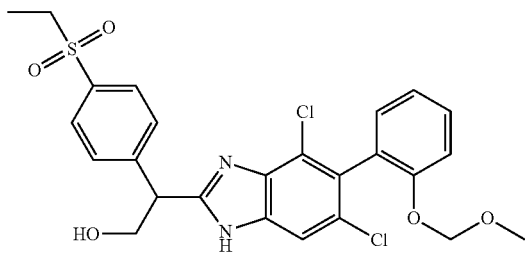

This compound was prepared by essential the same method as of example 4 to afford the product as a white solid, MS (+) ES: 535 (M+H)+.

Example 15

Preparation of (4,6-dichloro-5-(2,5-dichlorophenyl)-1H-benzo[d]imidazol-2-yl)(4-(ethylsulfonyl)phenyl)methanol

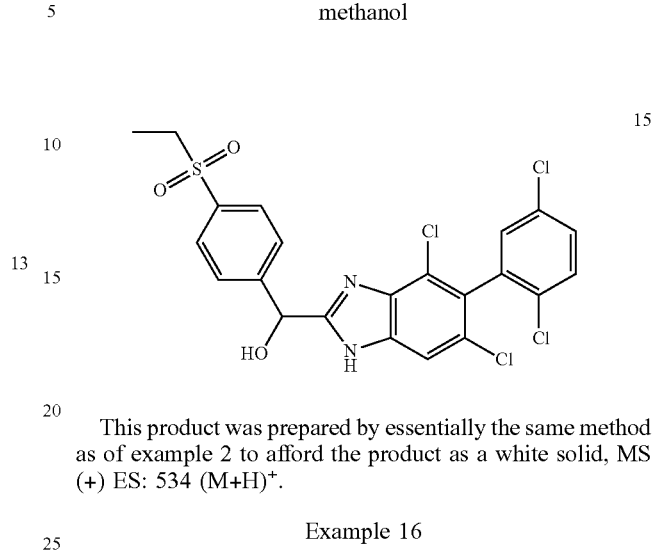

15

This product was prepared by essentially the same method as of example 2 to afford the product as a white solid, MS (+) ES: 534 (M+H)+.

Example 16

Preparation of 4,6-dichloro-5-(2-ethoxyphenyl)-2-(4-(ethylsulfonyl)benzyl)-1H-benzo[d]imidazole

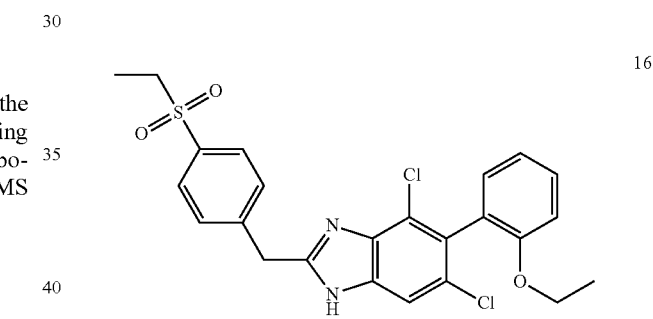

16

This compound was prepared by using essentially the same scope of example 1 except by using 2-ethoxyphenylboronic acid instead of phenylboronic acid in step 8 to afford the product as a white solid, MS (+) ES: 489 (M+H)+.

Example 17

Preparation of 2-(4,6-dichloro-5-(2-ethoxyphenyl)-1H-benzo[d]imidazol-2-yl)-2-(4-(ethylsulfonyl)phenyl)ethanol

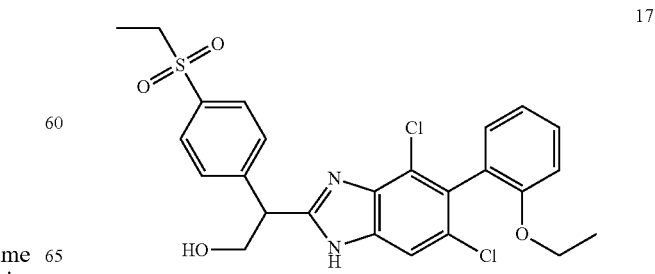

17

This compound was prepared by essential the same method as of example 4 to afford the product as a white solid, MS (+) ES: 519 (M+H)⁺.

Example 18

Preparation of (4,6-dichloro-5-(2-ethoxyphenyl)-1H-benzo[d]imidazol-2-yl)(4-(ethylsulfonyl)phenyl)methanol

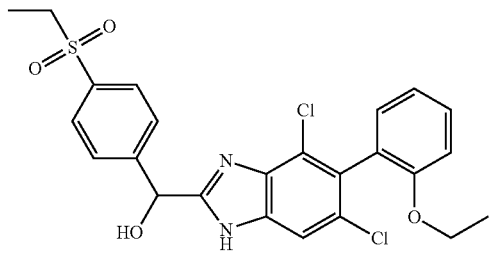

18

This product was prepared by essentially the same method as of example 2 to afford the product as a white solid, MS (+) ES: 505 (M+H)⁺.

Example 19

Preparation of 4,6-dichloro-2-(4-(ethylsulfonyl)benzyl)-5-(2-(2-methoxyethoxy)phenyl)-1H-benzo[d]imidazole

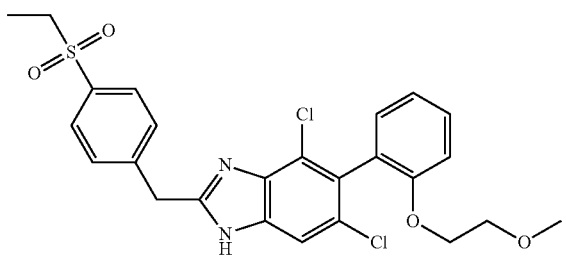

19

This compound was prepared by using essentially the same scope of example 1 except by using (2-(2-methoxyethoxy)phenyl)boronic acid instead of phenylboronic acid in step 8 to afford the product as a white solid, MS (+) ES: 519 (M+H)⁺.

Example 20

Preparation of 2-(4,6-dichloro-5-(2-(2-methoxyethoxy)phenyl)-1H-benzo[d]imidazol-2-yl)-2-(4-(ethylsulfonyl)phenyl)ethanol

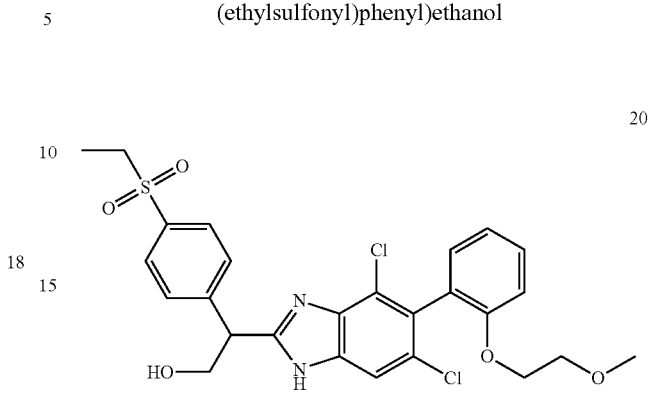

20

This compound was prepared by essential the same method as of example 4 to afford the product as a white solid, MS (+) ES: 549 (M+H)⁺.

Example 21

Preparation of (4,6-dichloro-5-(2-(2-methoxyethoxy)phenyl)-1H-benzo[d]imidazol-2-yl)(4-(ethylsulfonyl)phenyl)methanol

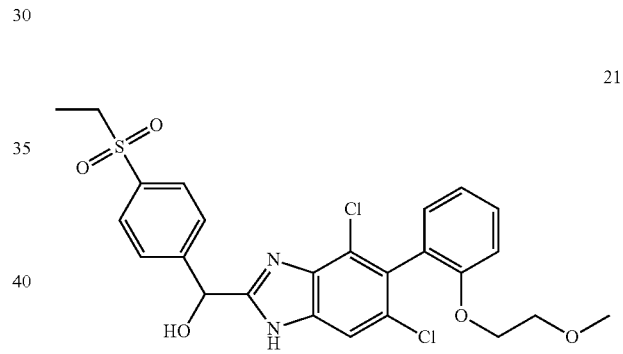

21

This product was prepared by essentially the same method as of example 2 to afford the product as a white solid, MS (+) ES: 535 (M+H)⁺.

Example 22

Preparation of 2-(4,6-dichloro-2-(1-(4-(ethylsulfonyl)phenyl)-2-hydroxyethyl)-1H-benzo[d]imidazol-5-yl)benzonitrile

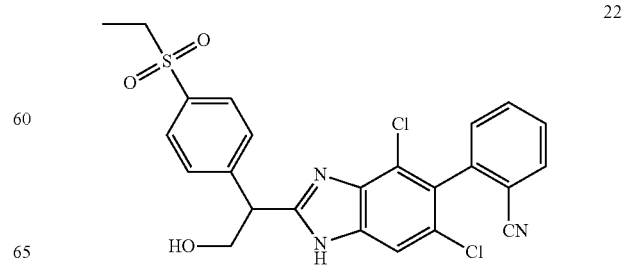

22

This compound was prepared by essential the same method as of example 4 to afford the product as a white solid, MS (+) ES: 500 (M+H)+.

Example 23

Preparation of 2-(4,6-dichloro-2-((4-(ethylsulfonyl)phenyl)(hydroxy)methyl)-1H-benzo[d]imidazol-5-yl)benzonitrile

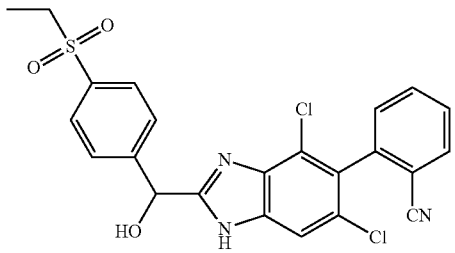

23

This product was prepared by essentially the same method as of example 2 to afford the product as a white solid, MS (+) ES: 486 (M+H)+.

Example 24

Preparation of 4,6-dichloro-2-(4-(ethylsulfonyl)benzyl)-5-(thiophen-3-yl)-1H-benzo[d]imidazole

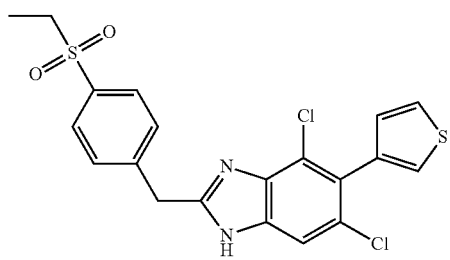

24

This compound was prepared by using essentially the same scope of example 1 except by using 3-thiophenylboronic acid instead of phenylboronic acid in step 8 to afford the product as a white solid, MS (+) ES: 451 (M+H)+.

Example 25

Preparation of 2-(4,6-dichloro-5-(thiophen-3-yl)-1H-benzo[d]imidazol-2-yl)-2-(4-(ethylsulfonyl)phenyl)ethanol

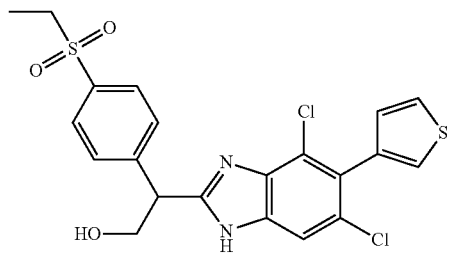

25

This compound was prepared by essential the same method as of example 4 to afford the product as a white solid, MS (+) ES: 481 (M+H)+.

Example 26

Preparation of (4,6-dichloro-5-(thiophen-3-yl)-1H-benzo[d]imidazol-2-yl)(4-(ethylsulfonyl)phenyl)methanol

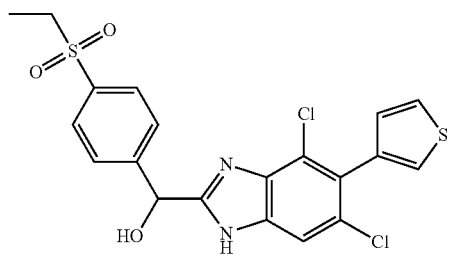

26

This product was prepared by essentially the same method as of example 2 to afford the product as a white solid, MS (+) ES: 467 (M+H)+.

Example 27

Preparation of 2-(4,6-dichloro-2-(4-(ethylsulfonyl)benzyl)-1H-benzo[d]imidazol-5-yl)-N,N-dimethylaniline

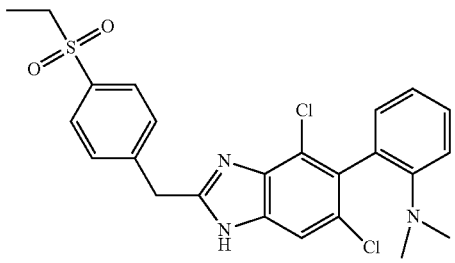

27

This compound was prepared by using essentially the same scope of example 1 except by using (2-(dimethylamino)phenyl)boronic acid instead of phenylboronic acid in step 8 to afford the product as a white solid, MS (+) ES: 488 (M+H)⁺.

Example 28

Preparation of 4,6-dichloro-5-(2-(difluoromethoxy)phenyl)-2-(4-(ethylsulfonyl)benzyl)-1H-benzo[d]imidazole

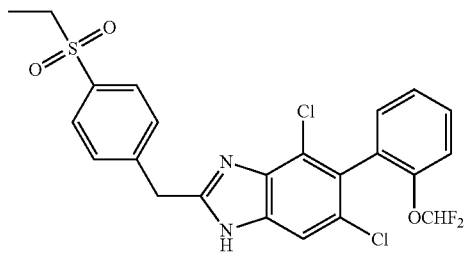

28

This compound was prepared by using essentially the same scope of example 1 except by using 2-difluoromethoxyphenylboronic acid pinacol ester instead of phenylboronic acid in step 8 to afford the product as a white solid, MS (+) ES: 511 (M+H)⁺.

Example 29

Preparation of 2-(4,6-dichloro-5-(2-(difluoromethoxy)phenyl)-1H-benzo[d]imidazol-2-yl)-2-(4-(ethylsulfonyl)phenyl)ethanol

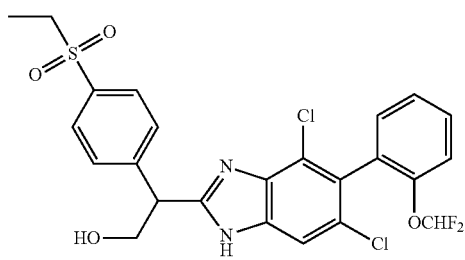

29

This compound was prepared by essential the same method as of example 4 to afford the product as a white solid, MS (+) ES: 541 (M+H)⁺.

Example 30

Preparation of (4,6-dichloro-5-(2-(difluoromethoxy)phenyl)-1H-benzo[d]imidazol-2-yl)(4-(ethylsulfonyl)phenyl)methanol

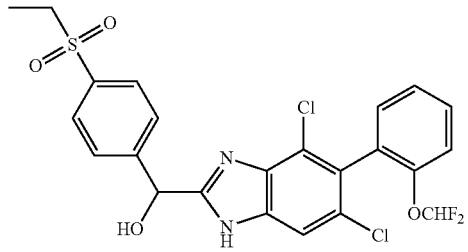

30

This product was prepared by essentially the same method as of example 2 to afford the product as a white solid, MS (+) ES: 527 (M+H)⁺.

Example 31

Preparation of 4,6-dichloro-2-(4-(ethylsulfonyl)benzyl)-5-(2-(2,2,2-trifluoroethoxy)phenyl)-1H-benzo[d]imidazole

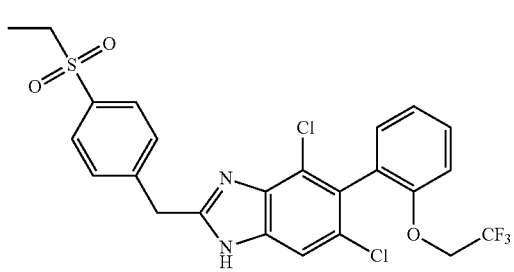

31

This compound was prepared by using essentially the same scope of example 1 except by using 4,4,5,5-tetramethyl-2-(2-(2,2,2-trifluoroethoxy)phenyl)-1,3,2-dioxaborolane instead of phenylboronic acid in step 8 to afford the product as a white solid, MS (+) ES: 543 (M+H)⁺.

Example 32

Preparation of 2-(4,6-dichloro-5-(2-(2,2,2-trifluoroethoxy)phenyl)-1H-benzo[d]imidazol-2-yl)-2-(4-(ethylsulfonyl)phenyl)ethanol

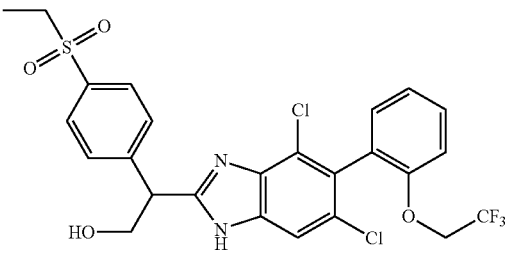

32

This compound was prepared by essential the same method as of example 4 to afford the product as a white solid, MS (+) ES: 573 (M+H)+.

Example 33

Preparation of (4,6-dichloro-5-(2-(2,2,2-trifluoroethoxy)phenyl)-1H-benzo[d]imidazol-2-yl)(4-(ethylsulfonyl)phenyl)methanol

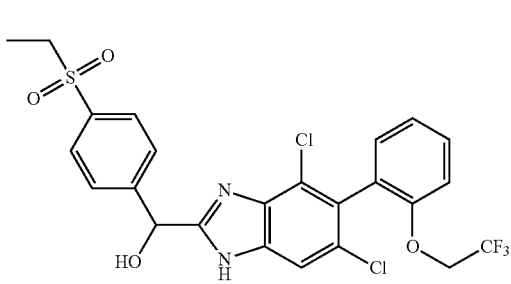

This product was prepared by essentially the same method as of example 2 to afford the product as a white solid, MS (+) ES: 559 (M+H)+.

Example 34

Preparation of 4,6-dichloro-2-(4-(ethylsulfonyl)benzyl)-5-(2-(3,3,3-trifluoropropyl)phenyl)-1H-benzo[d]imidazole

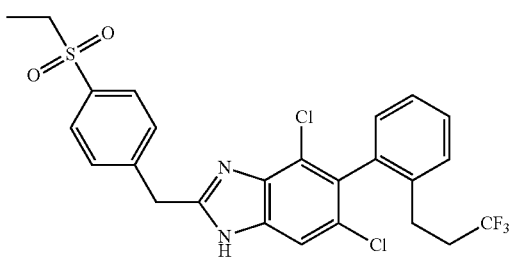

This compound was prepared by using essentially the same scope of example 1 except by using 4,4,5,5-tetramethyl-2-(2-(3,3,3-trifluoropropyl)phenyl)-1,3,2-dioxaborolane instead of phenylboronic acid in step 8 to afford the product as a white solid, MS (+) ES: 541 (M+H)+.

Example 35

Preparation of (4,6-dichloro-5-(2-(3,3,3-trifluoropropyl)phenyl)-1H-benzo[d]imidazol-2-yl)(4-(ethylsulfonyl)phenyl)methanol

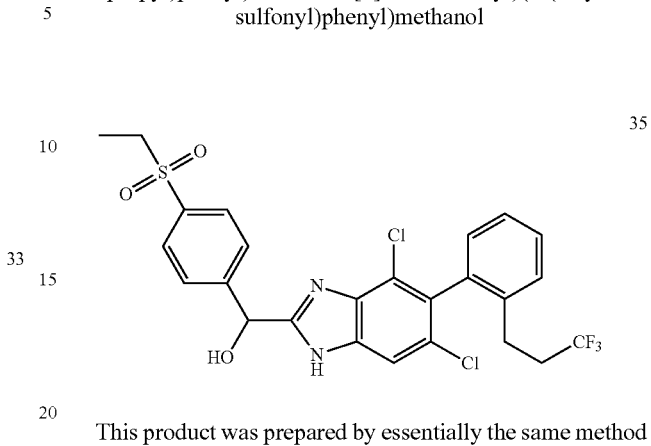

This product was prepared by essentially the same method as of example 2 to afford the product as a white solid, MS (+) ES: 557 (M+H)+.

Example 36

Preparation of 4,6-dichloro-2-(4-(ethylsulfonyl)benzyl)-5-(2-isopropylphenyl)-1H-benzol[d]imidazole

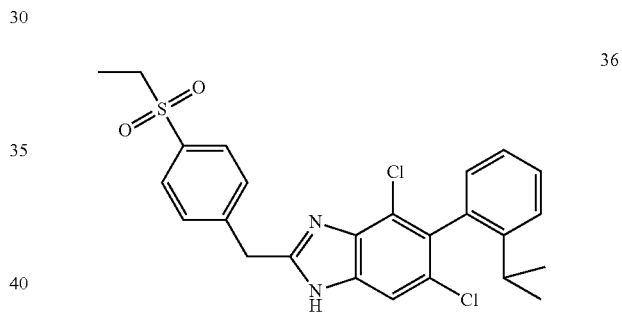

This compound was prepared by using essentially the same scope of example 1 except by using 2-isopropylphenylboronic acid instead of phenylboronic acid in step 8 to afford the product as a white solid, MS (+) ES: 487 (M+H)+.

Example 37

Preparation of 2-(4,6-dichloro-5-(2-isopropylphenyl)-1H-benzo[d]imidazol-2-yl)-2-(4-(ethylsulfonyl)phenyl)ethanol

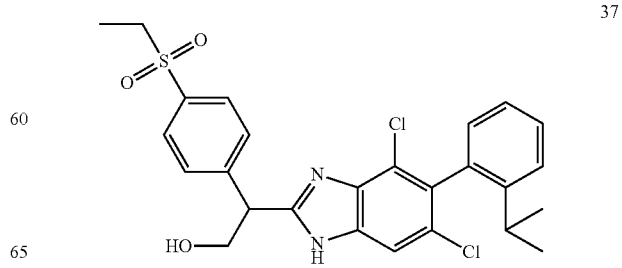

This compound was prepared by essential the same method as of example 4 to afford the product as a white solid, MS (+) ES: 517 (M+H)$^+$.

Example 38

Preparation of (E,Z)-(4,6-dichloro-5-(2-(difluoromethoxy)phenyl)-1H-benzo[d]imidazol-2-yl)(4-(ethylsulfonyl)phenyl)methanone oxime

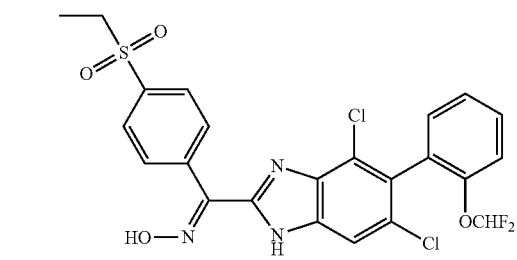

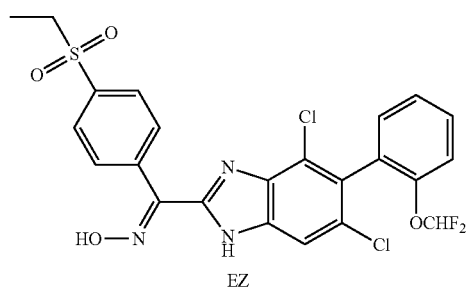

The mixture of (4,6-dichloro-5-(2-(difluoromethoxy)phenyl)-1H-benzo[d]imidazol-2-yl)(4-(ethylsulfonyl)phenyl)methanone (52 mg, 0.1 mmol) and hydroxylamine hydrochloride (14 mg, 0.2 mmol) in anhydrous pyridine (1 ml) was heated to 70° C. for 2 h. After cooling, the solvent was evaporated under reduced pressure to dryness. The product was purified by flash chromatography with hexane/ethyl acetate to afford the product as a white solid (42 mg, 78%), MS (+) ES: 540 (M+H)$^+$.

Example 39

Preparation of (4,6-dichloro-5-(2-(difluoromethoxy)phenyl)-1H-benzo[d]imidazol-2-yl)(4-(ethylsulfonyl)phenyl)methanamine

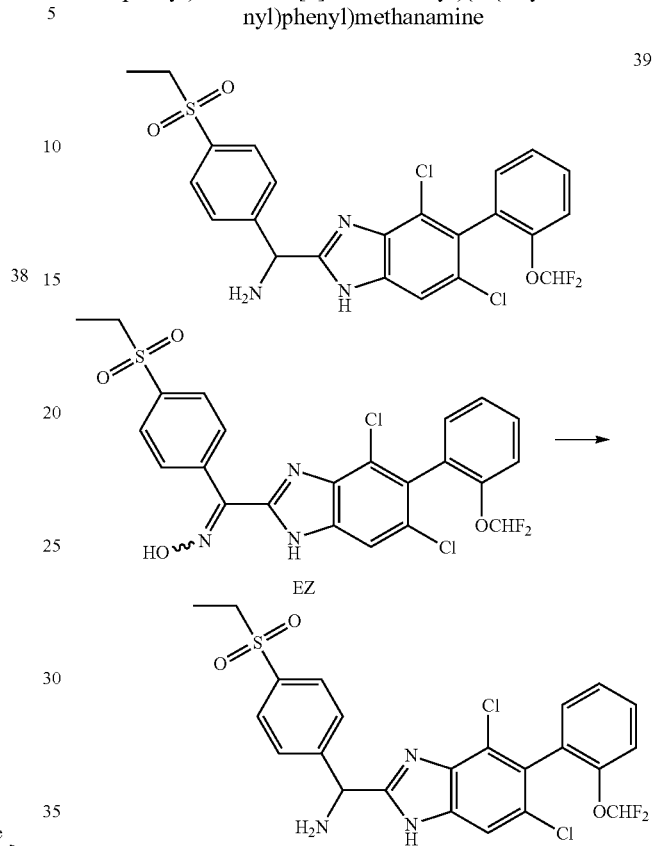

The mixture of (E,Z)-(4,6-dichloro-5-(2-(difluoromethoxy)phenyl)-1H-benzo[d]imidazol-2-yl)(4-(ethylsulfonyl)phenyl)methanone oxime (42 mg, 0.078 mmol) was dissolved in anhydrous THF (2 ml). To this solution was added borane 1M THF solution (4 ml) and the mixture was stirred at room temperature overnight. The volatile solvents were evaporated under reduced pressure and the residue was directly purified by Prep HPLC with elution system C to afford a white solid (18 mg, 45%), MS (+) ES: 526 (M+H)$^+$.

Example 40

Preparation of N-((4,6-dichloro-5-(2-(difluoromethoxy)phenyl)-1H-benzo[d]imidazol-2-yl)(4-(ethylsulfonyl)phenyl)methyl)acetamide

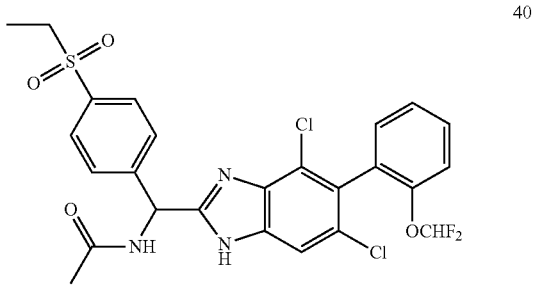

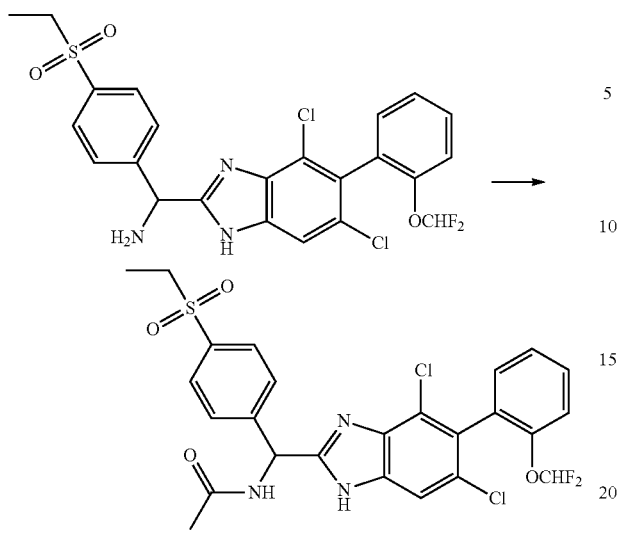

Acetyl chloride solution (in DCM) (1 eq) was added to a cooled solution (ice-water bath) of (4,6-dichloro-5-(2-(difluoromethoxy)phenyl)-1H-benzo[d]imidazol-2-yl)(4-(ethylsulfonyl)phenyl)methanamine (example 39) (4 mg, 0.0076 mmol) and triethyl amine (1 eq) in dichloromethane (0.5 ml). The mixture was stirred for 30 min before the dichloromethane was evaporated. The residue was directly separated by Prep HPLC with elution system C to afford a white solid (2.6 mg, 42%), MS (+) ES: 568 (M+H)+.

Example 41

Preparation of N-((4,6-dichloro-5-(2-(difluoromethoxy)phenyl)-1H-benzo[d]imidazol-2-yl)(4-(ethylsulfonyl)phenyl)methyl)-2-methoxyacetamide

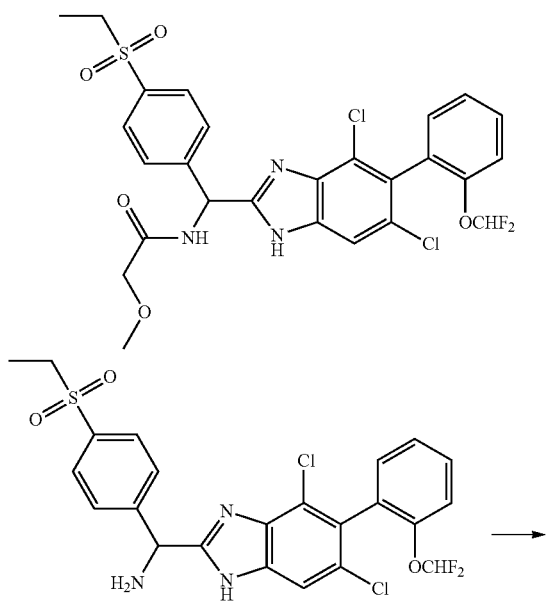

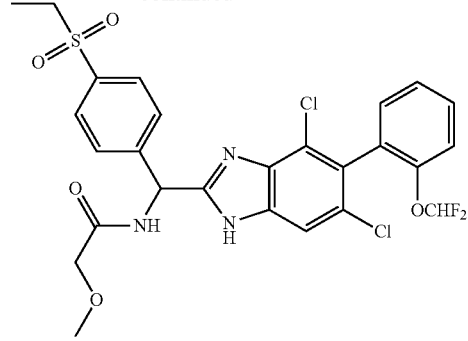

Similar method was applied as of example 40 to give the product as a white solid, MS (+) ES: 598 (M+H)+.

Example 42

Preparation of N-((4,6-dichloro-5-(2-(difluoromethoxy)phenyl)-1H-benzo[d]imidazol-2-yl)(4-(ethylsulfonyl)phenyl)methyl)-3,5-dimethylisoxazole-4-carboxamide

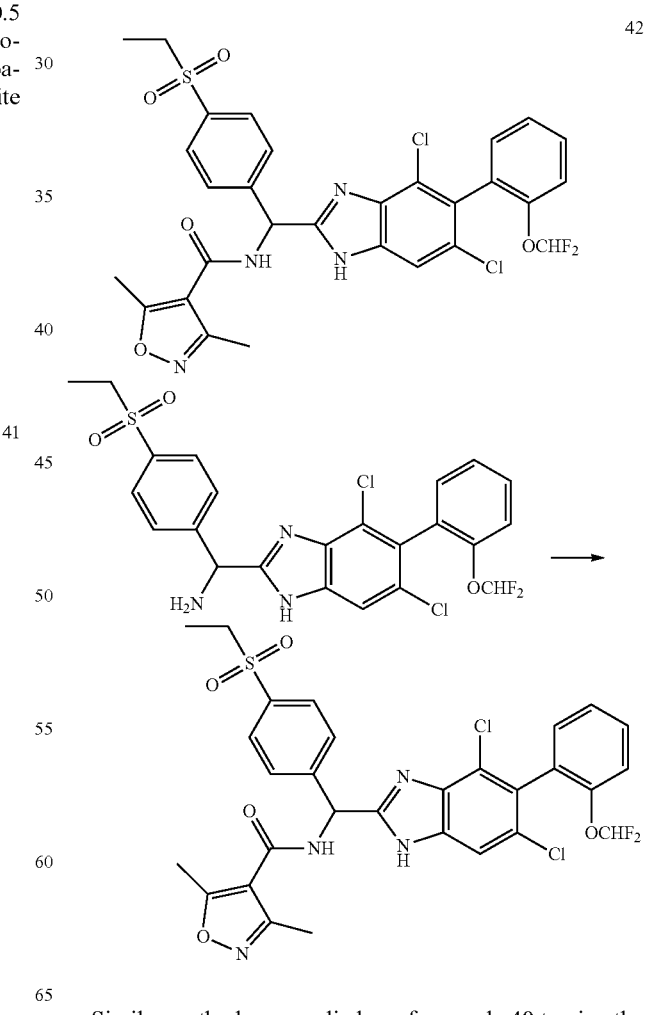

Similar method was applied as of example 40 to give the product as a white solid, MS (+) ES: 649 (M+H)+.

Example 43

Preparation of (4,6-dichloro-5-(2-(trifluoromethoxy)phenyl)-1H-benzo[d]imidazol-2-yl)(4-(ethylsulfonyl)phenyl)methanamine

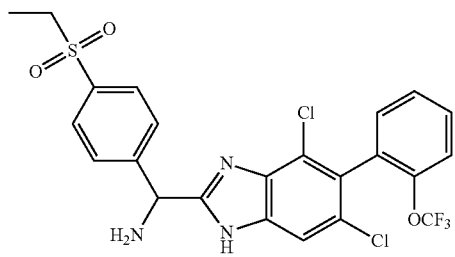

43

Similar method was applied as of example 39 to give the product as a white solid, MS (+) ES: 544 (M+H)⁺.

Example 44

Preparation of N-((4,6-dichloro-5-(2-(trifluoromethoxy)phenyl)-1H-benzo[d]imidazol-2-yl)(4-(ethylsulfonyl)phenyl)methyl)acetamide

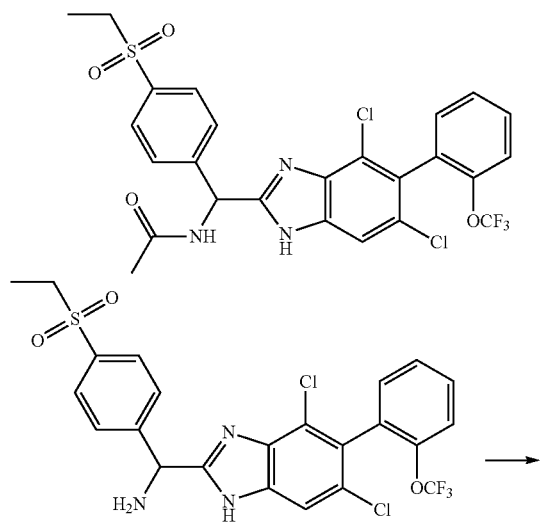

44

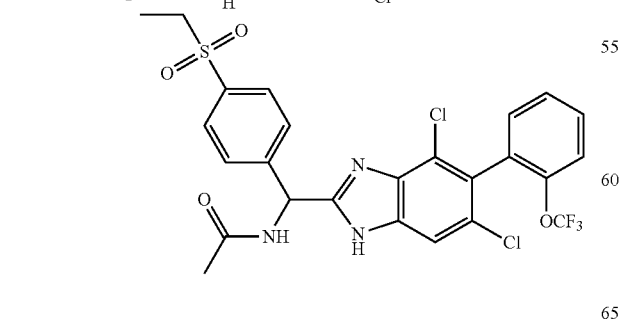

Similar method was applied as of example 40 to give the product as a white solid, MS (+) ES: 586 (M+H)⁺.

Example 45

Preparation of 4,6-dichloro-2-(4-(methylsulfonyl)benzyl)-5-(2-(trifluoromethyl)phenyl)-1H-benzo[d]imidazole

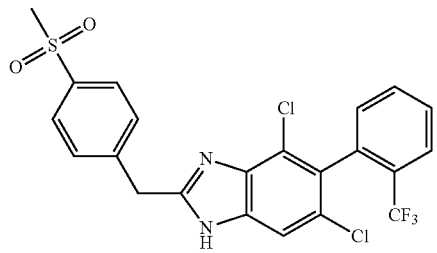

45

This compound was prepared by using essentially the same scope of example 1 to afford the product as a white solid, MS (+) ES: 499 (M+H)⁺.

Example 46

Preparation of 2-(4,6-dichloro-5-(2-(trifluoromethyl)phenyl)-1H-benzo[d]imidazol-2-yl)-2-(4-(methylsulfonyl)phenyl)ethanol

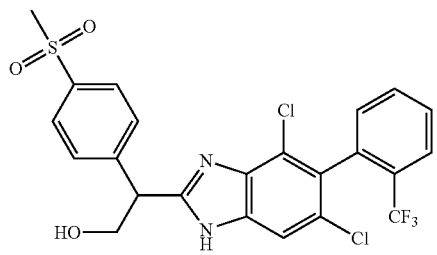

46

This compound was prepared by essential the same method as of example 4 to afford the product as a white solid, MS (+) ES: 529 (M+H)⁺.

Example 47

Preparation of 4,6-dichloro-5-(2-(difluoromethoxy)phenyl)-2-(4-(methylsulfonyl)benzyl)-1H-benzo[d]imidazole

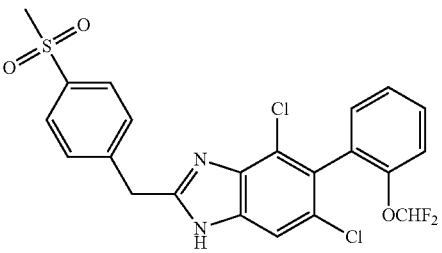

47

This compound was prepared by using essentially the same scope of example 28 to afford the product as a white solid, MS (+) ES: 497 (M+H)⁺.

Example 48

Preparation of 2-(4,6-dichloro-5-(2-(difluoromethoxy)phenyl)-1H-benzo[d]imidazol-2-yl)-2-(4-(methylsulfonyl)phenyl)ethanol

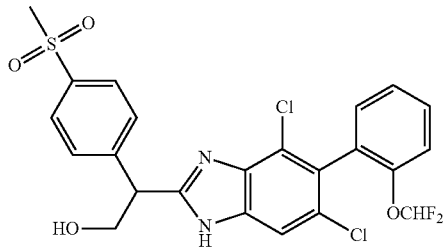

48

This compound was prepared by essential the same method as of example 29 to afford the product as a white solid, MS (+) ES: 527 (M+H)⁺.

Example 49

Preparation of (4,6-dichloro-5-(2-(difluoromethoxy)phenyl)-1H-benzo[d]imidazol-2-yl)(4-(methylsulfonyl)phenyl)methanol

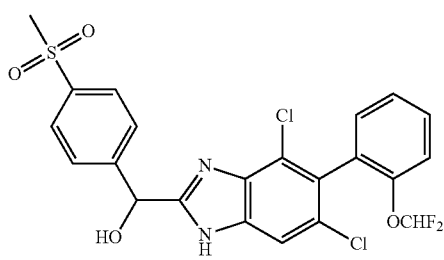

49

This product was prepared by essentially the same method as of example 30 to afford the product as a white solid, MS (+) ES: 513 (M+H)⁺.

Example 50

Preparation of 4,6-dichloro-2-(4-(propylsulfonyl)benzyl)-5-(2-(trifluoromethoxy)phenyl)-1H-benzo[d]imidazole

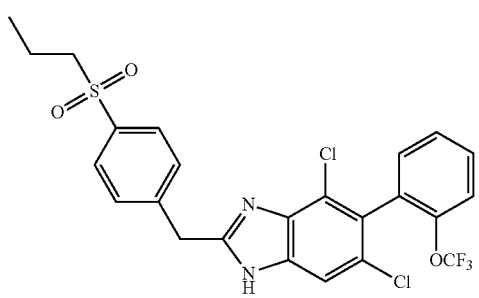

50

This compound was prepared by using essentially the same scope of example 1 to afford the product as a white solid, MS (+) ES: 543 (M+H)⁺.

Example 51

Preparation of 2-(4,6-dichloro-5-(2-(trifluoromethoxy)phenyl)-1H-benzo[d]imidazol-2-yl)-2-(4-(propylsulfonyl)phenyl)ethanol

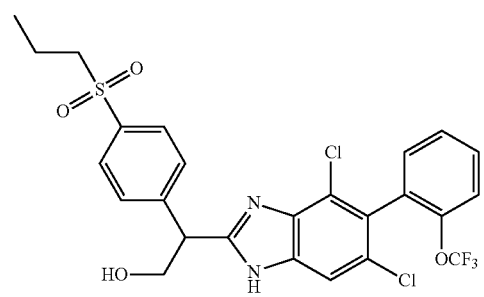

51

This compound was prepared by essential the same method as of example 6 to afford the product as a white solid, MS (+) ES: 573 (M+H)⁺.

Example 52

Preparation of (4,6-dichloro-5-(2-(trifluoromethoxy)phenyl)-1H-benzo[d]imidazol-2-yl)(4-(propylsulfonyl)phenyl)methanol

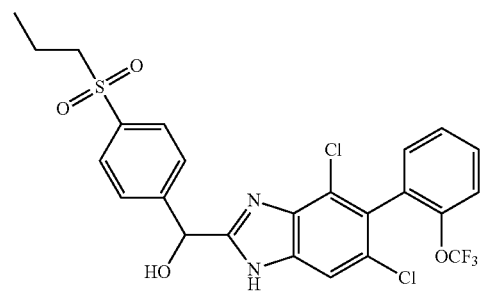

52

This product was prepared by essentially the same method as of example 7 to afford the product as a white solid, MS (+) ES: 559 (M+H)⁺.

Example 53

Preparation of 4,6-dichloro-2-(4-((2-methoxyethyl)sulfonyl)benzyl)-5-(2-(trifluoromethoxy)phenyl)-1H-benzo[d]imidazole

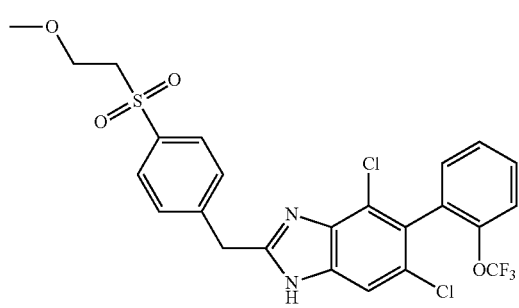

53

This compound was prepared by using essentially the same scope of example 1 to afford the product as a white solid, MS (+) ES: 559 (M+H)$^+$.

Example 54

Preparation of 2-(4,6-dichloro-5-(2-(trifluoromethoxy)phenyl)-1H-benzo[d]imidazol-2-yl)-2-(4-((2-methoxyethyl)sulfonyl)phenyl)ethanol

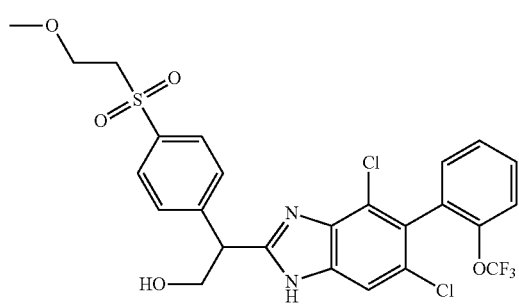

54

This compound was prepared by essential the same method as of example 6 to afford the product as a white solid, MS (+) ES: 589 (M+H)$^+$.

Example 55

Preparation of (4,6-dichloro-5-(2-(trifluoromethoxy)phenyl)-1H-benzo[d]imidazol-2-yl)(4-((2-methoxyethyl)sulfonyl)phenyl)methanol

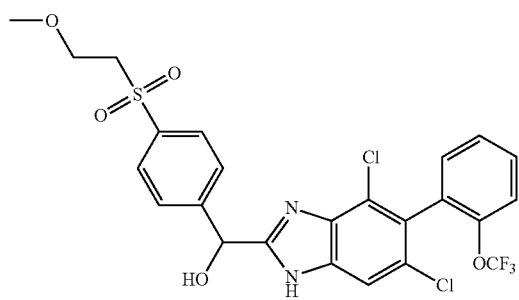

This product was prepared by essentially the same method as of example 7 to afford the product as a white solid, MS (+) ES: 575 (M+H)$^+$.

Example 56

Preparation of 4,6-dichloro-2-(4-(methylsulfonyl)benzyl)-5-(2-(trifluoromethoxy)phenyl)-1H-benzo[d]imidazole

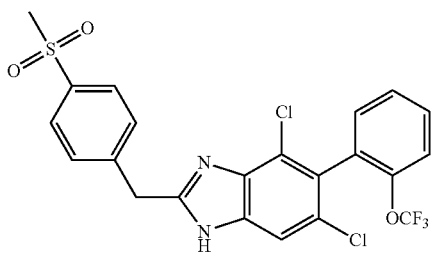

56

This compound was prepared by using essentially the same scope of example 1 to afford the product as a white solid, MS (+) ES: 515 (M+H)$^+$.

Example 57

Preparation of 2-(4,6-dichloro-5-(2-(trifluoromethoxy)phenyl)-1H-benzo[d]imidazol-2-yl)-2-(4-(methylsulfonyl)phenyl)ethanol

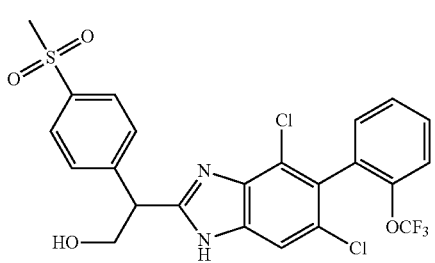

57

This compound was prepared by essential the same method as of example 6 to afford the product as a white solid, MS (+) ES: 545 (M+H)$^+$.

Example 58

Preparation of (4,6-dichloro-5-(2-(trifluoromethoxy)phenyl)-1H-benzo[d]imidazol-2-yl)(4-(methylsulfonyl)phenyl)methanol

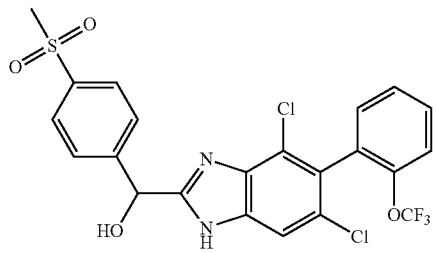

58

This product was prepared by essentially the same method as of example 7 to afford the product as a white solid, MS (+) ES: 531 (M+H)⁺.

Example 59

Preparation of 4,6-dichloro-2-(4-((2,2,2-trifluoroethyl)sulfonyl)benzyl)-5-(2-(trifluoromethoxy)phenyl)-1H-benzo[d]imidazole

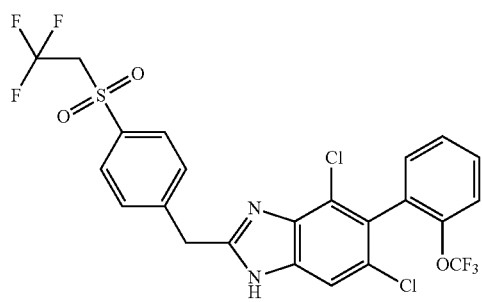

59

This compound was prepared by using essentially the same scope of example 1 to afford the product as a white solid, MS (+) ES: 583 (M+H)⁺.

Example 60

Preparation of 2-(4,6-dichloro-5-(2-(trifluoromethoxy)phenyl)-1H-benzo[d]imidazol-2-yl)-2-(4-((2,2,2-trifluoroethyl)sulfonyl)phenyl)ethanol

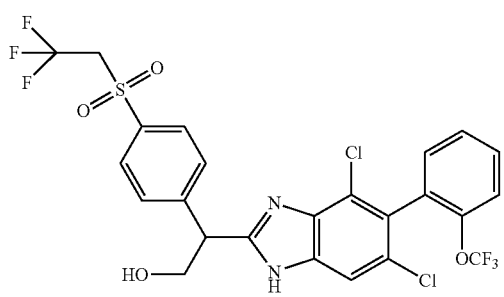

60

This compound was prepared by essential the same method as of example 6 to afford the product as a white solid, MS (+) ES: 613 (M+H)⁺.

Example 61

Preparation of 4,6-dichloro-2-(4-((2-fluoroethyl)sulfonyl)benzyl)-5-(2-(trifluoromethoxy)phenyl)-1H-benzo[d]imidazole

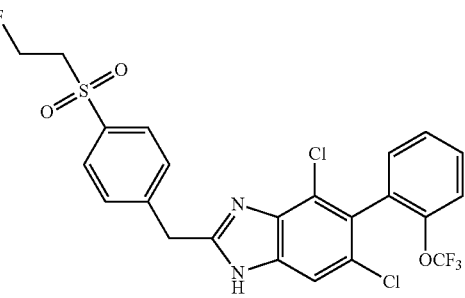

61

This compound was prepared by using essentially the same scope of example 1 to afford the product as a white solid, MS (+) ES: 547 (M+H)⁺.

Example 62

Preparation of 2-(4,6-dichloro-5-(2-(trifluoromethoxy)phenyl)-1H-benzo[d]imidazol-2-yl)-2-(4-((2-fluoroethyl)sulfonyl)phenyl)ethanol

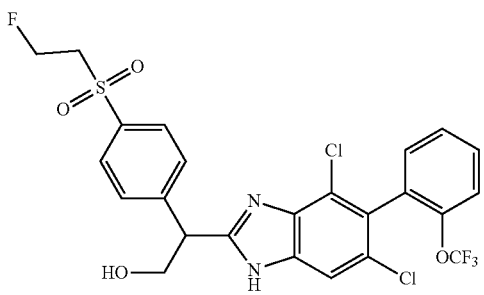

62

This compound was prepared by essential the same method as of example 4 to afford the product as a white solid, MS (+) ES: 577 (M+H)⁺.

Example 63

Preparation of 4,6-dichloro-2-(4-((2-fluoroethyl)sulfonyl)benzyl)-5-(2-(trifluoromethyl)phenyl)-1H-benzo[d]imidazole

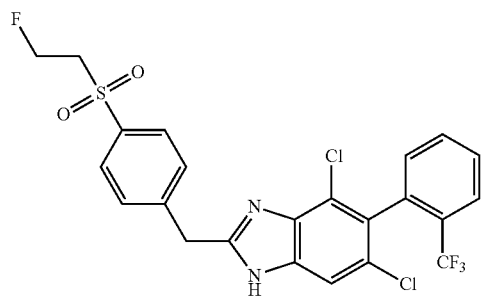

63

This compound was prepared by using essentially the same scope of example 1 to afford the product as a white solid, MS (+) ES: 531 (M+H)⁺.

Example 64

Preparation of 2-(4,6-dichloro-5-(2-(trifluoromethyl)phenyl)-1H-benzo[d]imidazol-2-yl)-2-(4-((2-fluoroethyl)sulfonyl)phenyl)ethanol

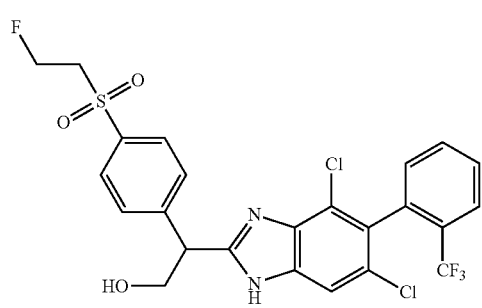

64

This compound was prepared by essential the same method as of example 4 to afford the product as a white solid, MS (+) ES: 561 (M+H)⁺.

Example 65

Preparation of 4,6-dichloro-5-(2-(trifluoromethyl)phenyl)-2-(4-((trifluoromethyl)sulfonyl)benzyl)-1H-benzo[d]imidazole

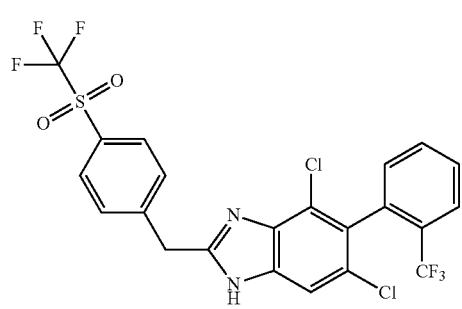

65

This compound was prepared by using essentially the same scope of example 1 to afford the product as a white solid, MS (+) ES: 553 (M+H)⁺.

Example 66

Preparation of 4,6-dichloro-2-(4-((cyclopropylmethyl)sulfonyl)benzyl)-5-(2-(trifluoromethoxy)phenyl)-1H-benzo[d]imidazole

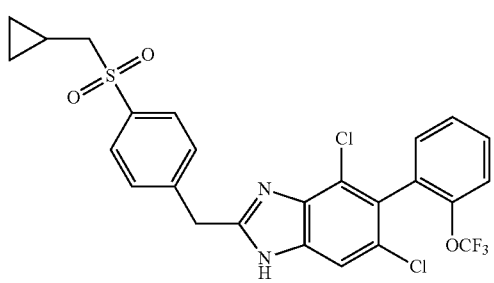

66

This compound was prepared by using essentially the same scope of example 1 to afford the product as a white solid, MS (+) ES: 555 (M+H)⁺.

Example 67

Preparation of 2-(4-((cyclopropylmethyl)sulfonyl)phenyl)-2-(4,6-dichloro-5-(2-(trifluoromethoxy)phenyl)-1H-benzo[d]imidazol-2-yl)ethanol

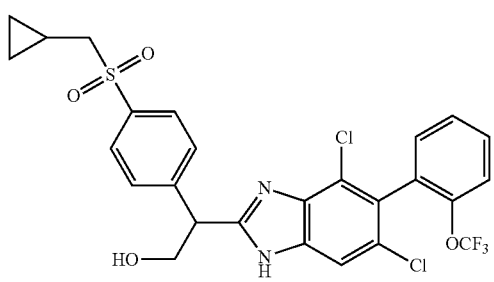

67

This compound was prepared by essential the same method as of example 4 to afford the product as a white solid, MS (+) ES: 585 (M+H)⁺.

Example 68

Preparation of (4-((cyclopropylmethyl)sulfonyl)phenyl)(4,6-dichloro-5-(2-(trifluoromethoxy)phenyl)-1H-benzo[d]imidazol-2-yl)methanol

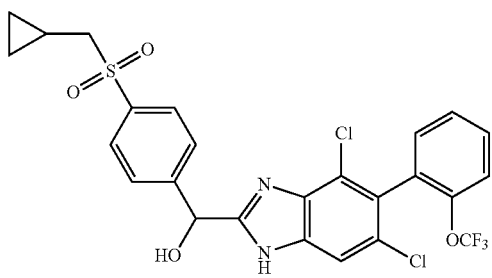

This product was prepared by essentially the same method as of example 2 to afford the product as a white solid, MS (+) ES: 571 (M+H)$^+$.

Example 69

Preparation of 4,6-dichloro-2-(4-((cyclopropylmethyl)sulfonyl)benzyl)-5-(2-(trifluoromethyl)phenyl)-1H-benzo[d]imidazole

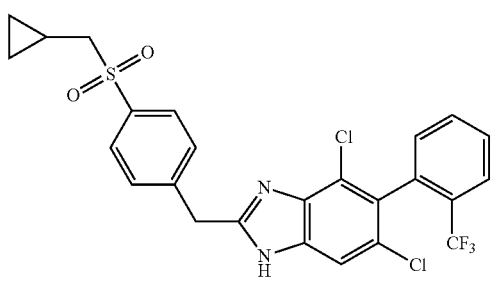

This compound was prepared by using essentially the same scope of example 1 to afford the product as a white solid, MS (+) ES: 539 (M+H)$^+$.

Example 70

Preparation of 2-(4-((cyclopropylmethyl)sulfonyl)phenyl)-2-(4,6-dichloro-5-(2-(trifluoromethyl)phenyl)-1H-benzo[d]imidazol-2-yl)ethanol

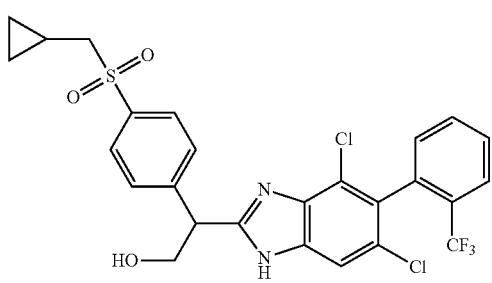

This compound was prepared by essential the same method as of example 4 to afford the product as a white solid, MS (+) ES: 569 (M+H)$^+$.

Example 71

Preparation of (4-((cyclopropylmethyl)sulfonyl)phenyl)(4,6-dichloro-5-(2-(trifluoromethyl)phenyl)-1H-benzo[d]imidazol-2-yl)methanol

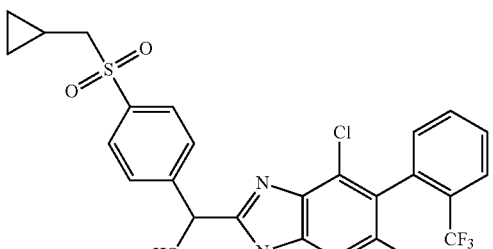

This product was prepared by essentially the same method as of example 2 to afford the product as a white solid, MS (+) ES: 555 (M+H)$^+$.

Example 72

Preparation of 4,6-dichloro-2-(4-((cyclopropylmethyl)sulfonyl)benzyl)-5-(2-(difluoromethoxy)phenyl)-1H-benzo[d]imidazole

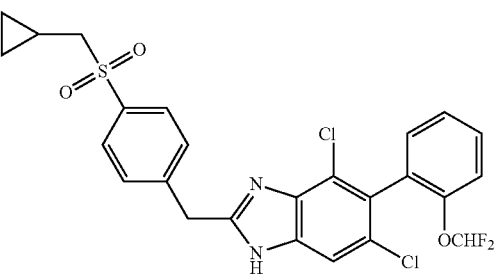

This compound was prepared by using essentially the same scope of example 1 to afford the product as a white solid, MS (+) ES: 537 (M+H)$^+$.

Example 73

Preparation of 2-(4-((cyclopropylmethyl)sulfonyl)phenyl)-2-(4,6-dichloro-5-(2-(difluoromethoxy)phenyl)-1H-benzo[d]imidazol-2-yl)ethanol

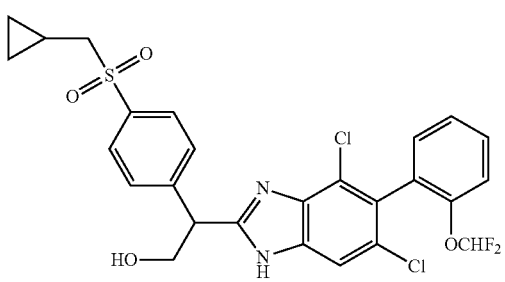

This compound was prepared by essential the same method as of example 4 to afford the product as a white solid, MS (+) ES: 567 (M+H)+.

Example 74

Preparation of 2-(4-((cyclopropylmethyl)sulfonyl)phenyl)-2-(4,6-dichloro-5-(2-fluorophenyl)-1H-benzo[d]imidazol-2-yl)ethanol

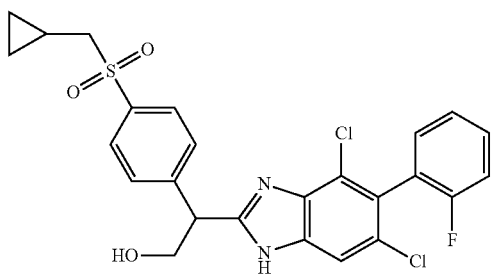

This compound was prepared by essential the same method as of example 4 to afford the product as a white solid, MS (+) ES: 519 (M+H)+.

Example 75

Preparation of (4-((cyclopropylmethyl)sulfonyl)phenyl)(4,6-dichloro-5-(2-fluorophenyl)-1H-benzo[d]imidazol-2-yl)methanol

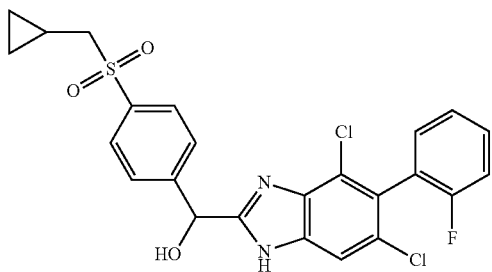

This product was prepared by essentially the same method as of example 2 to afford the product as a white solid, MS (+) ES: 505 (M+H)+.

Example 76

Preparation of 4,6-dichloro-2-(4-(ethylsulfonyl)-2-fluorobenzyl)-5-(2-(trifluoromethoxy)phenyl)-1H-benzo[d]imidazole

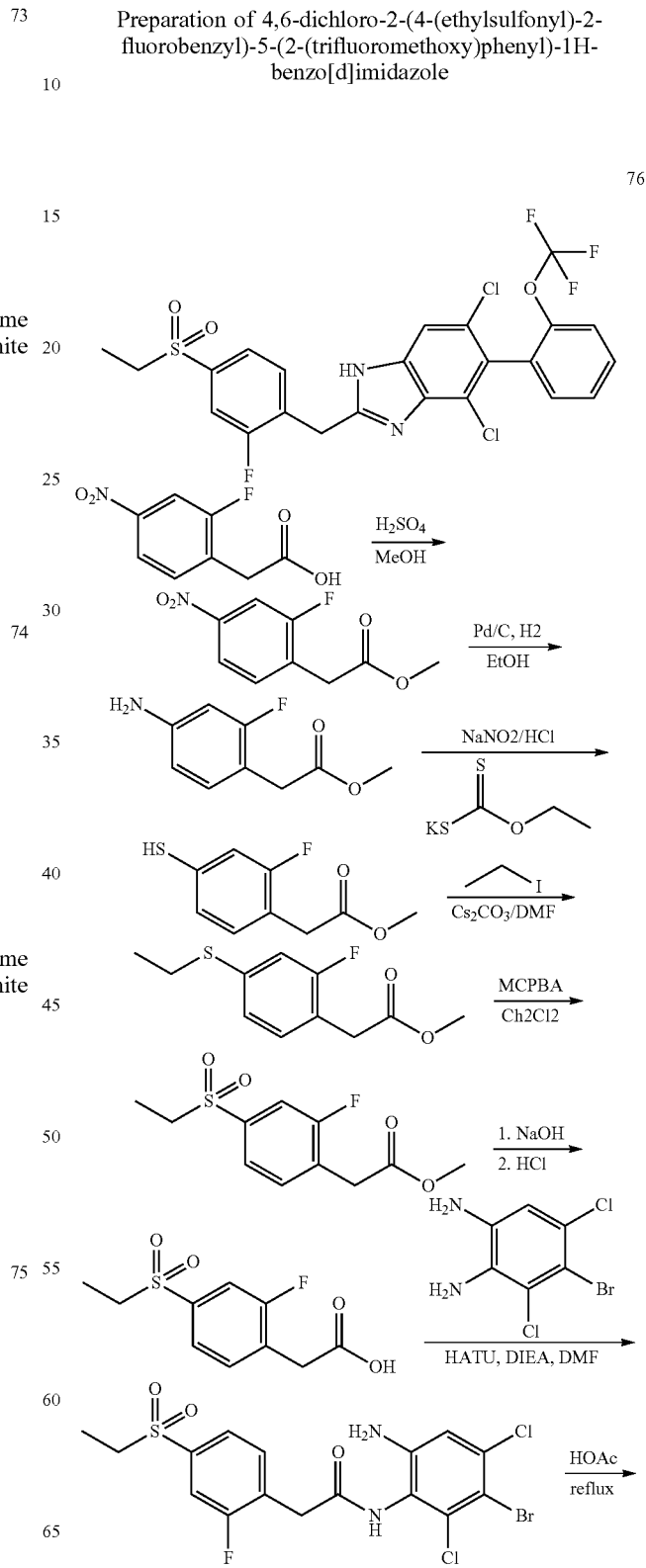

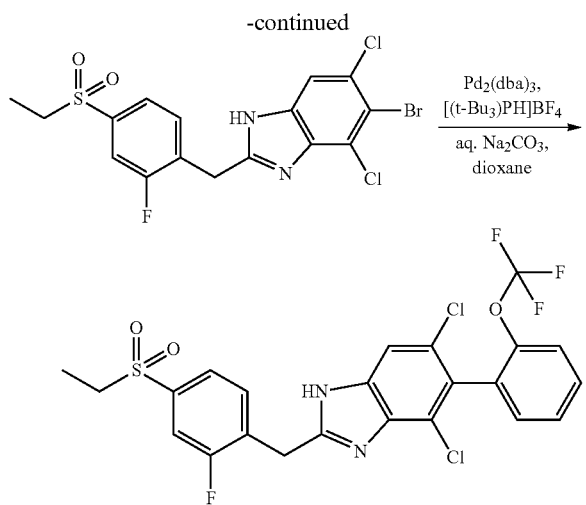

Step 1. Preparation of methyl 2-(2-fluoro-4-nitrophenyl)acetate

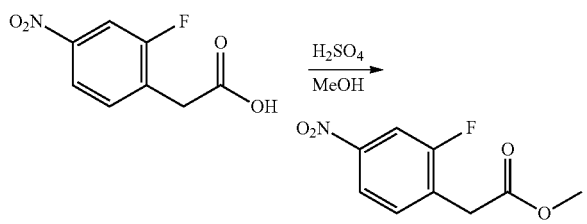

2-(2-fluoro-4-nitrophenyl)acetic acid (4.0 g, 0.02 mol) in methanol (20 ml) was added concentrated sulfuric acid (1 ml). The solution was heated to reflux overnight. After cooling, the mixture was concentrated to a small amount and partitioned between ether (30 ml) and water. The ether phase was separated and washed with saturated sodium bicarbonate solution (30 ml). The organic phase was then separated again and washed with water, dried over MgSO$_4$. The solid was filtered off and evaporation of the solvent to give the product pure enough for the next step (3.8 g, 88%), MS (+) ES: 214 (M+H)$^+$.

Step 2. Preparation of methyl 2-(4-amino-2-fluorophenyl)acetate

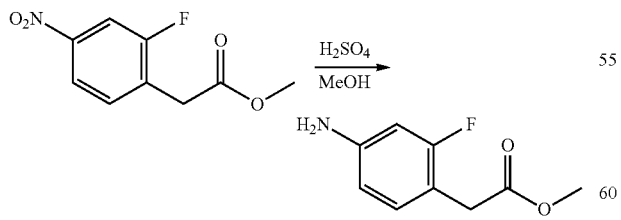

To a 50 ml round bottom flask, were added methyl 2-(2-fluoro-4-nitrophenyl)acetate (3.8 g, 0.018 mol) and ethyl acetate (30 ml). To the same flask, 10 percent palladium on activated carbon (0.5 g) was added. The reaction mixture was stirred under hydrogen gas (using bladder) atmosphere for 5 h. The reaction mixture was filtered through a pad of celite. The filtrate was evaporated under reduced pressure to get the title compound (2.8 g, 86%), MS (+) ES: 184 (M+H)$^+$.

Step 3. Preparation of 2-(2-fluoro-4-mercaptophenyl)acetic acid

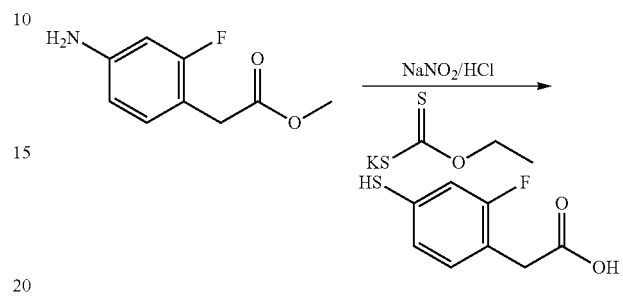

A solution of sodium nitrite (1.06 g, 0.015 mol) in 16 ml of water was added drop wise at 0° C., to a stirred suspension of methyl 2-(4-amino-2-fluorophenyl)acetate (2.8 g, 0.015 mol) in 50 ml of water and 3.8 ml of concentrated hydrochloric acid. After the addition was complete, the reaction mixture was stirred at the same temperature for a further 60 minutes. This cold diazonium salt solution was then added dropwise at room temperature to a mixture of potassium O-ethyl carbonodithioate (2.8 g), 50 ml of water and 16 ml of a 2 M sodium carbonate solution, and was heated to 45° C. until gas evolution stopped. The mixture was cooled to room temperature, and the pH was adjusted to 1 with concentrated hydrochloric acid. The oiled xanthogenate ester was extracted with ether. Solvent was evaporated to give a dark red liquid 2-(4-(ethoxycarbonothioyl)thio)-2-fluorophenyl)acetic acid methyl ester (3.5 g), MS (+) ES: 288 (M+H)$^+$.

The above oily product was dissolved in ethanol (10 ml), a solution of KOH (1.8 g) in water (10 ml) was added and the mixture heated to reflux overnight. The mixture was concentrated to a small amount and acidified with concentrated HCl. The product was extracted with ethyl acetate (10 ml×3). The combined organic phase was dried over MgSO$_4$, the solid was filtered off. Evaporation of the solvent to afford the crude product (2.5 g, 89%), MS (+) ES: 187 (M+H)$^+$.

Step 4. Preparation of ethyl 2-(4-(ethylthio)-2-fluorophenyl)acetate

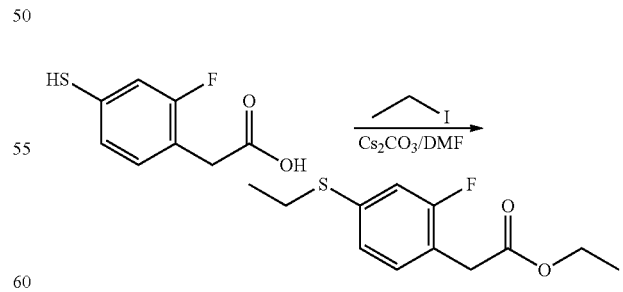

2-(2-fluoro-4-mercaptophenyl)acetic acid (2.5 g, 0.013 mol) was dissolved in DMF (25 ml), followed by the addition of cesium carbonate (13.0 g, 0.039 mol). The mixture was stirred for 10 min before Iodoethane (6 g, 0.039 mol) was added and the mixture was stirred at room temp overnight. The reaction mixture was partitioned between ethyl acetate (20 ml) and water (30 ml). The organic phase was separated and dried over MgSO₄. The solid was filtered off and the solvent was evaporated to dryness. This product was purified by flash chromatography with hexane/ethyl acetate to afford an oil (2.8 g, 86%), MS (+) ES: 243 (M+H)⁺.

Step 5. Preparation of ethyl 2-(4-(ethylsulfonyl)-2-fluorophenyl)acetate

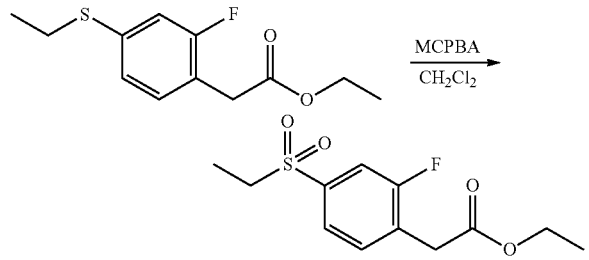

Ethyl 2-(4-(ethylthio)-2-fluorophenyl)acetate (2.8 g, 0.012 mol) was dissolved in DCM (50 ml). The solution was cooled to 0° C. with an ice bath. MCPBA (6.0 g) was added in portions. The reaction mixture was stirred at room temperature overnight, and then filtered to remove the solid. The filtrate was washed with sat. sodium carbonate solution (30 ml×2), water (30 ml), brine (30 ml), dried over magnesium sulfate, and concentrated. The residue was purified by column chromatography with hexane/ethyl acetate to afford the target compound ethyl 2-(4-(ethylsulfonyl)-2-fluorophenyl)acetate (2.0 g, 64%), MS (+) ES: 275 (M+H)⁺.

Step 6. Preparation of 2-(4-(ethylsulfonyl)-2-fluorophenyl)acetic acid

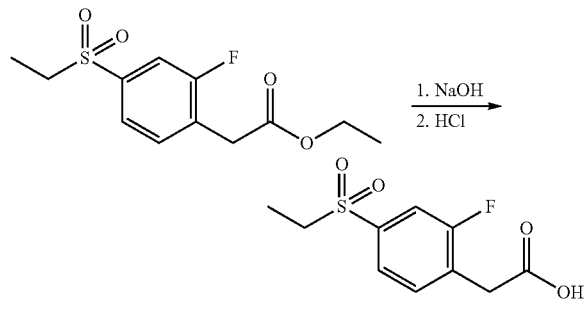

To a solution of ethyl 2-(4-(ethylsulfonyl)-2-fluorophenyl)acetate (2.0 g, 7.3 mmol) in ethanol (30 ml) was added a solution of NaOH (1.0 g) in water (10 ml). The reaction mixture was stirred at room temperature overnight. Ethanol was removed under reduced pressure, and 20 mL of water was added. The aqueous phase was acidified to pH=1 with 6 M HCl, and then extracted with ethyl acetate (50 ml×3). The combined organic phases were washed with brine (50 ml), dried over magnesium sulfate, and concentrated to afford an oil which solidified upon standing (1.6 g, 90%), MS(+) ES: 247 (M+H)⁺.

Step 7. Preparation of N-(6-amino-3-bromo-2,4-dichlorophenyl)-2-(4-(ethylsulfonyl)-2-fluorophenyl)acetamide

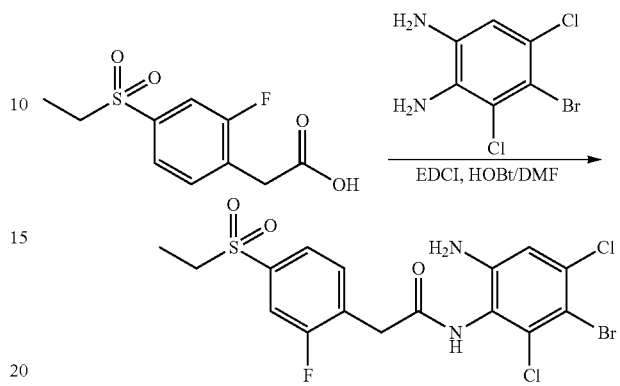

1-Ethyl-(3-(3-dimethylamino)propyl)-carbodiimide hydrochloride (1.0 g, 5 mmol) and benzotriazol-1-ol (0.7 g, 5 mmol) were added into a cooled solution (ice water bath) of 4-bromo-3,5-dichlorobenzene-1,2-diamine (1.28 g, 5 mmol) and 2-(4-(ethylsulfonyl)-2-fluorophenyl)acetic acid (example 93, step 6, 1.23 g, 5 mmol) in DMF (10 ml) portion wise. After the addition was completed, the mixture was stirred for 60 min and was allowed to warm-up to room temp, stirred overnight. The mixture was partitioned between water (50 ml) and ethyl acetate (50 ml). The organic phase was separated and dried over MgSO₄, filtered. The solvent was evaporated under reduced pressure to leave a off-white solid which was purified by flash chromatography with hexane/ethyl acetate to afford the product as a solid (1.7 g, 70%), MS (+) ES: 484 (M+H)⁺.

Step 8. Preparation of 5-bromo-4,6-dichloro-2-(4-(ethylsulfonyl)-2-fluorobenzyl)-1H-benzo[d]imidazole

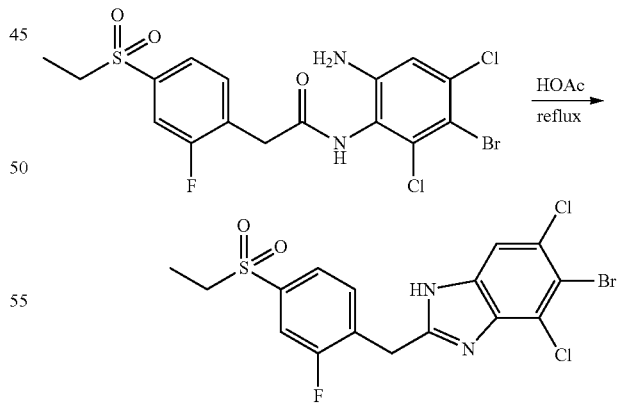

N-(6-amino-3-bromo-2,4-dichlorophenyl)-2-(4-(ethylsulfonyl)-2-fluorophenyl)acetamide (step 7) (1.7 g, 3.5 mmol) was mixed with acetic acid (10 ml) and the mixture was heated to 100° C. for 4 hours, cooled. The solvent was evaporated under reduce pressure and the residue was dissolved in dichloromethane and washed with saturated sodium bicarbonate, dried over MgSO₄. This product was purified by flash chromatography with hexane/ethyl acetate to afford the product as a white solid (1.2 g, 73%), MS (+) ES: 466 (M+H)+.

Step 9. Preparation of 4,6-dichloro-2-(4-(ethylsulfonyl)-2-fluorobenzyl)-5-(2-(trifluoromethoxy)phenyl)-1H-benzo[d]imidazole

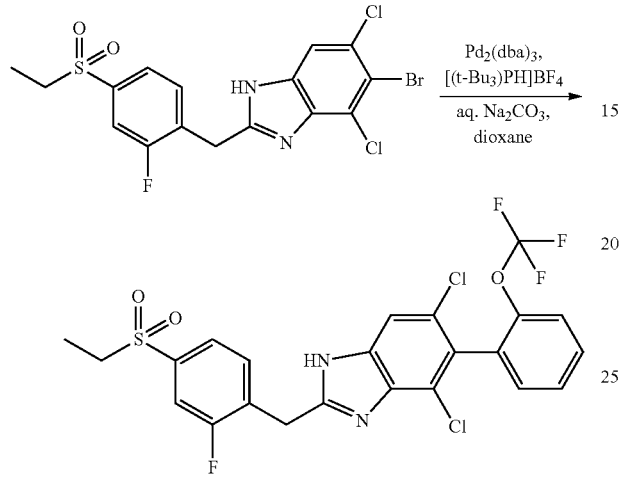

A mixture of 5-bromo-4,6-dichloro-2-(4-(ethylsulfonyl)-2-fluorobenzyl)-1H-benzo[d]imidazole (step 8) (47 mg, 0.1 mmol), 2-trifluoromethoxyphenylboronic acid (62 mg, 0.3 mmol), tris-(dibenzylideneacetone)dipalladium(0) (6 mg), tri(tert-butyl)phosphonium tetrafluoroborate (6 mg) and sodium carbonate (2M solution) in 1,4-dioxane (0.6 ml) was degassed and heated to 100° C. under Microwave irradiation for 1 h. The volatile solvents were removed under reduced pressure. The residue was directly loaded onto a ISCO solid cartridge and flashed with hexane/ethyl acetate to afford a white solid product (38 mg, 70% yield), MS (+) ES: 547 (M+H)+.

Example 77

Preparation of 2-(4,6-dichloro-5-(2-(trifluoromethoxy)phenyl)-1H-benzo[d]imidazol-2-yl)-2-(4-(ethylsulfonyl)-2-fluorophenyl)ethanol

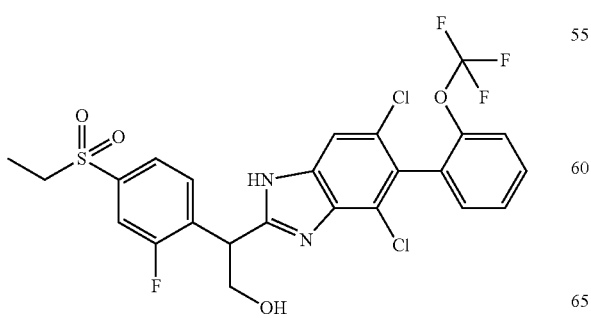

This compound was prepared by essential the same method as of example 4 to afford the product as a white solid, MS (+) ES: 577 (M+H)+.

Example 78

Preparation of (4,6-dichloro-5-(2-(trifluoromethoxy)phenyl)-1H-benzo[d]imidazol-2-yl)(4-(ethylsulfonyl)-2-fluorophenyl)methanol

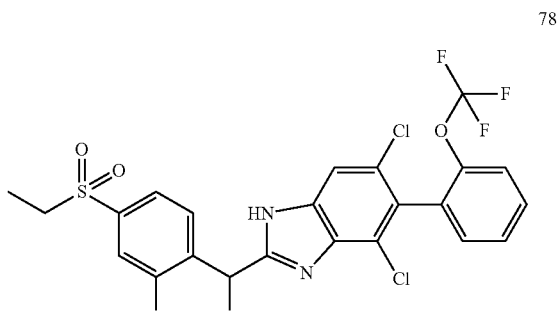

This compound was prepared by essential the same method as of example 2 to afford the product as a white solid, MS (+) ES: 563 (M+H)+.

Example 79

Preparation of (4,6-dichloro-5-(2-(trifluoromethyl)phenyl)-1H-benzo[d]imidazol-2-yl)(4-(ethylsulfonyl)-2-fluorophenyl)methanol

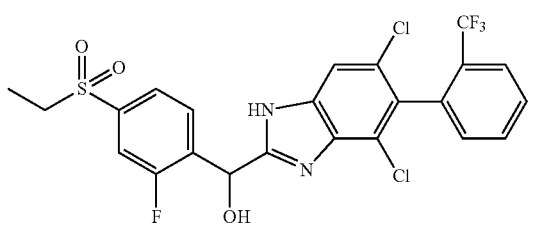

This compound was prepared by essential the similar method as of example 78 to afford the product as a white solid, MS (+) ES: 547 (M+H)+.

Example 80

Preparation of 4,6-dichloro-2-(4-((cyclopropylmethyl)sulfonyl)-2-fluorobenzyl)-5-(2-(trifluoromethoxy)phenyl)-1H-benzo[d]imidazole

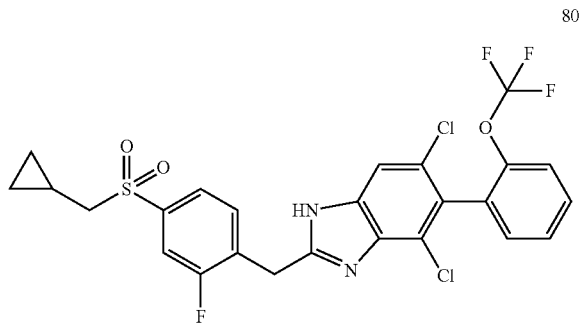 [SMILES: O=S(=O)(CC1CC1)c1ccc(Cc2nc3c(Cl)c(-c4ccccc4OC(F)(F)F)c(Cl)cc3[nH]2)c(F)c1]

80

This compound was prepared by essential the similar method as of example 76 to afford the product as a white solid, MS (+) ES: 573 (M+H)+.

Example 81

Preparation of 2-(4-((cyclopropylmethyl)sulfonyl)-2-fluorophenyl)-2-(4,6-dichloro-5-(2-(trifluoromethoxy)phenyl)-1H-benzo[d]imidazol-2-yl)ethanol

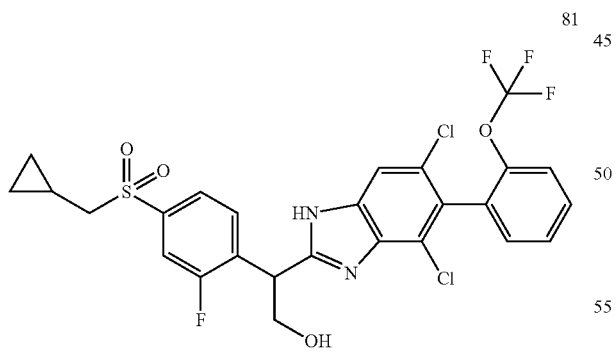

81

This compound was prepared by essential the similar method as of example 77 to afford the product as a white solid, MS (+) ES: 603 (M+H)+.

Example 82

Preparation of (4-((cyclopropylmethyl)sulfonyl)-2-fluorophenyl)(4,6-dichloro-5-(2-(trifluoromethoxy)phenyl)-1H-benzo[d]imidazol-2-yl)methanol

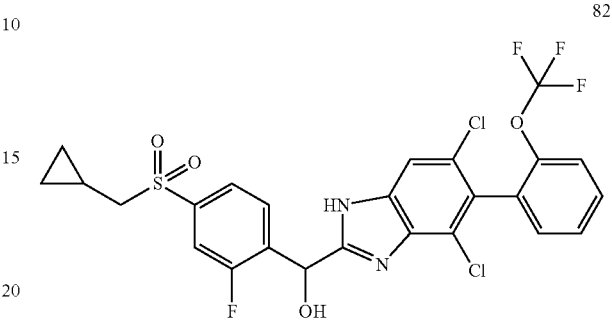

82

This compound was prepared by essential the similar method as of example 78 to afford the product as a white solid, MS (+) ES: 589 (M+H)+.

Example 83

Preparation of 4,6-dichloro-5-(2-(difluoromethoxy)phenyl)-2-(4-(ethylsulfonyl)-2-fluorobenzyl)-1H-benzo[d]imidazole

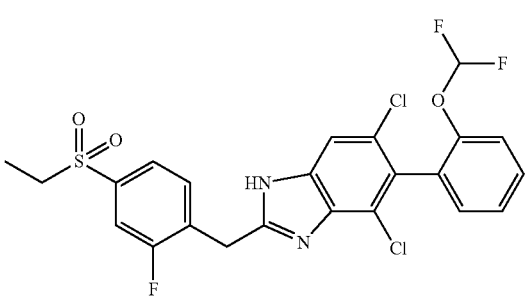

83

This compound was prepared by essential the same method as of example 76 by using 2-difluorophenylboronic acid instead of 2-trifluoromethoxyphenylboronic acid in step 9 to afford the product as a white solid, MS (+) ES: 529 (M+H)*.

Example 84

Preparation of 2-(4,6-dichloro-5-(2-(difluoromethoxy)phenyl)-1H-benzo[d]imidazol-2-yl)-2-(4-(ethylsulfonyl)-2-fluorophenyl)ethanol

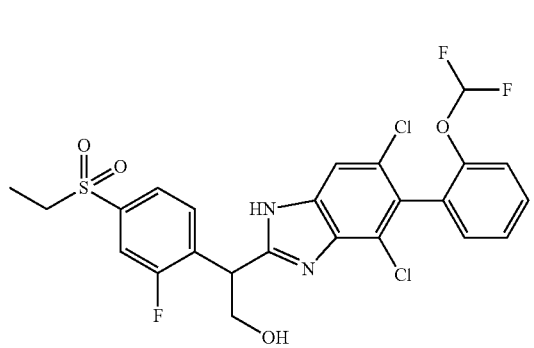

This compound was prepared by essential the similar method as of example 77 to afford the product as a white solid, MS (+) ES: 559 (M+H)+.

Example 85

Preparation of (4,6-dichloro-5-(2-(difluoromethoxy)phenyl)-1H-benzo[d]imidazol-2-yl)(4-(ethylsulfonyl)-2-fluorophenyl)methanol

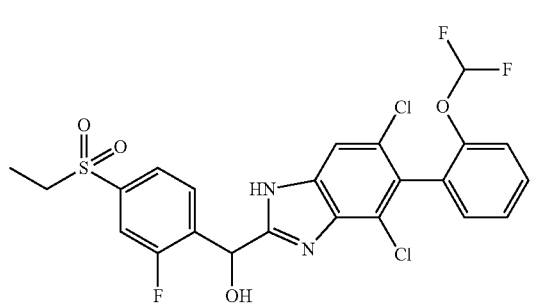

This compound was prepared by essential the similar method as of example 78 to afford the product as a white solid, MS (+) ES: 545 (M+H)+.

Example 86

Preparation of 4,6-dichloro-2-(2-chloro-4-(ethylsulfonyl)benzyl)-5-(2-(trifluoromethoxy)phenyl)-1H-benzo[d]imidazole

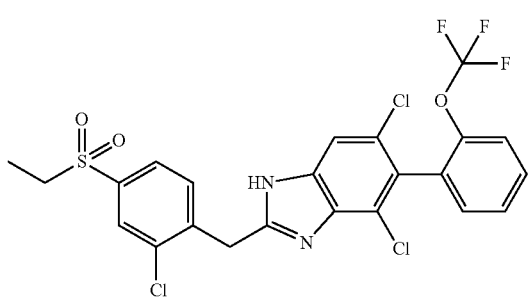

This compound was prepared by essential the similar method as of example 76 to afford the product as a white solid, MS (+) ES: 563 (M+H)+.

Example 87

Preparation of 2-(2-chloro-4-(ethylsulfonyl)phenyl)-2-(4,6-dichloro-5-(2-(trifluoromethoxy)phenyl)-1H-benzo[d]imidazol-2-yl)ethanol

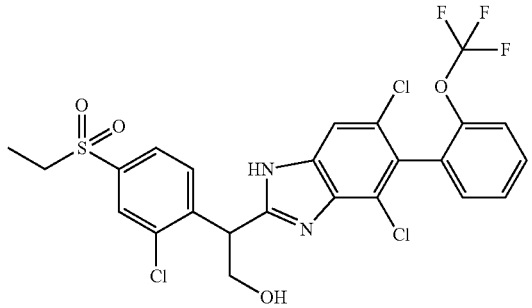

This compound was prepared by essential the similar method as of example 77 to afford the product as a white solid, MS (+) ES: 593 (M+H)+.

Example 88

Preparation of (2-chloro-4-(ethylsulfonyl)phenyl)(4,6-dichloro-5-(2-(trifluoromethoxy)phenyl)-1H-benzo[d]imidazol-2-yl)methanol

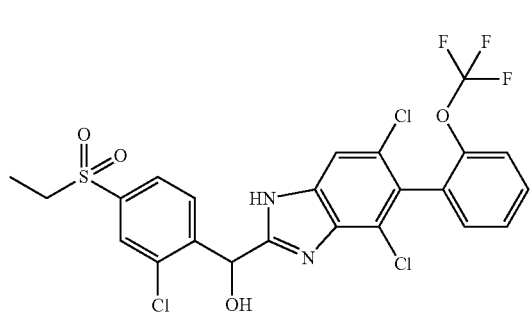

This compound was prepared by essential the similar method as of example 78 to afford the product as a white solid, MS (+) ES: 579 (M+H)$^+$.

Example 89

Preparation of 4,6-dichloro-2-(2-chloro-4-(ethylsulfonyl)benzyl)-5-(2-(difluoromethoxy)phenyl)-1H-benzo[d]imidazole

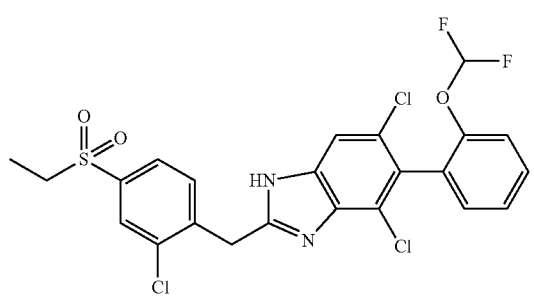

This compound was prepared by essential the similar method as of example 76 to afford the product as a white solid, MS (+) ES: 545 (M+H)$^+$.

Example 90

Preparation of 4,6-dichloro-2-(2-chloro-4-((cyclopropylmethyl)sulfonyl)benzyl)-5-(2-(trifluoromethoxy)phenyl)-1H-benzo[d]imidazole

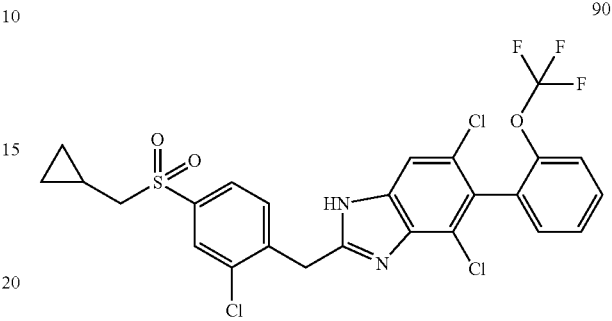

This compound was prepared by essential the similar method as of example 76 to afford the product as a white solid, MS (+) ES: 589 (M+H)$^+$.

Example 91

Preparation of 2-(2-chloro-4-((cyclopropylmethyl)sulfonyl)phenyl)-2-(4,6-dichloro-5-(2-(trifluoromethoxy)phenyl)-1H-benzo[d]imidazol-2-yl)ethanol

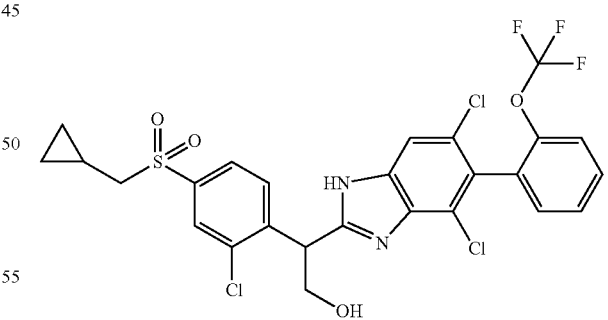

This compound was prepared by essential the similar method as of example 77 to afford the product as a white solid, MS (+) ES: 619 (M+H)$^+$.

Example 92

Preparation of (2-chloro-4-((cyclopropylmethyl)sulfonyl)phenyl)(4,6-dichloro-5-(2-(trifluoromethoxy)phenyl)-1H-benzo[d]imidazol-2-yl)methanol

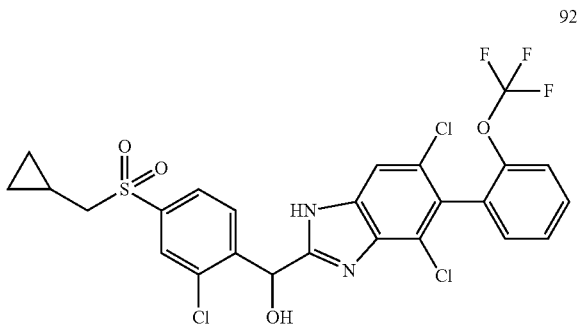 [SMILES: O=S(=O)(CC1CC1)c1ccc(C(O)c2nc3c(Cl)c(-c4ccccc4OC(F)(F)F)c(Cl)cc3[nH]2)c(Cl)c1]

This compound was prepared by essential the similar method as of example 78 to afford the product as a white solid, MS (+) ES: 605 (M+H)⁺.

Example 93

Preparation of 4,6-dichloro-5-(2-chlorophenyl)-2-(4-((cyclopropylmethyl)sulfonyl)benzyl)-1H-benzo[d]imidazole

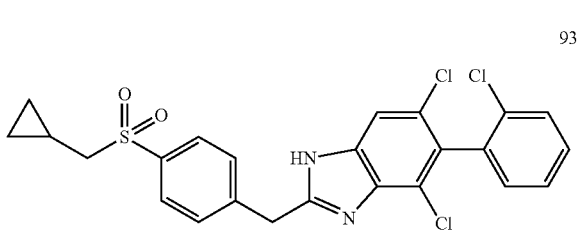 [SMILES: O=S(=O)(CC1CC1)c1ccc(Cc2nc3c(Cl)c(-c4ccccc4Cl)c(Cl)cc3[nH]2)cc1]

This compound was prepared by essential the similar method as of example 76 to afford the product as a white solid, MS (+) ES: 505 (M+H)⁺.

Example 94

Preparation of (4-((cyclopropylmethyl)sulfonyl)phenyl)(4,6-dichloro-5-(2-chlorophenyl)-1H-benzo[d]imidazol-2-yl)methanol

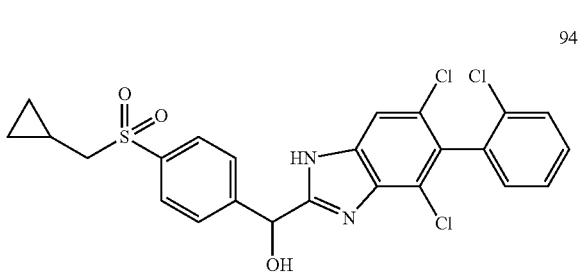 [SMILES: O=S(=O)(CC1CC1)c1ccc(C(O)c2nc3c(Cl)c(-c4ccccc4Cl)c(Cl)cc3[nH]2)cc1]

This compound was prepared by essential the similar method as of example 78 to afford the product as a white solid, MS (+) ES: 521 (M+H)⁺.

Example 95

Preparation of 2-(4,6-dichloro-2-(4-((cyclopropylmethyl)sulfonyl)benzyl)-1H-benzo[d]imidazol-5-yl)benzonitrile

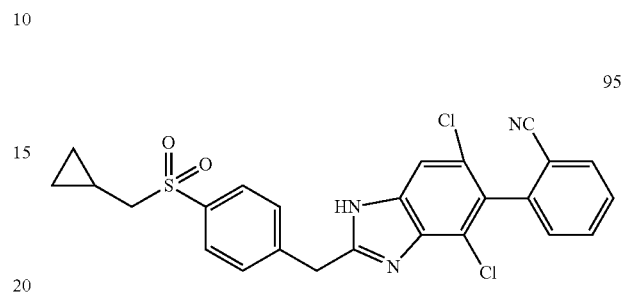

This compound was prepared by essential the similar method as of example 76 to afford the product as a white solid, MS (+) ES: 496 (M+H)⁺.

Example 96

Preparation of 2-(4,6-dichloro-2-(1-(4-((cyclopropylmethyl)sulfonyl)phenyl)-2-hydroxyethyl)-1H-benzo[d]imidazol-5-yl)benzonitrile

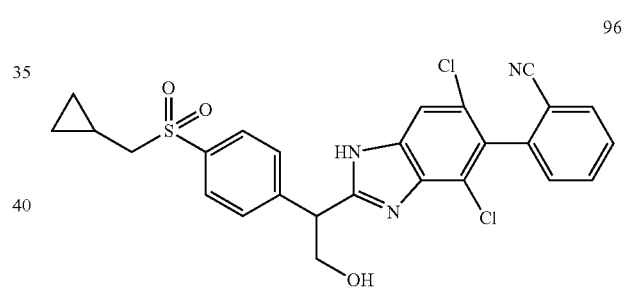

This compound was prepared by essential the similar method as of example 77 to afford the product as a white solid, MS (+) ES: 526 (M+H)⁺.

Example 97

Preparation of 2-(4,6-dichloro-2-((4-((cyclopropylmethyl)sulfonyl)phenyl)(hydroxy)methyl)-1H-benzo[d]imidazol-5-yl)benzonitrile

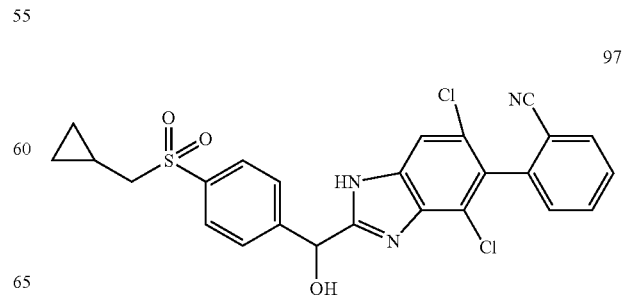

This compound was prepared by essential the similar method as of example 78 to afford the product as a white solid, MS (+) ES: 512 (M+H)+.

Example 98

Preparation of 4,6-dichloro-2-(4-((cyclopropylmethyl)sulfonyl)-2-fluorobenzyl)-5-(2-(difluoromethoxy)phenyl)-1H-benzo[d]imidazole

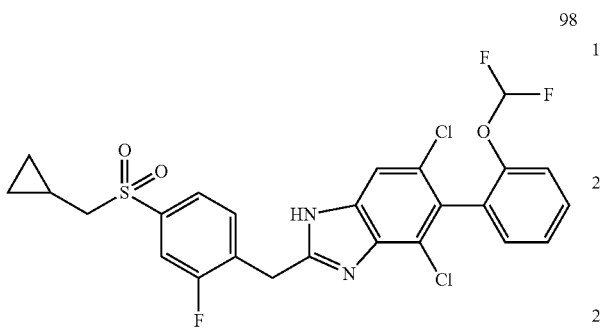

98

This compound was prepared by essential the similar method as of example 76 to afford the product as a white solid, MS (+) ES: 555 (M+H)+.

Example 99

Preparation of 2-(4-((cyclopropylmethyl)sulfonyl)-2-fluorophenyl)-2-(4,6-dichloro-5-(2-(difluoromethoxy)phenyl)-1H-benzo[d]imidazol-2-yl)ethanol

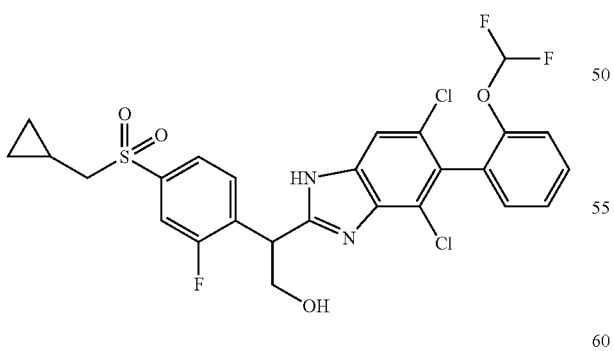

99

This compound was prepared by essential the similar method as of example 77 to afford the product as a white solid, MS (+) ES: 585 (M+H)+.

Example 100

Preparation of (4-((cyclopropylmethyl)sulfonyl)-2-fluorophenyl)(4,6-dichloro-5-(2-(difluoromethoxy)phenyl)-1H-benzo[d]imidazol-2-yl)methanol

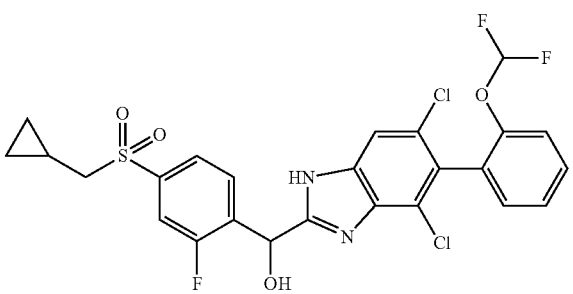

100

This compound was prepared by essential the similar method as of example 78 to afford the product as a white solid, MS (+) ES: 571 (M+H)+.

Example 101

Preparation of 4,6-dichloro-2-(2-chloro-4-(methylsulfonyl)benzyl)-5-(2-(trifluoromethoxy)phenyl)-1H-benzo[d]imidazole

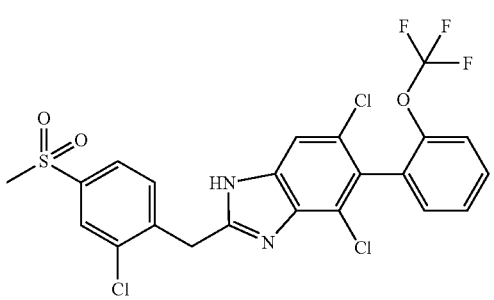

101

This compound was prepared by essential the similar method as of example 76 to afford the product as a white solid, MS (+) ES: 549 (M+H)+.

Example 102

Preparation of 2-(2-chloro-4-(methylsulfonyl)phenyl)-2-(4,6-dichloro-5-(2-(trifluoromethoxy)phenyl)-1H-benzo[d]imidazol-2-yl)ethanol

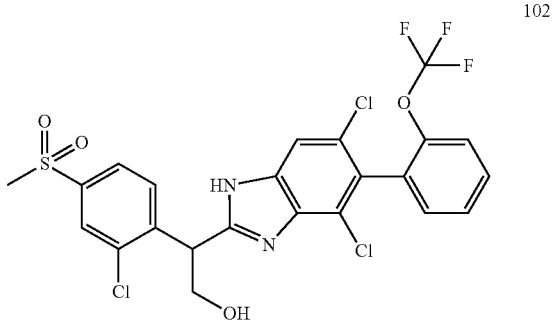 [SMILES: CS(=O)(=O)c1ccc(C(CO)c2nc3c(Cl)c(-c4ccccc4OC(F)(F)F)c(Cl)cc3[nH]2)c(Cl)c1]

102

This compound was prepared by essential the similar method as of example 77 to afford the product as a white solid, MS (+) ES: 579 (M+H)$^+$.

Example 103

Preparation of (2-chloro-4-(methylsulfonyl)phenyl)(4,6-dichloro-5-(2-(trifluoromethoxy)phenyl)-1H-benzo[d]imidazol-2-yl)methanol

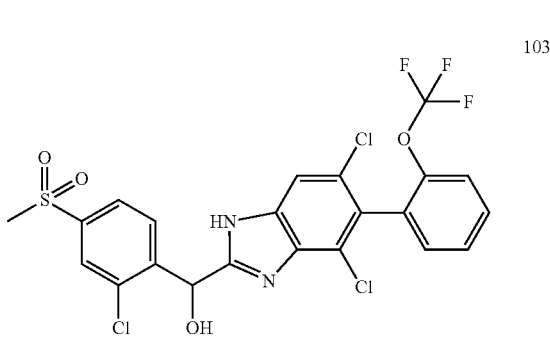 [SMILES: CS(=O)(=O)c1ccc(C(O)c2nc3c(Cl)c(-c4ccccc4OC(F)(F)F)c(Cl)cc3[nH]2)c(Cl)c1]

103

This compound was prepared by essential the similar method as of example 78 to afford the product as a white solid, MS (+) ES: 565 (M+H)$^+$.

Example 104

Preparation of 4,6-dichloro-2-(4-((isopropylsulfonyl)benzyl)-5-(2-(trifluoromethoxy)phenyl)-1H-benzo[d]imidazole

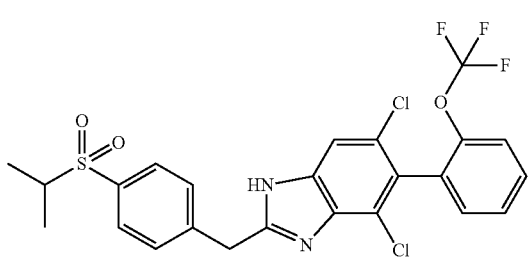

104

This compound was prepared by essential the similar method as of example 76 to afford the product as a white solid, MS (+) ES: 543 (M+H)$^+$.

Example 105

Preparation of 2-(4-((iso-propyl)sulfonyl)phenyl)-2-(4,6-dichloro-5-(2-(trifluoromethoxy)phenyl)-1H-benzo[d]imidazol-2-yl)ethanol

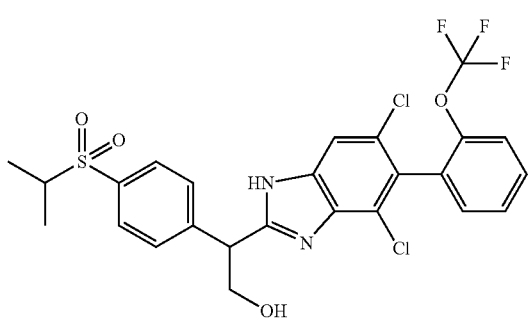

105

This compound was prepared by essential the similar method as of example 77 to afford the product as a white solid, MS (+) ES: 573 (M+H)$^+$.

Example 106

Preparation of (4-((iso-propyl)sulfonyl)phenyl)(4,6-dichloro-5-(2-(trifluoromethoxy)phenyl)-1H-benzo[d]imidazol-2-yl)methanol

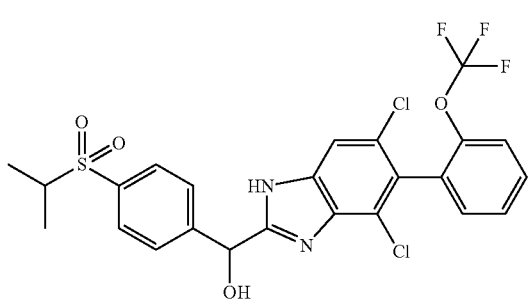

106

This compound was prepared by essential the similar method as of example 78 to afford the product as a white solid, MS (+) ES: 559 (M+H)$^+$.

Example 107

Preparation of 2-(4,6-dichloro-5-(2-(trifluoromethyl)phenyl)-1H-benzo[d]imidazol-2-yl)-2-(4-((isopropylsulfonyl)phenyl)ethanol

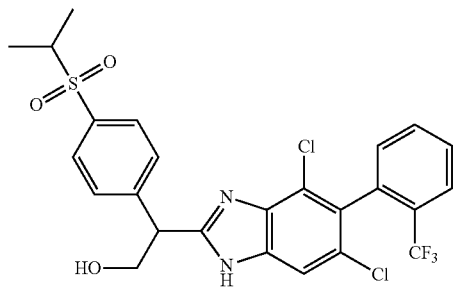

This compound was prepared by essential the same method as of example 4 to afford the product as a white solid, MS (+) ES: 557 (M+H)$^+$.

Example 108

Preparation of 2-(4-(ethylsulfonyl)benzyl)-4,6-difluoro-5-(2-(trifluoromethoxy)phenyl)-1H-benzo[d]imidazole

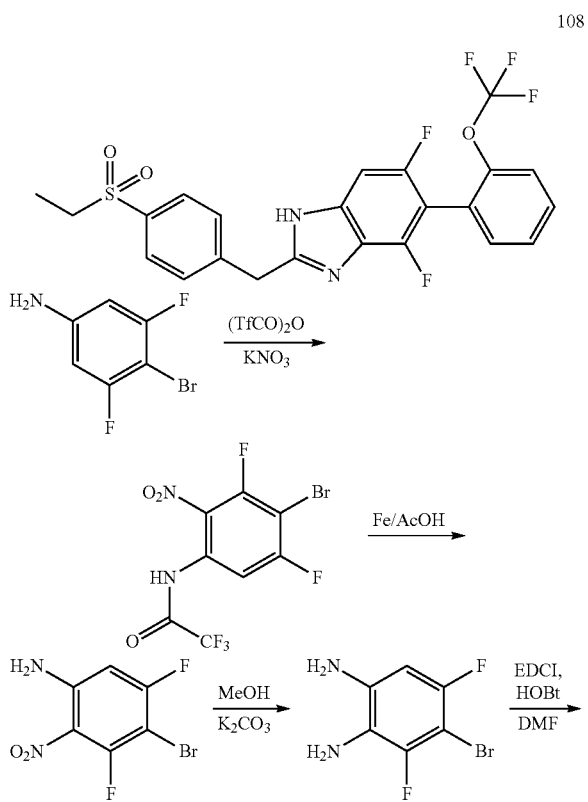

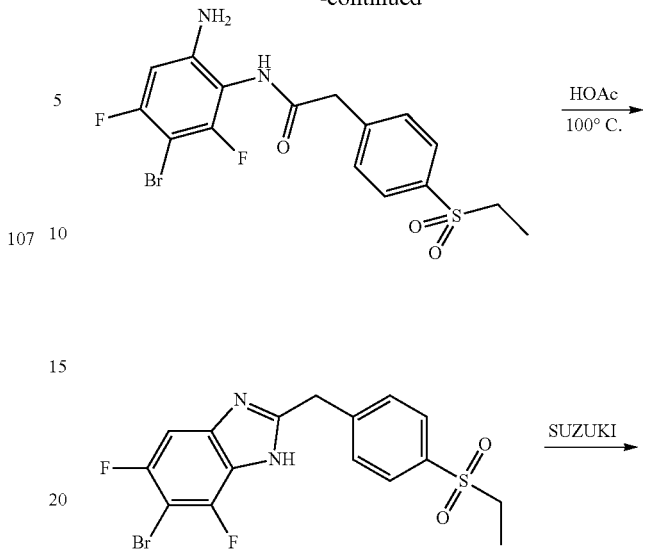

Step 1. Preparation of N-(4-bromo-3,5-difluoro-2-nitrophenyl)-2,2,2-trifluoroacetamide

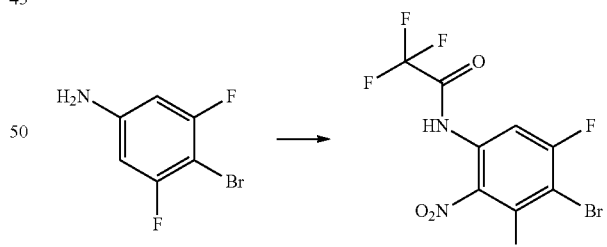

KNO$_3$ was added into a cooled (ice-water) solution of 4-bromo-3,5-difluoroaniline (2 g, 0.01 mol) in trifluoroacetic acid anhydride (10 ml) in one portion. Then the reaction mixture was allowed to worm-up to room temp with stirring overnight. The solvent was evaporated to dryness and the residue was treated with ethyl acetate, washed with sat. sodium bicarbonate solution, water, dried over MgSO$_4$. The solid was filtered off and the solvent was evaporated. The product was purified by flash chromatography with hexane/ethyl acetate to afford a off-white solid (1.8 g, 51%), MS (+) ES: 349 (M+H)$^+$.

Step 2. Preparation of 4-bromo-3,5-difluoro-2-nitroaniline

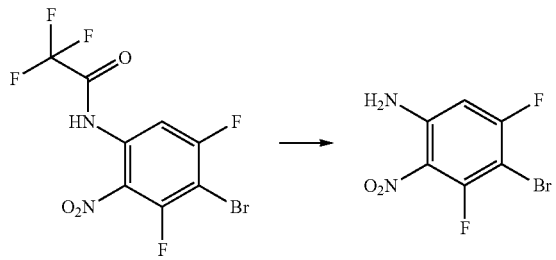 [SMILES: O=C(Nc1cc(F)c(Br)c(F)c1[N+](=O)[O-])C(F)(F)F ; Nc1cc(F)c(Br)c(F)c1[N+](=O)[O-]]

A mixture of K$_2$CO$_3$ (0.95 g, 6.9 mmol) and N-(4-bromo-3,5-difluoro-2-nitrophenyl)-2,2,2-trifluoroacetamide (2 g, 5.7 mmol) in methanol (20 ml) was heated to 50° C. for 3 h. After cooling, water (50 ml) was added and the precipitate was collected by filtration, washed thoroughly with water and dried in vacuum to afford the product as a off-white solid (1.4 g, 98%) which was used directly to the next step without purification, MS (+) ES: 253 (M+H)$^+$.

Step 3. Preparation of 4-bromo-3,5-difluorobenzene-1,2-diamine

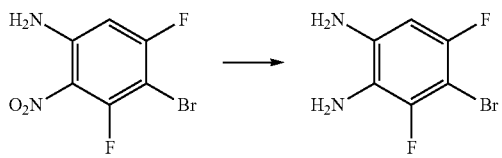 [SMILES: Nc1cc(F)c(Br)c(F)c1[N+](=O)[O-] ; Nc1cc(F)c(Br)c(F)c1N]

To a stirred mixture of AcOH (50 ml) and EtOH (100 ml) was suspended 4-bromo-3,5-difluoro-2-nitroaniline (2.5 g, 0.01 mol) and iron powder (4.4 g, 0.08 mol). The reaction was heated slowly to reflux and allowed to stir for 1 hour. The reaction was cooled to room temperature then diethyl ether (50 ml) and water (50 ml) was added. The solution was carefully neutralized by the addition of sodium carbonate. The combined organic extracts were washed with saturated NaHCO$_3$ (2×30 ml), H$_2$O (2×30 ml) and brine (1×30 ml) then dried over Na$_2$SO$_4$, filtered and concentrated to dryness under vacuum to yield the title compound as a white solid (1.6 g, 71%), MS (+) ES: 223 (M+H)$^+$.

Step 4. Preparation of N-(6-amino-3-bromo-2,4-difluorophenyl)-2-(4-(ethylsulfonyl)phenyl)acetamide

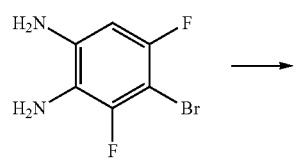

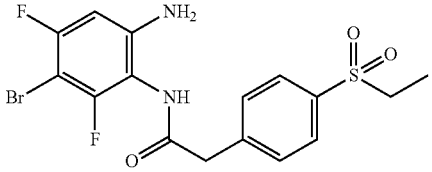

1-Ethyl-(3-(3-dimethylamino)propyl)-carbodiimide hydrochloride (2.0 g, 0.01 mol) and benzotriazol-1-ol (1.35 g, 0.01 mol) were added into a cooled solution (ice-water bath) of 4-bromo-3,5-difluorobenzene-1,2-diamine (2.2 g, 0.01 mol) and 2-(4-(ethylsulfonyl)phenyl)acetic acid (example 1, step 3, 2.28 g, 0.01 mol) in DMF (10 ml) portion-wise over 30 min. After the addition was completed, the mixture was stirred for 60 min at 0-5° C., and then was allowed to warm-up to room temp with stirring overnight. The mixture was partitioned between water (50 ml) and ethyl acetate (50 ml). The organic phase was separated and dried over MgSO$_4$, filtered. The solvent was evaporated under reduced pressure to leave a off-white solid that was purified by flash chromatography with hexane/ethyl acetate to afford the product as a solid (3.5 g, 80%), MS (+) ES: 433 (M+H)$^+$.

Step 5. Preparation of 5-bromo-2-(4-(ethylsulfonyl)benzyl)-4,6-difluoro-1H-benzo[d]imidazole

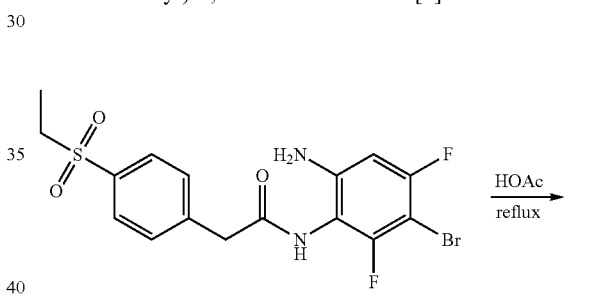

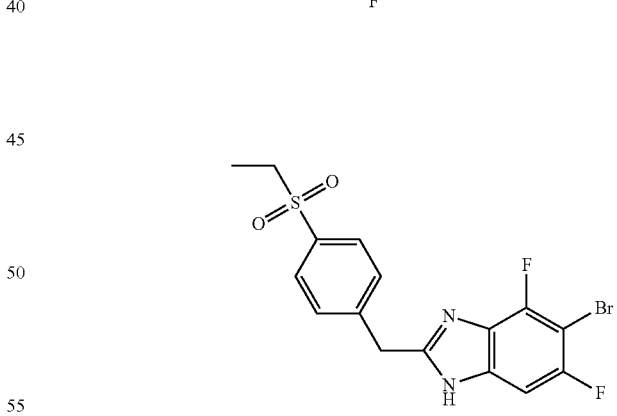

N-(6-amino-3-bromo-2,4-difluorophenyl)-2-(4-(ethylsulfonyl)phenyl)acetamide (step 4) (3.5 g, 0.0075 mol) was mixed with acetic acid (25 ml) and the mixture was heated to 100° C. for 4 hours, cooled. The solvent was evaporated under reduce pressure and the residue was dissolved in dichloromethane and washed with saturated sodium bicarbonate, dried over MgSO$_4$. This product was purified by flash chromatography with hexane/ethyl acetate to afford the product as a white solid (2.8 g, 85%), MS (+) ES: 415 (M+H)$^+$.

Step 6. Preparation of 2-(4-(ethylsulfonyl)benzyl)-4,6-difluoro-5-(2-(trifluoromethoxy)phenyl)-1H-benzo[d]imidazole

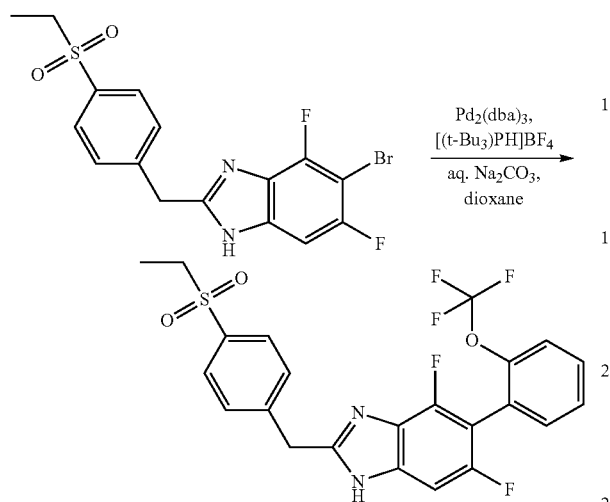

A mixture of 5-bromo-2-(4-(ethylsulfonyl)benzyl)-4,6-difluoro-1H-benzo[d]imidazole (42 mg, 0.1 mmol), 2-trifluoromethoxyphenylboronic acid (62 mg, 0.003 mol), tris-(dibenzylideneacetone)dipalladium(0) (6 mg), tri(tert-butyl)phosphonium tetrafluoroboronate (6 mg) and sodium carbonate (2M solution, 0.2 ml) in 1,4-dioxane (0.5 ml) was degassed, sealed and heated to 100° C. under Microwave irradiation for 1 h. The volatile solvents were removed under reduced pressure. The residue was directly loaded onto a flash solid cartridge and flash chromatographed with hexane/ethyl acetate to afford a white solid product (34 mg, 68% yield), MS (+) ES: 497 (M+H)+.

Example 109

Preparation of 2-(4,6-difluoro-5-(2-(trifluoromethoxy)phenyl)-1H-benzo[d]imidazol-2-yl)-2-(4-(ethylsulfonyl)phenyl)ethanol

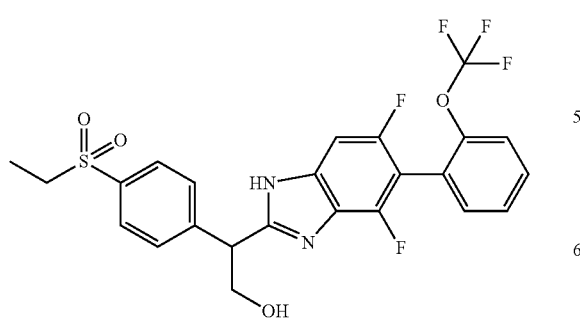

This compound was prepared by essential the similar method as of example 77 to afford the product as a white solid, MS (+) ES: 527 (M+H)+.

Example 110

Preparation of (4,6-difluoro-5-(2-(trifluoromethoxy)phenyl)-1H-benzo[d]imidazol-2-yl)(4-(ethylsulfonyl)phenyl)methanol

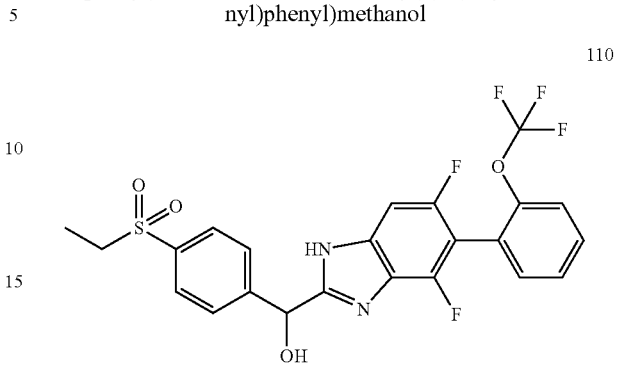

This compound was prepared by essential the similar method as of example 78 to afford the product as a white solid, MS (+) ES: 513 (M+H)+.

Example 111

Preparation of 2-(4-(ethylsulfonyl)benzyl)-4,6-difluoro-5-(2-(trifluoromethyl)phenyl)-1H-benzo[d]imidazole

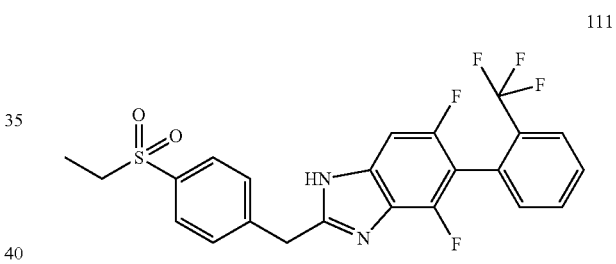

This compound was prepared by essential the same method as of example 91, except by using 2-trifluoromethylphenylboronic acid instead of 2-trifluoromethoxyphenylboronic acid in step 6, to afford the product as a white solid, MS (+) ES: 481 (M+H)+.

Example 112

Preparation of 2-(4,6-difluoro-5-(2-fluorophenyl)-1H-benzo[d]imidazol-2-yl)-2-(4-(ethylsulfonyl)phenyl)ethanol

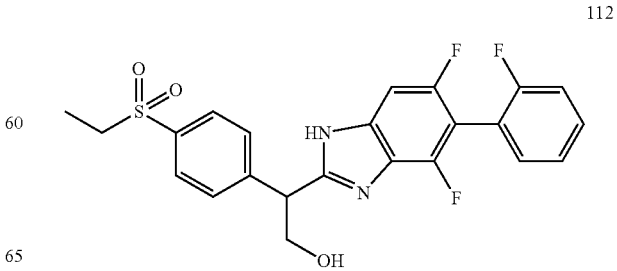

This compound was prepared by essential the similar method as of example 92 to afford the product as a white solid, MS (+) ES: 461 (M+H)⁺.

Example 113

Preparation of (4,6-difluoro-5-(2-methoxyphenyl)-1H-benzo[d]imidazol-2-yl)(4-(ethylsulfonyl)phenyl)methanol

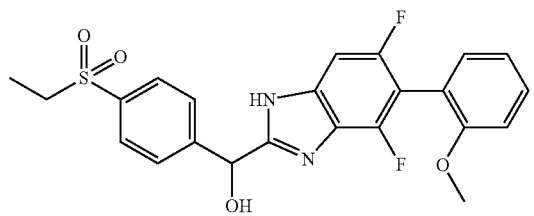

113

This compound was prepared by essential the similar method as of example 93 to afford the product as a white solid, MS (+) ES: 459 (M+H)⁺.

Example 114

Preparation of 2-(4,6-difluoro-5-phenyl-1H-benzo[d]imidazol-2-yl)-2-(4-(ethylsulfonyl)phenyl)ethanol

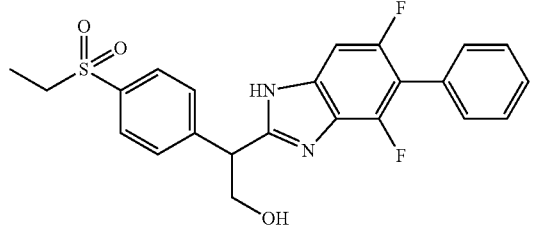

114

This compound was prepared by essential the similar method as of example 92 to afford the product as a white solid, MS (+) ES: 443 (M+H)⁺.

Example 115

Preparation of 2-(4-(ethylsulfonyl)benzyl)-4,6-dimethyl-5-(2-(trifluoromethyl)phenyl)-1H-benzo[d]imidazole

115

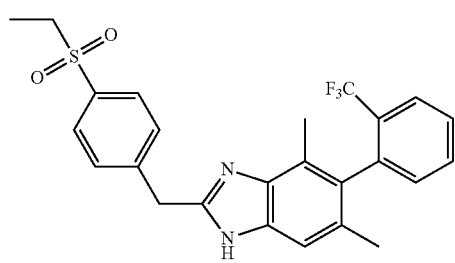

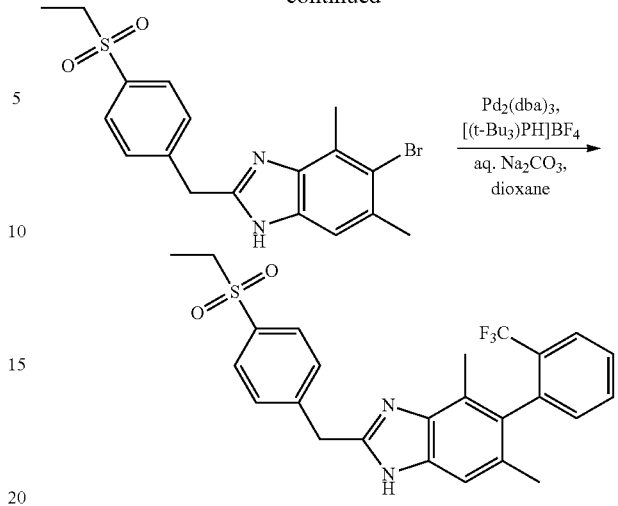

This compound was prepared by the same procedure as described in example 108 to afford the product as a white solid, MS (+) ES: 473 (M+H)⁺.

Example 116

Preparation of 2-(4,6-dimethyl-5-(2-(trifluoromethyl)phenyl)-1H-benzo[d]imidazol-2-yl)-2-(4-(ethylsulfonyl)phenyl)ethanol

116

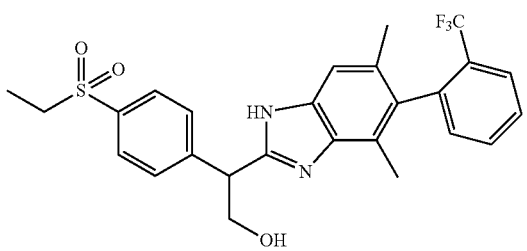

This compound was prepared by essential the similar method as of example 77 to afford the product as a white solid, MS (+) ES: 503 (M+H)⁺.

Example 117

Preparation of 2-(4-(ethylsulfonyl)phenyl)-2-(5-(2-methoxyphenyl)-4,6-dimethyl-1H-benzo[d]imidazol-2-yl)ethanol

117

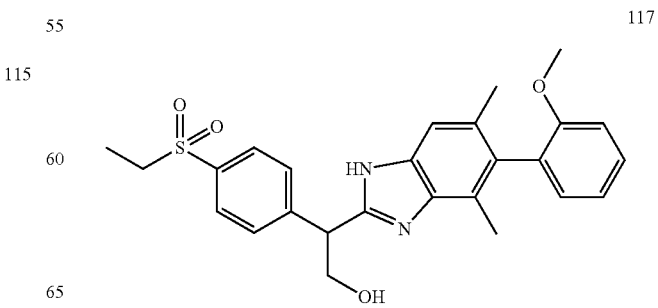

This compound was prepared by essential the similar method as of example 77 to afford the product as a white solid, MS (+) ES: 465 (M+H)⁺.

Example 118

Preparation of (4-(ethylsulfonyl)phenyl)(5-(2-methoxyphenyl)-4,6-dimethyl-1H-benzo[d]imidazol-2-yl)methanol

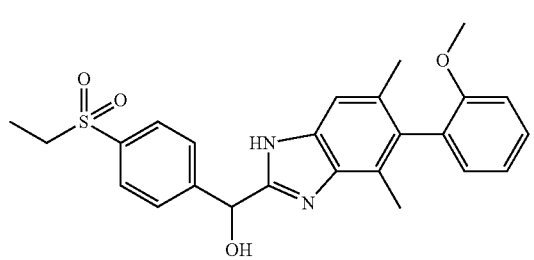

This compound was prepared by essential the similar method as of example 78 to afford the product as a white solid, MS (+) ES: 451 (M+H)⁺.

Example 119

Preparation of 2-(6-chloro-5-(2-(trifluoromethoxy)phenyl)-1H-benzo[d]imidazol-2-yl)-2-(4-(ethylsulfonyl)phenyl)ethanol

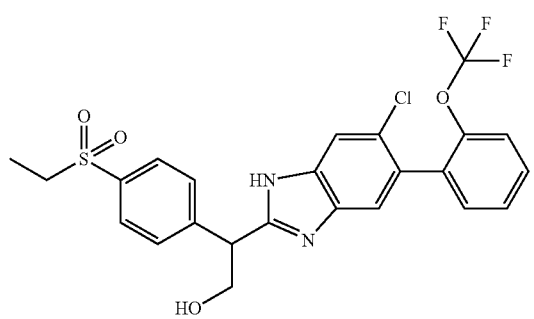

This compound was prepared by essential the similar method as of example 4 to afford the product as a white solid, MS (+) ES: 525 (M+H)⁺.

Example 120

Preparation of 2-(4-(ethylsulfonyl)phenyl)-2-(6-fluoro-5-(2-(trifluoromethoxy)phenyl)-1H-benzo[d]imidazol-2-yl)ethanol

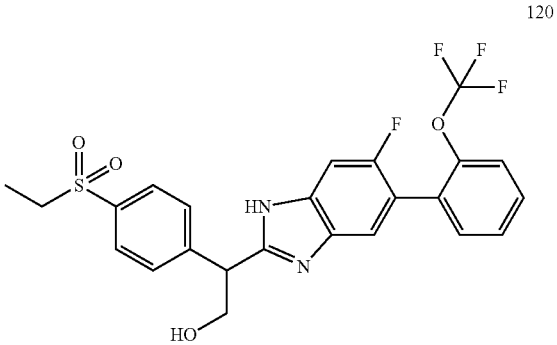 [SMILES: CCS(=O)(=O)c1ccc(C(CO)c2nc3cc(-c4ccccc4OC(F)(F)F)c(F)cc3[nH]2)cc1]

This compound was prepared by essential the similar method as of example 4 to afford the product as a white solid, MS (+) ES: 509 (M+H)⁺.

Example 121

Preparation of (4-(ethylsulfonyl)phenyl)(6-fluoro-5-(2-(trifluoromethoxy)phenyl)-1H-benzo[d]imidazol-2-yl)methanol

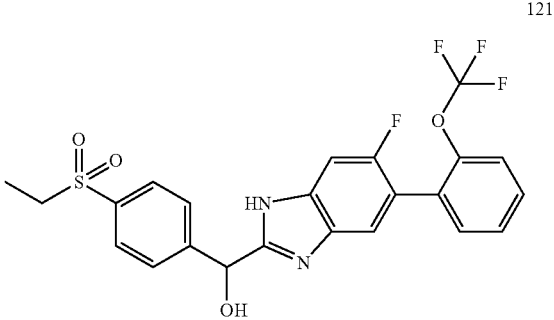 [SMILES: CCS(=O)(=O)c1ccc(C(O)c2nc3cc(-c4ccccc4OC(F)(F)F)c(F)cc3[nH]2)cc1]

This compound was prepared by essential the similar method as of example 2 to afford the product as a white solid, MS (+) ES: 495 (M+H)⁺.

Example 122

Preparation of N-cyclopropyl-4-((4,6-dichloro-5-(2-(trifluoromethoxy)phenyl)-1H-benzo[d]imidazol-2-yl)methyl)benzenesulfonamide

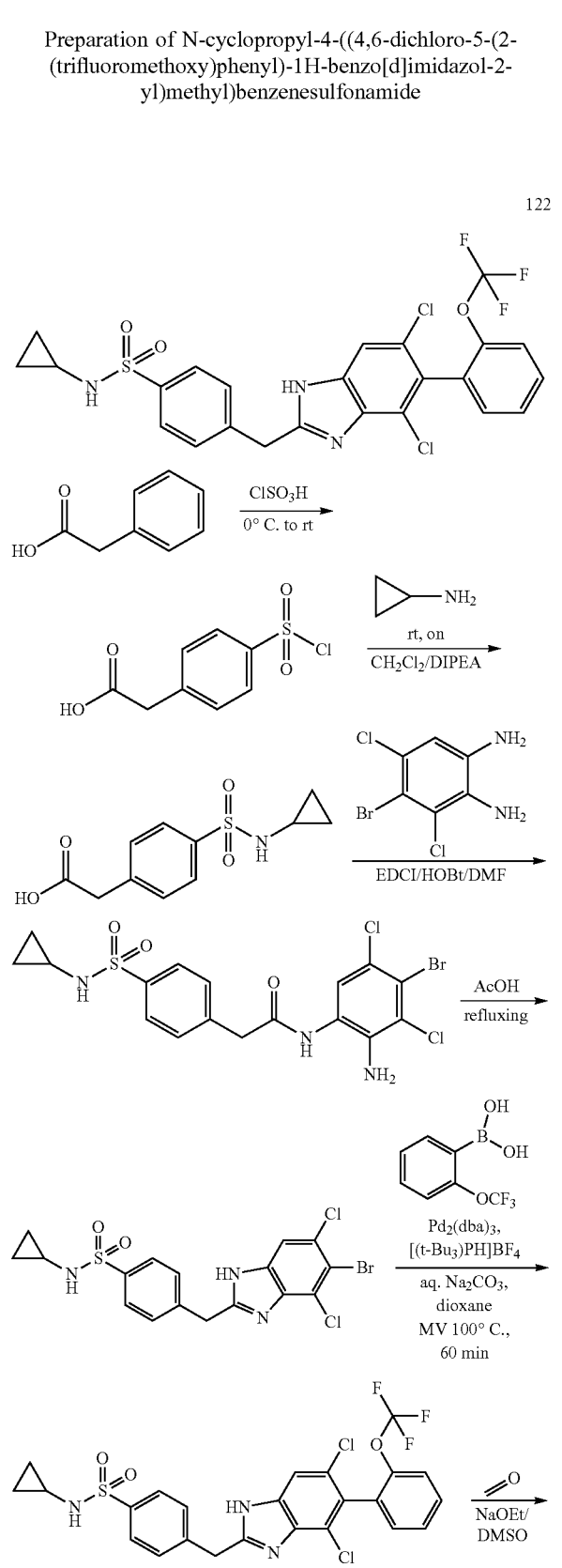

Step 1. Preparation of 2-(4-(chlorosulfonyl)phenyl)acetic acid

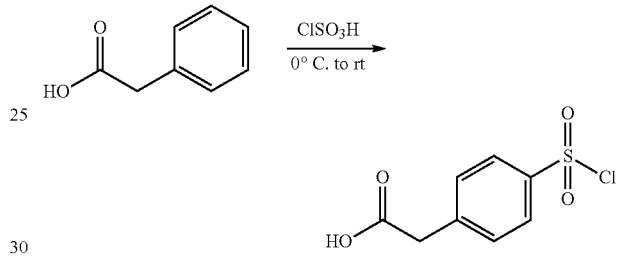

To chlorosulfonic acid (35 ml) was dropped 2-phenylacetic acid (5 g, 36.724 mmol) at 0° C., and the reaction mixture was stirred at 0° C. for 1 hour and then at room temperature over night. After the reaction was completed, the reaction mixture was slowly cooled to 0° C. and poured on to ice carefully. The resulting solid was extracted with ethyl acetate (3×10 mL) and dried over MaSO₄. The solid was filtered off and the solvent was evaporated under reduced pressure to leave a off-white solid to give the target compound (6.8 g, 78%), MS (+) ES: 235 (M+H)⁺.

Step 2. Preparation of 2-(4-(N-cyclopropylsulfamoyl)phenyl)acetic acid

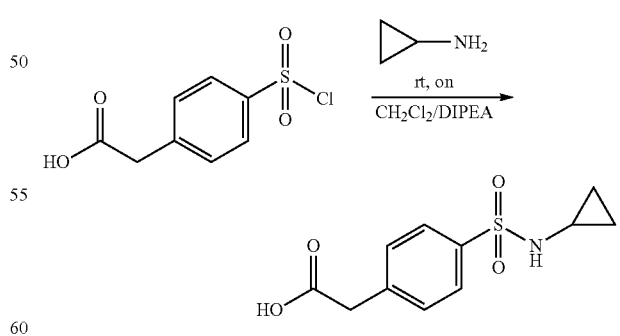

To a stirred solution of 2-(4-(chlorosulfonyl)phenyl)acetic acid (234 mg, 1.0 mmol) and i-Pr2NEt (0.52 mL, 2.86 mmol) in CH₂Cl₂ (10 mL) was added cyclopropylamine (0.076 mL, 1.1 mmol). The mixture was stirred overnight at rt, diluted with EtOAc (80 mL), washed with 5 percent aq HCl (2×10 mL) and brine (10 mL), and dried over Mg₂SO₄.

Removal of the solvent left the product as a gummy solid (180 mg, 70%). MS (+) ES: 256 (M+H)+.

Step 3. Preparation of N-(2-amino-4-bromo-3,5-dichlorophenyl)-2-(4-(N-cyclopropylsulfamoyl)phenyl)acetamide

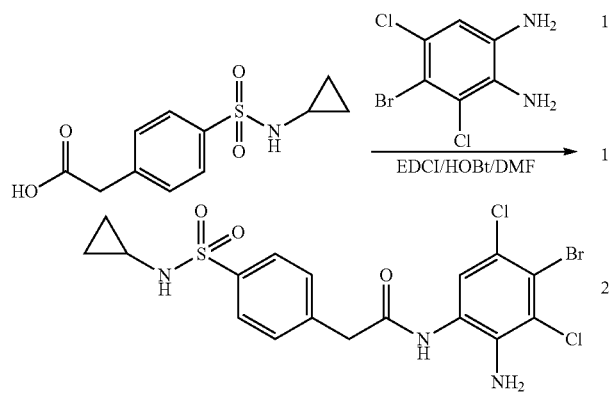

To 2-(4-(N-cyclopropylsulfamoyl)phenyl)acetic acid (255 mg, 1 mmol) in DMF was added 4-bromo-3,5-dichlorobenzene-1,2-diamine (255 mg, 1 mmol), HOBt (135 mg, 1 mmol), triethylamine (202 mg, 2 mmol), followed by the addition of EDCI (191 mg, 1 mmol) at 0° C. The mixture was stirred at 0° C. for 30 min and was allowed to reach room temperature and stirred over night. The reaction solution was partitioned between ethyl acetate (15 ml) and water (15 ml). The organic phase was separated and dried over MgSO4. Evaporation of the solvent to leave a tan solid that was directly used for the next step without purification (490 mg, 99% yield), MS (+) ES: 492 (M+H)+.

Step 4. Preparation of 4-((5-bromo-4,6-dichloro-1H-benzo[d]imidazol-2-yl)methyl)-N-ethylbenzenesulfonamide

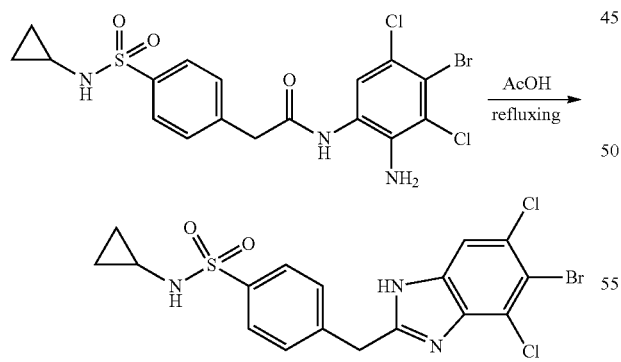

N-(2-amino-4-bromo-3,5-dichlorophenyl)-2-(4-(N-cyclopropylsulfamoyl)phenyl)acetamide (490 mg, 1 mmol) in acetic acid (5 ml) was heated to 80° C. for 3 h. After cooling, the solvent was evaporated to dryness and dissolved in ethyl acetate 910 ml), washed with saturated sodium bicarbonate solution and brine, dried over MgSO4. Evaporation of the ethyl acetate to leave a solid that was purified with flash chromatography with solvent hexane/ethyl acetate (containing 10% MeOH), to afford the product as a white solid 288 mg (60% yield), MS (+) ES: 474 (M+H)+.

Step 5. Preparation of N-cyclopropyl-4-((4,6-dichloro-5-(2-(trifluoromethoxy)phenyl)-1H-benzo[d]imidazol-2-yl)methyl)benzenesulfonamide (example 164)

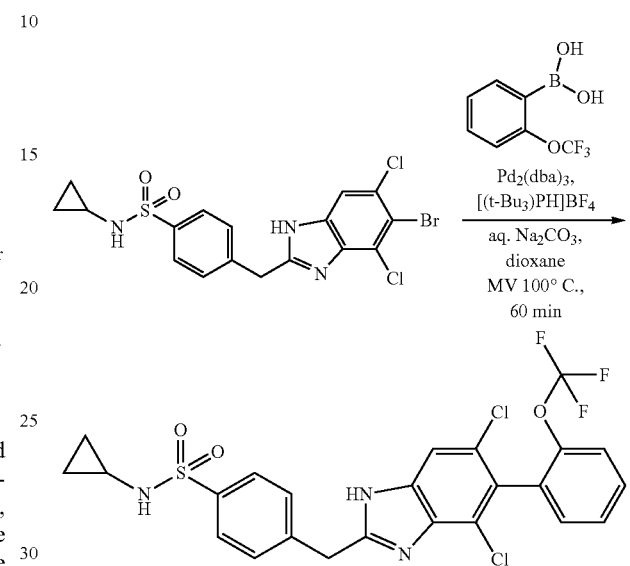

A mixture of 4-((5-bromo-4,6-dichloro-1H-benzo[d]imidazol-2-yl)methyl)-N-cyclopropylbenzenesulfinamide (step 4) (238 mg, 0.5 mmol), 2-trifluoromethoxyphenylboronic acid (308 mg, 1.5 mmol), tris-(dibenzylideneacetone)dipalladium(0) (24 mg), tri(tert-butyl)phosphonium tetrafluoroboronate (24 mg) and sodium carbonate (1 ml, 2M solution) in 1,4-dioxane (2.5 ml) was degassed, sealed and heated to 100° C. under Microwave irradiation for 1 h. The volatile solvents were removed under reduced pressure. The residue was directly loaded onto a ISCO solid cartridge and flashed with hexane/ethyl acetate to afford a white solid product 83 mg (30% yield), MS (+) ES: 556 (M+H)+.

Example 123

Preparation of N-cyclopropyl-4-(1-(4,6-dichloro-5-(2-(trifluoromethoxy)phenyl)-1H-benzo[d]imidazol-2-yl)-2-hydroxyethyl)benzenesulfonamide

123

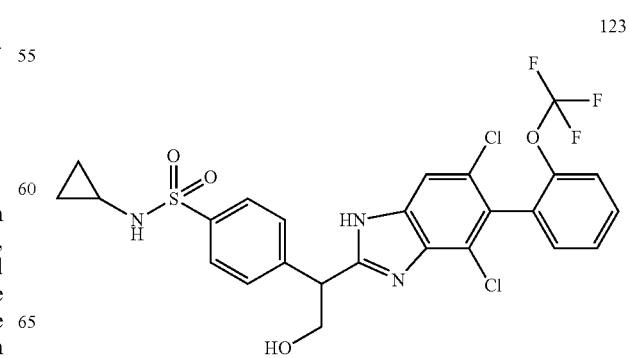

207

-continued

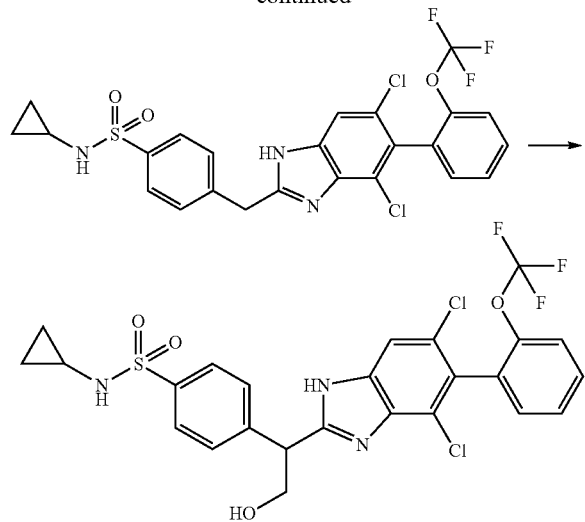

To N-cyclopropyl-4-((4,6-dichloro-5-(2-(trifluoromethoxy)phenyl)-1H-benzo[d]imidazol-2-yl)methyl)benzenesulfonamide (5.7 mg, 0.01 mmol) in DMSO (0.05 ml) was added paraformaldehyde (0.6 mg, 0.02 mmol), followed by the addition of sodium ethoxide (1.3 mg, 0.002 mmol) at room temperature. The reaction mixture was stirred for 60 min and by directly by Prep HPLC with elution system C to afford the product as a white solid 3.8 mg (66% yield), MS (+) ES: 586 (M+H)+.

Example 124

Preparation of 2-(6-chloro-5-(2-isopropoxyphenyl)-1H-benzo[d]imidazol-2-yl)-2-(4-((cyclopropylmethyl)sulfonyl)phenyl)ethanol

124

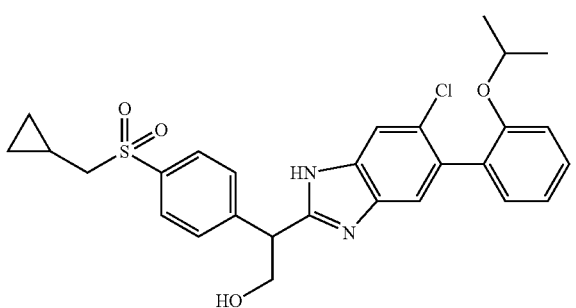

Step 1. Preparation of cyclopropylmethyl 2-(4-((cyclopropylmethyl)thio)phenyl)acetate

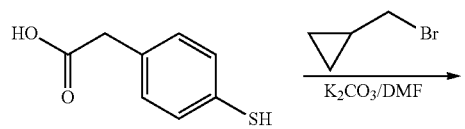

208

-continued

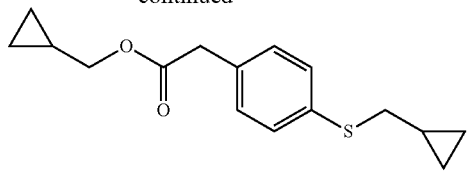

To a solution of (4-mercaptophenyl) acetic acid (3.4 g, 0.02 mol) in N, N-dimethylformamide (DMF) (20 ml) was added K₂CO₃ (11 g, 0.08 mol) and (bromomethyl)cyclopropane (8.1 g, 0.06 mol). The reaction mixture was stirred at RT. After 2.5 hours, the starting material was totally consumed. The reaction mixture was partitioned between ethyl acetate (30 ml) and water (30 ml). The organic phase was washed with water (30 ml) and brine (20 ml), dried over sodium sulphate, filtered, and concentrated to give the desired product. %), MS (+) ES: 277 (M+H)+.

Step 2. Preparation of cyclopropylmethyl 2-(4-((cyclopropylmethyl)sulfonyl)phenyl)acetate

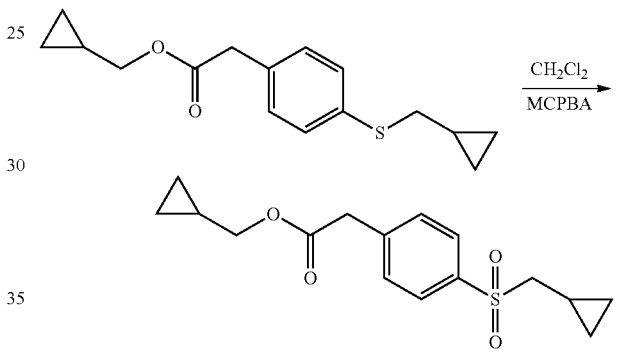

To a 250 ml round bottom flask, were added cyclopropylmethyl 2-(4-((cyclopropylmethyl)thio)phenyl)acetate (6.76 g, 0.0245 mol) and dichloromethane (82.5 ml). The reaction mixture was cooled to 0° C. To the same flask, m-chloroperbenzoic acid (12.6 g, 0.073 mol) was added at 0° C. The reaction mixture was stirred at room temperature for 12 h. The resulting suspension was filtered through a pad of celite. The filtrate was washed with water. The organic layer was separated, washed with saturated sodium bicarbonate solution three times, followed by brine and dried over anhydrous sodium sulfate. The solvent was evaporated under reduced pressure to get the crude product. The crude product was purified by flash column chromatography with hexane/ethyl acetate to get the title compound as oil, MS (+) ES: 309 (M+H)+.

Step 3. Preparation of 2-(4-((cyclopropylmethyl)sulfonyl)phenyl)acetic acid

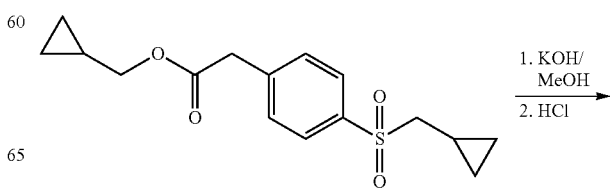

-continued

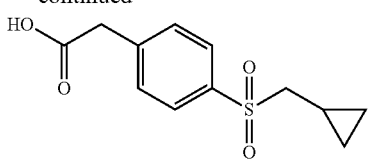

To a 50 mL round bottom flask, were added cyclopropylmethyl 2-(4-((cyclopropylmethyl)sulfonyl)phenyl)acetate (3.08 g, 0.01 mol) and ethanol (18 ml). To the same flask, a solution of sodium hydroxide in water (1.42 g, 0.0355 mol in 18 ml of water) was added. The reaction mixture was stirred at room temperature for 12 h. The volatiles were evaporated under reduced pressure. The residue was acidified with 1N HCl to pH 5.0 and extracted with ethyl acetate (15 ml×3). The organic layer was separated and combined, washed with brine and dried over sodium sulfate. The solvent was evaporated under reduced pressure to get the title compound as a colorless oil that was solidified upon standing (85%). MS (+) ES: 255 (M+H)+.

Step 4. Preparation of N-(2-amino-5-bromo-4-chlorophenyl)-2-(4-((cyclopropylmethyl)sulfonyl)phenyl)acetamide

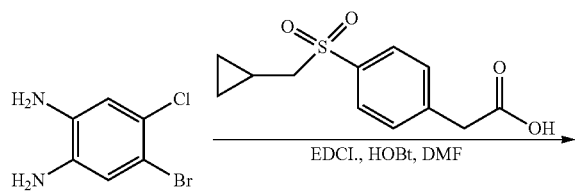

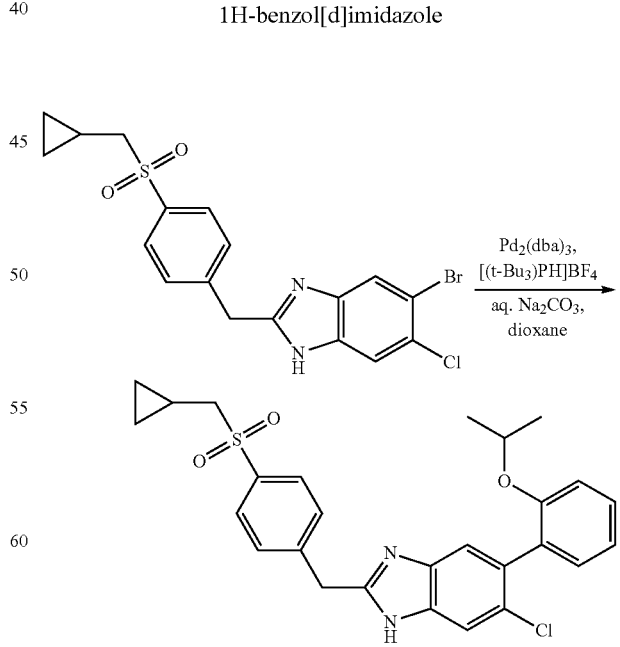

1-Ethyl-(3-(3-dimethylamino)propyl)-carbodiimide hydrochloride (2.0 g, 0.01 mol) and hydroxybenzotriazol-1-ol (1.35 g, 0.01 mol) were added into a cooled solution (ice water bath) of 4-bromo-5-chlorobenzene-1,2-diamine (2.21 g, 0.01 mol) and 2-(4-((cyclopropylmethyl)sulfonyl)phenyl) acetic acid (step 3, 2.54 g, 0.01 mol) in DMF (10 ml), portion wise over 30 min. After the addition was completed, the mixture was stirred for 60 min and was allowed to warm-up to room temp, stirred overnight. The mixture was partitioned between water (50 ml) and ethyl acetate (50 ml). The organic phase was separated and dried over MgSO4, filtered. The solvent was evaporated under reduced pressure to leave an off-white solid which was purified by flash chromatography with hexane/ethyl acetate to afford the product as an off-white solid (75%), MS (+) ES: 457 (M+H)+.

Step 5. Preparation of 5-bromo-6-chloro-2-(4-((cyclopropylmethyl)sulfonyl)benzyl)-1H-benzo[d]imidazole

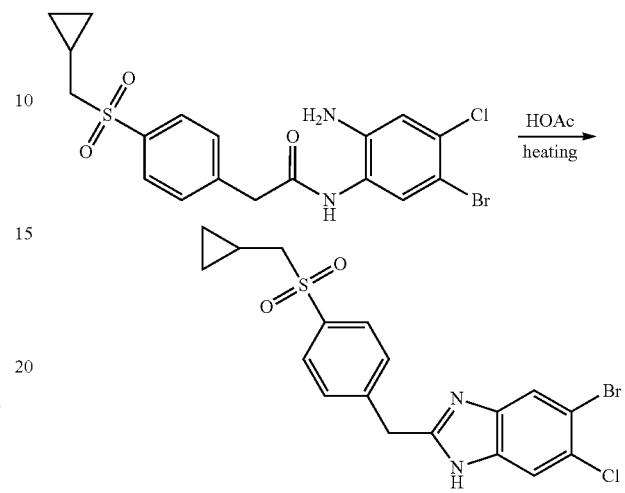

N-(2-amino-5-bromo-4-chlorophenyl)-2-(4-((cyclopropylmethyl)sulfonyl)phenyl)acetamide (step 4) (3.42 g, 7.5 mmol) was mixed with acetic acid (25 ml) and the mixture was heated to 80° C. for 4 hours, cooled. The solvent was evaporated under reduce pressure and the residue was dissolved in EtOAc and washed with saturated sodium bicarbonate, dried over MgSO4. This product was purified by flash chromatography with hexane/ethyl acetate to afford the product as a white solid 2.6 g (80%), MS (+) ES: 439 (M+H)+.

Step 6. Preparation of 6-chloro-2-(4-((cyclopropylmethyl)sulfonyl)benzyl)-5-(2-isopropoxyphenyl)-1H-benzol[d]imidazole A mixture of 5-bromo-6-chloro-2-(4-((cyclopropylmethyl)sulfonyl)benzyl)-1H-benzo[d]imidazole (step 5) (439 mg, 1 mmol), (2-isopropoxyphenyl)boronic acid (495 mg, 3 mmol), tris-(dibenzylideneacetone)dipalladium(0) (60 mg), tri(tert-butyl)phosphonium tetrafluoroboronate (60 mg) and sodium carbonate (2 ml, 2M solution) in 1,4-dioxane (8 ml) was degassed, sealed and heated to 100° C. under Microwave irradiation for 60 min. The volatile solvents were removed under reduced pressure. The residue was directly taken into DCM and loaded onto an ISCO solid cartridge and flashed with hexane/ethyl acetate to afford a white solid product 355 mg (72% yield), MS (+) ES: 495 (M+H)$^+$.

Step 7. Preparation of 2-(6-chloro-5-(2-isopropoxyphenyl)-1H-benzo[d]imidazol-2-yl)-2-(4-((cyclopropylmethyl)sulfonyl)phenyl)ethanol

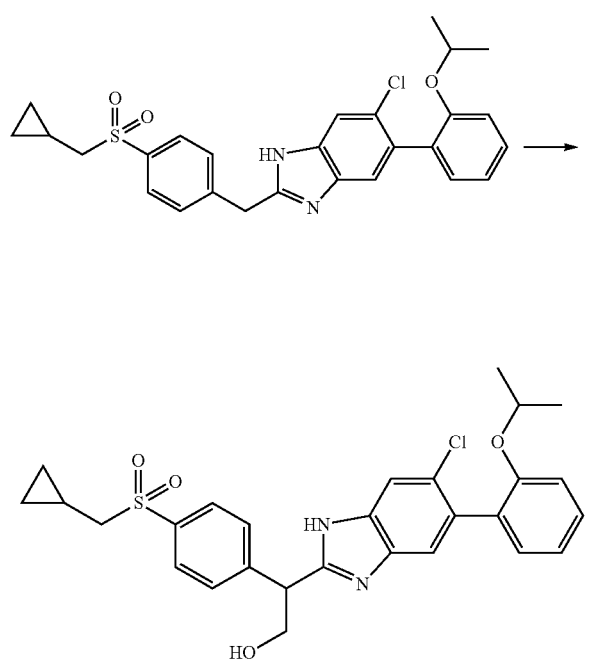 [SMILES: CC(C)Oc1ccccc1-c1cc2nc(Cc3ccc(S(=O)(=O)CC4CC4)cc3)[nH]c2cc1Cl ; CC(C)Oc1ccccc1-c1cc2nc(C(CO)c3ccc(S(=O)(=O)CC4CC4)cc3)[nH]c2cc1Cl]

6-chloro-2-(4-((cyclopropylmethyl)sulfonyl)benzyl)-5-(2-isopropoxyphenyl)-1H-benzo[d]imidazole (49.5 mg, 0.1 mmol) was dissolved in 1 ml anhydrous DMSO, paraformylaldehyde (6 mg, 0.2 mmol) wan added with stirring, followed by the addition of powder sodium ethoxide (12 mg, 0.2 mmol). The mixture was stirred at room temp for 60 min. (Check LCMS for completion). The mixture then was treated with EtOAc (10 ml) and washed with sat. NH$_4$Cl solution, followed by water. The organic phase was dried with MgSO$_4$. The product was purified by flash chromatography with hexane/EtOAc (10% 2N NH3 in MeOH) to afford a white solid 37 mg (70% yield example 124). MS (+) ES: 525 (M+H)$^+$.

Examples 124-1 and 124-2

Preparation of (S)-2-(6-chloro-5-(2-isopropoxyphenyl)-1H-benzo[d]imidazol-2-yl)-2-(4-((cyclopropylmethyl)sulfonyl)phenyl)ethanol (example 124-1) and (R)-2-(6-chloro-5-(2-isopropoxyphenyl)-1H-benzo[d]imidazol-2-yl)-2-(4-((cyclopropylmethyl)sulfonyl)phenyl)ethanol (example 124-2)

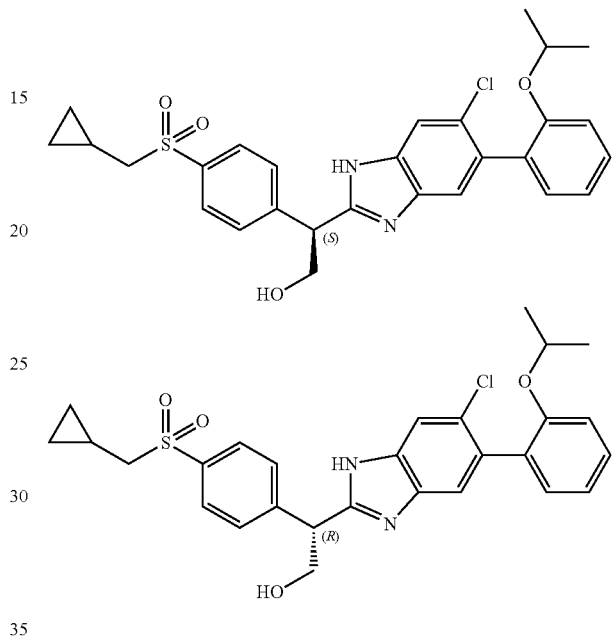

Example 124 was separated chirally (separation conditions: Dasail 20*200 mm, 5 um; mobile phase: ethanol/hexane=1:4 (v/v); flow rate: 30 mL/min), The corresponding fractions were collected and concentrated under reduced pressure to obtain the title compounds (400 mg, 400 mg).

Single configuration compound (the shorter retention time)

MS (+) ES: 525 (M+H)$^+$

Chiral HPLC analysis: retention time 6.296 minutes, chiral purity: 100% (chromatographic column: OZ Phenomenex Lux Cellulose-2 150*4.6 mm, 5 um; mobile phase: ethanol/hexane=3:2 (v/v));

$^1$H NMR (400 mHz, DMSO-d$_6$): 12.53 (s, 1H), 7.87 (d, 8.0 Hz, 2H), 7.71 (s, 0.6H) (due to benzoimidazole taumeriazation), 7.67 (d, 12.0 Hz, 2H), 7.57 (s, 0.4H), 7.43 (s, 0.48H), 7.34 (t, 8.0 Hz, 1H), 7.31 (s, 0.44H), 7.16-7.11 (m, 1H), 7.08 (d, 8.0 Hz, 1H), 6.98 (t, 8.0 Hz, 1H), 5.16 (t, 4.0 Hz, 1H), 4.59-4.43 (m, 2H), 4.29-4.15 (m, 1H), 4.06-3.95 (m, 1H), 3.23 (d, 8.0 Hz, 2H), 1.12 (d, 4.0 Hz, 6H), 0.89-0.75 (m, 1H), 0.49-0.39 (m, 2H), 0.18-0.09 (m, 2H).

Single configuration compound (the longer retention time)

MS (+) ES: 525 (M+H)$^+$

Chiral HPLC analysis: retention time 11.837 minutes, chiral purity: 98.875% (chromatographic column: OZ Phenomenex Lux Cellulose-2 150*4.6 mm, 5 um; mobile phase: ethanol/hexane=3:2 (v/v);

$^1$H NMR (400 mHz, DMSO-d$_6$): 12.53 (s, 1H), 7.87 (d, 8.0 Hz, 2H), 7.71 (s, 0.6H) (due to benzoimidazole taumeriazation), 7.67 (d, 12.0 Hz, 2H), 7.57 (s, 0.4H), 7.43 (s, 0.48H), 7.34 (t, 8.0 Hz, 1H), 7.31 (s, 0.44H), 7.16-7.11 (m, 1H), 7.08 (d, 8.0 Hz, 1H), 6.98 (t, 8.0 Hz, 1H), 5.16 (t, 4.0

Hz, 1H), 4.59-4.43 (m, 2H), 4.29-4.15 (m, 1H), 4.06-3.95 (m, 1H), 3.23 (d, 8.0 Hz, 2H), 1.12 (d, 4.0 Hz, 6H), 0.89-0.75 (m, 1H), 0.49-0.39 (m, 2H), 0.18-0.09 (m, 2H).

Example 125

Preparation of 4,6-dichloro-5-(4,4-difluoropiperidin-1-yl)-2-(4-(ethylsulfonyl)benzyl)-1H-benzo[d]imidazole

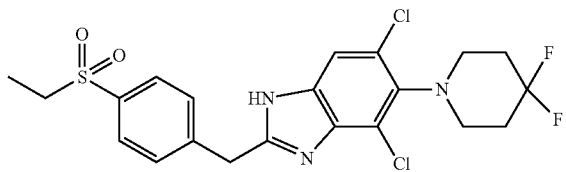

Step 1. Preparation of 2,4-dichloro-3-(4,4-difluoropiperidin-1-yl)-6-nitroaniline

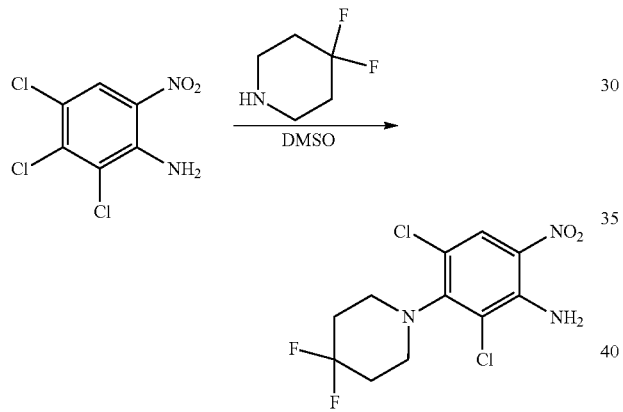

The mixture of 2,3,4-trichloro-6-nitroaniline (241 mg, 1 mmol), 4,4-difluoropiperidine (190 mg, 1.2 mmol) and DIEA (390 mg, 3 mmol) in 8 ml DMSO was heated in a sealed vessel to 108° C. over night. After cooling, the reaction mixture was partitioned between water (30 ml) and ethyl acetate (10 ml). The organic phase was separated and dried over MgSO$_4$. The solid was filtered off and the solvent was evaporated, the residue was directly flashed with hexane/ethyl acetate to afford a yellow solid 280 mg (yield 85%), MS (+) ES: 326 (M+H)$^+$.

Step 2. Preparation of 3,5-dichloro-4-(4,4-difluoropiperidin-1-yl)benzene-1,2-diamine

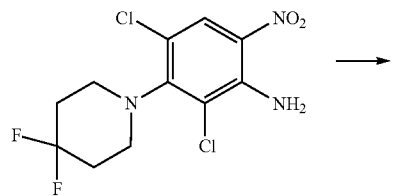

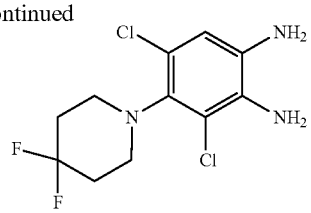

The mixture of 2,4-dichloro-3-(4,4-difluoropiperidin-1-yl)-6-nitroaniline (200 mg, 0.68 mmol), and Pd/C (20 mg) in 15 ml methanol was hydrogenated with a nitrogen balloon for 2 h. The catalyst was filtered off and the solvent was evaporated to leave tan residue that was directly flashed with hexane/ethyl acetate to afford an oil product 120 mg (yield 66%), (MS (+) ES: 296 (M+H)$^+$.

Step 3. Preparation of 4,6-dichloro-5-(4,4-difluoropiperidin-1-yl)-2-(4-(ethylsulfonyl)benzyl)-1H-benzo[d]imidazole

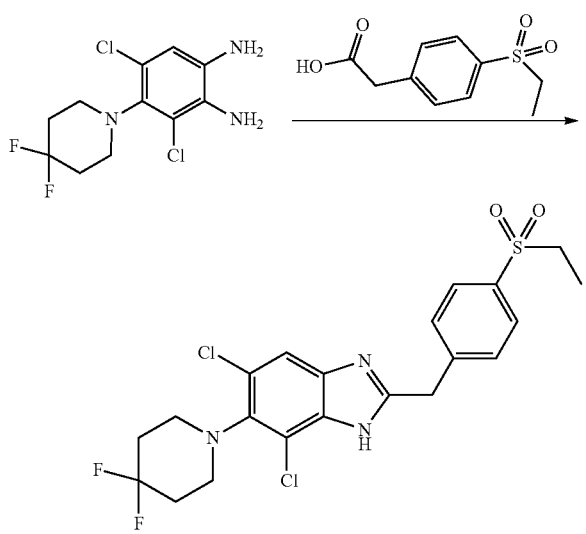

1-Ethyl-(3-(3-dimethylamino)propyl)-carbodiimide hydrochloride (20 mg, 0.1 mmol) and hydroxybenzotriazol-1-ol (13.5 mg, 0.1 mmol) were added into a cooled solution (ice water bath) of 3,5-dichloro-4-(4,4-difluoropiperidin-1-yl)benzene-1,2-diamine (29.6 mg, 0.1 mmol) and 2-(4-(ethylsulfonyl)phenyl)acetic acid (22.8 mg, 0.01 mmol) in DMF (1 ml). After the addition was completed, the mixture was stirred and allowed to warm up to room temp, stirred overnight. The mixture was partitioned between water (50 ml) and ethyl acetate (50 ml). The organic phase was separated and dried over MgSO$_4$, filtered. The solvent was evaporated under reduced pressure to leave an off-white solid which was mixed with acetic acid (1 ml). The mixture was heated to 80° C. for 2 hours, cooled. The solvent was evaporated under reduce pressure and the residue was dissolved in EtOAc and washed with saturated sodium bicarbonate, dried over MgSO$_4$. This product was purified by flash chromatography with hexane/ethyl acetate to afford the product as a white solid 26 mg (60%), MS (+) ES: 488 (M+H)$^+$.

Example 126

Preparation of 2-(5,7-dichloro-6-(4,4-difluoropiperidin-1-yl)-1H-benzo[d]imidazol-2-yl)-2-(4-(ethylsulfonyl)phenyl)ethanol

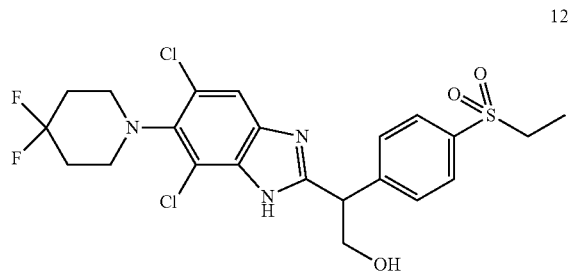

126

Step 1. Preparation of 2,3,4-Trichloro-6-nitrobenzenamine

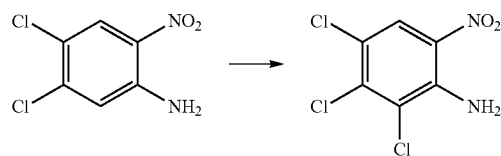 [SMILES: Nc1cc(Cl)c(Cl)cc1[N+](=O)[O-] ; Nc1c([N+](=O)[O-])cc(Cl)c(Cl)c1Cl]

A suspension of 4,5-dichloro-2-nitrobenzenamine (30 g, 145 mmol) and N-chlorosuccinimide (24.2 g, 181.2 mmol) in 250 mL of DMF was stirred at 100° C. for 2 hours. It was cooled to room temperature, and poured into ice-cooled water (1 mL). The precipitate formed was collected by filtration. It was dissolved in dichloromethane and washed with water. The organic layer was concentrated to get 2,3,4-trichloro-6-nitrobenzenamine (34.2 g, 97.5% yield) as a brightly yellow solid Step 2. Preparation of 2,4-dichloro-3-(4,4-difluoropiperidin-1-yl)-6-nitrobenzenamine

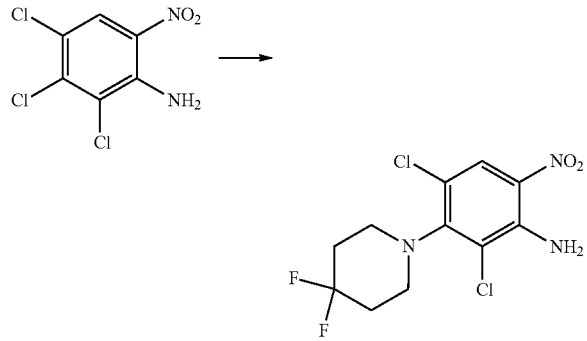

A solution of 2,3,4-trichloro-6-nitrobenzenamine (5 g, 20.7 mmol), N,N-diisopropyl ethylamine (11.8 mL, 62.1 mmol), and 4,4-difluoropiperidine (3.8 g, 31.06 mmol) in 20 mL of DMF was stirred at 105° C. over the weekend. The reaction solution was absorbed onto 20 g of silica gel, loaded to a silica gel column, and eluted with 30% ethyl acetate in hexanes, to get the 2,4-dichloro-3-(4,4-difluoropiperidin-1-yl)-6-nitrobenzenamine (4.72 g, 70.0% yield) as a brightly yellow solid MS (+) ES: 326 (M+H)+.

Step 3. Preparation of 3,5-Dichloro-4-(4,4-difluoropiperidin-1-yl)benzene-1,2-diamine

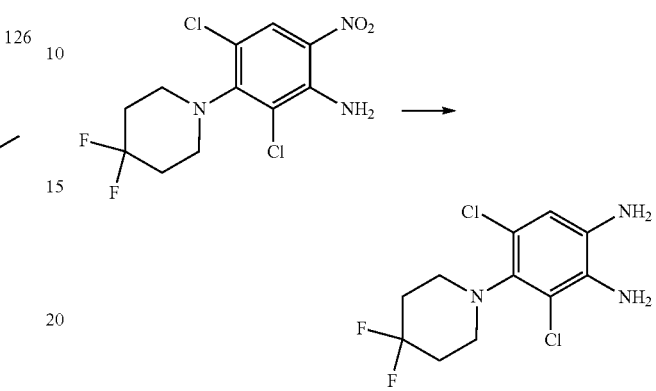

To a solution of 2,4-dichloro-3-(4,4-difluoropiperidin-1-yl)-6-nitrobenzenamine (3.5 g, 10.8 mmol) in 30 mL of THF was added zinc powder (7 g) and concentrated hydrochloric acid (2 mL). The reaction mixture was stirred at room temperature overnight. It was filtered. The filtrate was concentrated, and purified on a silica gel column, eluting with ethyl acetate, to get 3,5-dichloro-4-(4,4-difluoropiperidin-1-yl)benzene-1,2-diamine (1.85 g, 57.8% yield) as a pale solid MS (+) ES: 296 (M+H)+.

Step 4. Preparation of N-(6-amino-2,4-dichloro-3-(4,4-difluoropiperidin-1-yl)phenyl)-2-(4-(ethylsulfonyl)phenyl)acetamide and N-(2-amino-3,5-dichloro-4-(4,4-difluoropiperidin-1-yl)phenyl)-2-(4-(ethylsulfonyl)phenyl)acetamide

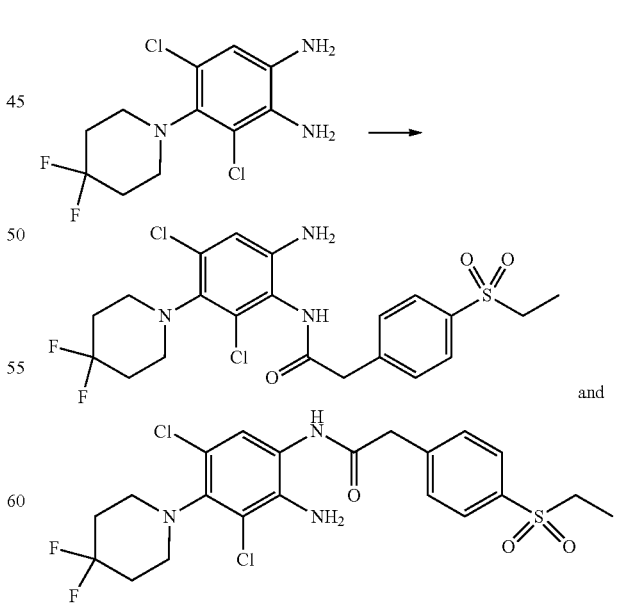

and

To a solution of 3,5-dichloro-4-(4,4-difluoropiperidin-1-yl)benzene-1,2-diamine (350 mg, 1.18 mmol) and 2-(4-

(ethylsulfonyl)phenyl)acetic acid (225 mg, 0.99 mmol) in dichloromethane (10 mL) was added EDCI (285 mg, 1.49 mmol) and HBTU (565 mg, 1.49 mmol). The reaction solution was stirred at room temperature for 2 hours. It was absorbed onto 5 g of silica gel, and loaded onto a silica gel column. The column was eluted with 45% of ethyl acetate in hexanes to get a mixture of N-(2-amino-3,5-dichloro-4-(4,4-difluoropiperidin-1-yl)phenyl)-2-(4-(ethylsulfonyl)phenyl)acetamide and N-(6-amino-2,4-dichloro-3-(4,4-difluoropiperidin-1-yl)phenyl)-2-(4-(ethylsulfonyl)phenyl)acetamide (410 mg, 81.8% yield) as a white solid MS (+) ES: 506 (M+H)+.

Step 5. Preparation of 2-(4-(Ethylsulfonyl)benzyl)-4,6-dichloro-5-(4,4-difluoropiperidin-1-yl)-1H-benzo[d]imidazole

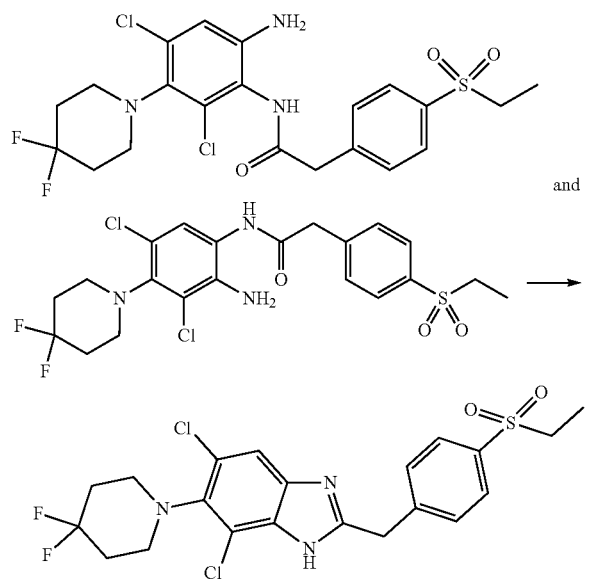

The mixture of N-(2-amino-3,5-dichloro-4-(4,4-difluoropiperidin-1-yl)phenyl)-2-(4-(ethylsulfonyl)phenyl)acetamide and N-(6-amino-2,4-dichloro-3-(4,4-difluoropiperidin-1-yl)phenyl)-2-(4-(ethylsulfonyl)phenyl)acetamide (410 mg) obtained from the previous step was treated with 15 mL of glacial acetic acid at 80° C. for 2 hours. It was concentrated, and purified on a silica gel column, eluting with 60% ethyl acetate in hexanes, to get 2-(4-(ethylsulfonyl)benzyl)-4,6-dichloro-5-(4,4-difluoropiperidin-1-yl)-1H-benzo[d]imidazole (375 mg, 94.8% yield) as a pale solid MS (+) ES: 488 (M+H)+.

Step 6. 2-(5,7-dichloro-6-(4,4-difluoropiperidin-1-yl)-1H-benzo[d]imidazol-2-yl)-2-(4-(ethylsulfonyl)phenyl)ethanol

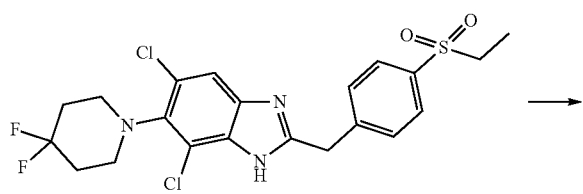

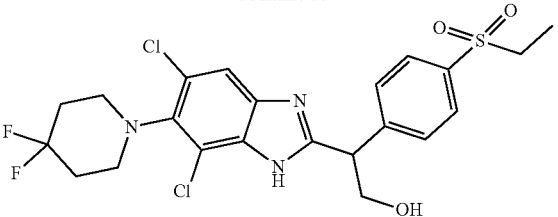

To a solution of get 2-(4-(ethylsulfonyl)benzyl)-4,6-dichloro-5-(4,4-difluoropiperidin-1-yl)-1H-benzo[d]imidazole (20 mg, 0.04 mmol) and paraformaldehyde (6.3 mg, 0.21 mmol) in 3 mL of DMSO, was added sodium ethoxide (8.2 mg, 0.12 mmol). The reaction solution was stirred at room temperature for 2 hours. Then, it was directly loaded to a reverse phase column with elution system D, and purified to get 2-(4,6-dichloro-5-(4,4-difluoropiperidin-1-yl)-1H-benzo[d]imidazole-2-yl)-2-(4-(ethylsulfonyl)phenyl)ethanol (9 mg, 42.5% yield) as a white solid; MS (+) ES: 518 (M+H)+.

Examples 126-1 and 126-2

Preparation of (R)-2-(5,7-dichloro-6-(4,4-difluoropiperidin-1-yl)-1H-benzo[d]imidazol-2-yl)-2-(4-(ethylsulfonyl)phenyl)ethanol (Example 126-1) and (S)-2-(5,7-dichloro-6-(4,4-difluoropiperidin-1-yl)-1H-benzo[d]imidazol-2-yl)-2-(4-(ethylsulfonyl)phenyl)ethanol (Example 126-2)

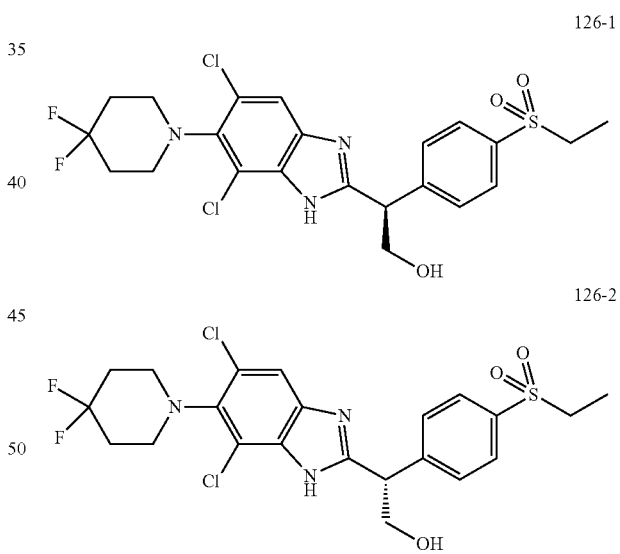

Example 126 was separated chirally (separation conditions: cellulose-1 20*250 mm, 5 um; mobile phase: ethanol/hexane=1:4 (v/v); flow rate: 20 mL/min), The corresponding fractions were collected and concentrated under reduced pressure to obtain the title compounds (420 mg, 410 mg).

Single configuration compound (the shorter retention time)

MS (+) ES: 518 (M+H)+;

Chiral HPLC analysis: retention time 7.275 minutes, chiral purity: 100% (chromatographic column: OD Phenomenex Lux Cellulose-1 150*4.6 mm, 5 um; mobile phase: ethanol/hexane=15:85 (v/v);

¹H NMR (400 mHz, CD₃OD): 7.90 (d, 8.0 Hz, 2H), 7.67 (d, 8.0 Hz, 2H), 7.62 (s, 0.5H), 7.49 (s, 0.5H), 4.59 (t, 8.0 Hz, 1H), 4.38 (dd, 8.0, 11.0 Hz, 1H), 4.27-4.11 (m, 1H), 3.44-3.28 (m, 4H), 3.20 (q, 8.0 Hz, 2H), 2.24-2.01 (m, 4H), 1.21 (t, 8.0 Hz, 3H).

Single configuration compound (the longer retention time)

MS (+) ES: 518 (M+H)+;

Chiral HPLC analysis: retention time 9.290 minutes, chiral purity: 100% (chromatographic column: OD Phenomenex Lux Cellulose-1 150*4.6 mm, 5um; mobile phase: ethanol/hexane=15:85 (v/v);

¹H NMR (400 mHz, CD₃OD): 7.90 (d, 8.0 Hz, 2H), 7.67 (d, 8.0 Hz, 2H), 7.62 (s, 0.5H), 7.49 (s, 0.5H), 4.59 (t, 8.0 Hz, 1H), 4.38 (dd, 8.0, 11.0 Hz, 1H), 4.27-4.11 (m, 1H), 3.44-3.28 (m, 4H), 3.20 (q, 8.0 Hz, 2H), 2.24-2.01 (m, 4H), 1.21 (t, 8.0 Hz, 3H).

Example 127

Preparation of 5,7-dichloro-2-(4-((cyclopropylmethyl)sulfonyl)benzyl)-6-(4,4-difluoropiperidin-1-yl)-1H-benzo[d]imidazole

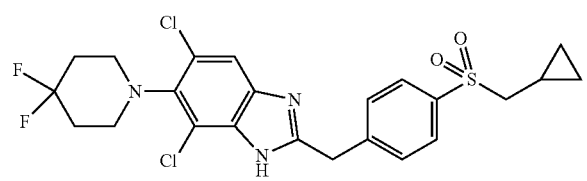

Step 1: Preparation of cyclopropylmethyl 2-(4-(cyclopropylmethylthio) phenyl)acetate

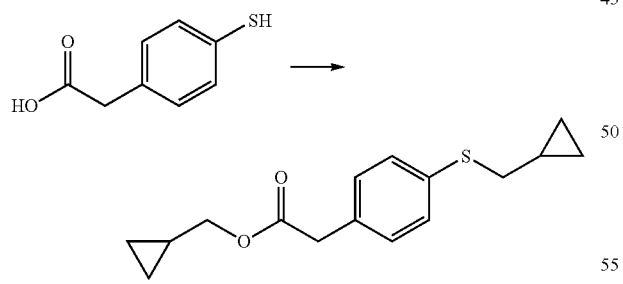

To a solution of 2-(4-mercaptophenyl)acetic acid (5 g, 29.7 mmol) in DMF (50 mL), was added cesium carbonate (29.3 g, 89.1 mmol) and cyclopropylmethyl bromide (10 g, 74.21 mmol). The reaction mixture was stirred at room temperature overnight. It was distribute between water and ethyl acetate. The organic layer was dried over sodium sulfate, concentrated, and purified on a silica gel column, eluting with 25% ethyl acetate in hexanes, to get cyclopropylmethyl 2-(4-(cyclopropylmethylthio)phenyl)acetate (7.7 g, 93.7% yield) as a colorless oil. MS (+) ES: 277 (M+H)⁺.

Step 2: Preparation of cyclopropylmethyl 2-(4-(cyclopropylmethylsulfonyl)phenyl)acetate

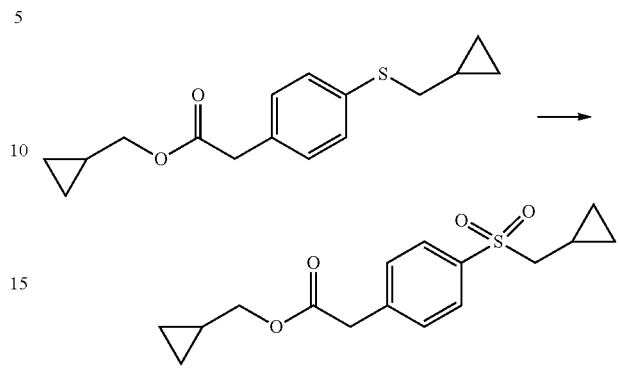

To a solution of cyclopropylmethyl 2-(4-(cyclopropylmethylthio)phenyl)acetate (4.07 g, 14.7 mmol) in dichloromethane (20 mL), was added MCPBA (7.61 g, 44.3 mmol) at room temperature. After addition, the reaction mixture was stirred at ambient temperature for 14 hours. It was distributed between dichloromethane and saturated sodium thiosulfate. The organic layer was washed with 2N aqueous sodium hydroxide solution and brine. It was concentrated and purified on a silica gel column, eluting with 60% ethyl acetate in hexanes, to get cyclopropylmethyl 2-(4-(cyclopropylmethylsulfonyl)phenyl)acetate (4.23 g, 93.0% yield) as a white solid. MS (+) ES: 309 (M+H)⁺.

Step 3: Preparation of 2-(4-(cyclopropylmethyl)sulfonyl)phenyl)acetic acid

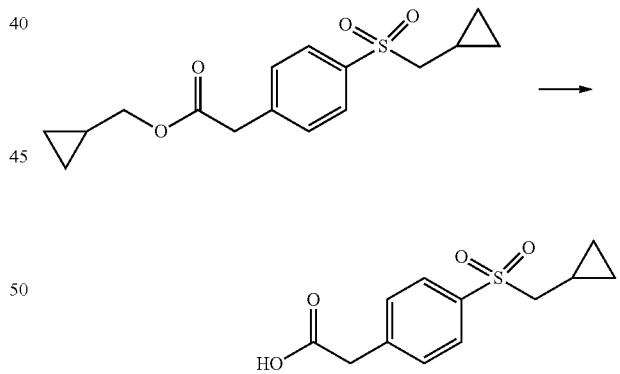

To a solution of cyclopropylmethyl 2-(4-(cyclopropylmethylsulfonyl)phenyl)acetate (2.50 g, 8.1 mmol) in dioxane (10 mL), was added lithium hydroxide nomohydrate (4.1 g, 40.6 mmol) and water (10 mL). The reaction mixture was stirred at ambient temperature overnight. It was acidified with hydrochloric acid to pH 5, and concentrated to dryness. The solid collected was dissolved in 15% methanol in dichloromethane, and filtered through a silica gel pad, eluting with 15% methanol in dichloromethane, and concentrated to get 2-(4-(cyclopropylmethyl)sulfonyl)phenyl) acetic acid (2.1 g, 97% yield) as a white solid. MS (+) ES: 255 (M+H)⁺.

221

Step 4: Preparation of N-(6-amino-2,4-dichloro-3-(4,4-difluoropiperidin-1-yl)phenyl)-2-(4-(cyclopropylmethylsulfonyl)phenyl)acetamide and N-(2-amino-3,5-dichloro-4-(4,4-difluoropiperidin-1-yl)phenyl)-2-(4-(cyclopropylmethylsulfonyl)phenyl)acetamide

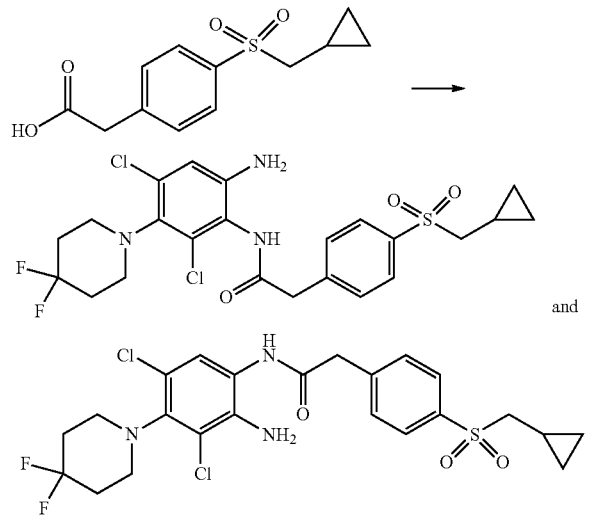

To a solution of 3,5-dichloro-4-(4,4-difluoropiperidin-1-yl)benzene-1,2-diamine (175 mg, 0.193 mmol) and 2-(4-(cyclopentylmethyl sulfonyl)phenyl)acetic acid (181 mg 0.711 mmol) in dichloromethane (5 mL) was added EDCI (171 mg, 0.89 mmol) and HBTU (334 mg, 0.89 mmol). The reaction solution was stirred at room temperature for 2 hours. It was absorbed onto 5 g of silica gel, and loaded onto a silica gel column. The column was eluted with 45% of ethyl acetate in hexanes to get a mixture of N-(2-amino-3,5-dichloro-4-(4,4-difluoropiperidin-1-yl)phenyl)-2-(4-(cyclopropylmethylsulfonyl)phenyl)acetamide and N-(6-amino-2,4-dichloro-3-(4,4-difluoropiperidin-1-yl)phenyl)-2-(4-(cyclopropylmethylsulfonyl)phenyl)acetamide (230 mg, 73.2% yield) as a white solid. MS (+) ES: 532 (M+H)+).

Step 5: Preparation of 2-(4-(cyclopropylmethylsulfonyl)benzyl)-4,6-dichloro-5-(4,4-difluoropiperidin-1-yl)-1H-benzo[d]imidazole

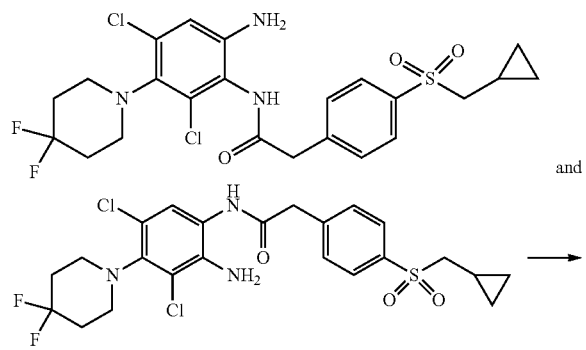

and

222

-continued

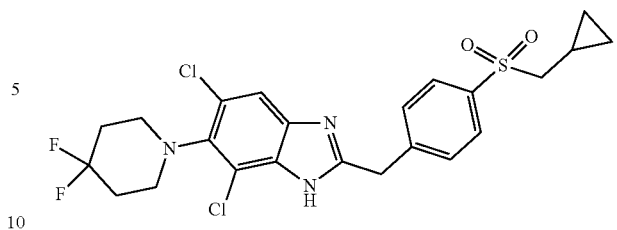

The mixture of N-(2-amino-3,5-dichloro-4-(4,4-difluoropiperidin-1-yl)phenyl)-2-(4-(cyclopropylmethylsulfonyl)phenyl)acetamide and N-(6-amino-2,4-dichloro-3-(4,4-difluoropiperidin-1-yl)phenyl)-2-(4-(cyclopropylmethylsulfonyl)phenyl)acetamide (230 mg) obtained from the previous step was treated with 15 mL of glacial acetic acid at 80° C. for 2 hours. It was concentrated, and purified on a reverse phase column, eluting with 60% acetonitrile in water, to get 2-(4-(cyclopropylmethylsulfonyl)benzyl)-4,6-dichloro-5-(4,4-difluoropiperidin-1-yl)-1H-benzo[d]imidazole (375 mg, 94.8% yield) as a pale solid; MS (+) ES: 514 (M+H)+;

1H NMR (500 mHz, CDCl$_3$): 7.85 (d, 5.00 Hz, 2H), 7.66 (s, 0.5H), 7.50 (d, 5.00 Hz, 2H), 7.30 (s, 0.5H), 4.45 (m, 2H), 3.30 (m, 4H), 3.00 (m, 2H), 2.12 (m, 5H), 0.51 (m, 2H), 0.35 (m, 2H).

Example 128

Preparation of 2-(7-chloro-6-(2-(difluoromethoxy)phenyl)-1H-benzo[d]imidazol-2-yl)-2-(4-((cyclopropylmethyl)sulfonyl)phenyl)ethanamine

128

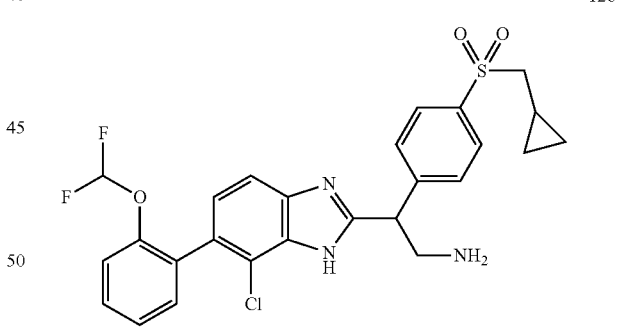

Step 1. Preparation of benzyl 2-(4-((cyclopropylmethyl)sulfonyl)phenyl)acetate

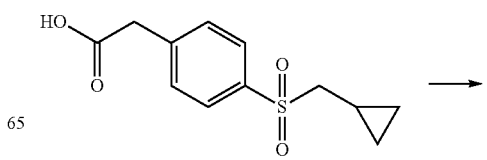

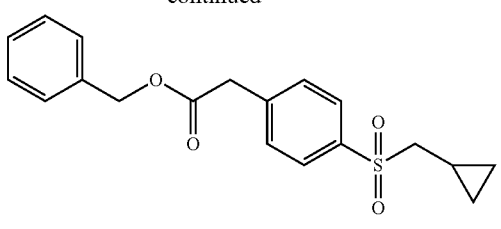

To a suspended CH$_2$Cl$_2$ (10 ml) solution of 2-bromo-1-methylpyridinium iodide (2.16 g, 7.2 mmol) was added a mixture of benzyl alcohol (648 mg, 6.0 mmol), 2-(4-((cyclopropylmethyl)sulfonyl)phenyl)acetic acid (1.5 g, 6.0 mmol) and tri-n-butylamine (2.66 g, 14.4 mmol) in CH$_2$Cl$_2$ (8 ml), and the resulting mixture was refluxed for 3 hours. After evaporation of the solvent, the residue was separated by silica gel column chromatography, and benzyl the product was isolated as a white solid 1.8 g (90% yield). MS (+) ES: 344 (M+H)$^+$.

Step 2. Preparation of benzyl 2-(4-((cyclopropylmethyl)sulfonyl)phenyl)-3-(1,3-dioxoisoindolin-2-yl)propanoate

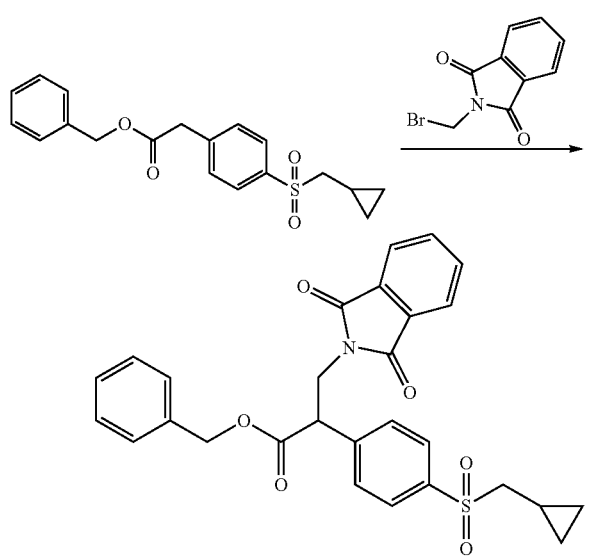

A solution of n-butyllithium in THF (1.8 ml, 2.5 M, 4.5 mmol) was added in to a cooled mixture of HMDS (608 mg, 4.56 mmol) in THF (20 ml) dropwise over 20 min with stirring. The mixture was stirred for 30 min before benzyl 2-(4-((cyclopropylmethyl)sulfonyl)phenyl)acetate (1.3 g, 3.8 mmol) in THF (5 ml) was added through a syringe dropwise over 10 min. Stirred for another 30 min at −78° C. followed by the addition of 2-(bromomethyl)isoindoline-1,3-dione (912 mg, 3.8 mmol) in THF (5 ml) was added through a syringe over 10 min. The mixture was stirred at −78° C. and allowed to reach to room temperature overnight. The mixture was treated with methanol carefully and the solvents were evaporated. The product was purified by flash chromatography to afford the product as a White solid 1.4 g (74% yield). MS (+) ES: 504 (M+H)$^+$.

Step 3. Preparation of 2-(4-((cyclopropylmethyl)sulfonyl)phenyl)-3-(1,3-dioxoisoindolin-2-yl)propanoic acid

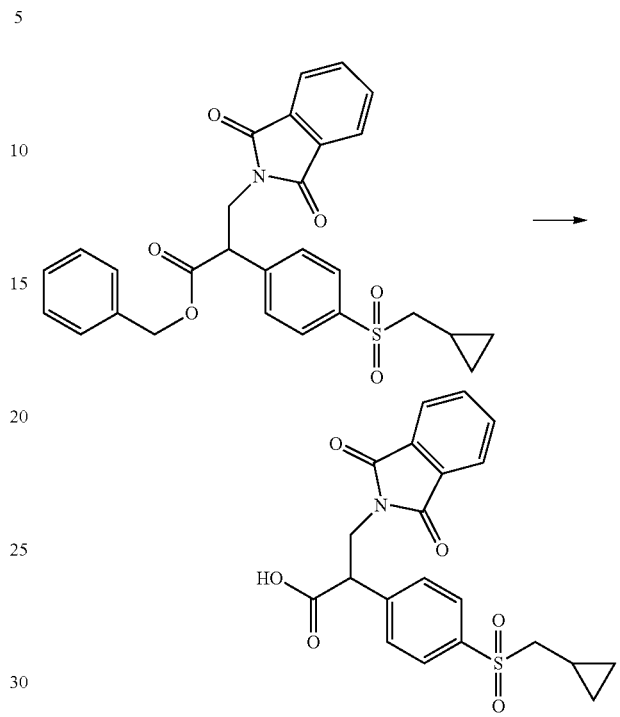

Benzyl 2-(4-((cyclopropylmethyl)sulfonyl)phenyl)-3-(1,3-dioxoisoindolin-2-yl) propanoate in step 2 (1.4 g, 2.8 mmol) was dissolved in ethyl acetate (20 mL) and Pd(OH)$_2$ (140 mg) was added and the mixture was hydrogenated with a hydrogen balloon for 8 h. Catalyst was filtered off and the solvent was evaporated to leave a White solid product 900 mg (78% yield). MS (+) ES: 414 (M+H)$^+$.

Step 4. Preparation of 6-chloro-2'-(difluoromethoxy)-[1,1'-biphenyl]-3,4-diamine

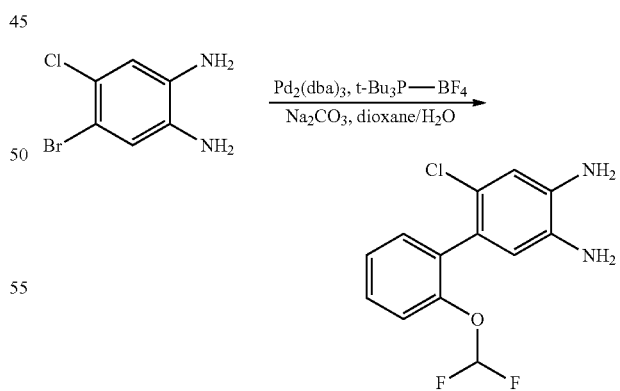

A mixture of 4-bromo-5-chlorobenzene-1,2-diamine (1.5 g, 6.78 mmol), 2-(2-(difluoromethoxy)phenyl)-4,4,5,5-tetramethyl-1,3,2-dioxaborolane (2.2 g, 8.15 mmol), tris-(dibenzylideneacetone)dipalladium(0) (620 mg), tri(tert-butyl) phosphonium tetrafluoroboronate (393 mg) and sodium carbonate (1.7 g, 13.7 mmol) in 1,4-dioxane (50 ml) and water (10 mL) was degassed, heated to 90° C. under for Step 5. Preparation of 2-(2-(5-chloro-6-(2-(difluoromethoxy)phenyl)-1H-benzo[d]imidazol-2-yl)-2-(4-((cyclopropylmethyl)sulfonyl)phenyl)ethyl)isoindoline-1,3-dione

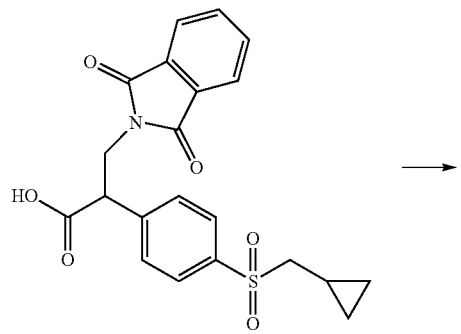

Step 6. Preparation of 2-(5-chloro-6-(2-(difluoromethoxy)phenyl)-1H-benzo[d]imidazol-2-yl)-2-(4-((cyclopropylmethyl)sulfonyl)phenyl)ethanamine

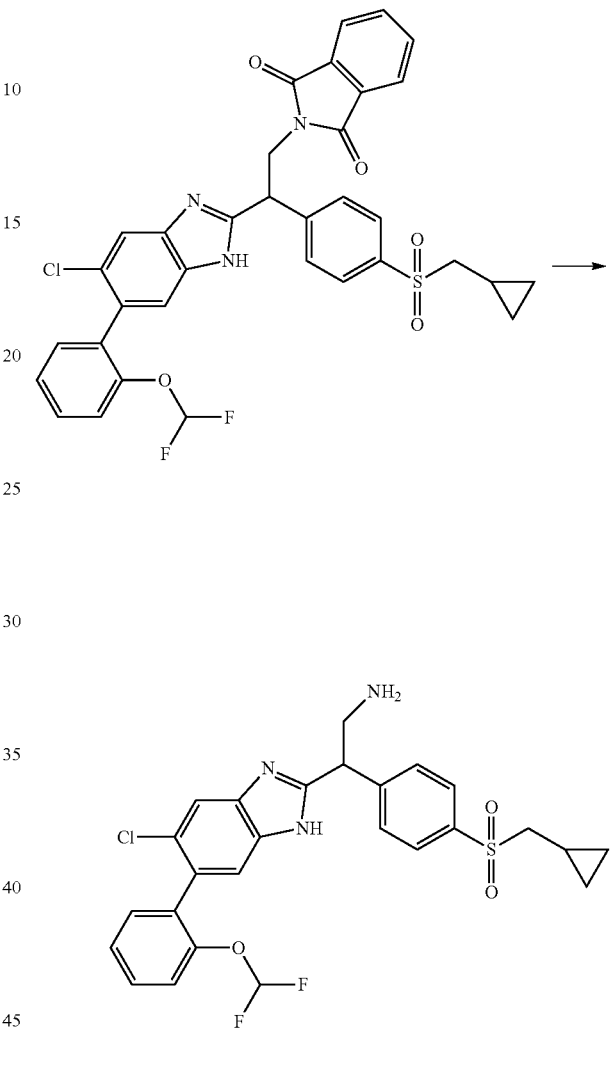

To a mixture of 2-(4-((cyclopropylmethyl)sulfonyl)phenyl)-3-(1,3-dioxoisoindolin-2-yl)propanoic acid (step 3, 400 mg, 0.97 mmol) and 6-chloro-2'-(difluoromethoxy)-[1,1'-biphenyl]-3,4-diamine (step 4; 275 mg, 0.98 mmol) in DMF (8 ml) was added N-(3-Dimethylaminopropyl)-N-ethylcarbodiimide hydrochloride 224 mg, 1.2 mmol) and 1-Hydroxybenzotriazole (162 mg, 1.2 mmol). The mixture was stirred at room temperature overnight, partitioned between ethyl acetate (10 ml) and water (15 ml). The organic phase was separated and dried over MgSO$_4$. After filtration and evaporation of the solvent the residue was treated with acetic acid (5 ml) and heated to 80° C. for two hours. The mixture was cooled and the acetic acid was evaporated to dryness, dissolved in ethyl acetate (10 ml) washed with saturated sodium bicarbonate and brine. The organic phase was separated and dried over MgSO$_4$. The product was purified by flash chromatography to afford a white solid 454 mg (70% yield). MS (+) ES: 662 (M+H)$^+$.

2-(2-(5-chloro-6-(2-(difluoromethoxy)phenyl)-1H-benzo[d]imidazol-2-yl)-2-(4-((cyclopropylmethyl)sulfonyl)phenyl)ethyl)isoindoline-1,3-dione (step 4, 454 mg, 0.68 mmol) was dissolved in ethanol (5 ml). hydrazine hydrate (0.1 mL) was added and the mixture was stirred overnight. The solid precipitate was filtered off and the volatile solvents was evaporated to dryness. The product was purified by flash chromatography to afford the product as a white solid 280 mg (76% yield). MS (+) ES: 532 (M+H)$^+$.

Example 129

Preparation of N-(2-(5-chloro-6-(2-(difluoromethoxy)phenyl)-1H-benzo[d]imidazol-2-yl)-2-(4-((cyclopropylmethyl)sulfonyl)phenyl)ethyl)acetamide

Example 130

Preparation of 3-(4,6-dichloro-5-(4,4-difluoropiperidin-1-yl)-1H-benzo[d]imidazol-2-yl)-3-(4-(ethylsulfonyl)phenyl)propanoic acid

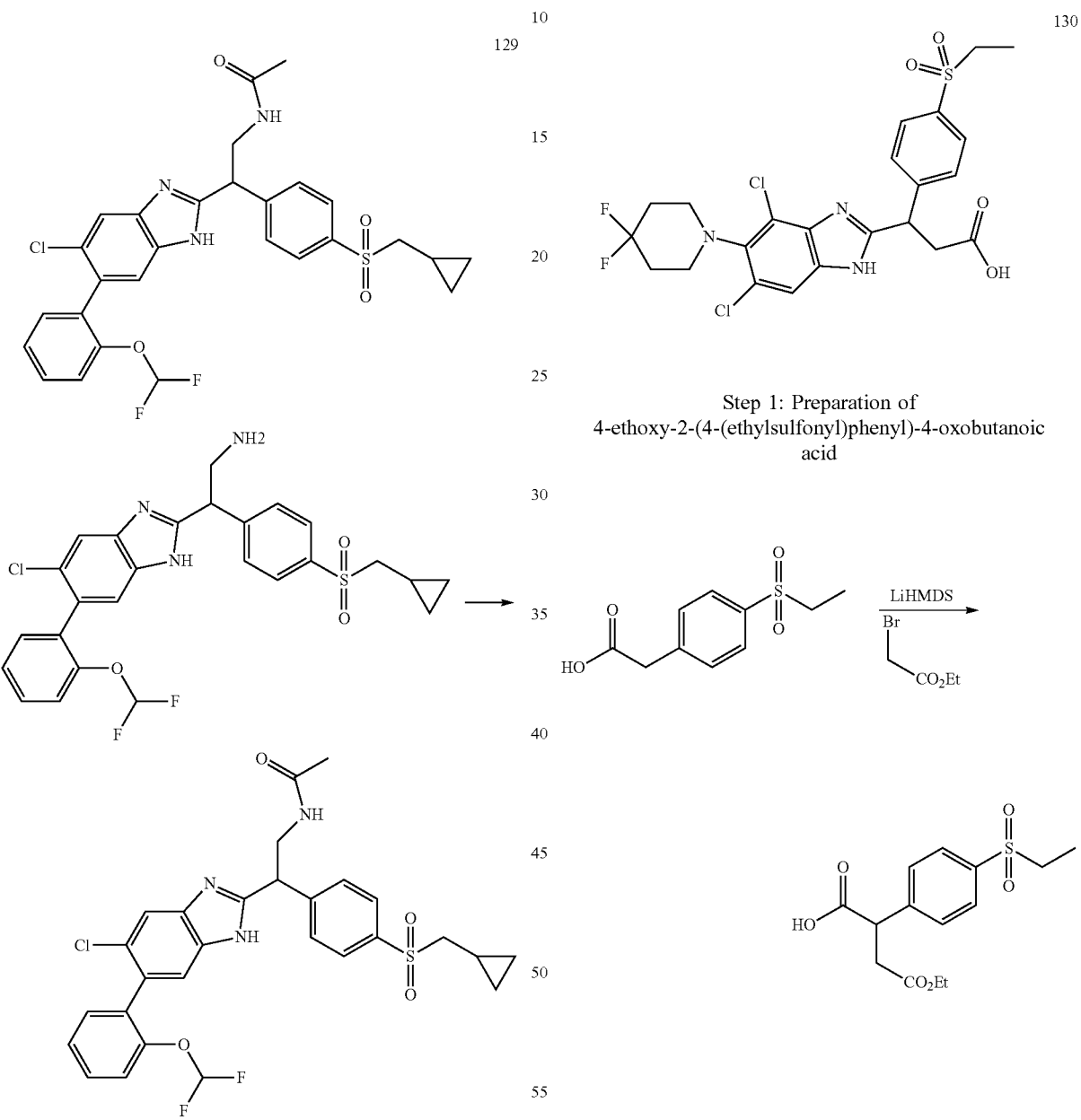

Step 1: Preparation of 4-ethoxy-2-(4-(ethylsulfonyl)phenyl)-4-oxobutanoic acid To a solution of 2-(5-chloro-6-(2-(difluoromethoxy)phenyl)-1H-benzo[d]imidazol-2-yl)-2-(4-((cyclopropylmethyl)sulfonyl)phenyl)ethanamine (example 128) (5.3 mg, 0.01 mmol) and triethyl amine (3 mg, 0.03 mmol) in DCM (0.4 mL) was added acetic anhydride (1.2 mg, 0.012 mmol). The mixture was stirred for 4 h. Solvent was evaporated under reduced pressure and the product was purified by Prep HPLC to afford the product as a white solid 3.5 mg (66% yield). MS (+) ES: 574 (M+H)+

To 2-(4-(ethylsulfonyl)phenyl)acetic acid (250 mg, 1.1 mmol) in THF (8 mL) at −78° C. was added LiHMDS (1M in THF, 2.31 mL). After 50 min, ethyl 2-bromoacetate (147 µL, 1.32 mmol) was added. The reaction mixture was stirred at −78° C. for 3.5 h. 0.1N HCl solution was added to adjust pH to around 4. Extracted with EtOAc three times, dried over Na$_2$SO$_4$, filtered, concentrated. The residue was purified by silica gel column with elution system A to give yellow oil 29 mg. MS (ESI): 315 (M+H)+.

Step 2: Preparation of ethyl 4-((2-amino-3,5-di-chloro-4-(4,4-difluoropiperidin-1-yl)phenyl)amino)-3-(4-(ethylsulfonyl)phenyl)-4-oxobutanoate

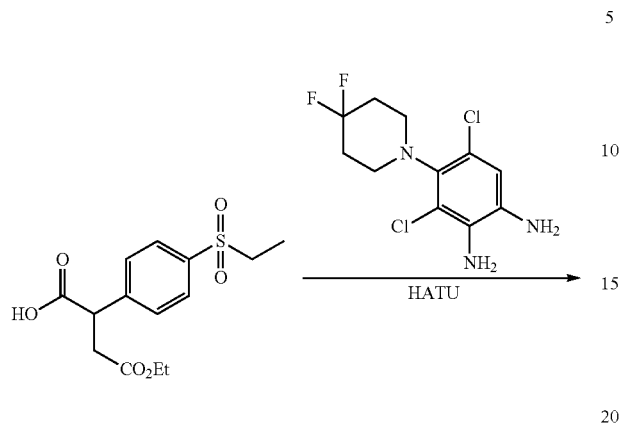

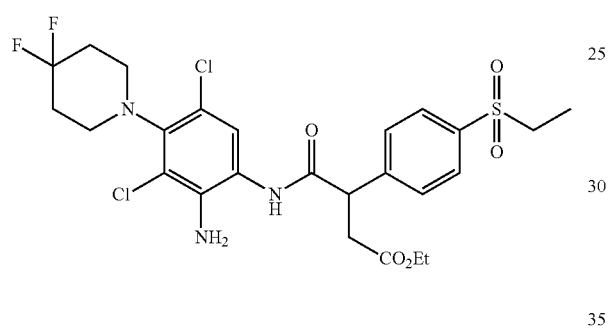

To a solution of 4-ethoxy-2-(4-(ethylsulfonyl)phenyl)-4-oxobutanoic acid (27 mg) in DCM (1 mL), 3,5-dichloro-4-(4,4-difluoropiperidin-1-yl)benzene-1,2-diamine (65 mg), HATU (150 mg), DIEA (0.1 mL) were added. The mixture was stirred at room temperature for 18 h. A solution of saturated NaHCO₃ was added, extracted EtOAc three times, dried over Na₂SO₄, filtered, concentrated. The residue was purified by silica gel column with elution system A to obtain the title compound 40 mg. MS (ESI): 593 (M+H)⁺.

Step 3: Preparation of ethyl 3-(4,6-dichloro-5-(4,4-difluoropiperidin-1-yl)-1H-benzo[d]imidazol-2-yl)-3-(4-(ethylsulfonyl)phenyl)propanoate

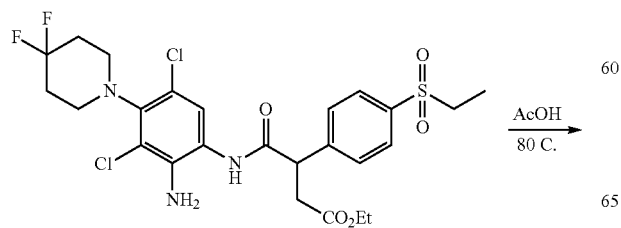

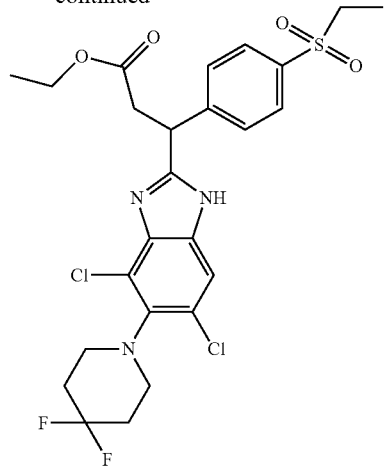

Ethyl 4-((2-amino-3,5-dichloro-4-(4,4-difluoropiperidin-1-yl)phenyl)amino)-3-(4-(ethylsulfonyl) phenyl)-4-oxobutanoate (39 mg) in AcOH (2 mL) was heated to 80° C. for 3 h. The mixture was purified by silica gel column with elution system C to give the title compound (18 mg). MS (ESI): 574 (M+H)⁺.

Step 4: Preparation of 3-(4,6-dichloro-5-(4,4-difluoropiperidin-1-yl)-1H-benzo[d]imidazol-2-yl)-3-(4-(ethylsulfonyl)phenyl)propanoic acid

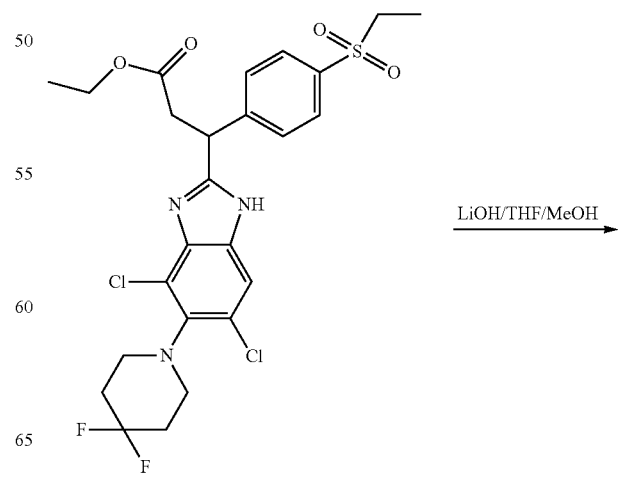

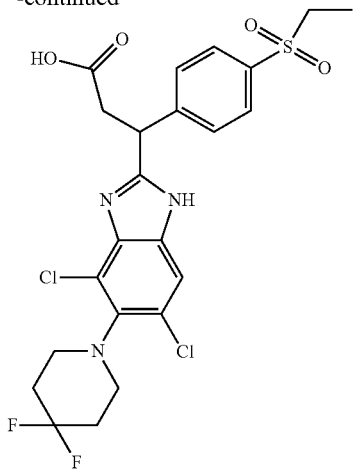

Ethyl 3-(4,6-dichloro-5-(4,4-difluoropiperidin-1-yl)-1H-benzo[d]imidazol-2-yl)-3-(4-(ethylsulfonyl)phenyl)propanoate (18 mg) in THF (1.5 mL)/MeOH (0.5 mL) was treated with LiOH (1M, 0.2 mL). The mixture was stirred at room temperature for 3 h until no ethyl 3-(4,6-dichloro-5-(4,4-difluoropiperidin-1-yl)-1H-benzo[d]imidazol-2-yl)-3-(4-(ethylsulfonyl)phenyl) propanoate left by LCMS. 1M HCl was added to adjust pH<5. Solvent was evaporated under reduced pressure and the product was purified by reverse phase preparative HPLC (elution system: 0.075% TFA in water and 0.075% TFA in MeOH) to afford the title compounds as a white solid (11 mg). MS (ESI): m/z=546 (M+H)$^+$.

Example 131

Preparation of 3-(4,6-dichloro-5-(4,4-difluoropiperidin-1-yl)-1H-benzo[d]imidazol-2-yl)-3-(4-(ethylsulfonyl)phenyl)propanamide To a solution Example 172 (9 mg) in DMF (1 mL) were added NH$_4$Cl (30 mg), HATU (17 mg), DIEA (60 μL). The mixture was stirred a room temperature for 20 h. The solid was filtered off. The filtrate was purified by reverse phase preparative HPLC (elution system: 0.075% TFA in water and 0.075% TFA in MeOH) to afford the title compounds as a white solid (3 mg). MS (ESI): m/z=545 (M+H)$^+$.

Examples 132

Preparation of 5,7-dichloro-2-(4-((cyclopropylmethyl)sulfonyl)benzyl)-6-(2-isopropoxyphenyl)-1H-benzol[d]imidazole

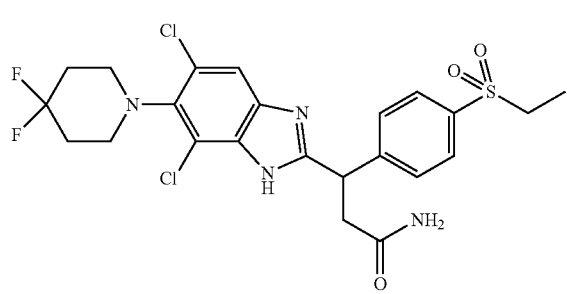

131

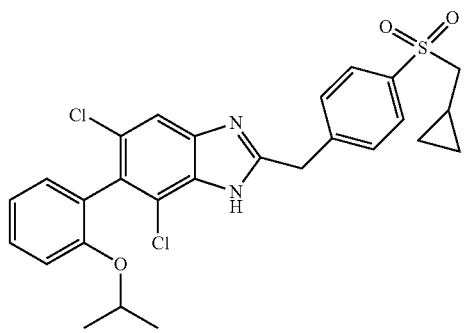

132

This compound was prepared by essential the similar method as of example 124 to afford the product as a white solid, MS (+) ES: 529 (M+H)⁺.

Examples 133

Preparation of (4-((cyclopropylmethyl)sulfonyl)phenyl)(5,7-dichloro-6-(2-isopropoxyphenyl)-1H-benzo[d]imidazol-2-yl)methanol

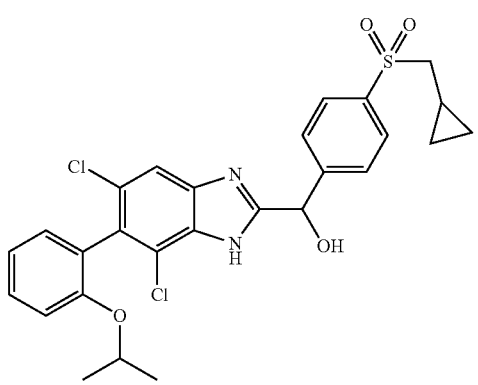

This compound was prepared by essential the similar method of example 2 and 124 to afford the product as a white solid, MS (+) ES: 545 (M+H)⁺.

Examples 134

Preparation of 2-(4-((cyclopropylmethyl)sulfonyl)phenyl)-2-(5,7-dichloro-6-(2-isopropoxyphenyl)-1H-benzo[d]imidazol-2-yl)ethanol

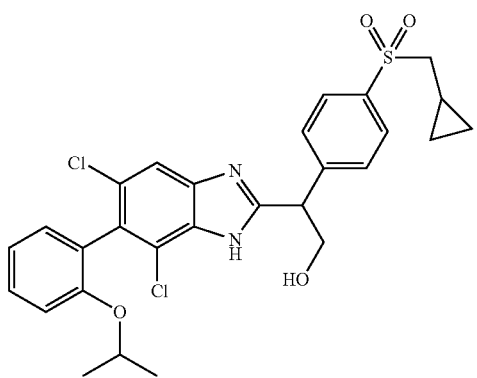

This compound was prepared by essential the similar method as of example 124 to afford the product as a white solid, MS (+) ES: 559 (M+H)⁺.

Examples 135

Preparation of 2-(4-((cyclopropylmethyl)sulfonyl)phenyl)-2-(5,7-dichloro-6-(2-methoxyphenyl)-1H-benzo[d]imidazol-2-yl)ethanol

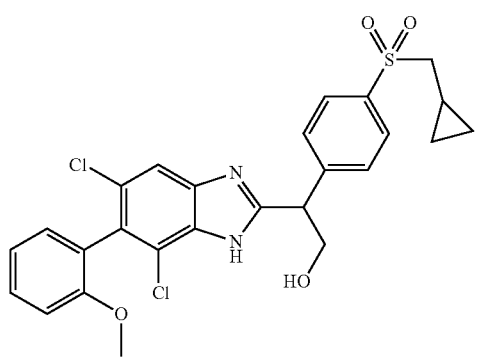

This compound was prepared by essential the similar method as of example 124 to afford the product as a white solid, MS (+) ES: 531 (M+H)⁺.

Examples 136

Preparation of 5,7-dichloro-2-(4-((cyclopropylmethyl)sulfonyl)benzyl)-6-(2-ethoxyphenyl)-1H-benzo[d]imidazole

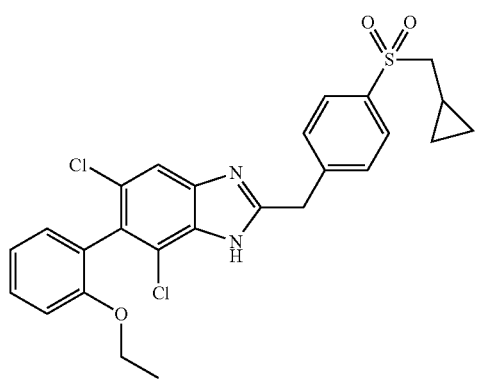

This compound was prepared by essential the similar method as of example 124 to afford the product as a white solid, MS (+) ES: 515 (M+H)⁺.

Examples 137

Preparation of 2-(4-((cyclopropylmethyl)sulfonyl)phenyl)-2-(5,7-dichloro-6-(2-ethoxyphenyl)-1H-benzo[d]imidazol-2-yl)ethanol

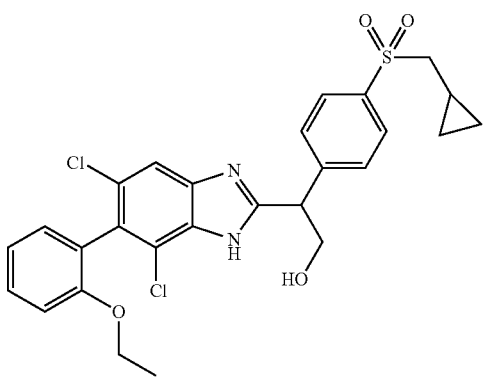

This compound was prepared by essential the similar method as of example 124 to afford the product as a white solid, MS (+) ES: 545 (M+H)$^+$.

Examples 138

Preparation of (4-((cyclopropylmethyl)sulfonyl)phenyl)(5,7-dichloro-6-(2-ethoxyphenyl)-1H-benzo[d]imidazol-2-yl)methanol

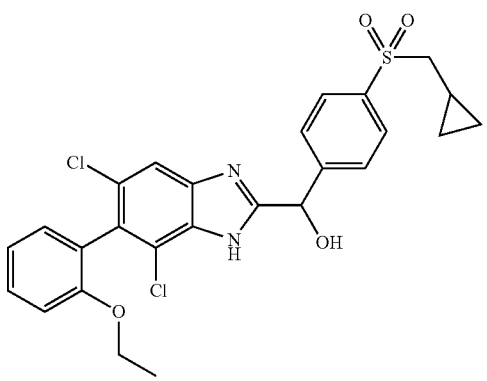

This compound was prepared by essential the similar method as of example 2 and 124 to afford the product as a white solid, MS (+) ES: 531 (M+H)$^+$.

Examples 139 and 140

Preparation of (S)-3-(4,6-dichloro-5-(4,4-difluoropiperidin-1-yl)-1H-benzo[d]imidazol-2-yl)-3-(4-(ethylsulfonyl)phenyl)propan-1-ol and (R)-3-(4,6-dichloro-5-(4,4-difluoropiperidin-1-yl)-1H-benzo[d]imidazol-2-yl)-3-(4-(ethylsulfonyl)phenyl) propan-1-ol

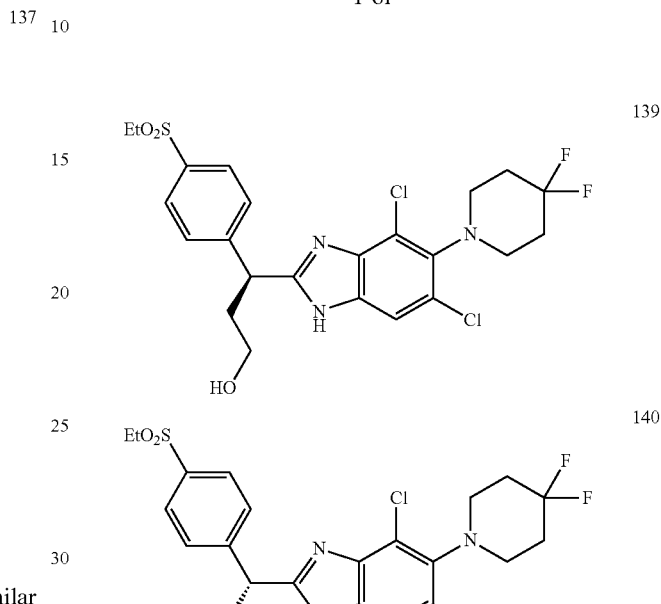

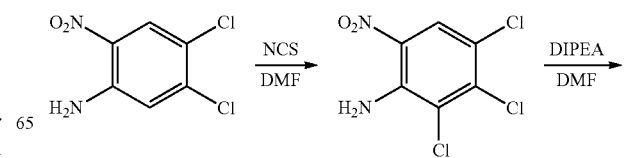

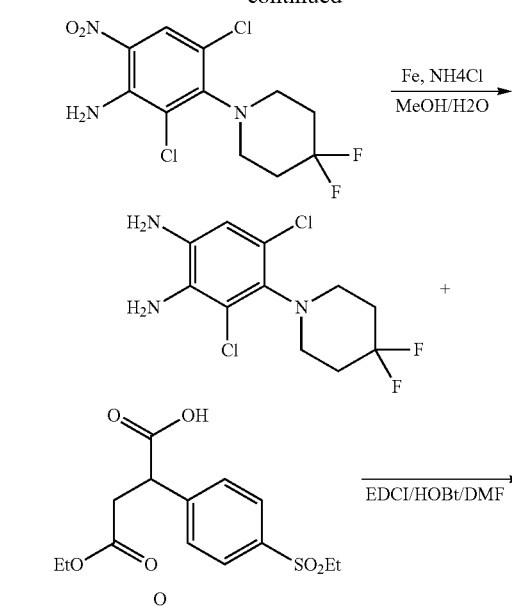

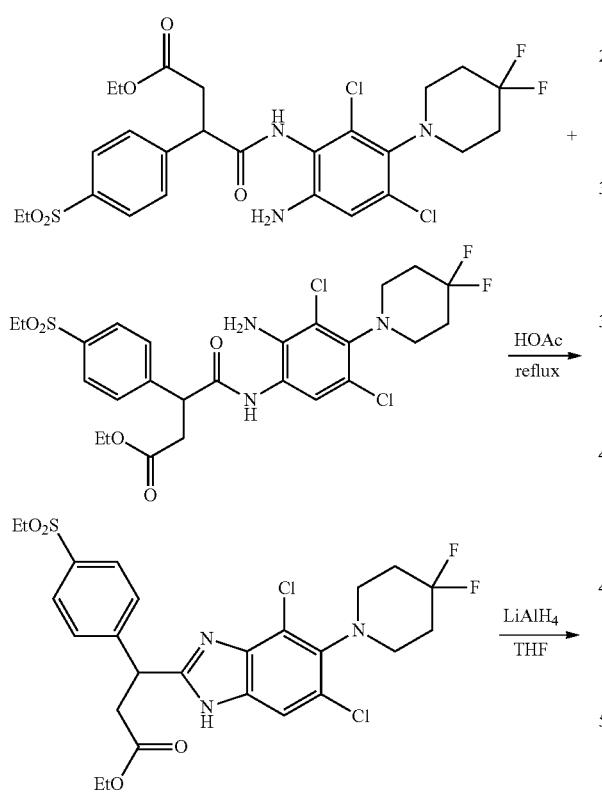

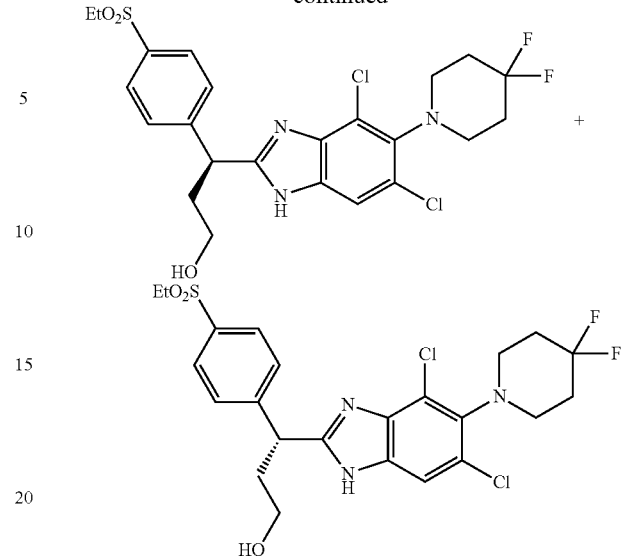

Step 1. Preparation of ethyl 2-(4-(ethylthio)phenyl)acetate

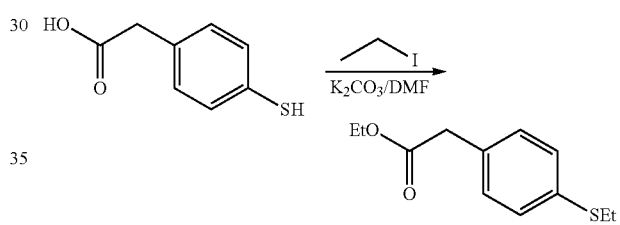

To a solution of (4-mercaptophenyl) acetic acid (5.0 g, 29.7 mmol) in N,N-dimethylformamide (DMF) (100 ml) was added $K_2CO_3$ (16.4 g, 118.8 mmol) and Iodoethane (9.7 g, 62.2 mmol). The reaction mixture was stirred at RT. After 12 hours, the starting material was totally consumed. The reaction mixture was partitioned between ethyl acetate (100 ml) and water (50 ml). The organic phase was washed with water (30 ml) and brine (20 ml), dried over sodium sulphate, filtered, and concentrated to give the desired product ethyl 2-(4-(ethylthio)phenyl)acetate (6.0 g, 90%) as a pale yellow solid, MS (+) ES: 225 (M+H)$^+$ Step 2. Preparation of ethyl 2-(4-(ethylsulfonyl)phenyl)acetate

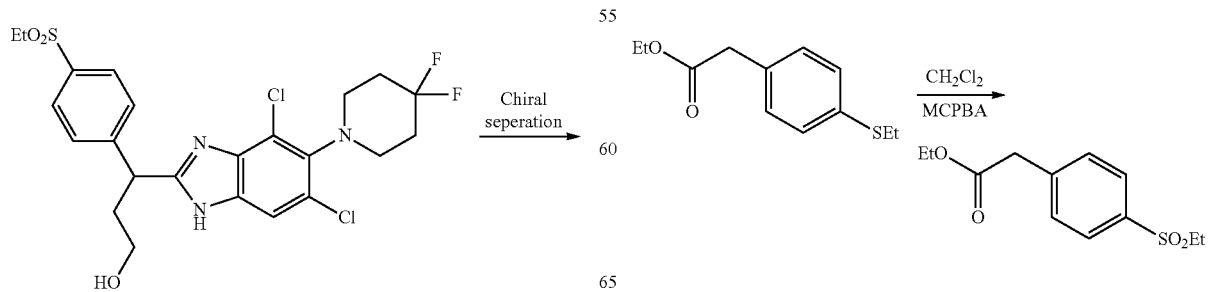

To a 250 ml round bottom flask, were added ethyl 2-(4-(ethylthio)phenyl)acetate (6.0 g, 26.7 mmol) and dichloromethane (300 ml). The reaction mixture was cooled to 0° C. To the same flask, m-chloroperbenzoic acid (13.8 g, 80.0 mmol) was added at 0° C. The reaction mixture was stirred at room temperature for 12 h. The resulting suspension was filtered through a pad of celite. The filtrate was washed with water. The organic layer was separated, washed with saturated sodium bicarbonate solution followed by brine and dried over anhydrous sodium sulfate. The solvent was evaporated under reduced pressure to get the crude product. The crude product was purified by flash column chromatography with hexane/ethyl acetate to get the title compound as an oil that was solidified upon standing (6.0 g, 87.5%), MS (+) ES: 257 (M+H)$^+$.

Step 3. Preparation of 2-(4-(ethylsulfonyl)phenyl)acetic acid

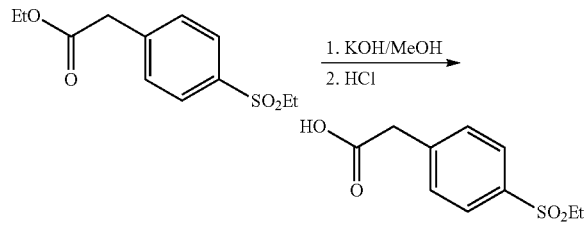

To a 250 mL round bottom flask, were added ethyl 2-(4-(ethylsulfonyl)phenyl)acetate (6.8 g, 26.5 mmol) and methanol (80 ml). To the same flask, a solution of sodium hydroxide in water (2.1 g, 52.5 mmol in 20 ml of water) was added. The reaction mixture was heated to reflux for 12 h. The volatiles were evaporated under reduced pressure. The residue was acidified with 1N HCl to pH 5.0 and extracted with ethyl acetate (50 ml×3). The organic layer was separated and combined, washed with brine and dried over sodium sulfate. The solvent was evaporated under reduced pressure to get the title compound as a white solid (3.3 g, 54.5%), MS (+) ES: 229 (M+H)$^+$.

Step 4. Preparation of 4-ethoxy-2-(4-(ethylsulfonyl)phenyl)-4-oxobutanoic acid

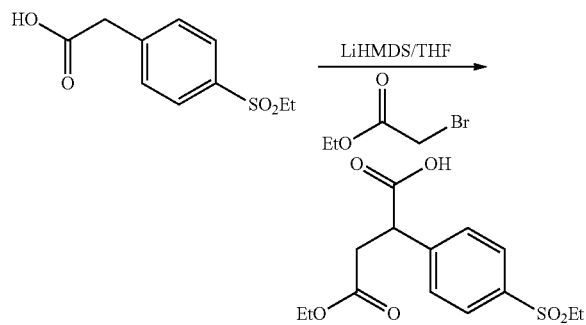

To 2-(4-(ethylsulfonyl)phenyl)acetic acid (1.0 g, 4.4 mmol) in THF (20 mL) at −78° C. was added LiHMDS (1M in THF, 9.0 mL). After 15 min, ethyl 2-bromoacetate (1.1 g, 6.58 mmol) was added. The reaction mixture was stirred at −78° C. for 3.5 h. 0.1N HCl solution was added to adjust pH to around 4. Extracted with EtOAc three times, dried over Na$_2$SO$_4$, filtered, concentrated. The residue was purified by silica gel column with elution system A to give yellow oil 0.45 g. MS (ESI): 315 (M+H)$^+$.

Step 5. Preparation of 2,3,4-Trichloro-6-nitrobenzenamine

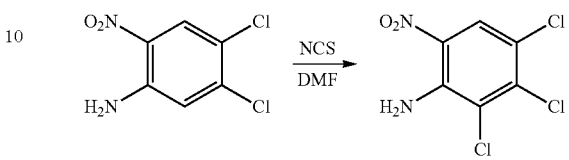

A suspension of 4,5-dichloro-2-nitrobenzenamine (10 g, 48.3 mmol) and N-chlorosuccinimide (7.7 g, 57.6 mmol) in 100 mL of DMF was stirred at 100° C. for 2 hours. It was cooled to room temperature, and poured into ice-cooled water (500 mL). The precipitate formed was collected by filtration. It was dissolved in dichloromethane and washed with water. The organic layer was concentrated to get 2,3,4-trichloro-6-nitrobenzenamine (11.0 g, 94.3% yield) as a brightly yellow solid.

Step 6. Preparation of 2,4-Dichloro-3-(4,4-difluoropiperidin-1-yl)-6-nitrobenzenamine

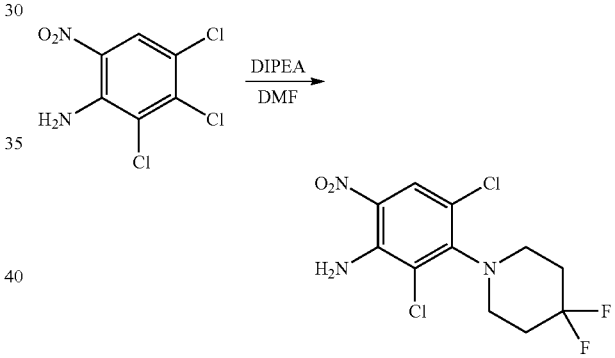

A solution of 2,3,4-trichloro-6-nitrobenzenamine (5 g, 20.7 mmol), N,N-diisopropyl ethylamine (8.0 g, 61.9 mmol), and 4,4-difluoropiperidine (10.0 g, 157.6 mmol) in 50 mL of DMF was stirred at 105° C. for 2 days. The reaction solution was absorbed onto 40 g of silica gel, loaded to a silica gel column, and eluted with 30% ethyl acetate in hexanes, to get the 2,4-dichloro-3-(4,4-difluoropiperidin-1-yl)-6-nitrobenzenamine (2.0 g, 29.6% yield) as a brightly yellow solid. MS (ESI): 326 (M+H)$^+$.

Step 7. Preparation of 3,5-Dichloro-4-(4,4-difluoropiperidin-1-yl)benzene-1,2-diamine

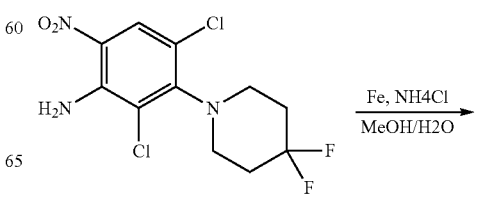

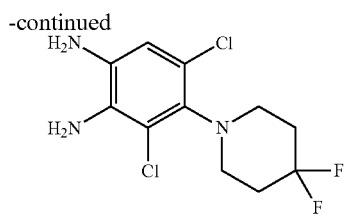

To a solution of 2,4-dichloro-3-(4,4-difluoropiperidin-1-yl)-6-nitrobenzenamine (2.0 g, 6.1 mmol) in 120 mL of methanol and 30 mL of water was added Fe powder (1.0 g, 18.0 mmol) and NH₄Cl (1.0 g, 18.5 mmol). The reaction mixture was stirred at 80° C. overnight. It was filtered. The filtrate was concentrated, and purified on a silica gel column, eluting with ethyl acetate, to get 3,5-dichloro-4-(4,4-difluoropiperidin-1-yl) benzene-1,2-diamine (0.6 g, 33.0% yield) as a pale solid (LCMS (M+1): 296).

Step 8. Preparation of ethyl 4-((2-amino-3,5-dichloro-4-(4,4-difluoropiperidin-1-yl)phenyl)amino)-3-(4-(ethylsulfonyl)phenyl)-4-oxobutanoate and ethyl 4-((6-amino-2,4-dichloro-3-(4,4-difluoropiperidin-1-yl)phenyl)amino)-3-(4-(ethylsulfonyl)phenyl)-4-oxobutanoate

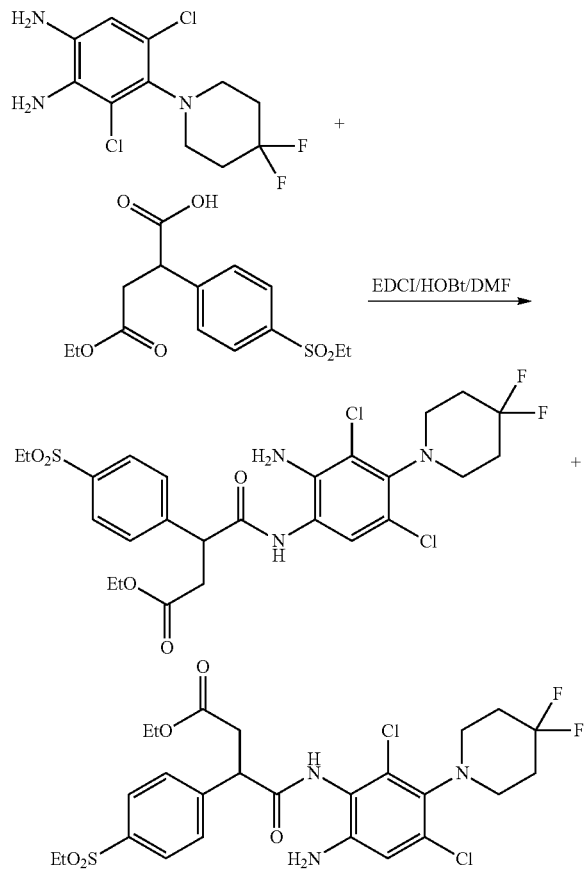

To a solution of 3,5-dichloro-4-(4,4-difluoropiperidin-1-yl)benzene-1,2-diamine (450 mg, 1.43 mmol) and 4-ethoxy-2-(4-(ethylsulfonyl)phenyl)-4-oxobutanoic acid (424 mg, 1.43 mmol) in DMF (10 mL) was added EDCI (410 mg, 2.15 mmol), HOBT (327 mg, 2.15 mmol) and DIPEA (554 mg, 4.30 mmol). The reaction solution was stirred at room temperature for 2 hours. It was absorbed onto 5 g of silica gel, and loaded onto a silica gel column. The column was eluted with 45% of ethyl acetate in hexanes to get a mixture of ethyl 4-((2-amino-3,5-dichloro-4-(4,4-difluoropiperidin-1-yl)phenyl)amino)-3-(4-(ethylsulfonyl)phenyl)-4-oxobutanoate and ethyl 4-((6-amino-2,4-dichloro-3-(4,4-difluoropiperidin-1-yl)phenyl)amino)-3-(4-(ethylsulfonyl)phenyl)-4-oxobutanoate (385 mg, 45.4% yield) as a white solid. MS (ESI): m/z=592 (M+H)⁺.

Step 9. Preparation of ethyl 3-(4,6-dichloro-5-(4,4-difluoropiperidin-1-yl)-1H-benzo[d]imidazol-2-yl)-3-(4-(ethylsulfonyl)phenyl)propanoate

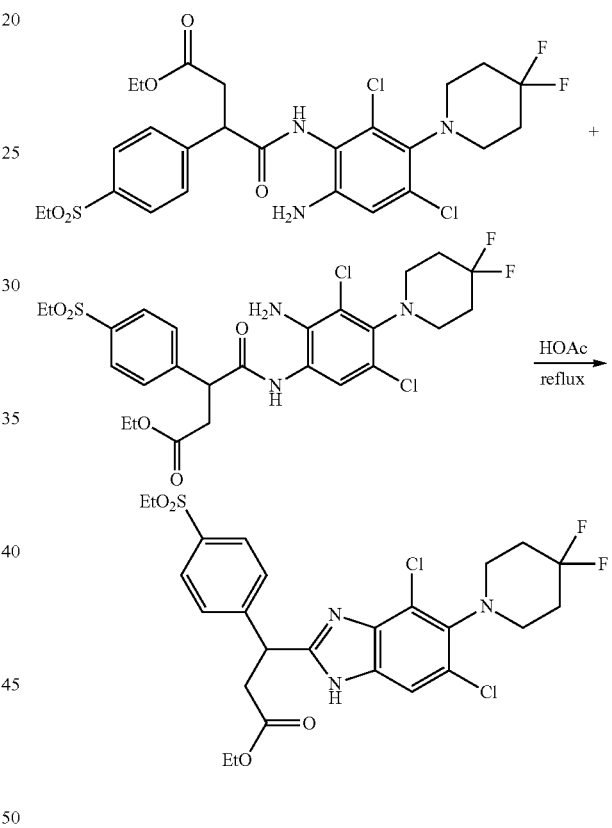

The mixture of ethyl 4-((6-amino-2,4-dichloro-3-(4,4-difluoropiperidin-1-yl)phenyl)amino)-3-(4-(ethylsulfonyl)phenyl)-4-oxobutanoate and ethyl 4-((2-amino-3,5-dichloro-4-(4,4-difluoropiperidin-1-yl)phenyl)amino)-3-(4-(ethylsulfonyl)phenyl)-4-oxobutanoate (385 mg) obtained from the previous step was treated with 15 mL of glacial acetic acid at 80° C. for 2 hours. It was concentrated, and purified on a silica gel column, eluting with 60% ethyl acetate in hexanes, to get ethyl 3-(4,6-dichloro-5-(4,4-difluoropiperidin-1-yl)-1H-benzo[d]imidazol-2-yl)-3-(4-(ethylsulfonyl)phenyl)propanoate (230 mg, 61.6% yield) as a pale solid. MS (ESI): 574 (M+H)⁺

Step 10. Preparation of (S)-3-(4,6-dichloro-5-(4,4-difluoropiperidin-1-yl)-1H-benzo[d]imidazol-2-yl)-3-(4-(ethylsulfonyl)phenyl)propan-1-ol and (R)-3-(4,6-dichloro-5-(4,4-difluoropiperidin-1-yl)-1H-benzo[d]imidazol-2-yl)-3-(4-(ethylsulfonyl)phenyl)propan-1-ol

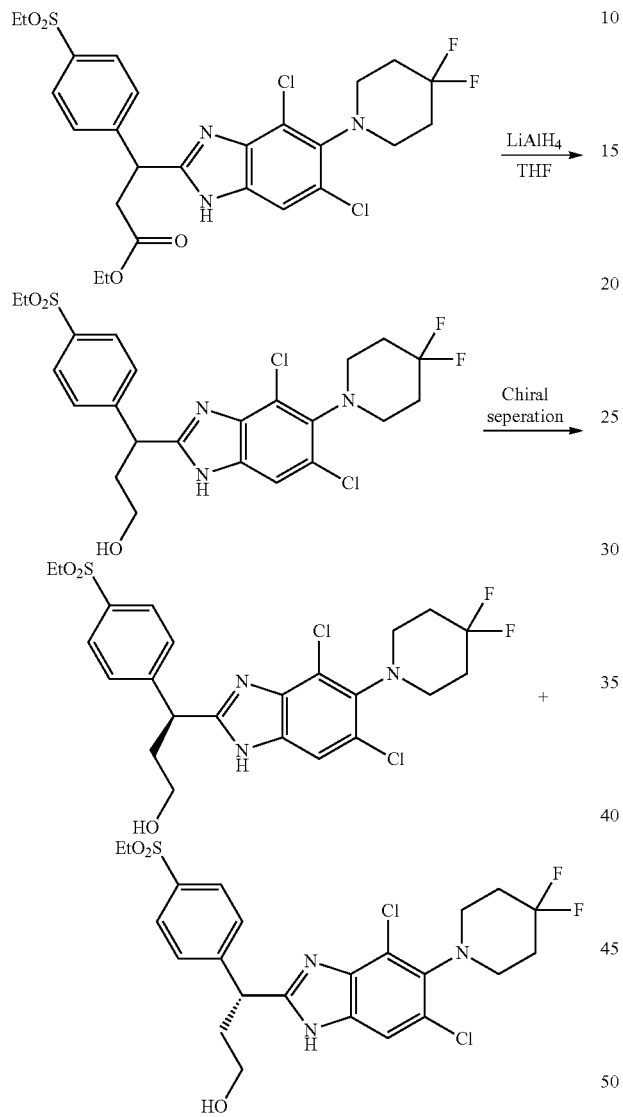

To a solution of ethyl 3-(4,6-dichloro-5-(4,4-difluoropiperidin-1-yl)-1H-benzo[d]imidazol-2-yl)-3-(4-(ethylsulfonyl)phenyl)propanoate (300 mg, 0.52 mmol) in THF (20 ml) was added LiAlH₄ (20 mg, 0.52 mmol) at 0° C. The reaction mixture was stirred at room temperature for 1 h. 5.0 mL water was added, the mixture was filtered. The filtrate was concentrated, the crude product was purified by flash column chromatography with hexane/ethyl acetate to get 3-(4,6-dichloro-5-(4,4-difluoropiperidin-1-yl)-1H-benzo[d]imidazol-2-yl)-3-(4-(ethylsulfonyl)phenyl)propan-1-ol (200 mg).

It was separated chirally (separation conditions: CHIRALCEL OZ—H(OZH00CD-VC005), 0.46 cm I.D.×15 cm L; mobile phase: Hexane/EtOH/DEA=70/30/0.1 (V/V/V); flow rate: 1.0 mL/min), The corresponding fractions were collected and concentrated under reduced pressure to obtain the title compounds (85 mg, 89 mg).

Single configuration compound (the shorter retention time)

MS (+) ES: 532 (M+H)+;

Chiral HPLC analysis: retention time 7.640 minutes, chiral purity: 100% (chromatographic column: OD Phenomenex Lux Cellulose-1 150*4.6 mm, 5 um; mobile phase: ethanol/hexane=15:85 (v/v);

¹H NMR (400 mHz, CD₃Cl): 7.90 (d, 8.0 Hz, 2H), 7.72 (s, 1H), 7.68 (d, 8.0 Hz, 2H), 4.68 (t, 8.0 Hz, 1H), 3.76 (t, 8.0 Hz, 2H), 3.71 (m, 4H), 3.14-3.12 (m, 2H), 2.65-2.60 (m, 1H), 2.38-2.35 (m, 1H), 2.10-2.10 (m, 4H), 1.23-1.19 (t, 8.0 Hz, 3H).

Single configuration compound (the longer retention time)

MS (+) ES: 532 (M+H)⁺.

Chiral HPLC analysis: retention time 9.398 minutes, chiral purity: 100% (chromatographic column: OD Phenomenex Lux Cellulose-1 150*4.6 mm, 5 um; mobile phase: ethanol/hexane=15:85 (v/v);

¹H NMR (400 mHz, CD₃OD): 7.90 (d, 8.0 Hz, 2H), 7.72 (s, 1H), 7.68 (d, 8.0 Hz, 2H), 4.68 (t, 8.0 Hz, 1H), 3.76 (t, 8.0 Hz, 2H), 3.71 (m, 4H), 3.14-3.12 (m, 2H), 2.65-2.60 (m, 1H), 2.38-2.35 (m, 1H), 2.10-2.10 (m, 4H), 1.23-1.19 (t, 8.0 Hz, 3H).

Example 141

Preparation of 3-(5-chloro-6-(2-(difluoromethoxy)phenyl)-1H-benzo[d]imidazol-2-yl)-3-(4-((cyclopropylmethyl)sulfonyl)phenyl)propanamide

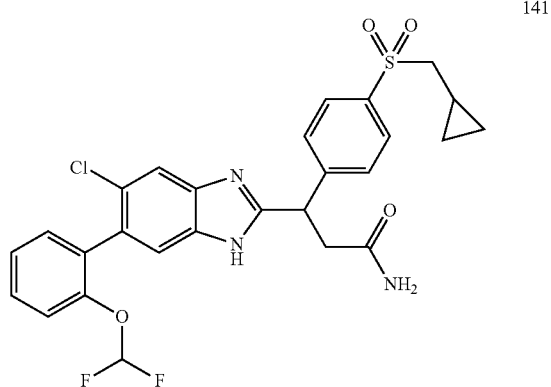 [SMILES: NC(=O)CC(c1ccc(S(=O)(=O)CC2CC2)cc1)c1nc2cc(Cl)c(-c3ccccc3OC(F)F)cc2[nH]1]

141

This compound was prepared by the same method as of racemic mixture of Examples 152 and 153. MS (+) ES: 560 (M+H)⁺.

Example 142

Preparation of 3-(5-chloro-6-(2-(difluoromethoxy)phenyl)-1H-benzo[d]imidazol-2-yl)-3-(4-((cyclopropylmethyl)sulfonyl)phenyl)propan-1-ol

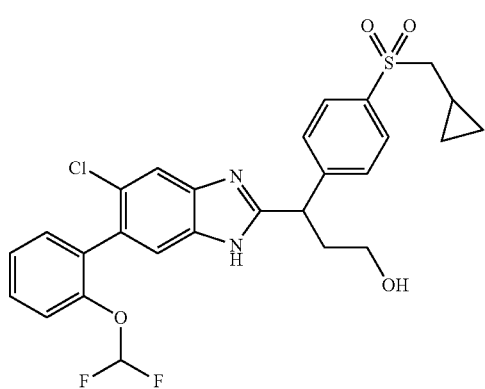

This compound was prepared by the same method as of racemic mixture of Examples 155 and 156. MS (+) ES: 547 (M+H)⁺.

Example 143

Preparation of 3-(5-chloro-6-(2-isopropoxyphenyl)-1H-benzo[d]imidazol-2-yl)-3-(4-((cyclopropylmethyl)sulfonyl)phenyl)propanamide

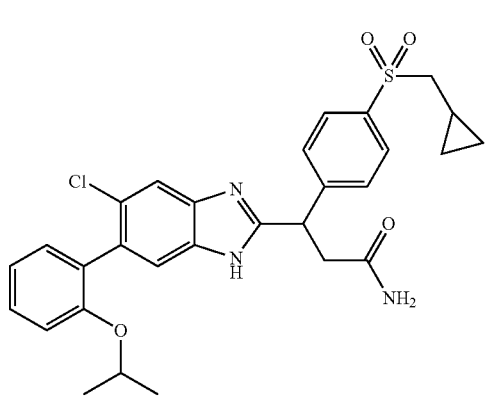

This compound was prepared by the same method as of racemic mixture of Examples 148 and 149. MS (+) ES: 552 (M+H)⁺.

Example 144

Preparation of 3-(5-chloro-6-(2-isopropoxyphenyl)-1H-benzo[d]imidazol-2-yl)-3-(4-((cyclopropylmethyl)sulfonyl)phenyl)propan-1-ol

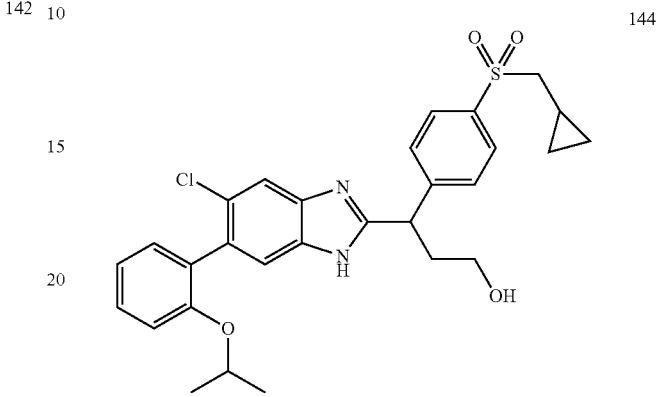

This compound was prepared by the same method as of racemic mixture of Examples 150 and 151. MS (+) ES: 539 (M+H)*.

Example 145

Preparation of 3-(4,6-dichloro-5-(4,4-difluoropiperidin-1-yl)-1H-benzo[d]imidazol-2-yl)-3-(4-(ethylsulfonyl)phenyl)propan-1-ol

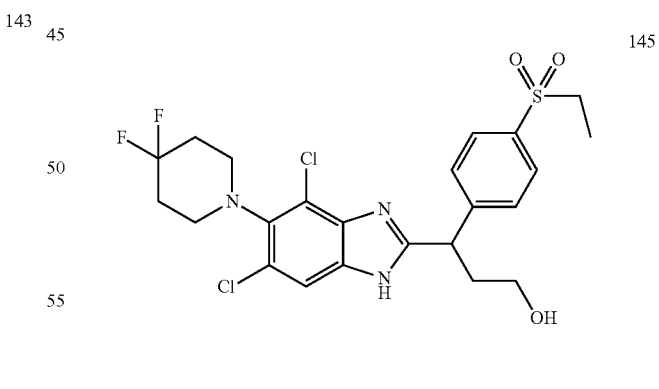

This compound was prepared by the same method as of racemic mixture of example 139 and 140. MS (+) ES: 532 (M+H)⁺.

Examples 146 and 147

Preparation of (S)-3-(4,6-dichloro-5-(4,4-difluoropiperidin-1-yl)-1H-benzo[d]imidazol-2-yl)-3-(4-(ethylsulfonyl)phenyl)propanamide and (R)-3-(4,6-dichloro-5-(4,4-difluoropiperidin-1-yl)-1H-benzo[d]imidazol-2-yl)-3-(4-(ethylsulfonyl)phenyl)propanamide

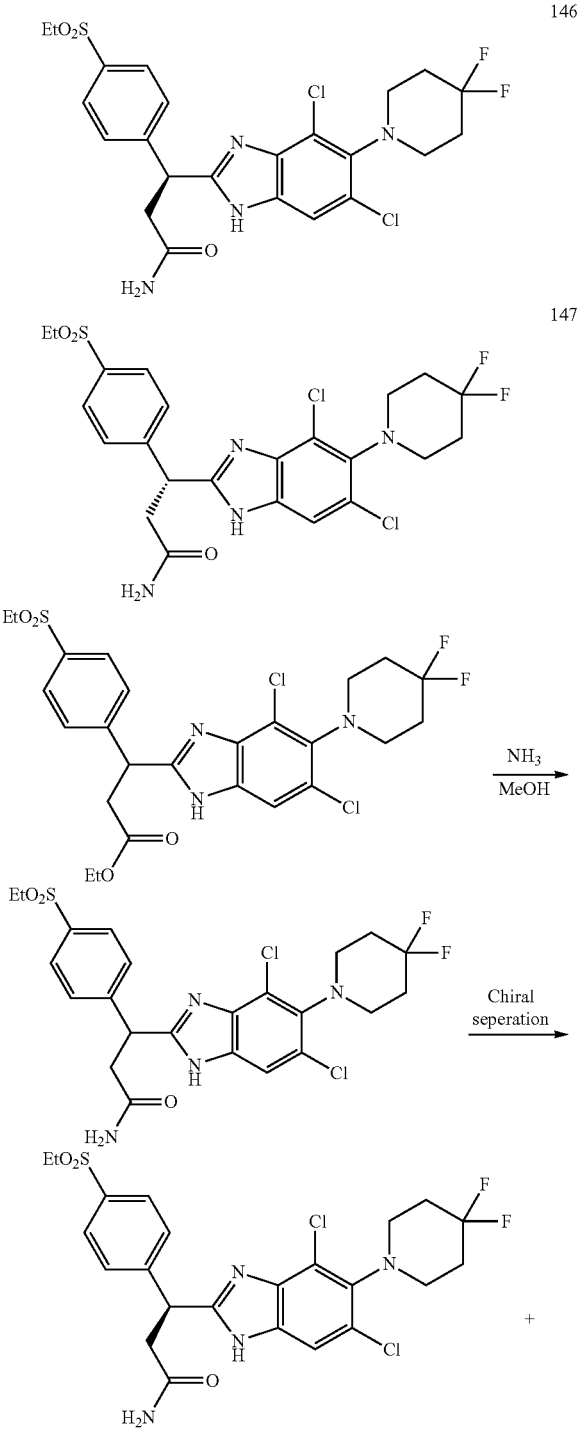

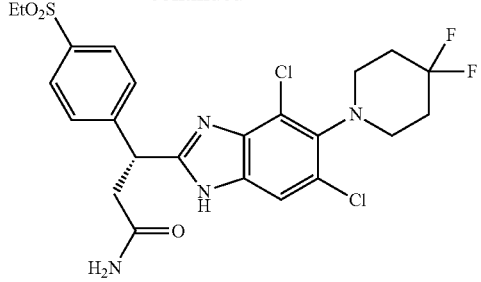

To a solution of ethyl 3-(4,6-dichloro-5-(4,4-difluoropiperidin-1-yl)-1H-benzo[d]imidazol-2-yl)-3-(4-(ethylsulfonyl)phenyl)propanoate (310 mg, 0.54 mmol) in methanol (20 ml) was added $NH_3$ (7.7 mL, 7N in methanol, 53.9 mmol). The reaction mixture was stirred at 60° C. for 12 h. the mixture was concentrated, the crude product was purified by flash column chromatography with hexane/ethyl acetate to get 3-(4,6-dichloro-5-(4,4-difluoropiperidin-1-yl)-1H-benzo[d]imidazol-2-yl)-3-(4-(ethylsulfonyl)phenyl)propanamide (300 mg).

It was separated chirally (separation conditions: CHIRALCEL OZ—H(OZH00CD-VC005), 0.46 cm I.D.×15 cm L; mobile phase:100% methanol; flow rate: 1.0 mL/min), The corresponding fractions were collected and concentrated under reduced pressure to obtain the title compounds (140 mg, 135 mg).

Single configuration compound (the shorter retention time)

MS (+) ES: 545 (M+H)+;

Chiral HPLC analysis: retention time 9.537 minutes, chiral purity: 100% (chromatographic column: OD Phenomenex Lux Cellulose-1 150*4.6 mm, 5 um; mobile phase: ethanol/hexane=15:85 (v/v);

$^1$H NMR (400 mHz, $CD_3OD$): 7.84 (d, 8.0 Hz, 2H), 7.63 (d, 8.0 Hz, 2H), 7.57 (s, 1H), 6.44 (s, 1H), 5.71 (s, 1H), 5.14 (t, 8.0 Hz, 1H), 3.74-3.68 (dd, 8.0 Hz, 1H), 3.2-3.22 (m, 4H), 3.15-3.09 (q, 2H), 3.09-3.03 (dd, 8.0 Hz, 1H), 2.18-2.10 (m, 4H), 1.31-1.27 (t, 8.0 Hz, 3H).

Single configuration compound (the longer retention time)

MS (+) ES: 545 (M+H)+;

Chiral HPLC analysis: retention time 11.851 minutes, chiral purity: 100% (chromatographic column: OD Phenomenex Lux Cellulose-1 150*4.6 mm, 5 um; mobile phase: ethanol/hexane=15:85 (v/v);

$^1$H NMR (400 mHz, $CD_3OD$): 7.84 (d, 8.0 Hz, 2H), 7.63 (d, 8.0 Hz, 2H), 7.57 (s, 1H), 6.44 (s, 1H), 5.71 (s, 1H), 5.14 (t, 8.0 Hz, 1H), 3.74-3.68 (dd, 8.0 Hz, 1H), 3.2-3.22 (m, 4H), 3.15-3.09 (q, 2H), 3.09-3.03 (dd, 8.0 Hz, 1H), 2.18-2.10 (m, 4H), 1.31-1.27 (t, 8.0 Hz, 3H).

Examples 148 and 149

Preparation of (S)-3-(6-chloro-5-(2-isopropoxyphenyl)-1H-benzo[d]imidazol-2-yl)-3-(4-((cyclopropylmethyl)sulfonyl)phenyl)propanamide and (R)-3-(6-chloro-5-(2-isopropoxyphenyl)-1H-benzo[d]imidazol-2-yl)-3-(4-((cyclopropylmethyl)sulfonyl)phenyl)propanamide

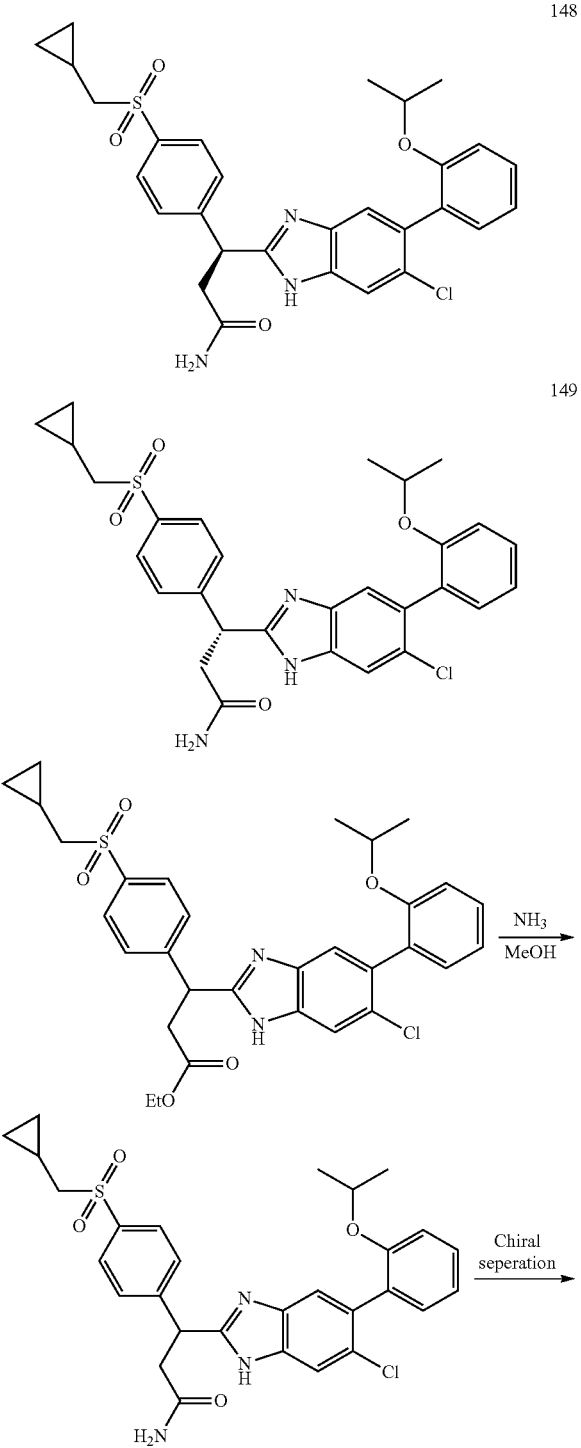

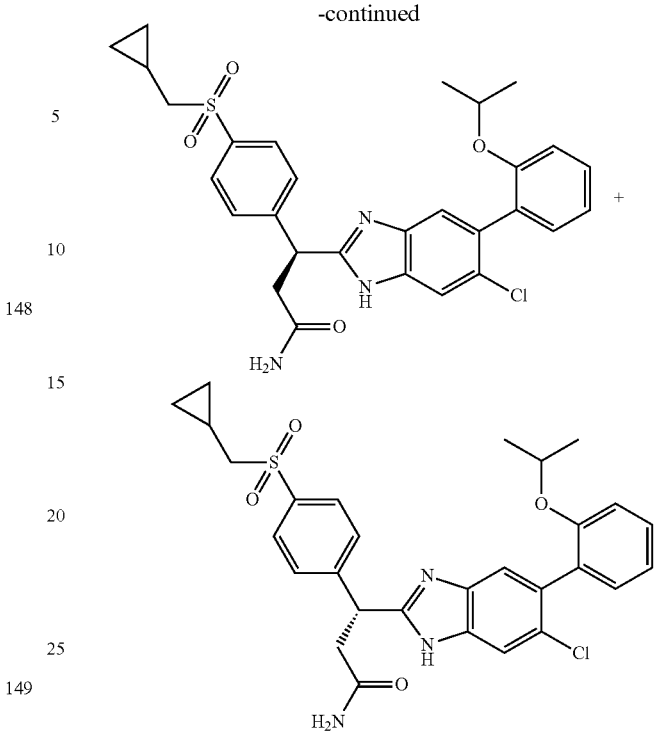

To a solution of ethyl 3-(6-chloro-5-(2-isopropoxyphenyl)-1H-benzo[d]imidazol-2-yl)-3-(4-((cyclopropylmethyl)sulfonyl)phenyl)propanoate (340 mg, 0.59 mmol) in methanol (5 ml) was added $NH_3$ (4.1 mL, 7N in methanol, 29.2 mmol). The reaction mixture was stirred at 60° C. for 12 h. the mixture was concentrated, the crude product was purified by flash column chromatography with hexane/ethyl acetate to get the title compound (220 mg).

It was separated chirally (separation conditions: CHIRALCEL OZ—H(OZH00CD-VCO005), 0.46 cm I.D.×15 cm L; mobile phase:100% methanol; flow rate: 1.0 m/min), The corresponding fractions were collected and concentrated under reduced pressure to obtain 3-(6-chloro-5-(2-isopropoxyphenyl)-1H-benzo[d]imidazol-2-yl)-3-(4-((cyclopropylmethyl)sulfonyl)phenyl)propanamide (97 mg, 87 mg).

Single configuration compound (the shorter retention time)

MS (+) ES: 552 (M+H)$^+$

Chiral HPLC analysis: retention time 5.617 minutes, chiral purity: 100% (chromatographic column: OD Phenomenex Lux Cellulose-1 150*4.6 mm, 5 um; mobile phase: ethanol/hexane=70:30 (v/v);

$^1$H NMR (400 mHz, $CD_3OD$): 7.92 (d, 8.0 Hz, 2H), 7.65 (d, 8.0 Hz, 2H), 7.51-7.49 (s, 1H), 7.35-7.31 (t, 8.0 Hz, 1H), 7.28 (s, 1H), 7.16-7.14 (d, 8.0 Hz, 1H), 7.05-7.03 (d, 8.0 Hz, 1H), 7.00-6.96 (d, 8.0 Hz, 1H), 4.95-4.91 (t, 8.0 Hz, 1H), 4.51-4.46 (m, 1H), 3.39-3.34 (dd, 8.0 Hz, 1H), 3.13-3.11 (d, 8.0 Hz, 2H), 3.12-3.06 (dd, 8.0 Hz, 1H), 1.16-1.15 (d, 4.0 Hz, 6H), 0.93-0.91 (m, 1H), 0.51-0.49 (d, 8.0 Hz, 2H), 0.13-0.11 (d, 8.0 Hz, 2H).

Single configuration compound (the longer retention time)

MS (+) ES: 552 (M+H)$^+$

Chiral HPLC analysis: retention time 15.283 minutes, chiral purity: 100% (chromatographic column: OD Phenomenex Lux Cellulose-1 150*4.6 mm, 5 um; mobile phase: ethanol/hexane=70:30 (v/v);

<sup>1</sup>H NMR (400 mHz, CD<sub>3</sub>OD): 7.92 (d, 8.0 Hz, 2H), 7.65 (d, 8.0 Hz, 2H), 7.51-7.49 (s, 1H), 7.35-7.31 (t, 8.0 Hz, 1H), 7.28 (s, 1H), 7.16-7.14 (d, 8.0 Hz, 1H), 7.05-7.03 (d, 8.0 Hz, 1H), 7.00-6.96 (d, 8.0 Hz, 1H), 4.95-4.91 (t, 8.0 Hz, 1H), 4.51-4.46 (m, 1H), 3.39-3.34 (dd, 8.0 Hz, 1H), 3.13-3.11 (d, 8.0 Hz, 2H), 3.12-3.06 (dd, 8.0 Hz, 1H), 1.16-1.15 (d, 4.0 Hz, 6H), 0.93-0.91 (m, 1H), 0.51-0.49 (d, 8.0 Hz, 2H), 0.13-0.11 (d, 8.0 Hz, 2H).
Examples 150 and 151
Preparation of (R)-3-(6-chloro-5-(2-isopropoxyphenyl)-1H-benzo[d]imidazol-2-yl)-3-(4-((cyclopropylmethyl)sulfonyl)phenyl)propan-1-ol and (S)-3-(6-chloro-5-(2-isopropoxyphenyl)-1H-benzo[d]imidazol-2-yl)-3-(4-((cyclopropylmethyl)sulfonyl)phenyl)propan-1-ol
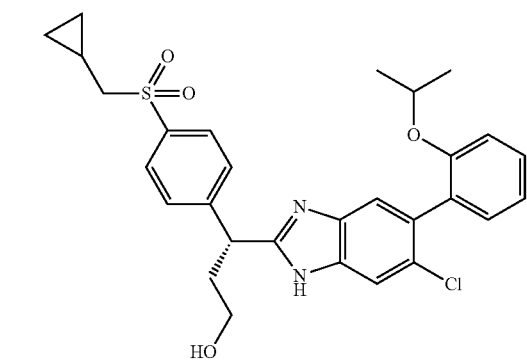
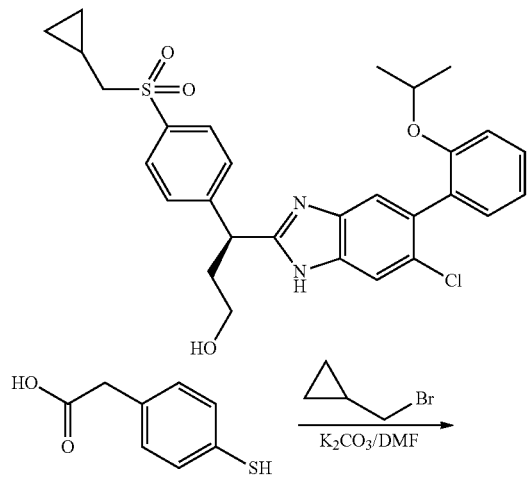
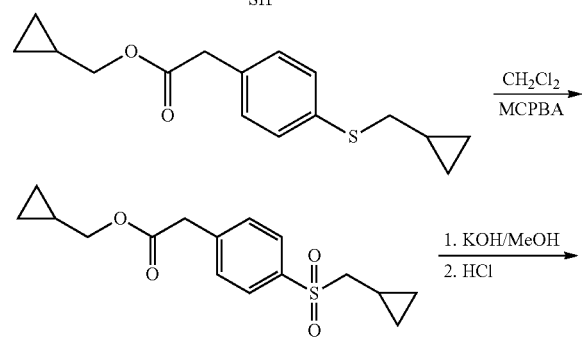
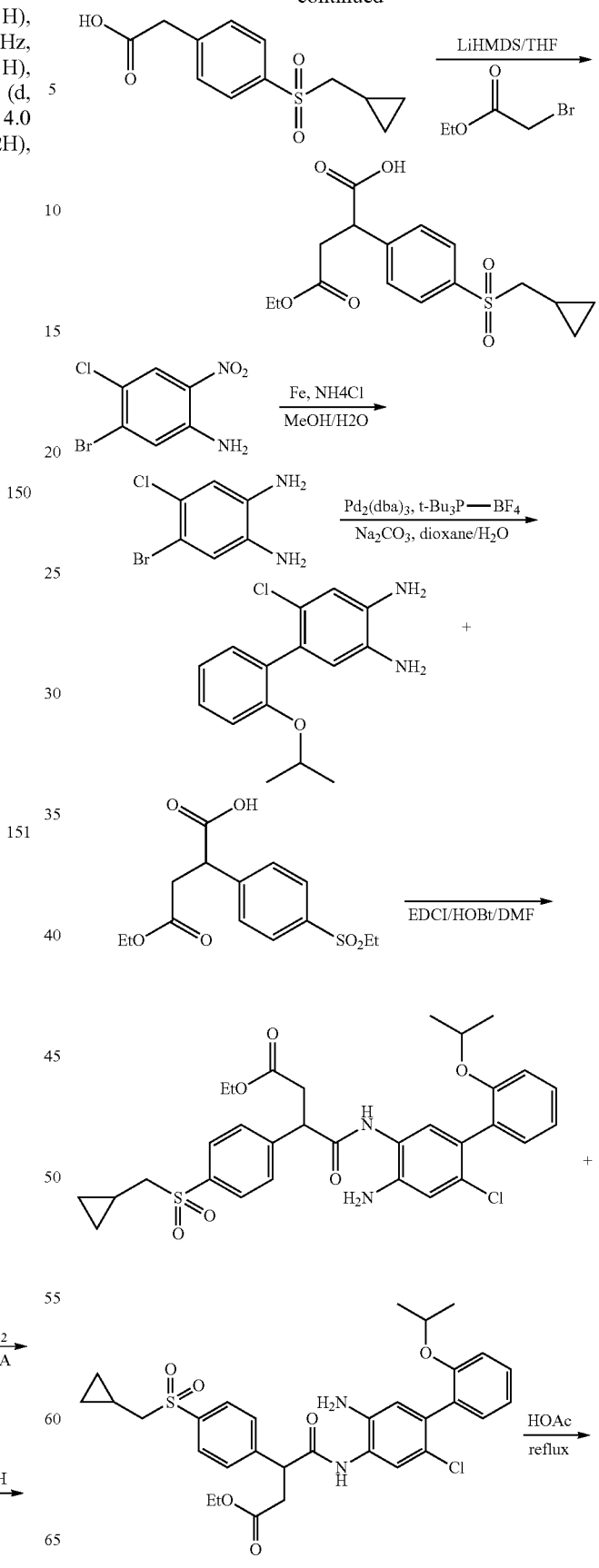

-continued

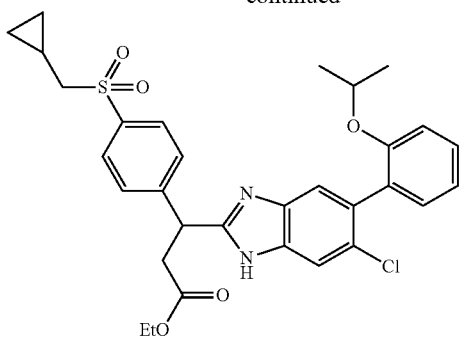

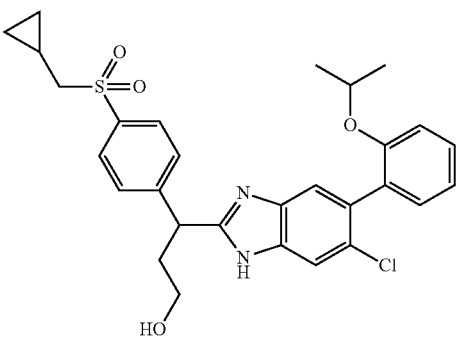

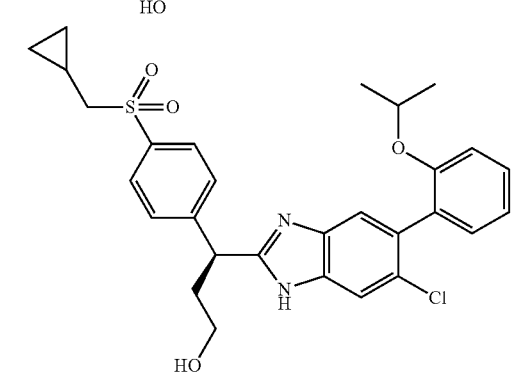

Step 1: Preparation of cyclopropylmethyl 2-(4-(cyclopropylmethylthio) phenyl)acetate

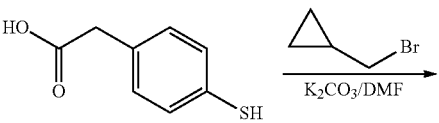

-continued

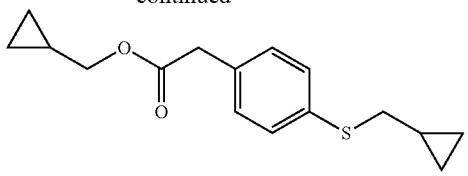

To a solution of 2-(4-mercaptophenyl)acetic acid (10 g, 59.4 mmol) in DMF (100 mL), was added potassium carbonate (25.0 g, 181.2 mmol) and cyclopropylmethyl bromide (20 g, 148.1 mmol). The reaction mixture was stirred at 50° C. overnight. It was distributed between water and ethyl acetate. The organic layer was dried over sodium sulfate, concentrated, and purified on a silica gel column, eluting with 25% ethyl acetate in hexanes, to get cyclopropylmethyl 2-(4-(cyclopropylmethylthio)phenyl)acetate (15.0 g, 91.3% yield) as a colorless oil.

Step 2: Preparation of cyclopropylmethyl 2-(4-(cyclopropylmethyl)sulfonyl)phenyl) acetate

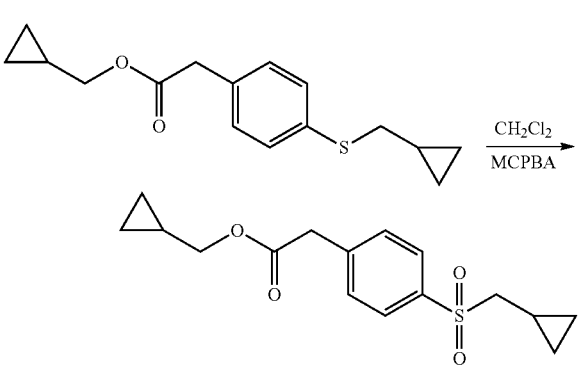

To a solution of cyclopropylmethyl 2-(4-(cyclopropylmethylthio)phenyl)acetate (15.0 g, 54.3 mmol) in dichloromethane (200 mL), was added MCPBA (23.4 g, 135.6 mmol) at 0° C. After addition, the reaction mixture was stirred at ambient temperature for 14 hours. It was distributed between dichloromethane and saturated sodium thiosulfate. The organic layer was washed with 2N aqueous sodium hydroxide solution and brine. It was concentrated and purified on a silica gel column, eluting with 60% ethyl acetate in hexanes, to get cyclopropylmethyl 2-(4-(cyclopropylmethyl)sulfonyl)phenyl)acetate (12 g, 71.6% yield) as a white solid.

Step 3: Preparation of 2-(4-(cyclopentylmethyl sulfonyl)phenyl)acetic acid

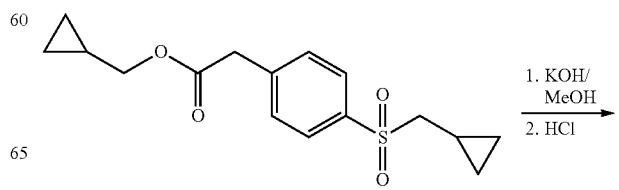

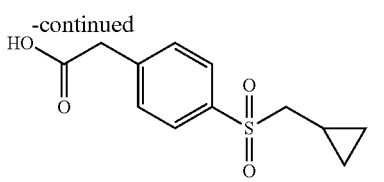

To a 250 mL round bottom flask, were added cyclopropylmethyl 2-(4-(cyclopropylmethyl)sulfonyl)phenyl)acetate (15.0 g, 48.6 mmol) and methanol (100 mL). a solution of sodium hydroxide in water (3.8 g, 95.0 mmol in 100 ml of water) was added. The reaction mixture was heated to reflux for 12 h. The volatiles were evaporated under reduced pressure. The residue was acidified with 1N HCl to pH 3.0 and extracted with ethyl acetate (100 ml×3). The organic layer was separated and combined, washed with brine and dried over sodium sulfate. The solvent was evaporated under reduced pressure to get the title compound as a white solid (9.0 g, 72.7%), MS (+) ES: 255 (M+H)$^+$.

Step 4. Preparation of 2-(4-((cyclopropylmethyl)sulfonyl)phenyl)-4-ethoxy-4-oxobutanoic acid

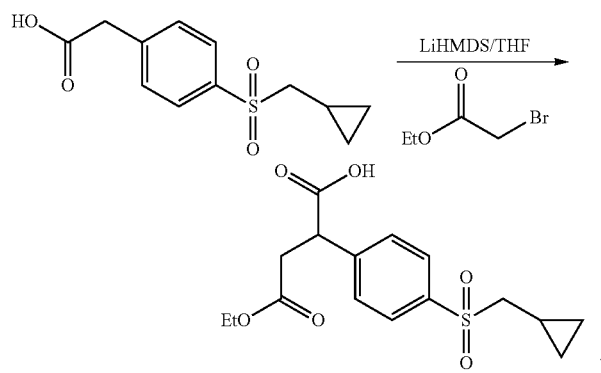

To 2-(4-(cyclopentylmethyl)sulfonyl)phenyl)acetic acid (1.0 g, 3.9 mmol) in THF (30 mL) at −78° C. was added LiHMDS (1M in THF, 8.4 mL). After 15 min, ethyl 2-bromoacetate (1.0 g, 5.9 mmol) was added. The reaction mixture was stirred at −78° C. for 1.0 h, then 0.1N HCl solution was added to adjust pH to 3-4. Extracted with EtOAc three times, dried over Na$_2$SO$_4$, filtered, concentrated. The residue was purified by silica gel column with elution system A to give yellow oil 0.8 g, MS (ESI): 341 (M+H)*.

Step 5. Preparation of 4-bromo-5-chlorobenzene-1,2-diamine

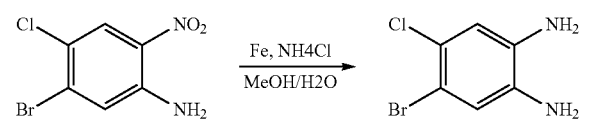 [SMILES: Nc1cc(Br)c(Cl)cc1[N+](=O)[O-] ; Nc1cc(Cl)c(Br)cc1N]

To a solution of 5-bromo-4-chloro-2-nitroaniline (9.0 g, 35.8 mmol) in 250 mL of methanol and 60 mL of water was added Fe powder (6.0 g, 107.4 mmol) and NH4Cl (5.7 g, 106.5 mmol). The reaction mixture was stirred at 80° C. overnight. It was filtered. The filtrate was concentrated, and purified on a silica gel column, eluting with ethyl acetate, to get 4-bromo-5-chlorobenzene-1,2-diamine (6.0 g, 75.7% yield) as a yellow solid.

Step 6. Preparation of 6-chloro-2'-isopropoxy-[1,1'-biphenyl]-3,4-diamine

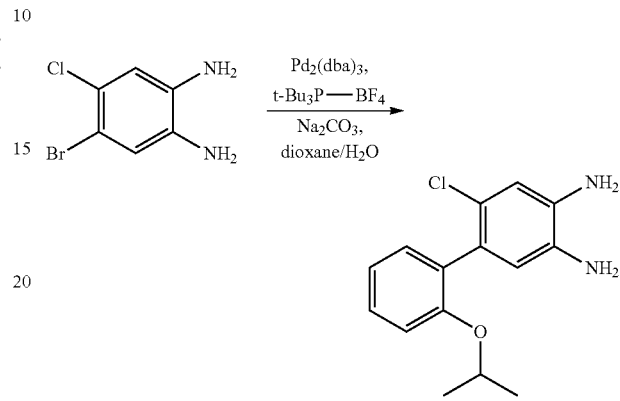

A mixture of 4-bromo-5-chlorobenzene-1,2-diamine (1.1 g, 5.0 mmol), (2-isopropoxyphenyl)boronic acid (1.1 g, 6.1 mmol), tris-(dibenzylideneacetone) dipalladium(0) (454 mg), tri(tert-butyl)phosphonium tetrafluoroboronate (288 mg) and sodium carbonate (1.8 g, 14.5 mmol) in 1,4-dioxane (100 ml) and water (10 mL) was degassed, heated to 90° C. under for 3 h. The volatile solvents were removed under reduced pressure. The residue was directly loaded onto a ISCO solid cartridge and flashed with hexane/ethyl acetate to afford a white solid product 1.1 g (80% yield), MS (+) ES: 277 (M+H)$^+$.

Step 7. Preparation of ethyl 4-((4-amino-6-chloro-2'-isopropoxy-[1,1'-biphenyl]-3-yl)amino)-3-(4-((cyclopropylmethyl)sulfonyl)phenyl)-4-oxobutanoate and ethyl 4-((5-amino-2-chloro-2'-isopropoxy-[1,1'-biphenyl]-4-yl)amino)-3-(4-((cyclopropylmethyl)sulfonyl)phenyl)-4-oxobutanoate

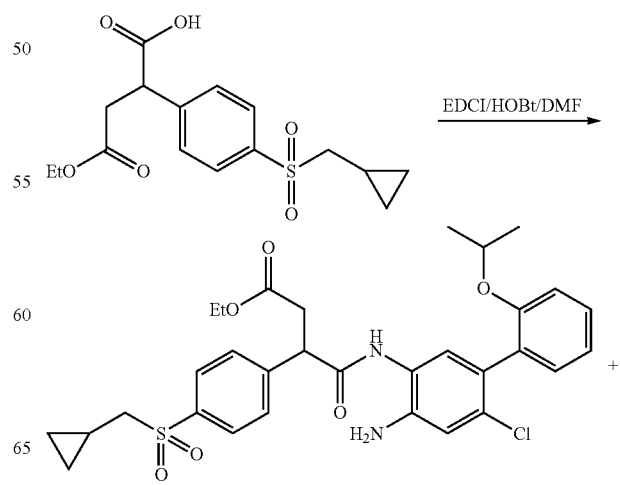

257

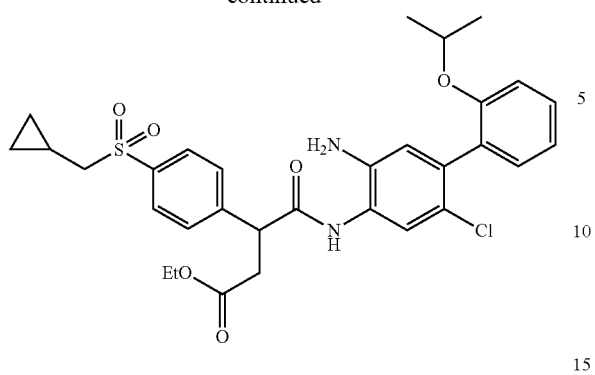

258

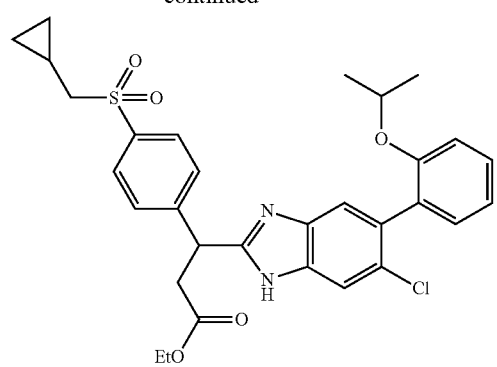

To a solution of 6-chloro-2'-isopropoxy-[1,1'-biphenyl]-3,4-diamine (600 mg, 1.76 mmol) and 2-(4-((cyclopropylmethyl)sulfonyl)phenyl)-4-ethoxy-4-oxobutanoic acid (585 mg, 2.11 mmol) in DMF (5 mL) was added EDCI (674 mg, 3.53 mmol), HOBT (537 mg, 3.53 mmol) and DIPEA (455 mg, 3.53 mmol). The reaction solution was stirred at room temperature for 2 hours. It was absorbed onto 5 g of silica gel, and loaded onto a silica gel column. The column was eluted with 45% of ethyl acetate in hexanes to get a mixture of ethyl 4-((4-amino-6-chloro-2'-isopropoxy-[1,1'-biphenyl]-3-yl)amino)-3-(4-((cyclopropylmethyl)sulfonyl)phenyl)-4-oxobutanoate and ethyl 4-((5-amino-2-chloro-2'-isopropoxy-[1,1'-biphenyl]-4-yl)amino)-3-(4-((cyclopropylmethyl)sulfonyl)phenyl)-4-oxobutanoate (750 mg, 71% yield) as a white solid. MS (ESI): 599 (M+H)$^+$.

Step 8. Preparation of ethyl 3-(6-chloro-5-(2-isopropoxyphenyl)-1H-benzo[d]imidazol-2-yl)-3-(4-((cyclopropylmethyl)sulfonyl)phenyl)propanoate The mixture of ethyl 4-((4-amino-6-chloro-2'-isopropoxy-[1,1'-biphenyl]-3-yl) amino)-3-(4-((cyclopropylmethyl)sulfonyl)phenyl)-4-oxobutanoate and ethyl 4-((5-amino-2-chloro-2'-isopropoxy-[1,1'-biphenyl]-4-yl)amino)-3-(4-((cyclopropylmethyl)sulfonyl)phenyl)-4-oxobutanoate (800 mg) was treated with 15 mL of glacial acetic acid at 80° C. for 2 hours. It was concentrated, and purified on a silica gel column, eluting with 60% ethyl acetate in hexanes, to get ethyl 3-(6-chloro-5-(2-isopropoxyphenyl)-1H-benzo[d]imidazol-2-yl)-3-(4-((cyclopropylmethyl)sulfonyl)phenyl)propanoate (700 mg, 90% yield) as a pale solid. MS (ESI): 581 (M+H)$^+$.

Step 9. Preparation of (R)-3-(6-chloro-5-(2-isopropoxyphenyl)-1H-benzo[d]imidazol-2-yl)-3-(4-((cyclopropylmethyl)sulfonyl)phenyl)propan-1-ol and (S)-3-(6-chloro-5-(2-isopropoxyphenyl)-1H-benzo[d]imidazol-2-yl)-3-(4-((cyclopropylmethyl)sulfonyl)phenyl)propan-1-ol

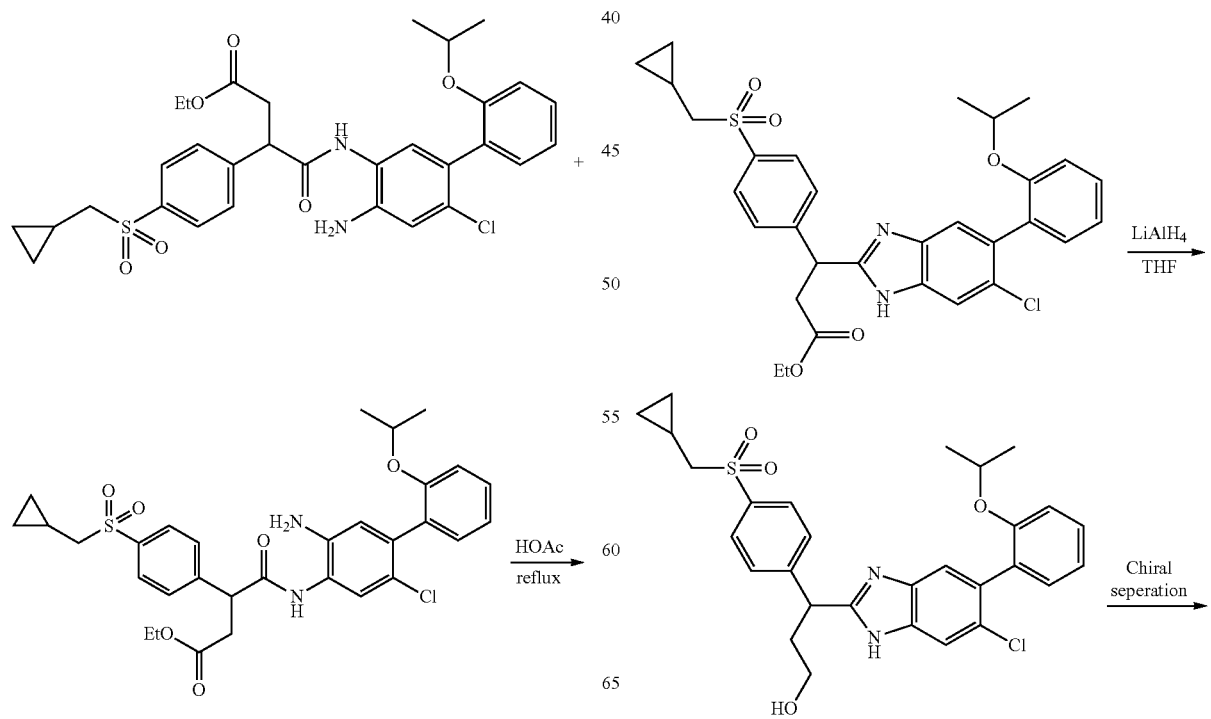

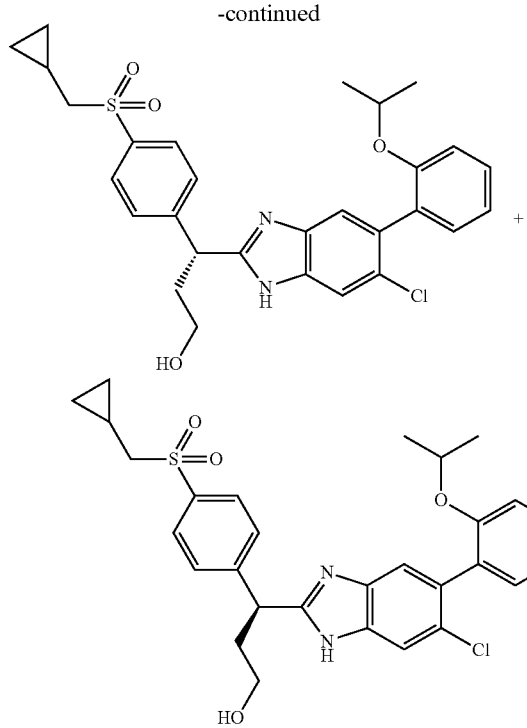

To a solution of ethyl 3-(6-chloro-5-(2-isopropoxyphenyl)-1H-benzo[d]imidazol-2-yl)-3-(4-((cyclopropylmethyl)sulfonyl)phenyl)propanoate (440 mg, 0.76 mmol) in THF (20 ml) was added LiAlH$_4$ (29 mg, 0.76 mmol) at 0° C. The reaction mixture was stirred at room temperature for 1 h. 5.0 mL water was added, the mixture was filtered. The filtrate was concentrated, the crude product was purified by flash column chromatography with hexane/ethyl acetate to get the 3-(6-chloro-5-(2-isopropoxyphenyl)-1H-benzo[d]imidazol-2-yl)-3-(4-((cyclopropylmethyl)sulfonyl)phenyl)propan-1-ol (400 mg).

It was separated chirally (separation conditions: CHIRALCEL OZ—H(OZH00CD-VCO005), 0.46 cm I.D.×15 cm L; mobile phase: ethanol/hexane=6:4 (v/v); flow rate: 1.0 mL/min), The corresponding fractions were collected and concentrated under reduced pressure to obtain the title compounds (183 mg, 165 mg).

Single configuration compound (the shorter retention time)

MS (+) ES: 539 (M+H)+;

Chiral HPLC analysis: retention time 6.938 minutes, chiral purity: 100% (chromatographic column: OD Phenomenex Lux Cellulose-1 150*4.6 mm, 5 um; mobile phase: ethanol/hexane=40:60 (v/v);

$^1$H NMR (400 mHz, CD$_3$OD): 7.90 (d, 8.0 Hz, 2H), 7.67 (d, 8.0 Hz, 2H), 7.62 (s, 0.5H), 7.49 (s, 0.5H), 4.59 (t, 8.0 Hz, 1H), 4.38 (dd, 8.0, 11.0 Hz, 1H), 4.27-4.11 (m, 1H), 3.44-3.28 (m, 4H), 3.20 (q, 8.0 Hz, 2H), 2.24-2.01 (m, 4H), 1.21 (t, 8.0 Hz, 3H). Single configuration compound (the longer retention time)

MS (+) ES: 539 (M+H)+;

Chiral HPLC analysis: retention time 11.098 minutes, chiral purity: 100% (chromatographic column: OD Phenomenex Lux Cellulose-1 150*4.6 mm, 5 um; mobile phase: ethanol/hexane=40:60 (v/v);

$^1$H NMR (400 mHz, CD$_3$OD): 7.90 (d, 8.0 Hz, 2H), 7.67 (d, 8.0 Hz, 2H), 7.62 (s, 0.5H), 7.49 (s, 0.5H), 4.59 (t, 8.0 Hz, 1H), 4.38 (dd, 8.0, 11.0 Hz, 1H), 4.27-4.11 (m, 1H), 3.44-3.28 (m, 4H), 3.20 (q, 8.0 Hz, 2H), 2.24-2.01 (m, 4H), 1.21 (t, 8.0 Hz, 3H).

Examples 152 and 153

Preparation of (S)-3-(6-chloro-5-(2-(difluoromethoxy)phenyl)-1H-benzo[d]imidazol-2-yl)-3-(4-((cyclopropylmethyl)sulfonyl)phenyl)propanamide and (R)-3-(6-chloro-5-(2-(difluoromethoxy)phenyl)-1H-benzo[d]imidazol-2-yl)-3-(4-((cyclopropylmethyl)sulfonyl)phenyl)propanamide

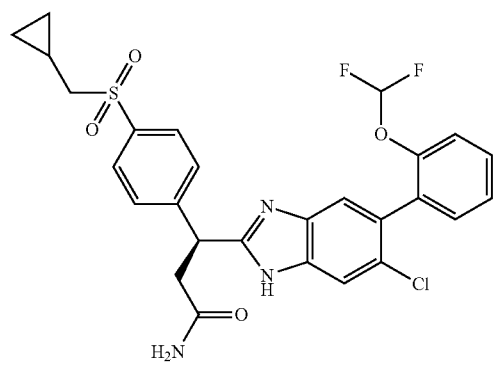

152

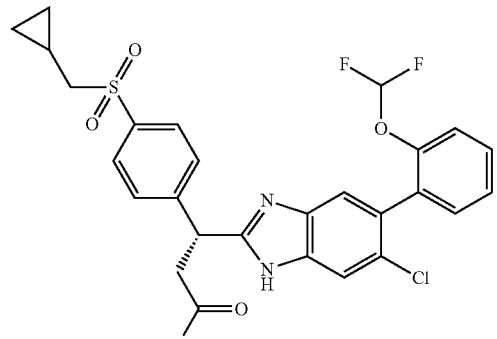

153

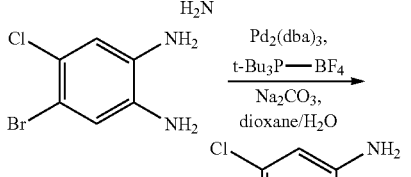

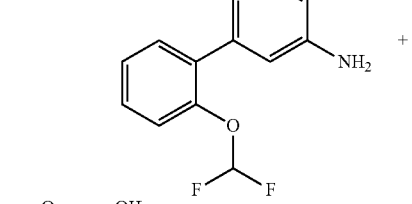

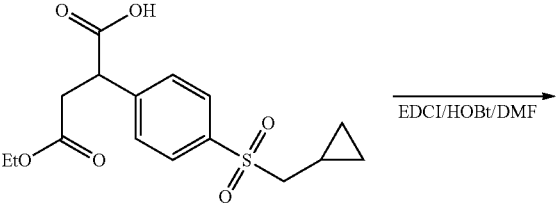

261
-continued

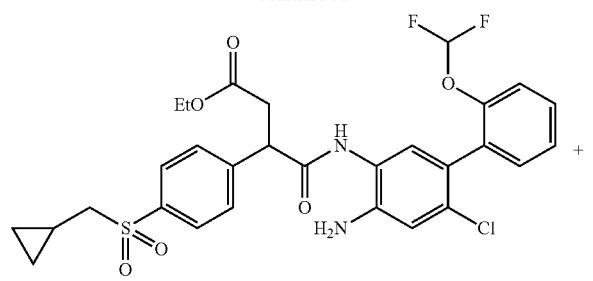

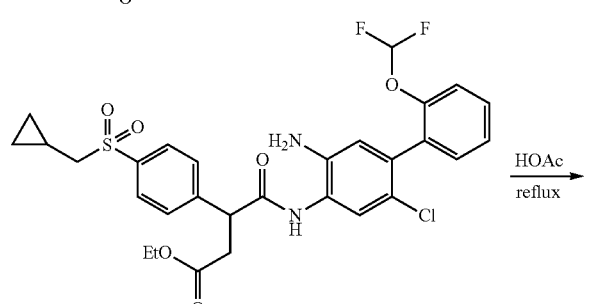

HOAc
reflux

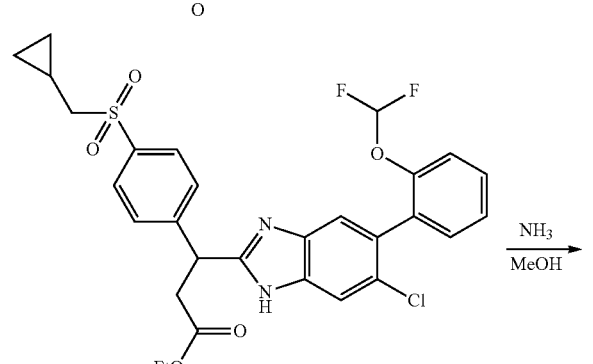

NH₃
MeOH

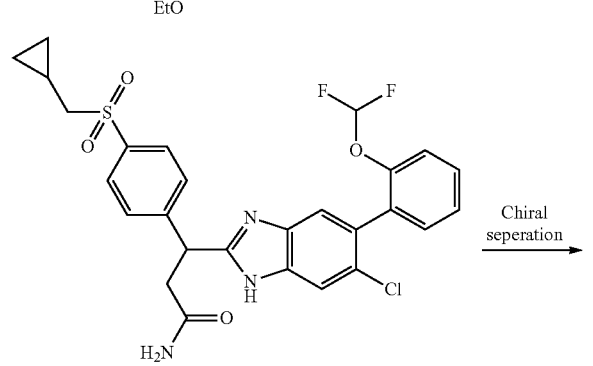

Chiral
seperation

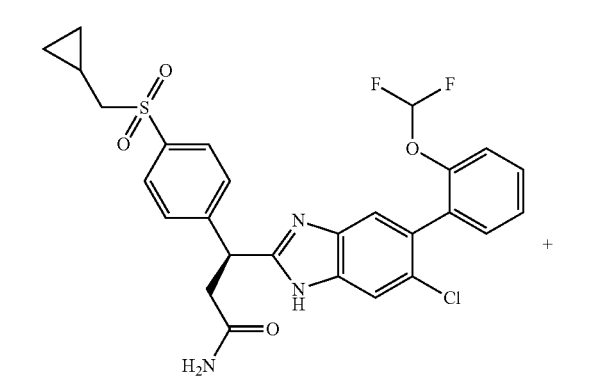

262
-continued

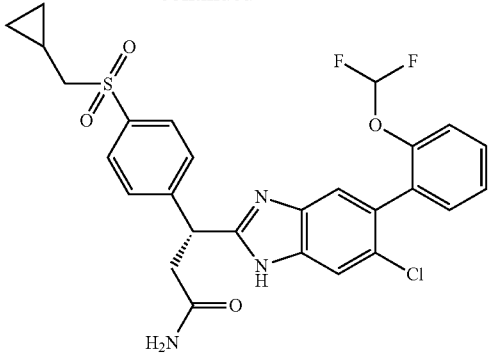

Step 1. Preparation of 6-chloro-2'-(difluoromethoxy)-[1,1'-biphenyl]-3,4-diamine

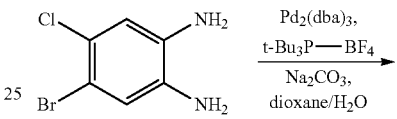

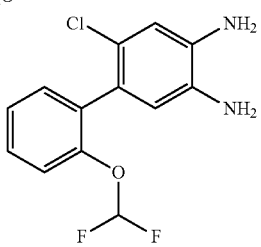

A mixture of 4-bromo-5-chlorobenzene-1,2-diamine (1.5 g, 6.78 mmol), 2-(2-(difluoromethoxy)phenyl)-4,4,5,5-tetramethyl-1,3,2-dioxaborolane (2.2 g, 8.15 mmol), tris-(dibenzylideneacetone)dipalladium(0) (620 mg), tri(tert-butyl) phosphonium tetrafluoroborate (393 mg) and sodium carbonate (1.7 g, 13.7 mmol) in 1,4-dioxane (50 ml) and water (10 mL) was degassed, heated to 90° C. under for 3 h. The volatile solvents were removed under reduced pressure. The residue was directly loaded onto a ISCO solid cartridge and flashed with hexane/ethyl acetate to afford a white solid product 1.0 g (51.9% yield), MS (+) ES: 285 (M+H)⁺.

Step 2. Preparation of ethyl 4-((4-amino-6-chloro-2'-(difluoromethoxy)-[1,1'-biphenyl]-3-yl)amino)-3-(4-((cyclopropylmethyl)sulfonyl)phenyl)-4-oxobutanoate and ethyl 4-((5-amino-2-chloro-2'-(difluoromethoxy)-[1,1'-biphenyl]-4-yl)amino)-3-(4-((cyclopropylmethyl)sulfonyl)phenyl)-4-oxobutanoate

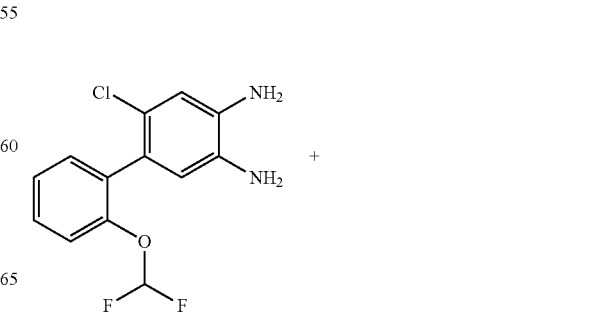

263
-continued

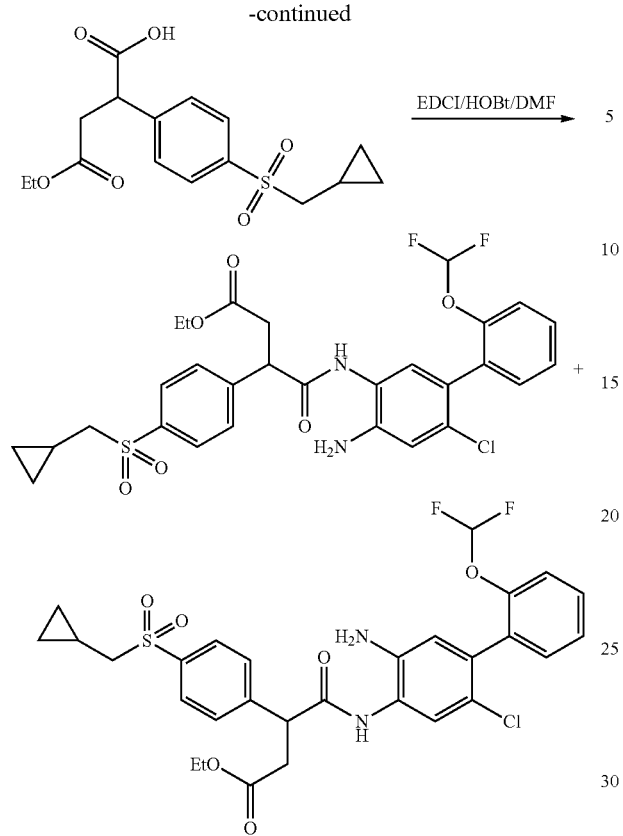

To a solution of 6-chloro-2'-(difluoromethoxy)-[1,1'-biphenyl]-3,4-diamine (543 mg, 1.9 mmol) and 2-(4-((cyclopropylmethyl)sulfonyl)phenyl)-4-ethoxy-4-oxobutanoic acid (500 mg, 1.47 mmol) in DMF (5 mL) was added EDCI (560 mg, 2.93 mmol), HOBT (447 mg, 2.93 mmol) and DIPEA (380 mg, 2.94 mmol). The reaction solution was stirred at room temperature for 2 hours. It was absorbed onto 5 g of silica gel, and loaded onto a silica gel column. The column was eluted with 45% of ethyl acetate in hexanes to get a mixture of ethyl 4-((4-amino-6-chloro-2'-(difluoromethoxy)-[1,1'-biphenyl]-3-yl)amino)-3-(4-((cyclopropylmethyl)sulfonyl)phenyl)-4-oxobutanoate and ethyl 4-((5-amino-2-chloro-2'-(difluoromethoxy)-[1,1'-biphenyl]-4-yl)amino)-3-(4-((cyclopropylmethyl) sulfonyl)phenyl)-4-oxobutanoate (600 mg, 62.3% yield) as a white solid. MS (ESI): 607 (M+H)⁺.

Step 3. Preparation of ethyl 3-(6-chloro-5-(2-(difluoromethoxy)phenyl)-1H-benzo[d]imidazol-2-yl)-3-(4-((cyclopropylmethyl)sulfonyl)phenyl)propanoate 264
-continued

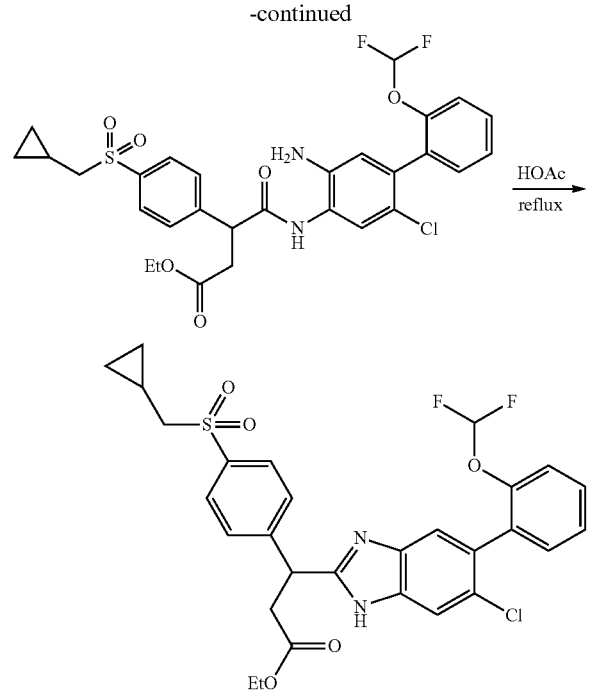

The mixture of ethyl 4-((4-amino-6-chloro-2'-(difluoromethoxy)-[1,1'-biphenyl]-3-yl)amino)-3-(4-((cyclopropylmethyl)sulfonyl)phenyl)-4-oxobutanoate and ethyl 4-((5-amino-2-chloro-2'-(difluoromethoxy)-[1,1'-biphenyl]-4-yl)amino)-3-(4-((cyclopropylmethyl)sulfonyl)phenyl)-4-oxobutanoate (800 mg) was treated with 15 mL of glacial acetic acid at 80° C. for 2 hours. It was concentrated, and purified on a silica gel column, eluting with 60% ethyl acetate in hexanes, to get ethyl 3-(6-chloro-5-(2-isopropoxyphenyl)-1H-benzo[d]imidazol-2-yl)-3-(4-((cyclopropylmethyl)sulfonyl) phenyl)propanoate (600 mg, 77.3% yield) as a pale solid. MS (ESI): 589 (M+H)⁺.

Step 4. Preparation of ethyl (S)-3-(6-chloro-5-(2-(difluoromethoxy)phenyl)-1H-benzo[d]imidazol-2-yl)-3-(4-((cyclopropylmethyl)sulfonyl)phenyl)propanamide and (R)-3-(6-chloro-5-(2-(difluoromethoxy)phenyl)-1H-benzo[d]imidazol-2-yl)-3-(4-((cyclopropylmethyl)sulfonyl)phenyl) propanamide

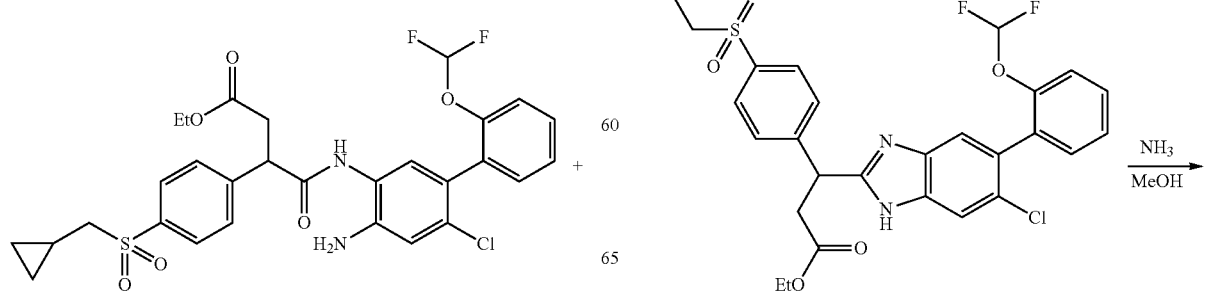

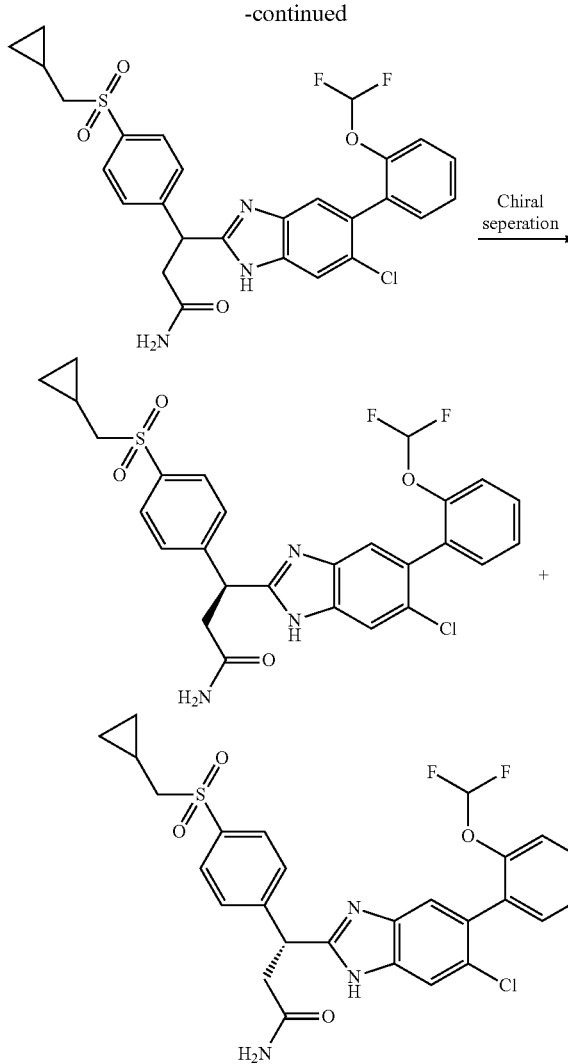

To a solution of ethyl 3-(6-chloro-5-(2-(difluoromethoxy)phenyl)-1H-benzo[d]imidazol-2-yl)-3-(4-((cyclopropylmethyl)sulfonyl)phenyl)propanoate (400 mg, 0.68 mmol) in methanol (5 ml) was added NH₃ (4.8 mL, 7N in methanol, 33.9 mmol). The reaction mixture was stirred at 60° C. for 12 h. the mixture was concentrated, the crude product was purified by flash column chromatography with hexane/ethyl acetate to get 3-(6-chloro-5-(2-(difluoromethoxy)phenyl)-1H-benzo[d]imidazol-2-yl)-3-(4-((cyclopropylmethyl)sulfonyl)phenyl)propanamide (177 mg).

It was separated chirally (separation conditions: CHIRALCEL OZ—H(OZH00CD-VC005), 0.46 cm I.D.×15 cm L; mobile phase:100% methanol; flow rate: 1.0 mL/min), The corresponding fractions were collected and concentrated under reduced pressure to obtain the title compounds (67 mg, 60 mg).

Single configuration compound (the shorter retention time)

MS (+) ES: 560 (M+H)⁺.

Chiral HPLC analysis: retention time 3.919 minutes, chiral purity: 100% (chromatographic column: OD Phenomenex Lux Cellulose-1 150*4.6 mm, 5 um; mobile phase: ethanol/hexane=80:20 (v/v);

¹H NMR (400 mHz, CD₃OD): 7.92 (d, 8.0 Hz, 2H), 7.51-7.49 (s, 1H), 7.65 (d, 8.0 Hz, 2H), 7.56-7.54 (m, 1H), 7.48-7.44 (m, 1H), 7.33-7.32 (m, 2H), 7.28-7.26 (d, 8.0 Hz, 1H), 6.86 (d, 8.0 Hz, 1H), 4.96-4.92 (t, 8.0 Hz, 1H), 3.41-3.35 (dd, 8.0 Hz, 1H), 3.13-3.11 (d, 8.0 Hz, 2H), 3.12-3.06 (dd, 8.0 Hz, 1H), 0.93-0.91 (m, 1H), 0.52-0.50 (d, 8.0 Hz, 2H), 0.13-0.11 (d, 8.0 Hz, 2H).

Single configuration compound (the longer retention time)

MS (+) ES: 560 (M+H)+;

Chiral HPLC analysis: retention time 8.942 minutes, chiral purity: 100% (chromatographic column: OD Phenomenex Lux Cellulose-1 150*4.6 mm, 5um; mobile phase: ethanol/hexane=80:20 (v/v);

¹H NMR (400 mHz, CD₃OD): 7.92 (d, 8.0 Hz, 2H), 7.51-7.49 (s, 1H), 7.65 (d, 8.0 Hz, 2H), 7.56-7.54 (m, 1H), 7.48-7.44 (m, 1H), 7.33-7.32 (m, 2H), 7.28-7.26 (d, 8.0 Hz, 1H), 6.86 (d, 8.0 Hz, 1H), 4.96-4.92 (t, 8.0 Hz, 1H), 3.41-3.35 (dd, 8.0 Hz, 1H), 3.13-3.11 (d, 8.0 Hz, 2H), 3.12-3.06 (dd, 8.0 Hz, 1H), 0.93-0.91 (m, 1H), 0.52-0.50 (d, 8.0 Hz, 2H), 0.13-0.11 (d, 8.0 Hz, 2H).

Example 154

Preparation of 3-(4-((cyclopropylmethyl)sulfonyl)phenyl)-3-(5,7-dichloro-6-(4,4-difluoropiperidin-1-yl)-1H-benzo[d]imidazol-2-yl)propanamide

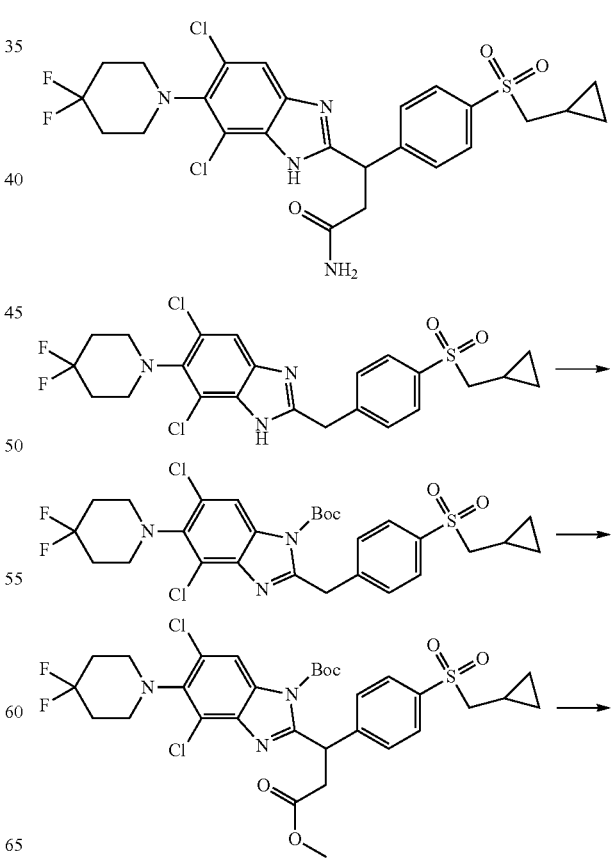

-continued

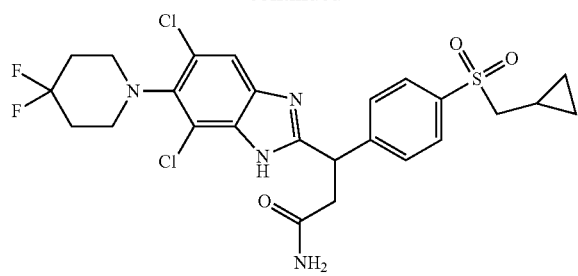

-continued

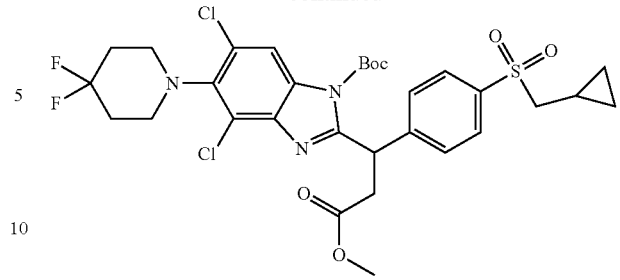

Step 1. Preparation of tert-butyl 4,6-dichloro-2-(4-((cyclopropylmethyl)sulfonyl)benzyl)-5-(4,4-difluoropiperidin-1-yl)-1H-benzo[d]imidazole-1-carboxylate

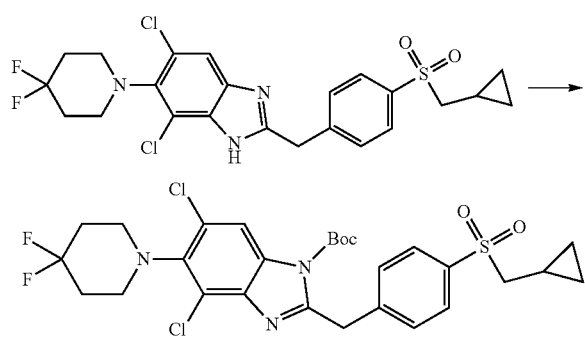

To a solution of 2-(4-(cyclopropylmethylsulfonyl)benzyl)-5,7-dichloro-6-(4,4-difluoropiperidin-1-yl)-1H-benzo[d]imidazole (3.35 g, 6.51 mmol) in DCM (25 mL) was added Boc anhydride (1.25 g, 9.77 mmol), DIEA (1.7 mL, 9.77 mmol), and catalytic amount of DMAP, at ambient temperature. After addition, the reaction solution was stirred at ambient temperature over night. It was concentrated. The residue was purified on a silica gel column, eluting with 25% EtOAc in DCM, to get a mixture of two isomers of the product as a pale solid (10.7 g, 90% yield).

MS (+) ES: 614 (M+H)⁺.

Step 2. Preparation of tert-butyl 4,6-dichloro-2-(1-(4-((cyclopropylmethyl) sulfonyl)phenyl)-3-methoxy-3-oxopropyl)-5-(4,4-difluoropiperidin-1-yl)-1H-benzo[d]imidazole-1-carboxylate

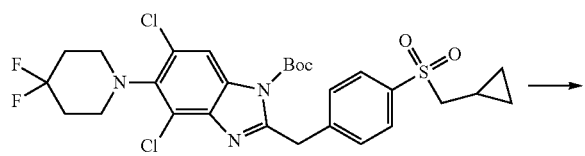

To a solution of tert-butyl 2-(4-(cyclopropylmethylsulfonyl)benzyl)-4,6-dichloro-5-(4,4-difluoropiperidin-1-yl)-1H-benzo[d]imidazole-1-carboxylate (465 mg, 0.76 mmol) in dry THF (10 mL) was added lithium hexamethyldisilyl amide solution (1M, 1 mL, 1 mmol), at −78° C. After it was stirred at −78° C. for 30 minutes, methyl bromoethylacetate (233 mg, 1.52 mmol) was added, and the reaction solution was slowly warmed to ambient temperature, and stirred over night. It was worked up with EtOAc and water. The organic layer was concentrated and purified on a silica gel column, eluting with 25% of EtOAc in DCM to get the desired product as a white solid (511 mg, 98% yield). MS (+) ES: 686 (M+H)⁺.

Step 3. Preparation of 3-(4-((cyclopropylmethyl)sulfonyl)phenyl)-3-(5,7-dichloro-6-(4,4-difluoropiperidin-1-yl)-1H-benzo[d]imidazol-2-yl)propanamide

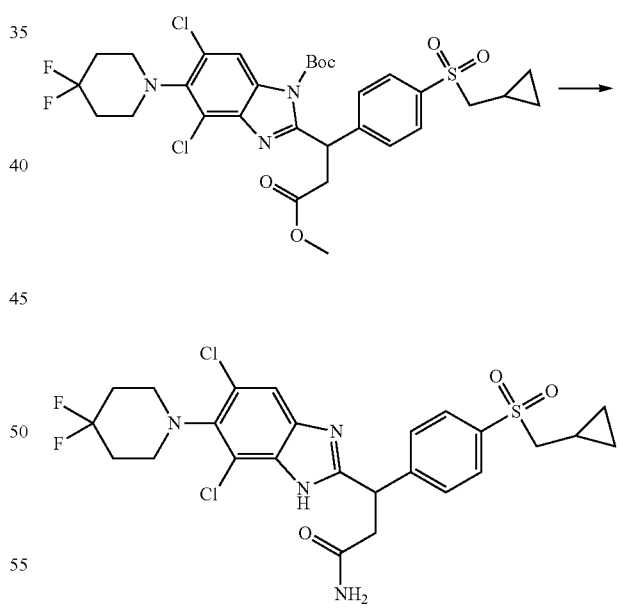

A solution of tert-butyl 4,6-dichloro-2-(1-(4-(cyclopropylmethyl)sulfonyl)phenyl)-3-methoxy-3-oxopropyl)-5-(4,4-difluoropiperidin-1-yl)-1H-benzo[d]imidazole-1-carboxylate (1 g, 1.45 mmol) in 20 mL of methanol (containing about 7 N ammonia) in a sealed reaction flask was stirred at 80° C. for 10 hours. It was concentrated and purified on a silica gel column, eluting with EtOAc to get the desired product as a white solid (0.65 g, 78% yield). MS (+) ES: 571 (M+H)⁺.

Examples 155 and 156

Preparation of (S)-3-(6-chloro-5-(2-(difluoromethoxy)phenyl)-1H-benzo[d]imidazol-2-yl)-3-(4-((cyclopropylmethyl)sulfonyl)phenyl)propan-1-ol and (R)-3-(6-chloro-5-(2-(difluoromethoxy)phenyl)-1H-benzo[d]imidazol-2-yl)-3-(4-((cyclopropylmethyl)sulfonyl)phenyl)propan-1-ol

155

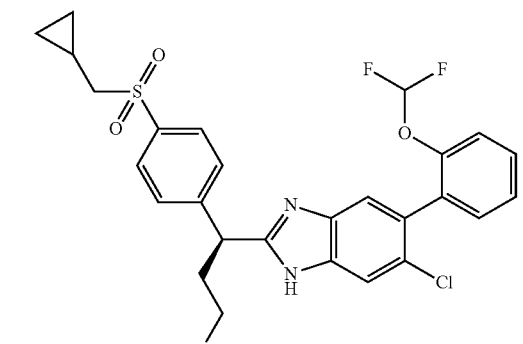

156

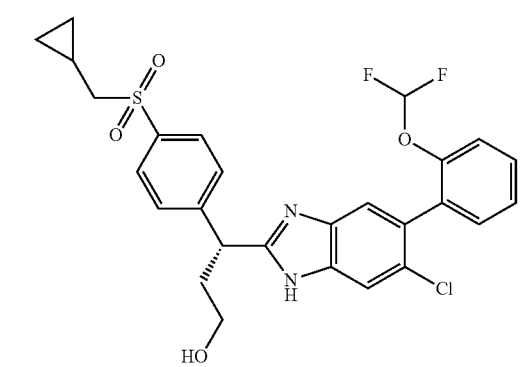

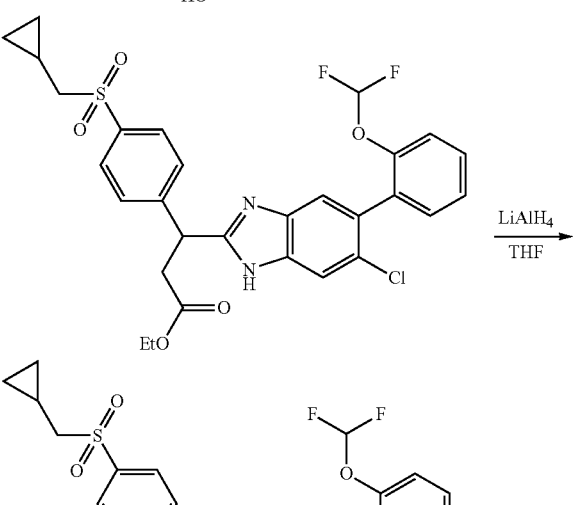

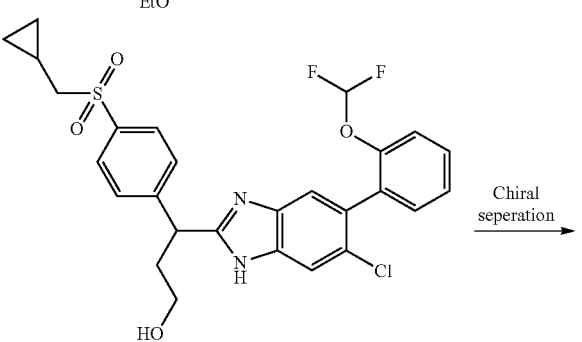

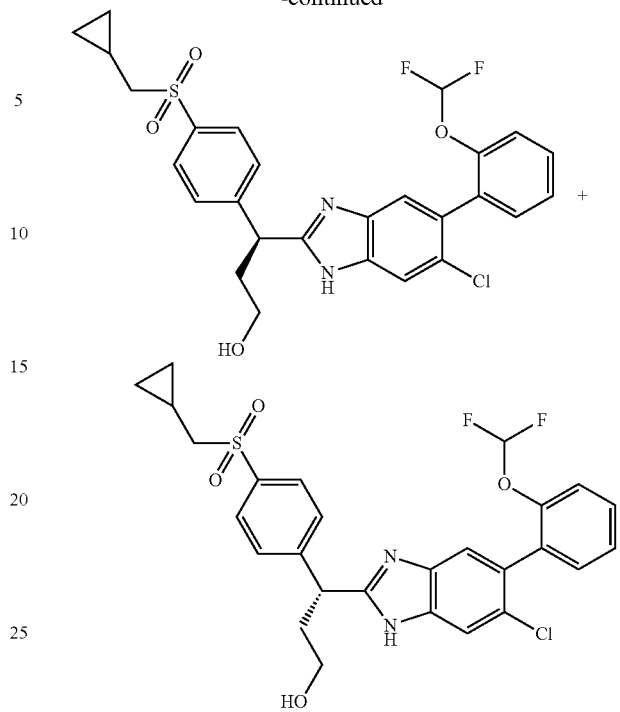

To a solution of ethyl 3-(6-chloro-5-(2-isopropoxyphenyl)-1H-benzo[d]imidazol-2-yl)-3-(4-((cyclopropylmethyl)sulfonyl)phenyl)propanoate (550 mg, 0.93 mmol) in THF (15 ml) was added LiAlH$_4$ (35 mg, 0.93 mmol) at 0° C. The reaction mixture was stirred at room temperature for 1 h. 5.0 mL water was added, the mixture was filtered. The filtrate was concentrated, the crude product was purified by flash column chromatography with hexane/ethyl acetate to get 3-(6-chloro-5-(2-(difluoromethoxy)phenyl)-1H-benzo[d]imidazol-2-yl)-3-(4-((cyclopropylmethyl)sulfonyl)phenyl)propan-1-ol (250 mg).

It was separated chirally (separation conditions: CHIRALCEL OZ—H(OZH00CD-VCO005), 0.46 cm I.D.×15 cm L; mobile phase:100% Hexane/Ethanol=80/20(V/V); flow rate: 1.0 mL/min), The corresponding fractions were collected and concentrated under reduced pressure to obtain the title compounds (110 mg, 100 mg).

Single configuration compound (the shorter retention time)

MS (+) ES: 547 (M+H)+;

Chiral HPLC analysis: retention time 6.374 minutes, chiral purity: 100% (chromatographic column: CHIRALPAK IG 150*4.6 mm, 5um; mobile phase: ethanol/hexane=20:80 (v/v);

$^1$H NMR (400 mHz, CD$_3$OD): 7.94-7.92 (d, 8.0 Hz, 2H), 7.67-7.65 (d, 8.0 Hz, 2H), 7.48-7.44 (m, 2H), 7.32-7.31 (m, 2H), 7.27-7.25 (m, 2H), 6.84-6.47 (t, 1H), 4.71-4.67 (t, 8.0 Hz, 1H), 3.64-3.53 (m, 1H), 3.13-3.12 (d, 4.0 Hz, 2H), 2.68-2.57 (m, 1H), 2.40-2.31 (m, 1H), 1.32-1.30 (m, 2H), 0.99-0.89 (m, 1H), 0.53-0.48 (q, 2H), 0.14-0.10 (q, 2H).

Single configuration compound (the longer retention time)

MS (+) ES: 547 (M+H)+;

Chiral HPLC analysis: retention time 7.719 minutes, chiral purity: 100% (chromatographic column: CHIRALPAK IG 150*4.6 mm, 5 um; mobile phase: ethanol/hexane=20:80 (v/v);

$^1$H NMR (400 mHz, CD$_3$OD): 7.94-7.92 (d, 8.0 Hz, 2H), 7.67-7.65 (d, 8.0 Hz, 2H), 7.48-7.44 (m, 1H), 7.32-7.31 (m, 2H), 7.27-7.25 (m, 2H), 6.84-6.47 (t, 1H), 4.71-4.67 (t, 8.0 Hz, 1H), 3.64-3.53 (m, 1H), 3.13-3.12 (d, 4.0 Hz, 2H), 2.68-2.57 (m, 1H), 2.40-2.31 (m, 1H), 1.32-1.30 (m, 2H), 0.99-0.89 (m, 1H), 0.53-0.48 (q, 2H), 0.14-0.10 (q, 2H).

Example 157

Preparation of 3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol

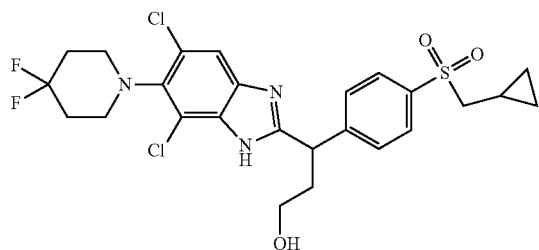

157

This compound was prepared by the similar method as of example 139,140 (racemic mixture) to produce the title compound as a white solid. MS (+) ES: 558 (M+H)$^+$.

Example 158

Preparation of 3-(4-((cyclopropylmethyl)sulfonyl)phenyl)-3-(5,7-dichloro-6-(2-(difluoromethoxy)phenyl)-1H-benzo[d]imidazol-2-yl)propanamide

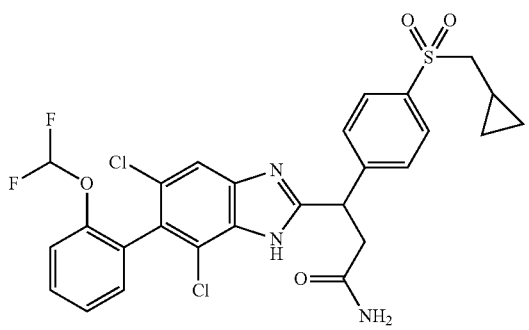

158

This compound was prepared by the similar method as of Examples 148, 149 (racemic mixture) to produce the title compound as a white solid. MS (+) ES: 594 (M+H)$^+$.

Example 159

Preparation of 3-(4-((cyclopropylmethyl)sulfonyl)phenyl)-3-(5,7-dichloro-6-(2-(difluoromethoxy)phenyl)-1H-benzo[d]imidazol-2-yl)propan-1-ol

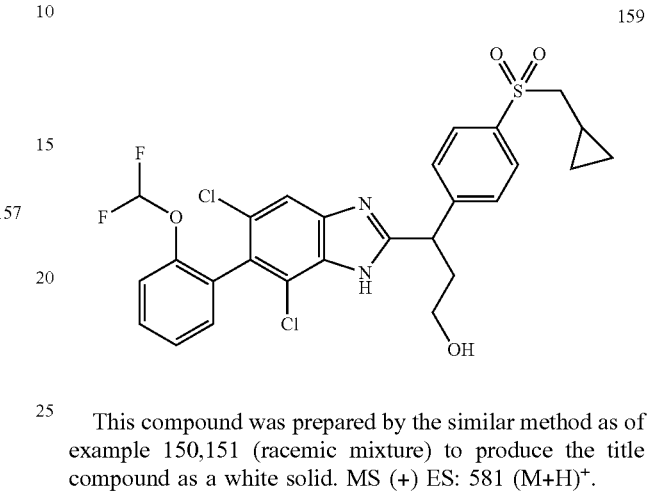

159

This compound was prepared by the similar method as of example 150,151 (racemic mixture) to produce the title compound as a white solid. MS (+) ES: 581 (M+H)$^+$.

Examples 160 and 161

Preparation of (S)-3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol (R)-3-(4-((cyclopropylmethyl)sulfonyl)phenyl)-3-(5,7-dichloro-6-(4,4-difluoropiperidin-1-yl)-1H-benzo[d]imidazol-2-yl)propan-1-ol

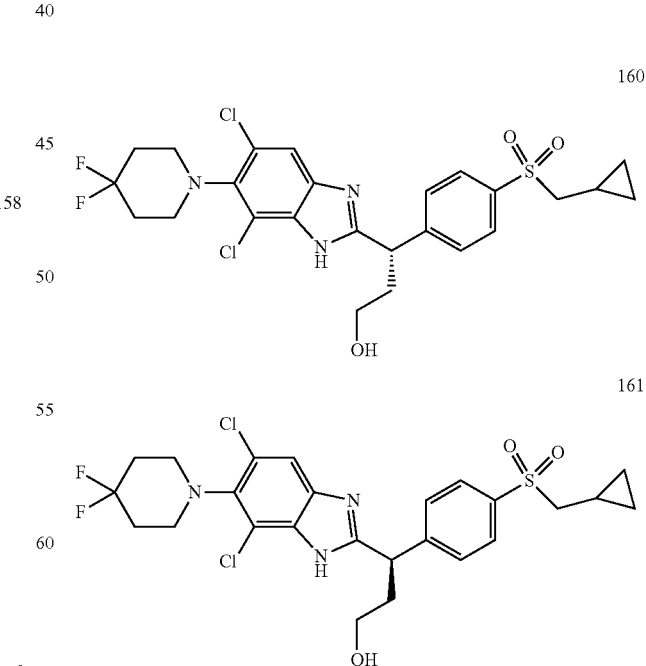

160

161

273
-continued

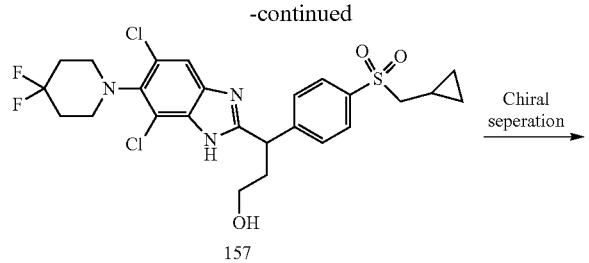

157

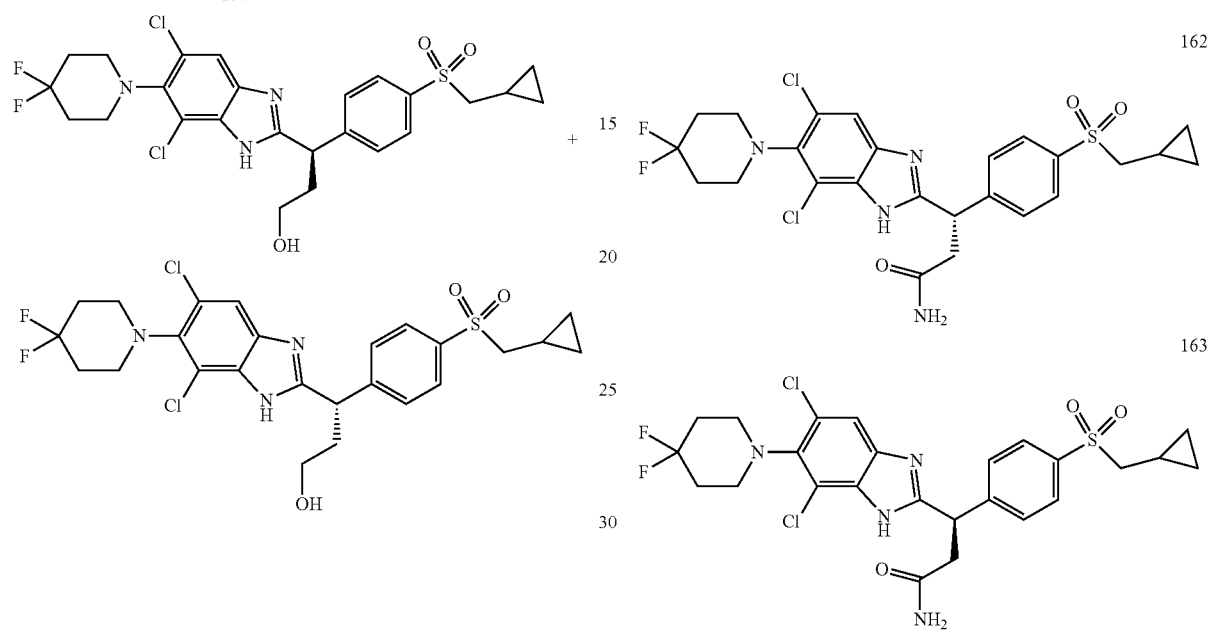

These two compounds were prepared from example 157 by chirally separation. (separation conditions: CHIRALCEL OZ—H(OZHOOCD-VC005), 0.46 cm I.D.×15 cm L; mobile phase:100% Hexane/Ethanol=70/30(V/V); flow rate: 1.0 mL/min), The corresponding fractions were collected and concentrated under reduced pressure to obtain the title compounds (350 mg, 350 mg).

Single configuration compound (the shorter retention time) MS m/z (ESI): 557.9 [M+1];

Chiral HPLC analysis: retention time 7.378 minutes, chiral purity: 100% (chromatographic column: OD Phenomenex Lux Cellulose-1 150*4.6 mm, 5um; mobile phase: ethanol/hexane=15:85 (v/v);

$^1$H NMR (400 mHz, CD$_3$OD): 7.91 (d, 2H), 7.66 (d, 2H), 7.44-7.40 (m, 1H), 4.68-4.66 (m, 1H), 3.55-3.53 (m, 2H), 3.13-3.11 (m, 2H), 2.68-2.57 (m, 2H), 2.40-2.31 (m, 2H), 2.11-2.14 (m, 4H), 1.32-1.30 (m, 1H), 0.91-0.89 (m, 2H), 0.50 (q, 2H), 0.12 (q, 2H).

Single configuration compound (the longer retention time) MS m/z (ESI): 557.9 [M+1];

Chiral HPLC analysis: retention time 8.738 minutes, chiral purity: 100% (chromatographic column: OD Phenomenex Lux Cellulose-1 150*4.6 mm, 5um; mobile phase: ethanol/hexane=15:85 (v/v);

$^1$H NMR (400 mHz, CD$_3$OD): 7.91 (d, 2H), 7.66 (d, 2H), 7.44-7.40 (m, 1H), 4.68-4.66 (m, 1H), 3.55-3.53 (m, 2H), 3.13-3.11 (m, 2H), 2.68-2.57 (m, 2H), 2.40-2.31 (m, 2H), 2.11-2.14 (m, 4H), 1.32-1.30 (m, 1H), 0.91-0.89 (m, 2H), 0.50 (q, 2H), 0.12 (q, 2H).

274

Examples 162 and 163

Preparation of (S)-3-(4-((cyclopropylmethyl)sulfonyl)phenyl)-3-(5,7-dichloro-6-(4,4-difluoropiperidin-1-yl)-1H-benzo[d]imidazol-2-yl)propanamide (R)-3-(4-((cyclopropylmethyl)sulfonyl)phenyl)-3-(5,7-dichloro-6-(4,4-difluoropiperidin-1-yl)-1H-benzo[d]imidazol-2-yl)propanamide

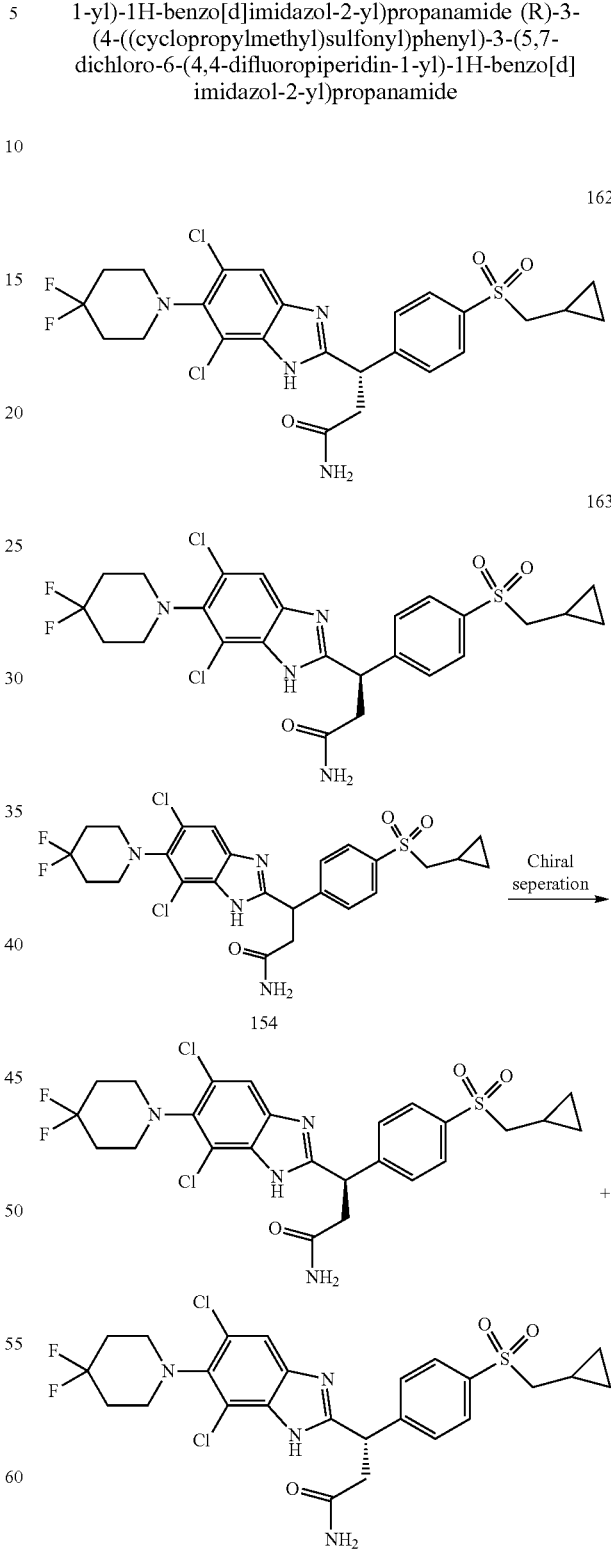

These two compounds were prepared from example 154 by chirally separation. (separation conditions: CHIRALCEL OZ—H(OZHOOCD-VCO005), 0.46 cm I.D.×15 cm L;

mobile phase:100% Hexane/Ethanol=45/55(V/V); flow rate: 1.0 mL/min), The corresponding fractions were collected and concentrated under reduced pressure to obtain the title compounds (250 mg, 250 mg).

Single configuration compound (the shorter retention time) MS m/z (ESI): 571.0 [M+1];

Chiral HPLC analysis: retention time 8.193 minutes, chiral purity: 100% (chromatographic column: OD Phenomenex Lux Cellulose-1 150*4.6 mm, 5um; mobile phase: ethanol/hexane=15:85 (v/v);

$^1$H NMR (400 mHz, CD$_3$OD): 7.90 (d, 2H), 7.65-7.63 (m, 3H), 4.94-4.92 (m, 1H), 3.13-3.03 (m, 3H), 2.68-2.57 (m, 1H), 2.40-2.31 (m, 2H), 2.11-2.14 (m, 4H), 1.38-1.30 (m, 1H), 0.94-0.91 (m, 2H), 0.50 (q, 2H), 0.11 (q, 2H).

Single configuration compound (the longer retention time) MS m/z (ESI): 571.0 [M+1];

Chiral HIPLC analysis: retention time 10.536 minutes, chiral purity: 100% (chromatographic column: OD Phenomenex Lux Cellulose-1 150*4.6 mm, 5um; mobile phase: ethanol/hexane=15:85 (v/v);

$^1$H NMR (400 mHz, CD$_3$OD): 7.90 (d, 2H), 7.65-7.63 (m, 3H), 4.94-4.92 (m, 1H), 3.13-3.03 (m, 3H), 2.68-2.57 (m, 1H), 2.40-2.31 (m, 2H), 2.11-2.14 (m, 4H), 1.38-1.30 (m, 1H), 0.94-0.91 (m, 2H), 0.50 (q, 2H), 0.11 (q, 2H).

Examples 164 and 165

Preparation of (S)-4-(3-(6-chloro-5-(2-(difluoromethoxy)phenyl)-1H-benzo[d]imidazol-2-yl)-3-(4-((cyclopropylmethyl)sulfonyl)phenyl)propyl)morpholine (R)-4-(3-(6-chloro-5-(2-(difluoromethoxy)phenyl)-1H-benzo[d]imidazol-2-yl)-3-(4-((cyclopropylmethyl)sulfonyl)phenyl)propyl) morpholine

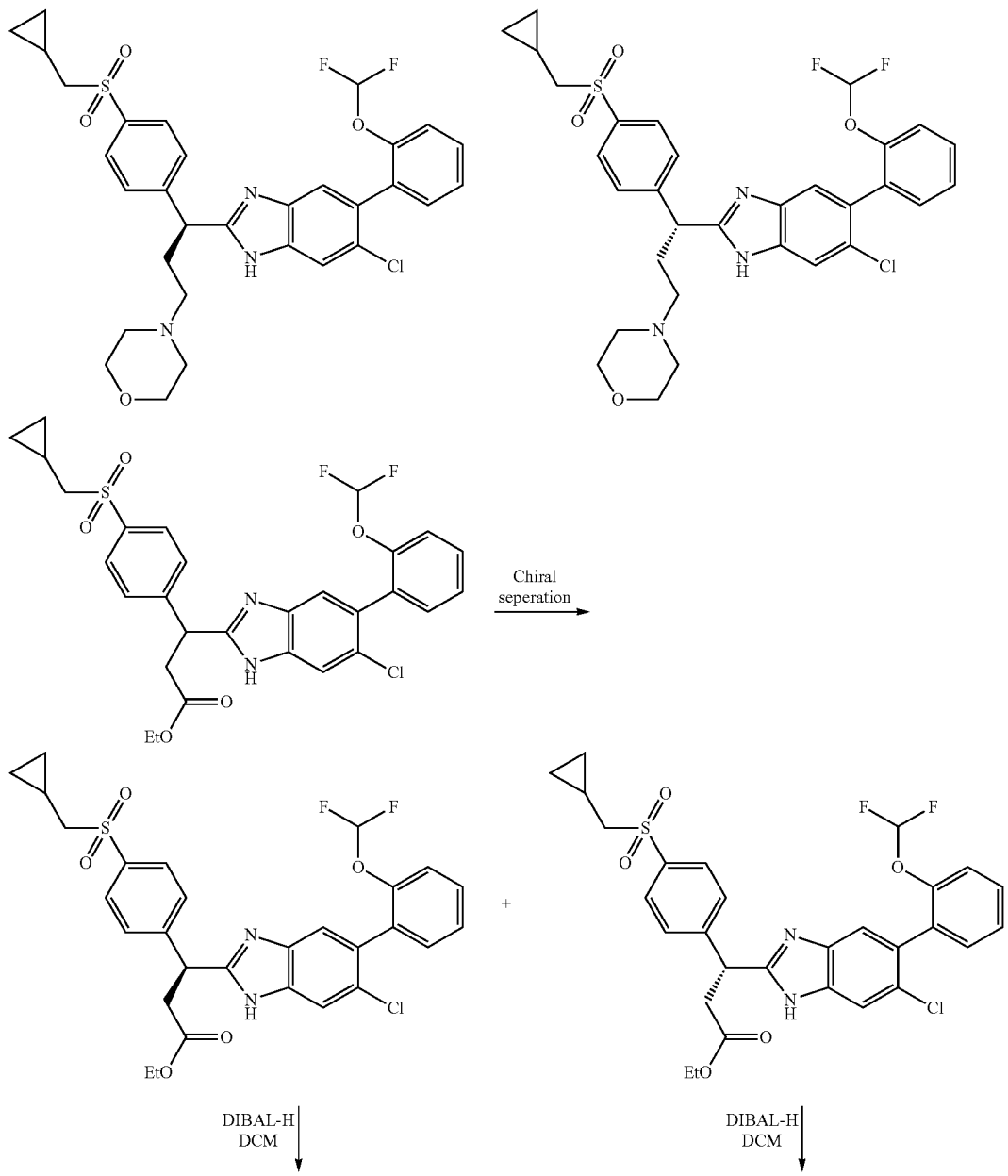

277
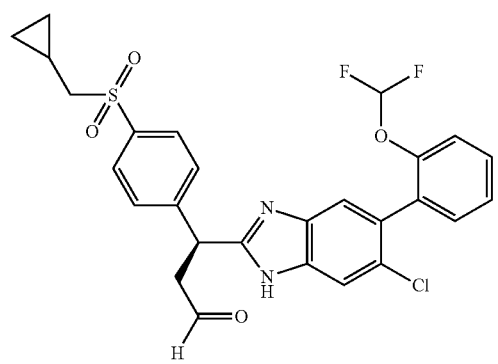
278
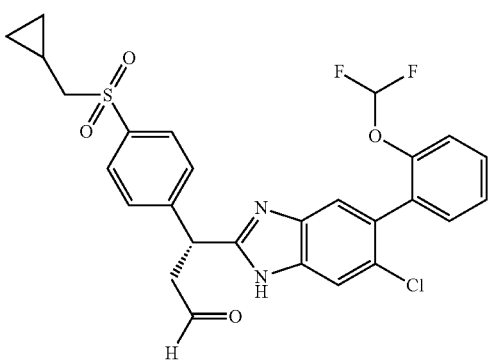
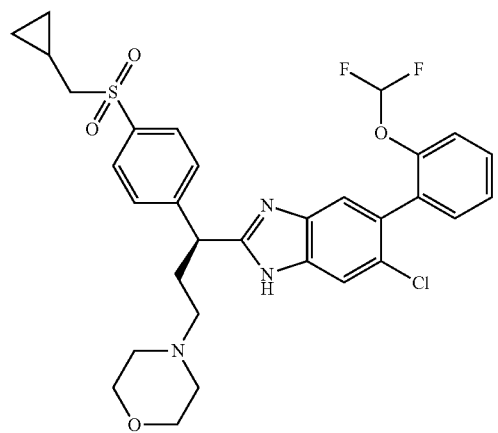
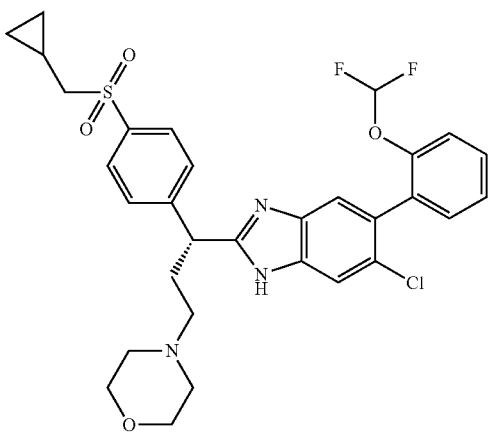
Step 1. Preparation of ethyl (R or S)-3(6-cloro-5-(2-difluoromethoxy)phenyl)-1H-benzo[d]imidazol-2-yl)-3-(4-((cyclopropylmethyl)sulfonyl)phenyl)propanoate
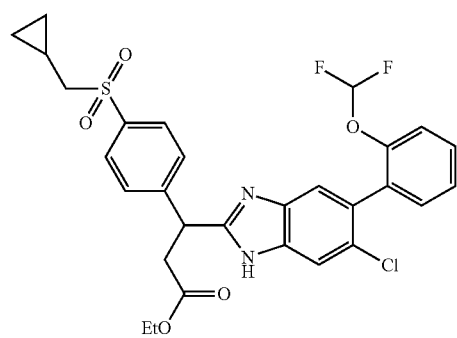
-continued
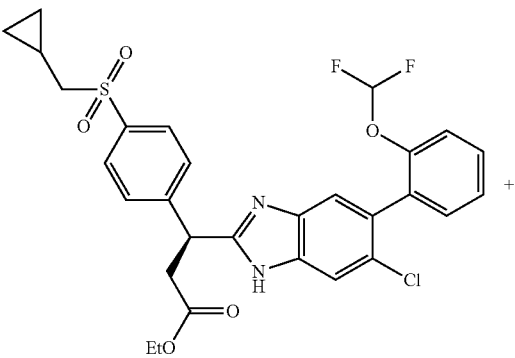

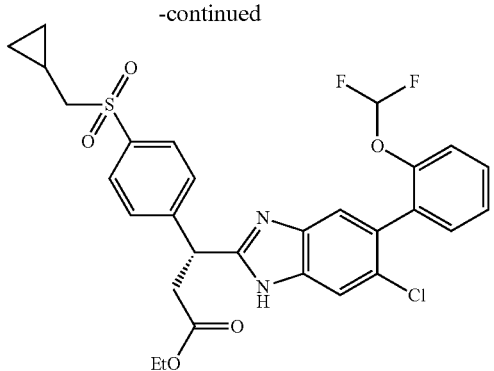

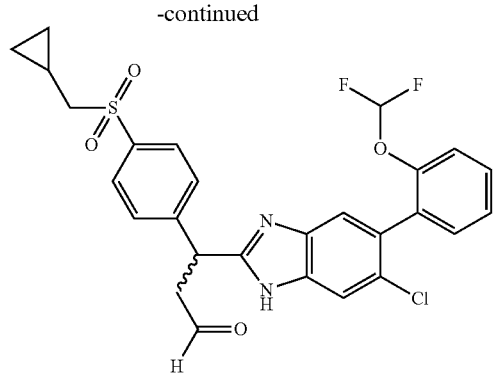

Step 1. Preparation of ethyl(R or S)-3-(6-chloro-5-(2-(difluoromethoxy)phenyl-1H-benzo[d]imidazol-2-yl)-3-(4-((cyclopropylmethyl)sulfonyl)phenyl) propanoate These two compounds were prepared by chirally separation. (separation conditions: CHIRALPAK IB—N (IBN5CD-VD005), 0.46 cm I.D.×15 cm L; mobile phase: 100% Hexane/Ethanol=80/20(V/V); flow rate: 1.0 mL/min), The corresponding fractions were collected and concentrated under reduced pressure to obtain the title compounds (690 mg, 490 mg).

Single configuration compound Int-164A (the shorter retention time)

MS m/z (ESI): 589.1 [M+1];

Chiral HPLC analysis: retention time 11.508 minutes, chiral purity: 100% (chromatographic column: CHIRAL-PAK IG150*4.6 mm, 5um; mobile phase: ethanol/hexane=20:80 (v/v);

Single configuration compound Int-164B (the longer retention time) MS m/z (ESI): 589.1 [M+1];

Chiral HIPLC analysis: retention time 17.164 minutes, chiral purity: 100% (chromatographic column: CHIRAL-PAK IG150*4.6 mm, 5um; mobile phase: ethanol/hexane=20:80 (v/v).

Step 2(1). Preparation of (R or S)-3-(6-chloro-5-(2-(difluoromethoxy)phenyl)-1H-benzo[d]imidazol-2-yl)-3-(4-((cyclopropylmethyl)sulfonyl)phenyl)propanal

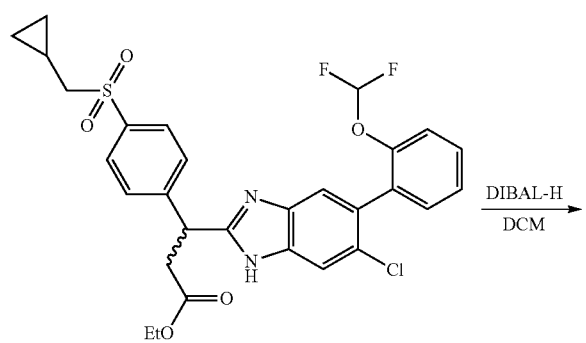

Ethyl (R or S)-3-(6-chloro-5-(2-(difluoromethoxy)phenyl)-1H-benzo[d]imidazol-2-yl)-3-(4-((cyclopropylmethyl)sulfonyl)phenyl)propanoate (the shorter retention time) (step 1) (45 mg, 0.076 mmol) was dissolved in DCM (3.0 mL), diisobutylaluminium hydride (0.16 mL, 0.16 mmol) was added and the mixture was stirred for 30 min until completion. The product was purified by flash chromatography with hexane/ethyl acetate to afford a white solid (22 mg, 52%), MS m/z (ESI): 543.0 [M−1].

Step 3(1). Preparation of (R or S)-4-(3-(6-chloro-5-(2-(difluoromethoxy)phenyl)-1H-benzo[d]imidazol-2-yl)-3-(4-((cyclopropylmethyl)sulfonyl)phenyl) propyl)morpholine

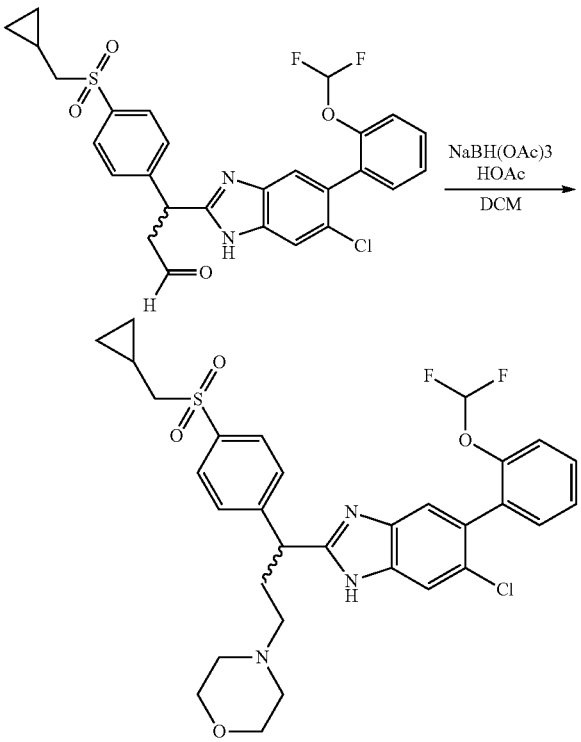

(R or S)-3-(6-chloro-5-(2-(difluoromethoxy)phenyl)-1H-benzo[d]imidazol-2-yl)-3-(4-((cyclopropylmethyl)sulfonyl) phenyl)propanal (step 2(1)) (22 mg, 0.04 mmol) and Morpholine (17 mg, 0.20 mmol) was dissolved in DCM (5.0 mL), acetic acid (14 mg, 0.24 mmol) was added and the mixture was stirred for 0.5 h, NaBH(OAc)₃ (25 mg, 0.12 mmol) was added at room temp. The mixture was stirred for 60 min until the completion (LC-MS monitor). The mixture was treated with small amount of diluted HCl and directly purified by flash chromatography with hexane/ethyl acetate to afford a white solid (7.3 mg, 29%), MS m/z (ESI): 616.0 [M+1].

¹H NMR (400 mHz, CDCl₃): 7.99 (d, 2H), 7.72 (s, 1H), 7.50 (s, 1H), 7.46-7.44 (m, 1H), 7.43 (d, 2H), 7.36-7.33 (m, 2H), 7.31-7.27 (m, 1H), 6.42 (d, 1H), 4.69 (t, 1H), 3.85-3.83 (m, 4H), 3.03-3.01 (m, 2H), 2.60-2.58 (m, 4H), 2.50-2.45 (m, 4H), 2.39-2.35 (m, 1H), 1.03-0.98 (m, 1H), 0.60 (d, 2H), 0.19 (d, 2H).

Step 2(2). Preparation of (R or S)-3-(6-chloro-5-(2-(difluoromethoxy)phenyl)-1H-benzo[d]imidazol-2-yl)-3-(4-((cyclopropylmethyl)sulfonyl)phenyl)propanal Step 3(2). Preparation of (R or S)-4-(3-(6-chloro-5-(2-(difluoromethoxy)phenyl)-1H-benzo[d]imidazol-2-yl)-3-(4-((cyclopropylmethyl)sulfonyl)phenyl)propyl)morpholine

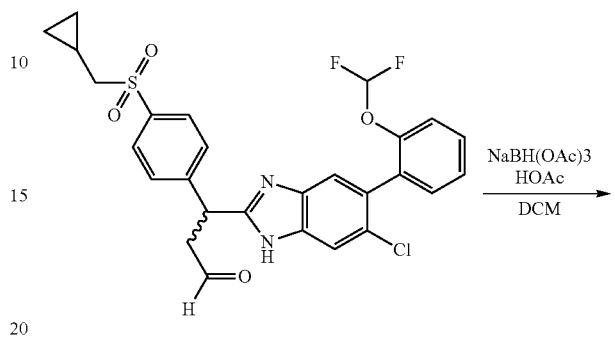

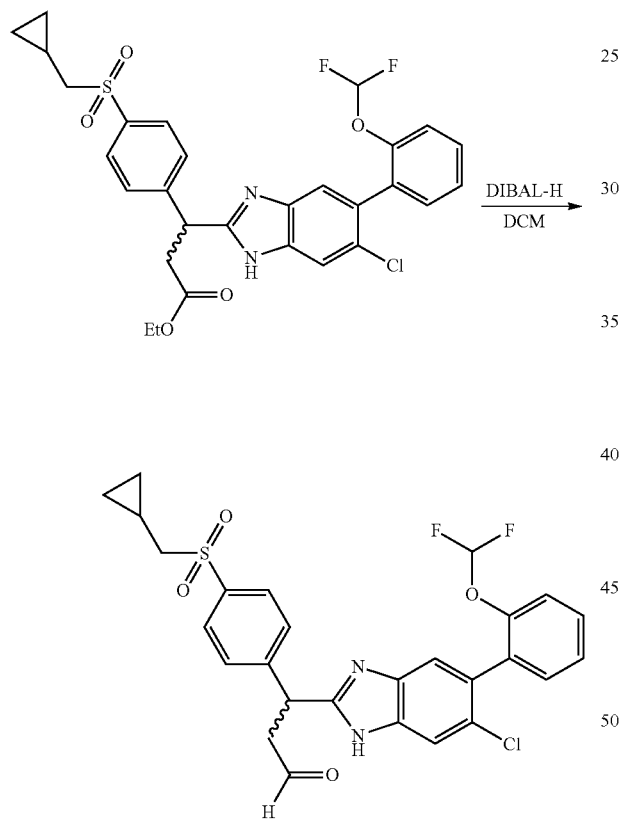

Ethyl (R or S)-3-(6-chloro-5-(2-(difluoromethoxy)phenyl)-1H-benzo[d]imidazol-2-yl)-3-(4-((cyclopropylmethyl)sulfonyl)phenyl)propanoate (the longer retention time) (example 164, step 1) (100 mg, 0.17 mmol) was dissolved in DCM (10.0 mL), diisobutylaluminium hydride (1.0 mL, 0.1 mmol) was added and the mixture was stirred for 30 min until completion. The mixture was treated with small amount of diluted HCl and directly purified by flash chromatography with hexane/ethyl acetate to afford a white solid (50 mg, 54%).

MS m/z (ESI): 543.0 [M−1].

(R or S)-3-(6-chloro-5-(2-(difluoromethoxy)phenyl)-1H-benzo[d]imidazol-2-yl)-3-(4-((cyclopropylmethyl)sulfonyl)phenyl)propanal (step 2(2)) (30 mg, 0.06 mmol) and Morpholine (48 mg, 0.55 mmol) was dissolved in DCM (10.0 mL), acetic acid (33 mg, 0.55 mmol) was added and the mixture was stirred for 0.5 h, NaBH(OAc)₃ (70 mg, 0.33 mmol) was added at room temp. The mixture was stirred for 60 min until the completion (LC-MS monitor). The mixture was treated with small amount of diluted HCl and directly purified by flash chromatography with hexane/ethyl acetate to afford a white solid (13.7 mg, 40%), MS m/z (ESI): 616.0 [M+1].

¹H NMR (400 mHz, CDCl₃): 7.89 (d, 2H), 7.72 (s, 1H), 7.50 (s, 1H), 7.46-7.44 (m, 1H), 7.43 (d, 2H), 7.36-7.33 (m, 2H), 7.31-7.27 (m, 1H), 6.42 (d, 1H), 4.69 (t, 1H), 3.85-3.83 (m, 4H), 3.03-3.01 (m, 2H), 2.60-2.58 (m, 4H), 2.50-2.45 (m, 4H), 2.39-2.35 (m, 1H), 1.03-0.98 (m, 1H), 0.60 (d, 2H), 0.19 (d, 2H).

Example 166, 167
Preparation of (S)—N-(3-(6-chloro-5-(2-(difluoromethoxy)phenyl)-1H-benzo[d]imidazol-2-yl)-3-(4-((cyclopropylmethyl)sulfonyl)phenyl)propyl)acetamide (R)—N-(3-(6-chloro-5-(2-(difluoromethoxy)phenyl)-1H-benzo[d]imidazol-2-yl)-3-(4-((cyclopropylmethyl)sulfonyl)phenyl)propyl)acetamide
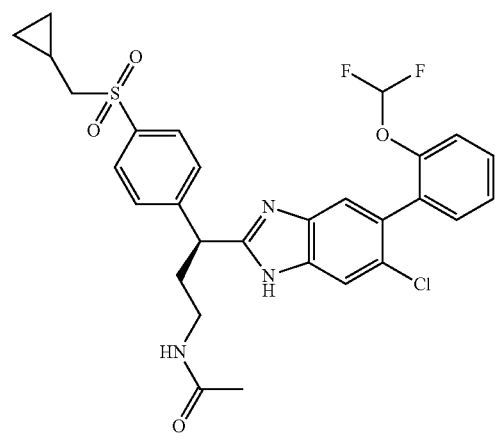
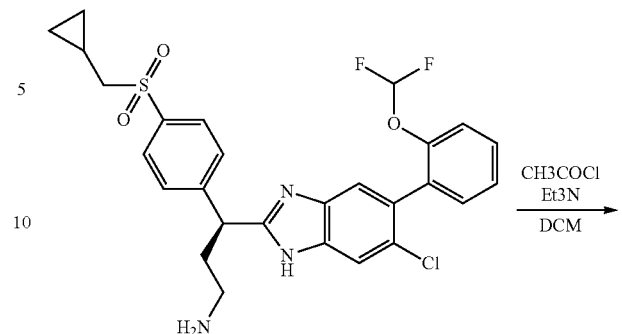
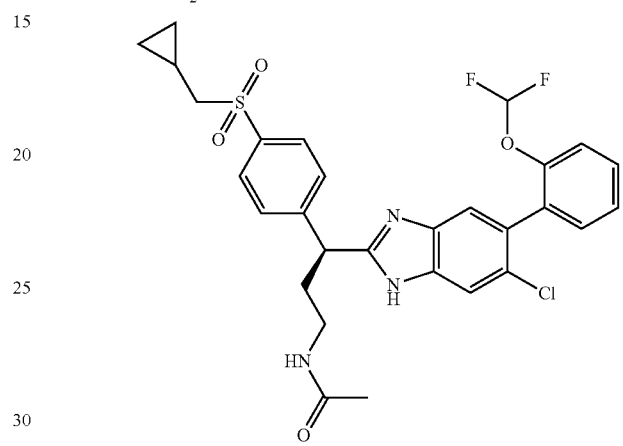
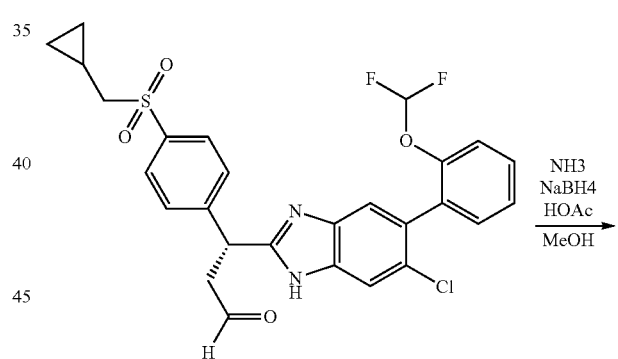
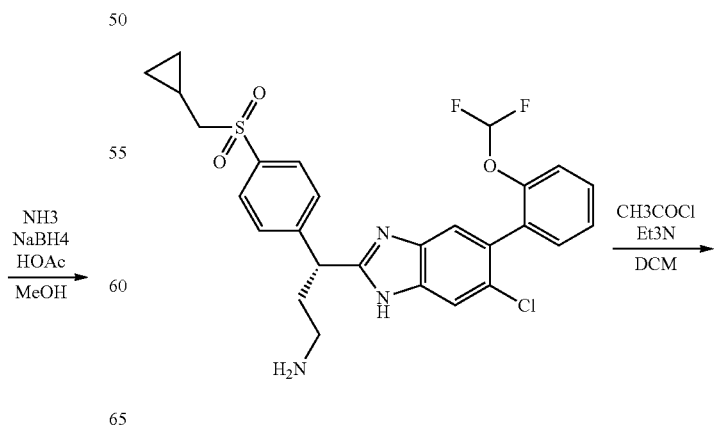

285

-continued

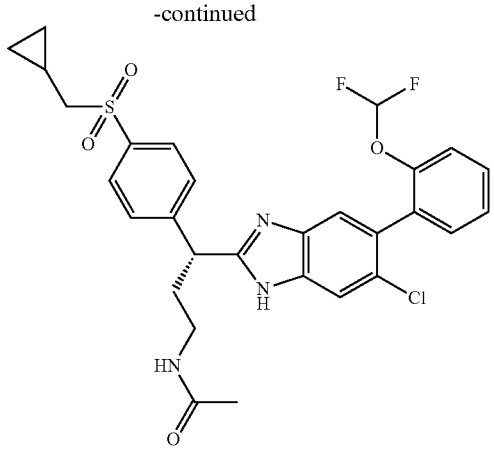

Step 1(1) Preparation of (R or S)-3-(6-chloro-5-(2-(difluoromethoxy)phenyl)-1H-benzo[d]imidazol-2-yl)-3-(4-((cyclopropylmethyl)sulfonyl)phenyl)propan-1-amine

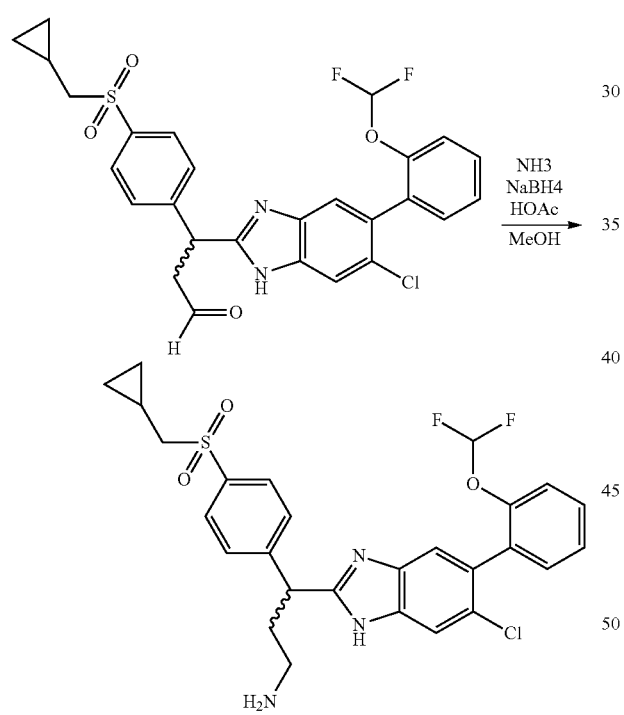

(R or S)-3-(6-chloro-5-(2-(difluoromethoxy)phenyl)-1H-benzo[d]imidazol-2-yl)-3-(4-((cyclopropylmethyl)sulfonyl)phenyl)propanal (example 164,165, step 2(1)) (45 mg, 0.08 mmol) was dissolved in MeOH (3.0 mL), acetic acid (50 mg, 0.83 mmol) and 7N NH3 in MeOH (1.2 mL, 8.4 mmol) were added and the mixture was stirred for 0.5 h, NaBH₄ (31 mg, 0.84 mmol) was added at room temp. The mixture was stirred for 60 min until the completion (LC-MS monitor). The mixture was treated with small amount of diluted HCl and directly purified by flash chromatography with hexane/ethyl acetate to afford a white solid (45 mg, 99%), MS m/z (ESI): 546.1 [M+1].

286

Step 2(1). Preparation of (R or S)—N-(3-(6-chloro-5-(2-(difluoromethoxy)phenyl)-1H-benzo[d]imidazol-2-yl)-3-(4-((cyclopropylmethyl)sulfonyl)phenyl)propyl)acetamide

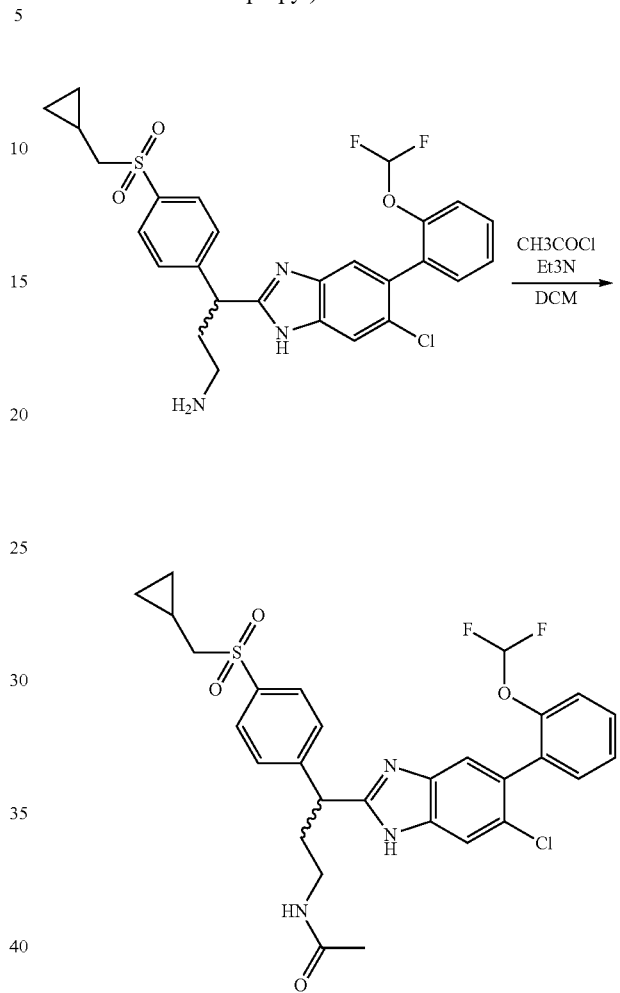

(R or S)-3-(6-chloro-5-(2-(difluoromethoxy)phenyl)-1H-benzo[d]imidazol-2-yl)-3-(4-((cyclopropylmethyl)sulfonyl)phenyl)propan-1-amine (45 mg, 0.083 mmol) was dissolved in DCM (2.0 mL), acetyl chloride (8.0 mg, 0.1 mmol) was added followed by the addition of Et₃N (9.0 mg, 0.1 mmol) and the mixture was stirred for 0.5 h, The mixture was treated with small amount of diluted HCl and directly purified by Prep HPLC with elution system C to afford the product as a white solid (10.7 mg, 22%), MS m/z (ESI): 587.9 [M+1].

¹H NMR (400 mHz, CD₃OD): 7.93 (d, 2H), 7.74-7.72 (m, 1H), 7.67-7.65 (m, 2H), 7.57-7.53 (m, 1H), 7.48-7.44 (m, 1H), 7.32 (d, 2H), 7.28-7.26 (m, 1H), 6.66 (d, 1H), 4.61 (s, 1H), 4.51-4.47 (m, 1H), 3.25-3.33 (m, 2H), 3.13 (d, 2H), 2.67-2.58 (m, 2H), 2.41-2.31 (m, 2H), 0.97-0.91 (m, 1H), 0.50 (q, 2H), 0.11 (q, 2H).

Step 1(2). Preparation of (R or S)-3-(6-chloro-5-(2-(difluoromethoxy)phenyl)-1H-benzo[d]imidazol-2-yl)-3-(4-((cyclopropylmethyl)sulfonyl)phenyl)propan-1-amine

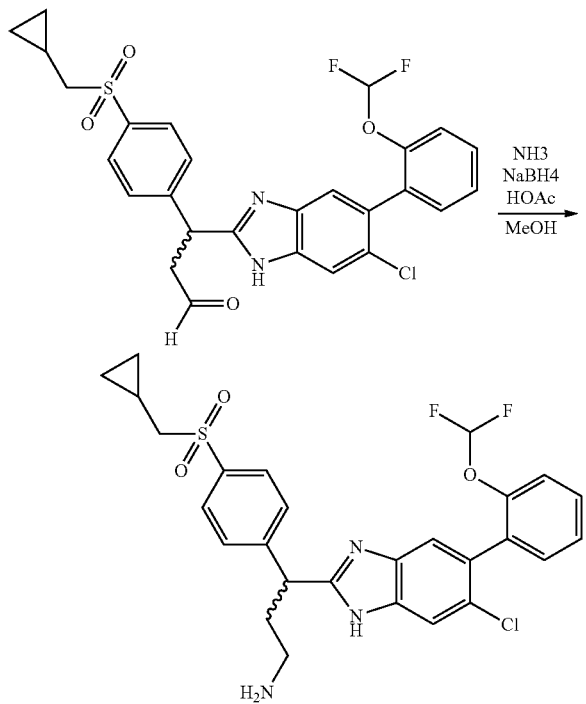

(R or S)-3-(6-chloro-5-(2-(difluoromethoxy)phenyl)-1H-benzo[d]imidazol-2-yl)-3-(4-((cyclopropylmethyl)sulfonyl)phenyl)propanal (example 164,165, step 2(2)) (50 mg, 0.09 mmol) was dissolved in MeOH (5.0 mL), acetic acid (55 mg, 0.92 mmol) and 7N NH₃ in MeOH (1.3 mL, 9.2 mmol) were added and the mixture was stirred for 0.5 h, NaBH₄ (21 mg, 0.55 mmol) was added at room temp. The mixture was stirred for 60 min until the completion (LC-MS monitor). The mixture was treated with small amount of diluted HCl and directly purified by flash chromatography with hexane/ethyl acetate to afford a white solid (45 mg, 90%), MS m/z (ESI): 546.1 [M+1].

Step 2(2). Preparation of (R or S)—N-(3-(6-chloro-5-(2-(difluoromethoxy)phenyl)-1H-benzo[d]imidazol-2-yl)-3-(4-((cyclopropylmethyl)sulfonyl)phenyl)propyl)acetamide

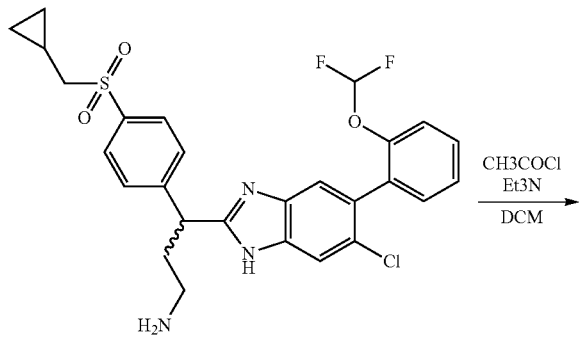

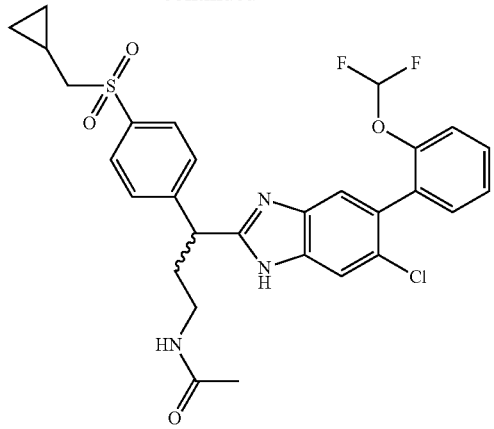

(R or S)-3-(6-chloro-5-(2-(difluoromethoxy)phenyl)-1H-benzo[d]imidazol-2-yl)-3-(4-((cyclopropylmethyl)sulfonyl)phenyl)propan-1-amine (40 mg, 0.073 mmol) was dissolved in DCM (5.0 mL), acetyl chloride (7.0 mg, 0.09 mmol) was added followed by the addition of Et₃N (15 mg, 0.15 mmol) and the mixture was stirred for 0.5 h, The mixture was treated with small amount of diluted HCl and directly purified by Prep HPLC with elution system C to afford the product as a white solid (20 mg, 46%)

MS m/z (ESI):587.9 [M+1].

¹H NMR (400 mHz, CD₃OD): 7.93 (d, 2H), 7.74-7.72 (m, 1H), 7.67-7.65 (m, 2H), 7.57-7.53 (m, 1H), 7.48-7.44 (m, 1H), 7.31 (d, 2H), 7.28-7.26 (m, 1H), 6.66 (d, 1H), 4.61 (s, 1H), 4.51-4.47 (m, 1H), 3.25-3.33 (m, 2H), 3.13 (d, 2H), 2.67-2.58 (m, 2H), 2.41-2.31 (m, 2H), 0.97-0.91 (m, 1H), 0.50 (q, 2H), 0.11 (q, 2H).

Example 168

Preparation of N-(3-(5-chloro-6-(2-(difluoromethoxy)phenyl)-1H-benzo[d]imidazol-2-yl)-3-(4-((cyclopropylmethyl)sulfonyl)phenyl)propyl)acetamide

168

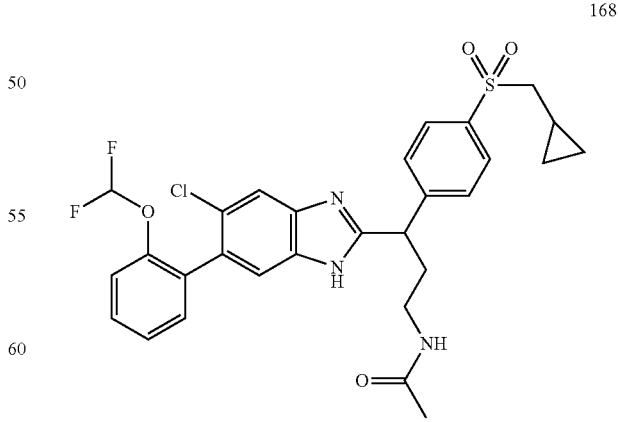

This compound can be prepared by the similar method as of example 166,167 from corresponding racemic starting material.

Example 169

Preparation of 4-(3-(5-chloro-6-(2-(difluoromethoxy)phenyl)-1H-benzo[d]imidazol-2-yl)-3-(4-((cyclopropylmethyl)sulfonyl)phenyl)propyl)morpholine

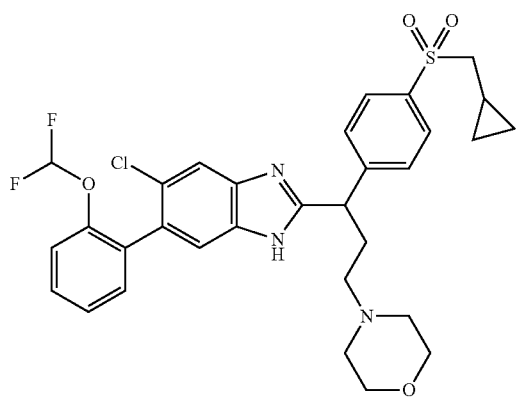

169

This compound can be prepared by the similar method as of example 164,165 from corresponding racemic starting material.

Example 170

Preparation of 4-(3-(4-((cyclopropylmethyl)sulfonyl)phenyl)-3-(5,7-dichloro-6-(4,4-difluoropiperidin-1-yl)-1H-benzo[d]imidazol-2-yl)propyl)morpholine

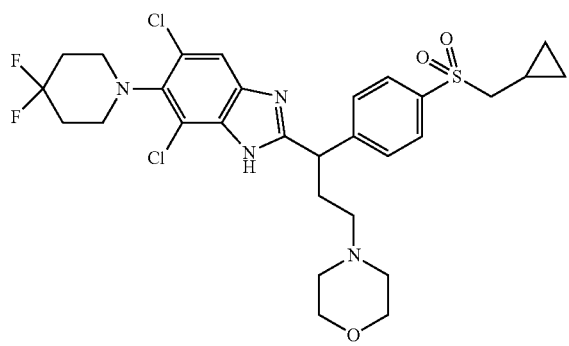

170

Step 1, preparation of cyclopropylmethyl 2-(4-((cyclopropylmethyl)thio)phenyl)acetate

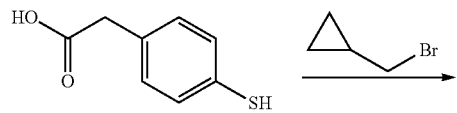

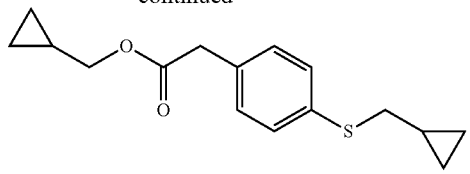

To a solution of 2-(4-mercaptophenyl)acetic acid (20 G, 118.9 mmol) in DMF (200 mL) was added (bromomethyl)cyclopropane (40.1 G, 297.2 mmol) and cesium carbonate (117 G, 356.7 mmol). After addition, the reaction was stirred at ambient temperature for 14 hours. The reaction mixture was concentrated to remove about half of the solvent. Then, it was worked up with EtOAc and water. The organic layer was concentrated, and purified on a silica gel column, eluting with 25% of EtOAc in hexanes, to get cyclopropylmethyl 2-(4-(cyclopropylmethylthio)phenyl)acetate (26.5 G, 81% yield) as a colorless oil.

Step 2 Preparation of cyclopropylmethyl 2-(4-((cyclopropylmethyl)sulfonyl)phenyl) acetate

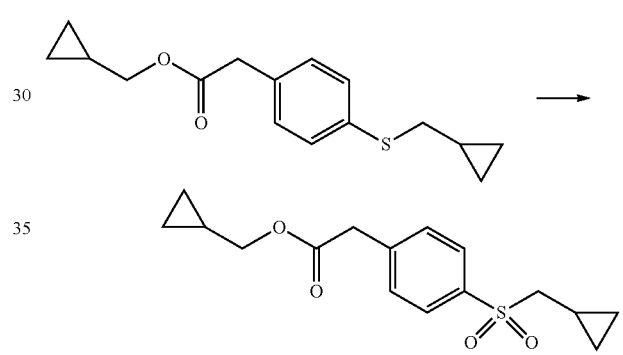

To a solution of cyclopropylmethyl 2-(4-(cyclopropylmethylthio)phenyl)acetate (31 g, 112.3 mmol) in dichloromethane (200 mL) was added meta-chloroperbenzoic acid (58 g, 337 mmol). After addition, the reaction was stirred at ambient temperature for 10 hours. It was distributed between DCM (1 L) and aqueous saturated Na2S2O3 (1 L). The organic layer was washed with 2N sodium hydroxide (200 mL) and brine. It was concentrated, and purified on a silica gel column, eluting with 60% of EtOAc in hexanes, to get cyclopropylmethyl 2-(4-(cyclopropylmethylsulfonyl)phenyl)acetate (33.5 G, 96.7% yield) as a white solid.

Step 3 Preparation of 2-(4-((cyclopropylmethyl)sulfonyl)phenyl)acetic acid

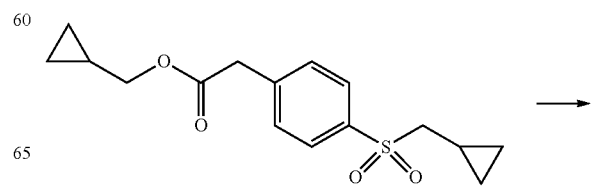

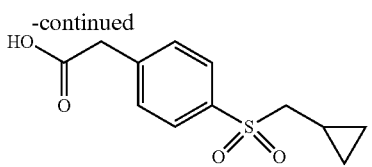

A mixture of cyclopropylmethyl 2-(4-(cyclopropylmethylsulfonyl)phenyl)acetate (32.6 G 105.7 mmol) and lithium hydroxide monohydrate (17.8 G, 423 mmol) in 1,4-dioxane (200 mL) and water (60 mL) was stirred at ambient temperature for 10 hours. It was acidified with concentrated hydrochloric acid to pH 5, and extracted with EtOAc (3×300 mL). The combined organic layers was concentrated to get the desired product, 2-(4-(cyclopropylmethylsulfonyl)phenyl)acetic acid (26.3 G, 98% yield), as a white solid.

Step 4 Preparation of 2,3,4-trichloro-6-nitroaniline

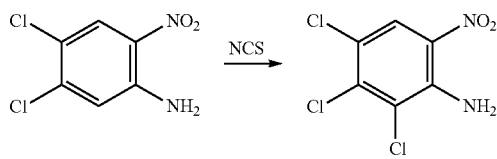 [SMILES: Nc1cc(Cl)c(Cl)cc1[N+](=O)[O-] ; "NCS" ; Nc1c([N+](=O)[O-])cc(Cl)c(Cl)c1Cl]

A suspension of 4,5-dichloro-2-nitrobenzenamine (30 G, 145 mmol), and NCS (24.2 G, 181.2 mmol) in DMF (250 mL) was heated to 100° C. for 2 hours. It was poured into ice-water. The bright yellow precipitate, 2,3,4-trichloro-6-nitrobenzenamine, was collected by filtration, and high vacuum drying overnight. (34.2 G, 98% yield).

Step 5 Preparation of 2,4-dichloro-3-(4,4-difluoropiperidin-1-yl)-6-nitroaniline

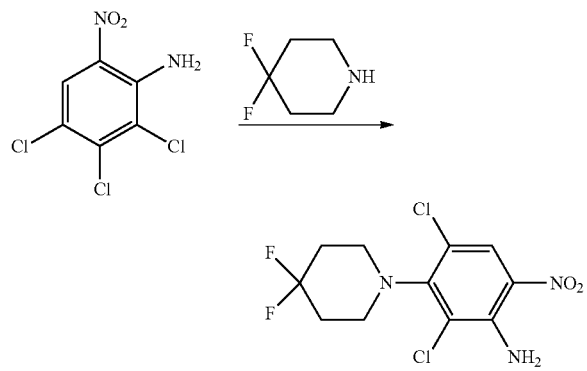

To a solution of (2,3,4-trichloro-6-nitrobenzenamine (5 G, 20.7 mmol) in 30 mL of DMF, was added 4,4-difluoropiperidine (3.8 G, 31.06 mmol) and DIEA (11.8 mL, 62.1 mmol). The reaction was stirred at 105° C. for 2 days. TLC showed mostly product. The majority of the DMF was vacuum removed. Then, it was absorbed onto silica gel, and purified on a silica gel column, eluting with 30% EtOAc in hexanes, to get the desired product, 2,4-dichloro-3-(4,4-difluoropiperidin-1-yl)-6-nitrobenzenamine, as a brightly yellow solid (4.72 G, 70% yield).

Step 6 Preparation of 3,5-dichloro-4-(4,4-difluoropiperidin-1-yl)benzene-1,2-diamine

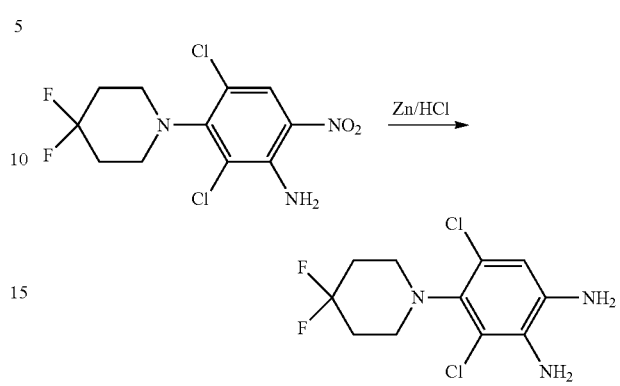

To a suspension of 2,4-dichloro-3-(4,4-difluoropiperidin-1-yl)-6-nitrobenzenamine (3.5 G, 10.8 mmol) in THF (30 mL) was added zinc powder (7 G, 108 mmol) and concentrated HCl (2 mL). The reaction mixture was stirred at room temperature for 14 hours. It was filtered and the filtrate was concentrated and purified on a silica gel column, eluting with straight EtOAc, to get 3,5-dichloro-4-(4,4-difluoropiperidin-1-yl)benzene-1,2-diamine as a pale solid (1.83 G, 57% yield).

Step 7 Preparation of N-(2-amino-3,5-dichloro-4-(4,4-difluoropiperidin-1-yl)phenyl)-2-(4-((cyclopropylmethyl)sulfonyl)phenyl)acetamide

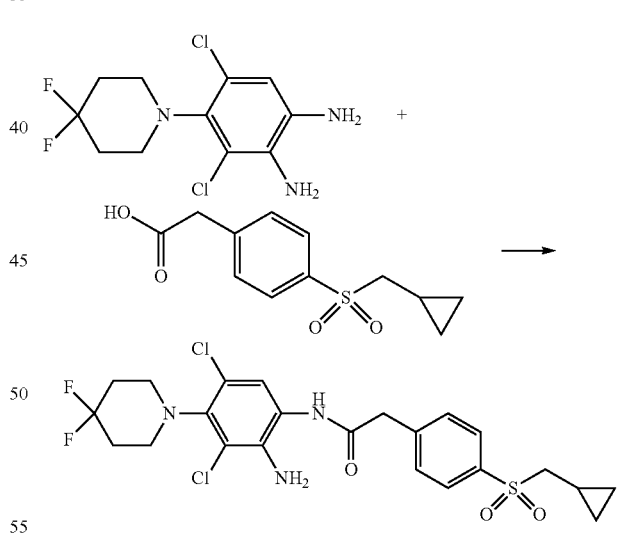

To a solution of 2-(4-(cyclopropylmethylsulfonyl)phenyl) acetic acid (1.71 g, 6.71 mmol) in dichloromethane (20 mL) was added EDC (1.61 g, 8.40 mmol), HBTU (3.15 G, 8.40 mmol), followed by 3,5-dichloro-4-(4,4-difluoropiperidin-1-yl)benzene-1,2-diamine (1.65 G, 5.59 mmol). After addition, the reaction solution was stirred at ambient temperature for 2 hours. It was absorbed onto silica gel and eluted with 50% ethyl acetate in hexanes to get N-(2-amino-3,5-dichloro-4-(4,4-difluoropiperidin-1-yl)phenyl)-2-(4-(cyclopropylmethylsulfonyl)phenyl)acetamide (2.9 G, 97% yield) as a off-white solid.

Step 8 Preparation of 5,7-dichloro-2-(4-((cyclopropylmethyl)sulfonyl)benzyl)-6-(4,4-difluoropiperidin-1-yl)-1H-benzo[d]imidazole

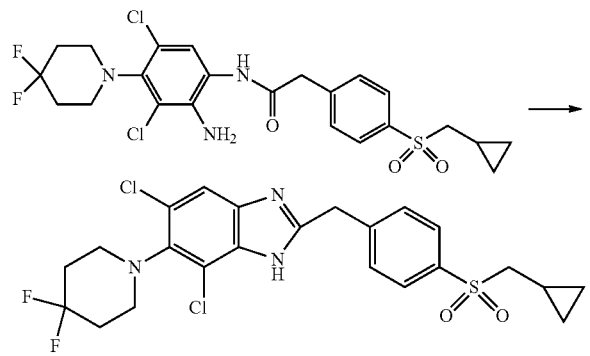

N-(2-amino-3,5-dichloro-4-(4,4-difluoropiperidin-1-yl)phenyl)-2-(4-(cyclopropylmethylsulfonyl)phenyl) acetamide (2.9 G, 5.45 mmol) was treated with acetic acid (20 mL), at 80° C., for 2 hours. The acid was removed with high vacuum. The residue was neutralized with NaHCO$_3$ and absorbed onto silica gel. It was purified with 40% ethyl acetate in dichloromethane as eluent to get 2-(4-(cyclopropylmethylsulfonyl)benzyl)-5,7-dichloro-6-(4,4-difluoropiperidin-1-yl)-1H-benzo[d]imidazole (2.3 G. 82% yield) as a brightly white solid.

Step 9 Preparation of tert-butyl 5,7-dichloro-2-(4-((cyclopropylmethyl)sulfonyl)benzyl)-6-(4,4-difluoropiperidin-1-yl)-1H-benzo[d]imidazole-1-carboxylate

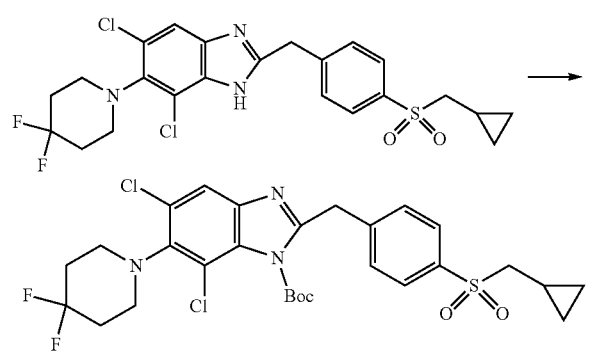

To a solution of 2-(4-(cyclopropylmethylsulfonyl)benzyl)-5,7-dichloro-6-(4,4-difluoropiperidin-1-yl)-1H-benzo[d]imidazole (3.35 G, 6.51 mmol) in dichloromethane (50 mL) was added di-t-butyl-di-carbonate (1.25 G, 9.77 mmol), N, N-Diisopropylethylamine (1.7 mL, 9.77 mmol), and catalytic amount of DMAP. After addition, the reaction solution was stirred at ambient temperature for 6 hours. It was concentrated, and purified on a silica gel column, eluting with 50% ethyl acetate in dichloromethane, to get tert-butyl 2-(4-(cyclopropylmethylsulfonyl)benzyl)-5,7-dichloro-6-(4,4-difluoropiperidin-1-yl)-1H-benzo[d]imidazole-1-carboxylate (3.62 G, 90% yield) as a white solid.

Step 10 Preparation of tert-butyl 5,7-dichloro-2-(1-(4-(cyclopropylmethylsulfonyl) phenyl)-3-methoxy-3-oxopropyl)-6-(4,4-difluoropiperidin-1-yl)-1H-benzo[d]imidazole-1-carboxylate

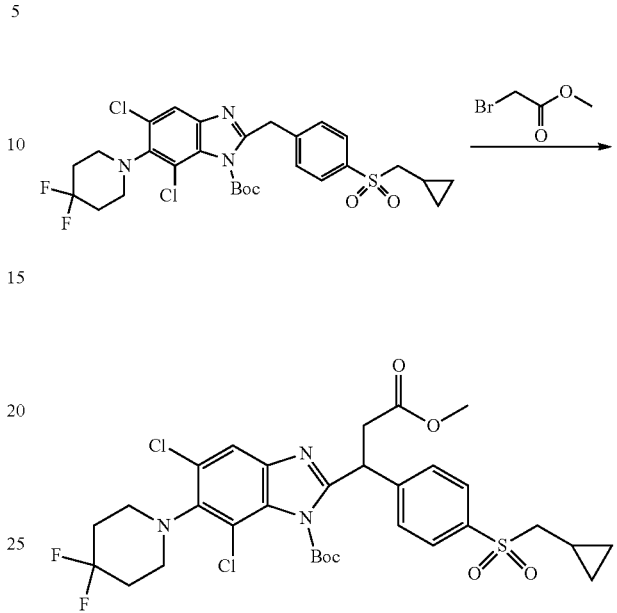

To a solution of tert-butyl 2-(4-(cyclopropylmethylsulfonyl)benzyl)-5,7-dichloro-6-(4,4-difluoropiperidin-1-yl)-1H-benzo[d]imidazole-1-carboxylate (8.2 G, 13.35 mmol) in THF (150 mL) was added lithium bis(trimethylsilyl)amide (1 M in THF, 17.4 mL), at −78° C. After stirring at −78° C. for half hour, methyl 2-bromoacetate (4.1 g, 26.70 mmol) was added, and the reaction was slowly warmed to ambient temperature, and stirred for 12 hours. It was worked up with ethyl acetate and water. The organic layer was concentrated, and purified on a silica gel column, eluting with 40% ethyl acetate in dichloromethane, to get tert-butyl 5,7-dichloro-2-(1-(4-(cyclopropylmethylsulfonyl)phenyl)-3-methoxy-3-oxopropyl)-6-(4,4-difluoropiperidin-1-yl)-1H-benzo[d]imidazole-1-carboxylate (6.3 g, 68.7% yield) as a white solid.

Step 11 Preparation of 3-(4-((cyclopropylmethyl)sulfonyl)phenyl)-3-(5,7-dichloro-6-(4,4-difluoropiperidin-1-yl)-1H-benzo[d]imidazol-2-yl)-1-morpholinopropan-1-one

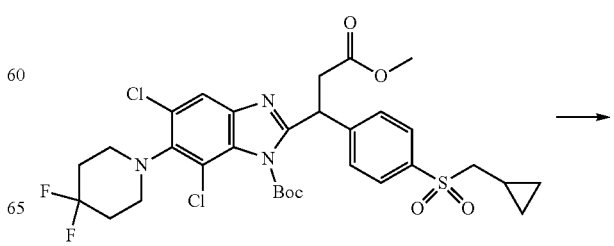

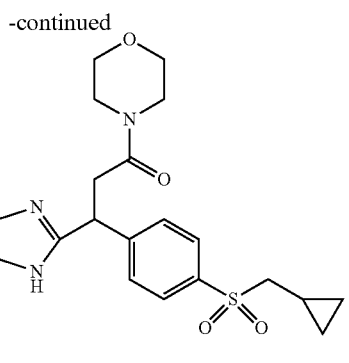

To a solution of tert-butyl 5,7-dichloro-2-(1-(4-(cyclopropylmethylsulfonyl)phenyl)-3-methoxy-3-oxopropyl)-6-(4,4-difluoropiperidin-1-yl)-1H-benzo[d]imidazole-1-carboxylate (350 mg, 0.51 mmol) in methanol (3 mL) was added morpholine (1 mL). The reaction solution was stirred at 100° C. for 14 hours. It was absorbed onto silica gel, and eluted with 60% ethyl acetate, to get 3-(4-(cyclopropylmethylsulfonyl)phenyl)-3-(5,7-dichloro-6-(4,4-difluoropiperidin-1-yl)-1H-benzo[d]imidazol-2-yl)-1-morpholinopropan-1-one (310 mg, 94% yield) as an off-white solid.

Step 12 Preparation of 4-(3-(4-((cyclopropylmethyl)sulfonyl)phenyl)-3-(5,7-dichloro-6-(4,4-difluoropiperidin-1-yl)-1H-benzo[d]imidazol-2-yl)propyl)morpholine

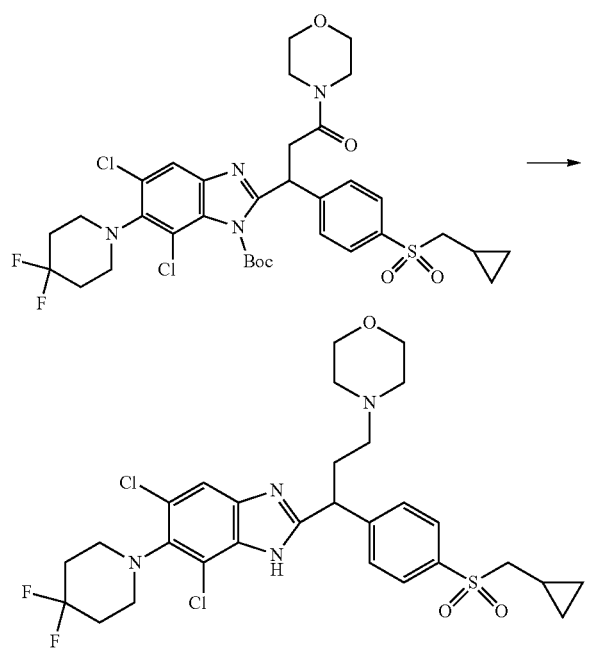

To a solution of 3-(4-(cyclopropylmethylsulfonyl)phenyl)-3-(5,7-dichloro-6-(4,4-difluoropiperidin-1-yl)-1H-benzo[d]imidazol-2-yl)-1-morpholinopropan-1-one (305 g, 0.48 mmol) in dry THF (10 mL) was added LAH (1 M in THF, 10 mL), at 0° C. After addition, the reaction solution was stirred at 0° C. for 14 hours. It was purified on a reverse phase column to get 5,7-dichloro-2-(1-(4-(cyclopropylmethylsulfonyl)phenyl)-3-morpholinopropyl)-6-(4,4-difluoropiperidin-1-yl)-1H-benzo[d]imidazole (100 mg, 33% yield) as a white solid.

MS m/z (ESI): 627 [M+1].

$^1$H NMR (400 mHz, CD$_3$OD): 7.92 (d, 10 Hz, 2H), 7.69 (d, 10 Hz, 2H), 7.55 (s, 1H), 3.67 (m, 6H), 3.58 (m, 1H), 3.13 (m, 2H), 2.62 (m, 1H), 2.48-2.41 (m, 4H), 2.38-2.31 (m, 2H), 2.13 (m, 4H), 1.61 (m, 1H), 1.32 (m, 2H), 0.95-0.91 (m, 2H), 0.50 (m, 2H), 0.11 (m, 2H).

Example 171

Preparation of N-(3-(4-((cyclopropylmethyl)sulfonyl)phenyl)-3-(5,7-dichloro-6-(4,4-difluoropiperidin-1-yl)-1H-benzo[d]imidazol-2-yl)propyl)acetamide

171

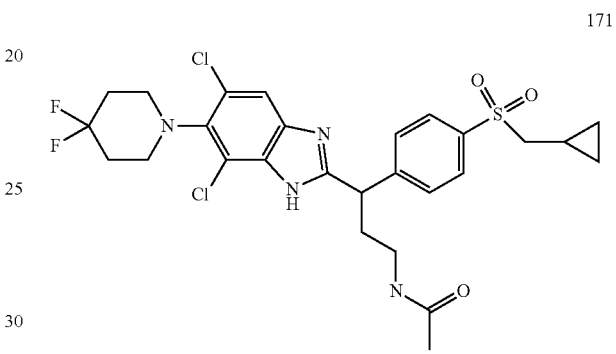

This compound can be prepared by the similar method as of example 170.

BIOLOGICAL ASSAY

The present invention will be further described with reference to the following test examples, but the examples should not be considered as limiting the scope of the invention.

Test Example 1. LanthaScreen TR-FRET Retinoid-Related Orphan Receptor Gamma (RORγ) Coactivator Assay Materials and Reagents
1. RORγ LBD-GST tagged (Cat No. RORC-114H, Creative Biomart)
2. Fluorescein-D22 coactivator peptide (Cat No. PV4386, Invitrogen)
3. LanthaScreen™ Tb anti-GST antibody (Cat No. PV3550, Invitrogen)
4. TR-FRET coregulatory buffer D (Cat No, PV4420, Invitrogen)
5. DTT (Cat No. P2325, Fisher)
6. 384-well assay plate (Cat No. 6008280, Perkin Elmer)
7. Tecan Infinite M1000 plate reader (Tecan)

Experimental Procedure

Prepare Complete TR-FRET Coregulator Buffer D by adding 1 M DTT to TR-FRET Coregulator Buffer D to the final concentration of 5 mM DTT. Make compound dilution in Complete TR-FRET Coregulator Buffer D. Highest dose is 3 μM, 7-folder dilution for total 7 doses. Add 10 μL to each well of a 384-well plate. For the negative and positive controls, add 10 μL of Complete TR-FRET Coregulator Buffer D.

Prepare RORγ LBD using Complete TR-FRET Coregulator Buffer D. The final concentration of RORγ LBD is 25 ng/reaction. Add 5 μL RORγ LBD to all the wells of the 384-well assay plate except negative wells which adding 5 μL Complete TR-FRET Coregulator Buffer D.

Prepare a solution containing 0.6 μM Fluorescein-D22 and 8 nM Tb anti-GST antibody using Complete TR-FRET Coregulator Buffer D. Add 5 μL to all wells of the 384-well assay plate.

Briefly and gently mix the 384-well plate on a plate shaker and incubate at room temperature protected from light for 1 hour. The plate may be sealed with a cover to minimize evaporation.

Read the plate at wavelengths of 520 nm and 495 nm on Tecan Infinite M1000. $IC_{50}$ values were calculated using GraphPad Prism by plotting the logarithm of compounds concentration versus percent inhibition. The $IC_{50}$ values for the example compounds were shown in Table I.

Test Example 2. IL-17 Production Assay Using Human PBMC

Materials and Reagents
1. Human PBMC cells (Cat No. 70025.1, Zenbio)
2. Lymphocyte medium (Cat No. LYMPH-1, Zenbio)
3. TexMACS (Cat No. 130-097-196, Miltenyi)
4. Cytostim-human (Cat No. 1130-092-173, Miltenyi)
5. Human IL-17 ELISA (Cat No. D1700, R&D systems)
6. Tecan Infinite M1000 plate reader (Tecan)

Experimental Procedure for IL-17 Production Assay

Cryopreserved peripheral blood human mononuclear cells (PBMCs) were rapidly thawed in warmed Lymphocyte media, and centrifuged cell suspension at 1000 rpm for 10 minutes. The supernatant was removed, and the cell pellets were gently resuspended in TexMACS media.

Human PBMC cells in TexMACS media were plated at $1 \times 10^5$ each well in triplicate. The test compounds at various concentrations or vehicle control (<0.5% DMSO) were added into cell culture. The cells were stimulated by cytostim (10 μL/mL) for 3 days in a humidified, 5% $CO_2$ incubator at 37° C.

After incubation, the cell culture supernatant was harvested, and then removed particulates by centrifugation. Human IL-17 in the supernatant was measured using human IL-17 ELISA kit according to the manufacturer's protocol. $IC_{50}$ values were determined using GraphPad Prism by plotting the compounds concentration versus percent inhibition. The $IC_{50}$ values for the example compounds were shown in Table I.

TABLE I

| Example No. | RORγ Coactivator Assay ($IC_{50}$ μM) | IL-17 production ($IC_{50}$ μM) |
| --- | --- | --- |
| 2 | 0.467 | N/T |
| 3 | 0.373 | 0.052 |
| 4 | 0.160 | 0.053 |
| 5 | 0.626 | 0.025 |
| 6 | 0.003 | 0.022 |
| 7 | 0.086 | 0.223 |
| 8 | 0.903 | N/T |
| 9 | 0.475 | 0.01 |
| 10 | 0.056 | N/T |
| 11 | 0.242 | N/T |
| 12 | 0.106 | N/T |
| 13 | 0.675 | 0.082 |
| 14 | 0.086 | 0.022 |
| 15 | 0.787 | N/T |
| 16 | 0.626 | N/T |
| 17 | 0.097 | N/T |
| 18 | 0.013 | N/T |
| 19 | 0.052 | 0.343 |
| 20 | 0.013 | 0.056 |
| 21 | 0.083 | 0.453 |
| 22 | 0.219 | N/T |
| 23 | 0.318 | 0.075 |
| 24 | 0.701 | N/T |
| 25 | 0.789 | N/T |
| 26 | 0.465 | N/T |
| 27 | 0.489 | N/T |
| 28 | 0.045 | N/T |
| 29 | 0.269 | 0.009 |
| 30 | 0.062 | 0.007 |
| 31 | 0.01 | 0.011 |
| 32 | 0.052 | 0.007 |
| 33 | 0.031 | 0.015 |
| 34 | 0.016 | 0.049 |
| 35 | 0.061 | 0.008 |
| 36 | 0.348 | N/T |
| 37 | 0.433 | N/T |
| 38 | 0.147 | 0.873 |
| 39 | 0.007 | 0.038 |
| 40 | 0.083 | N/T |
| 41 | 0.683 | N/T |
| 42 | 0.113 | N/T |
| 43 | 0.656 | N/T |
| 44 | 0.026 | N/T |
| 45 | 0.535 | N/T |
| 46 | 0.048 | 0.018 |
| 47 | 0.196 | N/T |
| 48 | 0.445 | N/T |
| 49 | 0.255 | N/T |
| 50 | 0.284 | N/T |
| 51 | 0.646 | N/T |
| 52 | 0.135 | N/T |
| 53 | 0.575 | N/T |
| 54 | 0.367 | N/T |
| 55 | 0.194 | N/T |
| 56 | 0.879 | N/T |
| 57 | 0.187 | N/T |
| 58 | 0.266 | N/T |
| 59 | 0.433 | N/T |
| 60 | 0.409 | N/T |
| 61 | 0.509 | N/T |
| 62 | 0.154 | N/T |
| 63 | 0.592 | N/T |
| 64 | 0.465 | N/T |
| 65 | 0.015 | N/T |
| 66 | 0.002 | 0.01 |
| 67 | 0.002 | 0.002 |
| 68 | 0.03 | 0.004 |
| 69 | 0.007 | 0.056 |
| 70 | 0.014 | 0.006 |
| 71 | 0.004 | N/T |
| 72 | 0.006 | 0.003 |
| 73 | 0.029 | 0.001 |
| 74 | 0.187 | N/T |
| 75 | 0.006 | N/T |
| 76 | 0.387 | N/T |
| 77 | 0.021 | 0.017 |
| 78 | 0.028 | 0.069 |
| 79 | 0.048 | N/T |
| 80 | 0.031 | 0.013 |
| 81 | 0.035 | 0.003 |
| 82 | 0.046 | N/T |
| 83 | 0.065 | N/T |
| 84 | 0.019 | 0.013 |
| 85 | 0.188 | N/D |
| 86 | 0.075 | 0.023 |
| 87 | 0.024 | N/T |
| 88 | 0.162 | N/T |
| 89 | 0.004 | N/T |
| 90 | 0.004 | N/T |

TABLE I-continued

| Example No. | RORγ Coactivator Assay (IC$_{50}$ μM) | IL-17 production (IC$_{50}$ μM) |
|---|---|---|
| 91 | 0.140 | N/T |
| 92 | 0.067 | N/T |
| 93 | 0.075 | N/T |
| 94 | 0.023 | N/T |
| 95 | 0.065 | N/T |
| 96 | 0.123 | N/T |
| 97 | 0.001 | N/T |
| 98 | 0.007 | N/T |
| 99 | 0.025 | 0.0024 |
| 100 | 0.014 | 0.0013 |
| 104 | 0.082 | N/T |
| 102 | 0.062 | N/T |
| 103 | 0.158 | N/T |
| 104 | 0.337 | N/T |
| 106 | 0.003 | N/T |
| 107 | 0.055 | N/T |
| 108 | 0.032 | N/T |
| 109 | 1.04 | N/T |
| 110 | 0.698 | N/T |
| 111 | 0.06 | N/T |
| 112 | 0.076 | N/T |
| 113 | 0.18 | N/T |
| 114 | 0.564 | N/T |
| 115 | 0.171 | N/T |
| 116 | 0.235 | N/T |
| 117 | 0.149 | N/T |
| 118 | 0.306 | N/T |
| 119 | 0.034 | 0.124 |
| 120 | 0.321 | N/T |
| 121 | 0.966 | N/T |
| 122 | 0.049 | N/T |
| 123 | 0.030 | 0.058 |
| 124 | 0.205 | 0.032 |
| the shorter retention time of 124-1 and 124-2 | 0.070 | 0.024 |
| the longer retention time of 124-1 and 124-2 | 0.026 | 0.041 |
| 125 | 0.059 | 0.047 |
| 126 | 0.135 | 0.008 |
| the shorter retention time of 126-1 and 126-2 | 0.014 | 0.045 |
| the longer retention time of 126-1 and 126-2 | 0.036 | 0.031 |
| 127 | 0.22 | 0.013 |
| 128 | 0.006 | 0.091 |
| 129 | 0.014 | 0.242 |
| 133 | 0.024 | 0.027 |
| 134 | 0.006 | 0.003 |
| 135 | 0.039 | 0.014 |
| 136 | 0.005 | 0.014 |
| 137 | 0.013 | 0.004 |
| 138 | 0.018 | 0.009 |
| the shorter retention time of 139 and 140 | 0.093 | 0.214 |
| the longer retention time of 139 and 140 | 0.035 | 0.026 |
| 141 | 0.01 | 0.02 |
| 142 | 0.013 | 0.028 |
| 143 | 0.01 | 0.027 |
| 144 | 0.011 | 0.023 |
| 145 | 0.068 | 0.01 |
| the shorter retention time of 146 and 147 | 0.057 | 0.315 |
| the longer retention time of 146 and 147 | 0.004 | 0.014 |
| the shorter retention time of 148 and 149 | 1.41 | 0.555 |
| the longer retention time of 148 and 149 | 0.083 | 0.022 |
| the shorter retention time of 150 and 151 | 0.787 | 0.718 |
| the longer retention time of 150 and 151 | 0.026 | 0.031 |
| the shorter retention time of 152 and 153 | 0.21 | 0.86 |
| the longer retention time of 152 and 153 | 0.013 | 0.010 |
| 154 | 0.049 | 0.077 |
| the shorter retention time of 155 and 156 | 0.081 | 0.135 |
| the longer retention time of 155 and 156 | 0.074 | 0.026 |
| 157 | 0.007 | 0.022 |
| 158 | 0.005 | 0.187 |
| 159 | 0.005 | 0.01 |
| the shorter retention time of 160 and 161 | 0.003 | 0.006 |
| the longer retention time of 160 and 161 | 0.003 | 0.004 |
| the shorter retention time of 162 and 163 | 0.014 | 0.069 |
| the longer retention time of 162 and 163 | 0.31 | 0.029 |
| 164 or 165 made from Int-164A | 1.25 | 0.28 |
| 164 or 165 made from Int-164B | 0.418 | 0.35 |
| 166 or 167 made from Int-164A | 0.01 | 0.066 |
| 166 or 167 made from Int-164B | 0.047 | 0.072 |
| 170 | 0.71 | 0.43 |

N/T: not tested

The foregoing examples and description of the preferred embodiments should be taken as illustrating, rather than as limiting, the present invention as defined by the claims. Numerous variations and combinations of the features set forth above may be utilized without departing from the present invention as set forth in the claims.

What is claimed is:

1. A compound of formula (I):

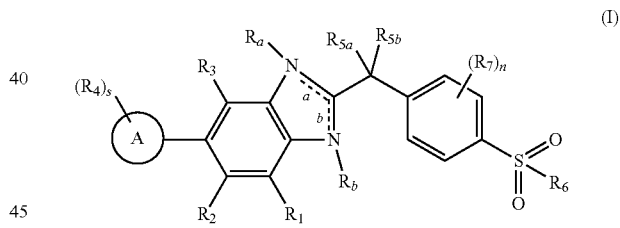

or a tautomer, mesomer, racemate, enantiomer, diastereomer, or mixture thereof, or a pharmaceutically acceptable salt, solvate, or prodrug thereof, wherein:

==== is a single bond or a double bond; when $\overset{a}{====}$ is a double bond, then $\overset{b}{====}$ is a single bond, R$_a$ is absent, and R$_b$ is hydrogen; and when $\overset{b}{====}$ is a double bond, then $\overset{a}{====}$ is single bond, R$_a$ is hydrogen, and R$_b$ is absent;

ring A is selected from the group consisting of cycloalkyl, heterocyclyl, aryl, and heteroaryl;

R$_1$, R$_2$, and R$_3$ are each independently selected from the group consisting of hydrogen, halogen, alkyl, haloalkyl, alkenyl, alkynyl, alkoxy, cyano, amino, hydroxy, cycloalkyl, heterocyclyl, aryl, and heteroaryl;

R$_4$ at each occurrence is independently selected from the group consisting of hydrogen, halogen, alkyl, haloalkyl, alkenyl, alkynyl, alkoxy, haloalkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$, and —S(O)$_2$NR$_{11}$R$_{12}$, wherein said alkyl, alkenyl, alkynyl, alkoxy, cycloalkyl, heterocyclyl, aryl, and heteroaryl are each optionally substituted by one or more groups independently selected from the group consisting of halogen, alkyl, alkenyl, alkynyl, alkoxy, cyano, amino, nitro, hydroxy, cycloalkyl, heterocyclyl, aryl, and heteroaryl;

R$_{5a}$ and R$_{5b}$ are each independently selected from the group consisting of hydrogen, halogen, alkyl, haloalkyl, hydroxy, hydroxyalkyl, alkoxy, cyano, amino, cycloalkyl, heterocyclyl, aryl, heteroaryl, —OR$_8$, —(CH$_2$)$_x$NR$_{10}$COR$_9$, —NR$_{10}$COR$_9$, —NR$_{10}$COCH$_2$OR$_8$, —(CH$_2$)$_x$C(O)OR$_8$, —(CH$_2$)$_x$CONR$_{11}$R$_{12}$, and —(CH$_2$)$_x$NR$_{11}$R$_{12}$, wherein said alkyl, alkoxy, cycloalkyl, heterocyclyl, aryl, and heteroaryl are each optionally substituted by one or more groups selected from the group consisting of halogen, alkyl, alkenyl, alkynyl, alkoxy, cyano, amino, nitro, hydroxy, —CONR$_{11}$R$_{12}$, —NR$_{10}$COR$_9$, cycloalkyl, heterocyclyl, aryl, and heteroaryl;

or R$_{5a}$ and R$_{5b}$ together form

R$_6$ is selected from the group consisting of alkyl, haloalkyl, alkenyl, alkynyl, cycloalkyl, heterocyclyl, aryl, heteroaryl, and —NR$_{11}$R$_{12}$, wherein said alkyl, cycloalkyl, heterocyclyl, aryl, and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl, and heteroaryl;

R$_7$ at each occurrence is independently selected from the group consisting of hydrogen, halogen, alkyl, haloalkyl, alkenyl, alkynyl, alkoxy, cyano, amino, hydroxy, hydroxyalkyl, cycloalkyl, heterocyclyl, aryl, heteroaryl, —OR$_8$, —C(O)OR$_8$, —COR$_9$, —NR$_{10}$COR$_9$, —S(O)$_2$R$_9$, —NR$_{10}$S(O)$_2$R$_9$, —CONR$_{11}$R$_{12}$, —NR$_{11}$R$_{12}$, and —S(O)$_2$NR$_{11}$R$_{12}$, wherein said alkyl, alkenyl, alkynyl, alkoxy, cycloalkyl, heterocyclyl, aryl, and heteroaryl are each optionally substituted by one or more group(s) selected from the group consisting of halogen, alkyl, alkenyl, alkynyl, alkoxy, cyano, amino, nitro, hydroxy, cycloalkyl, heterocyclyl, aryl, and heteroaryl;

R$_8$ is selected from the group consisting of hydrogen, alkyl, haloalkyl, cycloalkyl, and heterocyclyl, wherein said alkyl is optionally substituted by one or more groups selected from the group consisting of halogen and alkoxy;

R$_9$ is selected from the group consisting of hydrogen, alkyl, hydroxyl, alkoxy, cycloalkyl, aryl, and heteroaryl, wherein said alkyl, cycloalkyl, aryl, and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl, and heteroaryl;

R$_{10}$ is selected from the group consisting of hydrogen, alkyl, haloalkyl, cycloalkyl, and heterocyclyl;

R$_{11}$ and R$_{12}$ are each independently selected from the group consisting of hydrogen, alkyl, alkenyl, alkynyl, haloalkyl, cycloalkyl, heterocyclyl, COR$_{13}$, aryl, and heteroaryl, wherein said alkyl, alkenyl, alkynyl, cycloalkyl, heterocyclyl, aryl, and heteroaryl are each optionally substituted by one or more groups selected from the group consisting of halogen, alkyl, alkenyl, alkynyl, alkoxy, cyano, amino, nitro, hydroxy, cycloalkyl, heterocyclyl, aryl, and heteroaryl;

or R$_{11}$ and R$_{12}$ together with the nitrogen atom to which they are attached form a heterocyclyl group, wherein the heterocyclyl group comprises one or more additional heteroatoms independently selected from the group consisting of O, N and S, and wherein the heterocyclyl group is optionally substituted by one or more groups independently selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

R$_{13}$ is selected from the group consisting of hydrogen, alkyl, hydroxyl, alkoxy, cycloalkyl, aryl, and heteroaryl, wherein said alkyl, cycloalkyl, aryl, and heteroaryl are each optionally substituted by one or more groups independently selected from the group consisting of halogen, alkyl, alkenyl, alkynyl, alkoxy, cyano, amino, nitro, hydroxy, cycloalkyl, heterocyclyl, aryl, and heteroaryl;

n is 0, 1, 2, 3, or 4;
s is 0, 1, 2, 3 or 4; and
x is 0, 1, 2, 3 or 4.

2. The compound of claim 1, or a tautomer, mesomer, racemate, enantiomer, diastereomer, or mixture thereof, or a pharmaceutically acceptable salt, solvate, or prodrug thereof, having a structure of formula (Ia) or formula (Ib):

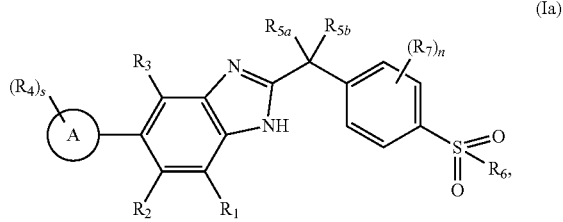

(Ia)

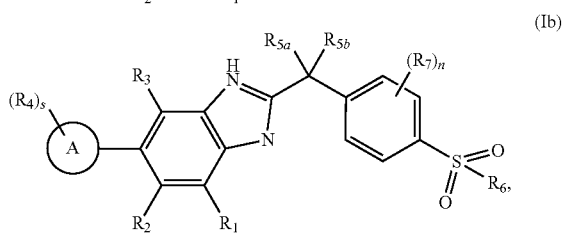

(Ib)

wherein:
R$_1$-R$_4$, R$_{5a}$, R$_{5b}$, R$_6$, R$_7$, n and s are as defined in claim 1.

3. The compound of claim 1, or a tautomer, mesomer, racemate, enantiomer, diastereomer, or mixture thereof, or a pharmaceutically acceptable salt, solvate, or prodrug thereof, wherein ring A is selected from the group consisting of phenyl, C$_{3-6}$ cycloalkyl, and 5 or 6 member heteroaryl.

4. The compound of claim 1, or a tautomer, mesomer, racemate, enantiomer, diastereomer, or mixture thereof, or a pharmaceutically acceptable salt, solvate, or prodrug thereof, having a structure of formula (II):

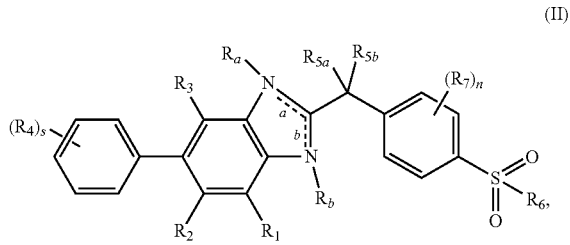

(II)

wherein:

$\stackrel{a}{\text{----}}$, $\stackrel{b}{\text{----}}$, $R_a$, $R_b$, $R_1$-$R_4$, $R_{5a}$, $R_{5b}$, $R_6$, $R_7$, n and s are as defined in claim 1.

5. The compound of claim 1, or a tautomer, mesomer, racemate, enantiomer, diastereomer, or mixture thereof, or a pharmaceutically acceptable salt, solvate, or prodrug thereof, having a structure of formula (III):

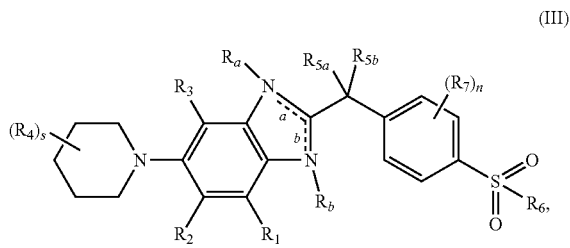

(III)

wherein:

$\stackrel{a}{\text{----}}$, $\stackrel{b}{\text{----}}$, $R_a$, $R_b$, $R_1$-$R_4$, $R_{5a}$, $R_{5b}$, $R_6$, $R_7$, n and s are as defined in claim 1.

6. The compound of claim 1, or a tautomer, mesomer, racemate, enantiomer, diastereomer, or mixture thereof, or a pharmaceutically acceptable salt, solvate, or prodrug thereof, wherein $R_4$ at each occurrence is independently selected from the group consisting of hydrogen, halogen, alkyl, haloalkyl, alkoxy, haloalkoxy, cyano, amino, —$OR_8$, and —$NR_{11}R_{12}$; and $R_8$, $R_{11}$ and $R_{12}$ are as defined in claim 1.

7. The compound of claim 1, or a tautomer, mesomer, racemate, enantiomer, diastereomer, or mixture thereof, or a pharmaceutically acceptable salt, solvate, or prodrug thereof, wherein $R_1$, $R_2$, and $R_3$ are each independently selected from the group consisting of hydrogen, halogen, and alkyl.

8. The compound of claim 1, or a tautomer, mesomer, racemate, enantiomer, diastereomer, or mixture thereof, or a pharmaceutically acceptable salt, solvate, or prodrug thereof, wherein $R_{5a}$ and $R_{5b}$ are each independently selected from the group consisting of hydrogen, hydroxy, hydroxyalkyl, —$OR_8$, —$(CH_2)_xNR_{10}COR_9$, —$NR_{10}COR_9$, —$NR_{10}COCH_2OR_8$, —$(CH_2)_xC(O)OR_8$, —$(CH_2)_xCONR_{11}R_{12}$, and —$(CH_2)_xNR_{11}R_{12}$;

or $R_{5a}$ and $R_{5b}$ together form

and $R_8$ to $R_{12}$ and x are as defined in claim 1.

9. The compound of claim 1, or a tautomer, mesomer, racemate, enantiomer, diastereomer, or mixture thereof, or a pharmaceutically acceptable salt, solvate, or prodrug thereof, wherein $R_6$ is selected from the group consisting of alkyl, haloalkyl, cycloalkyl, heterocyclyl, and —$NR_{11}R_{12}$, wherein said alkyl is optionally substituted by one or more groups independently selected from the group consisting of alkoxy and cycloalkyl; and $R_{11}$ and $R_{12}$ are as defined in claim 1.

10. The compound of claim 1, or a tautomer, mesomer, racemate, enantiomer, diastereomer, or mixture thereof, or a pharmaceutically acceptable salt, solvate, or prodrug thereof, wherein $R_7$ is selected from the group consisting of hydrogen, halogen, and alkyl.

11. The compound of claim 1, or a tautomer, mesomer, racemate, enantiomer, diastereomer, or mixture thereof, or a pharmaceutically acceptable salt, solvate, or prodrug thereof, wherein the compound is selected from the group consisting of:

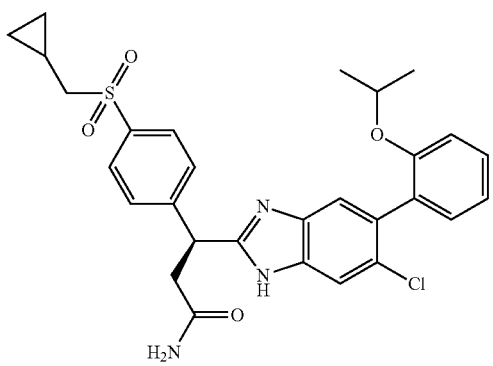

148

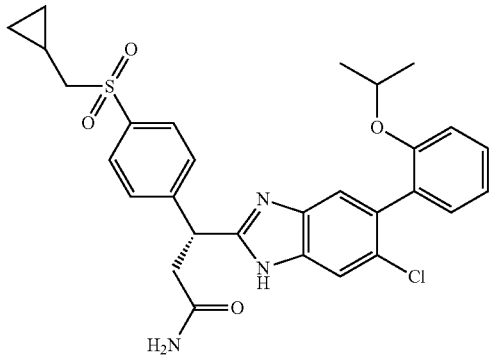

149

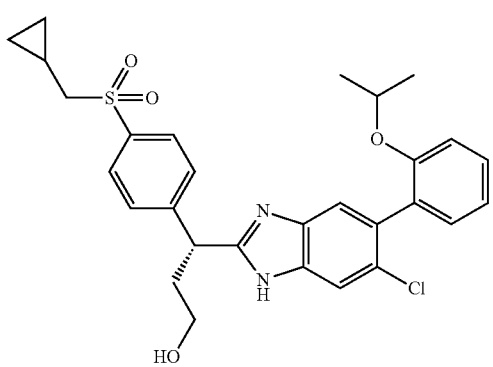

150

151

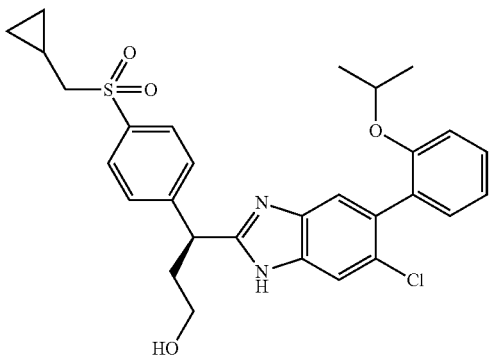

152

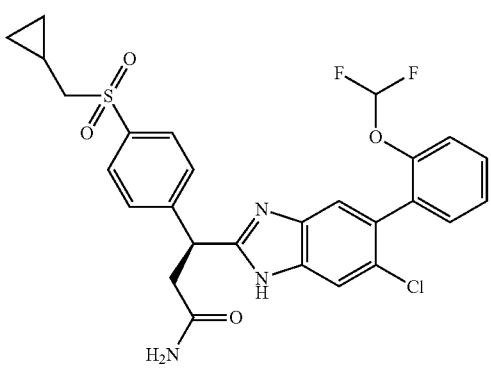

153

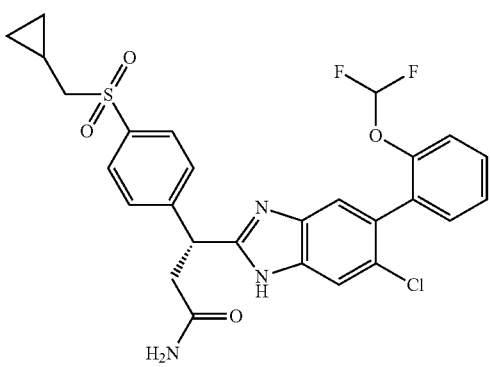

155

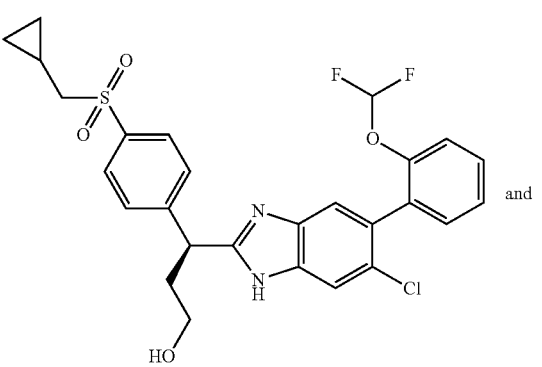 and

156

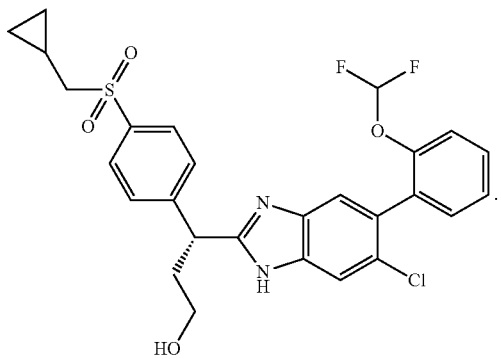

12. A pharmaceutical composition comprising a compound of claim 1, or a tautomer, mesomer, racemate, enantiomer, diastereomer, or mixture thereof, or a pharmaceutically acceptable salt, solvate or prodrug thereof, and one or more pharmaceutically acceptable carriers, diluents or excipients.

13. A method for treating a retinoid-related orphan receptor gamma (RORγ) mediated disease or disorder in a subject in need thereof, comprising administering to the subject a therapeutically effective amount of the compound of claim 1.

14. The method of claim 13, wherein the RORγ mediated disease or disorder is selected from the group consisting of inflammation, autoimmune diseases and cancers, wherein the inflammation and autoimmune diseases comprise arthritis, rheumatoid arthritis, juvenile rheumatoid arthritis, psoriasis, psoriatic arthritis, osteoarthritis, regional enteritis, ulcerative colitis, ankylosing spondylitis, autoimmune diabetes, type I diabetes, autoimmune ocular disease, autoimmune thyroid disease, autoimmune polyendocrine syndrome type I, autoimmune polyendocrine syndrome type II, multiple sclerosis, inflammatory bowel disease, inflammatory bowel syndrome, juvenile idiopathic arthritis syndrome, Crohn's disease, asthma, Kawasaki Disease, Hashimoto's thyroiditis, infectious diseases, ankylosing spondylitis, chronic obstructive pulmonary disease (COPD), pulmonary disease, glomerulonephritis, myocarditis, thyroiditis, dry eye, Uveitis, Behcet's disease, atopic dermatitis, contact dermatitis, allograft rejection, polymyositis, grad versus host disease, acne, ulcerative colitis, systemic lupus erythematosus, scleroderma, bronchitis, dermatomyositis, and allergic rhinitis.

15. The compound of claim 1, or a tautomer, mesomer, racemate, enantiomer, diastereomer, or mixture thereof, or a pharmaceutically acceptable salt, solvate, or prodrug thereof, wherein ring A is piperidinyl, phenyl, thienyl, furyl, or pyridinyl.

16. The compound of claim 1, or a tautomer, or a pharmaceutically acceptable salt, solvate, or prodrug thereof, wherein the compound is selected from the group consisting of:

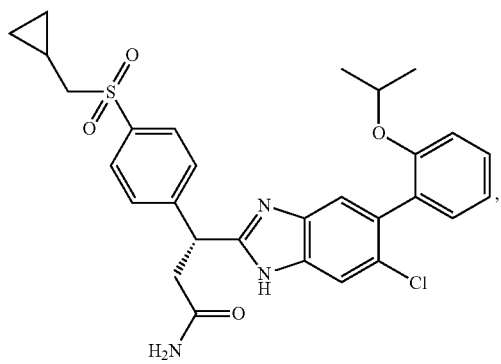
149
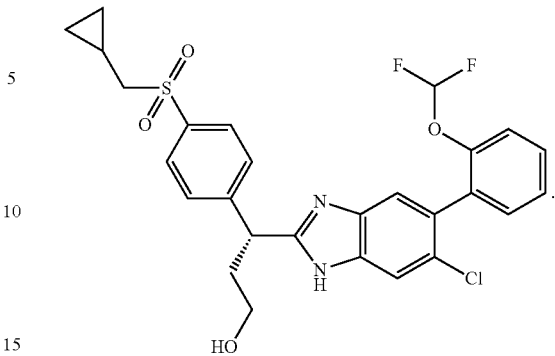
156
17. Compound of formula 153:
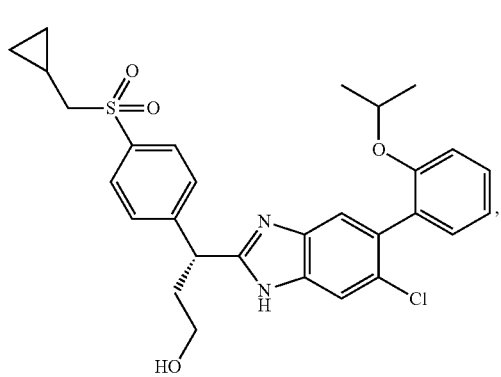
150
or a tautomer, or a pharmaceutically acceptable salt, solvate, or prodrug thereof.
18. Compound of formula 152:
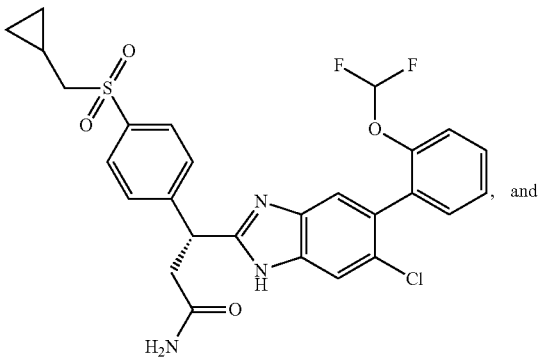
153, and
152
or a tautomer, or a pharmaceutically acceptable salt, solvate, or prodrug thereof.
* * * * *